United States Patent
Alper et al.

(10) Patent No.: US 10,954,233 B2
(45) Date of Patent: Mar. 23, 2021

(54) COMPOUNDS AND COMPOSITIONS AS INHIBITORS OF ENDOSOMAL TOLL-LIKE RECEPTORS

(71) Applicant: Novartis AG, Basel (CH)

(72) Inventors: Phillip Alper, San Diego, CA (US);
Jonathan Deane, San Diego, CA (US);
Songchun Jiang, San Diego, CA (US);
Tao Jiang, San Diego, CA (US);
Thomas Knoepfel, Basel (CH);
Pierre-Yves Michellys, San Diego, CA (US); Daniel Mutnick, Emeryville, CA (US); Wei Pei, San Diego, CA (US);
Peter Syka, San Diego, CA (US);
Guobao Zhang, Shanghai (CN); Yi Zhang, Belmont, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/330,820

(22) PCT Filed: Sep. 6, 2017

(86) PCT No.: PCT/IB2017/055375
§ 371 (c)(1),
(2) Date: Mar. 6, 2019

(87) PCT Pub. No.: WO2018/047081
PCT Pub. Date: Mar. 15, 2018

(65) Prior Publication Data
US 2019/0211009 A1   Jul. 11, 2019

Related U.S. Application Data

(60) Provisional application No. 62/385,726, filed on Sep. 9, 2016.

(51) Int. Cl.
| | |
|---|---|
| *C07D 471/04* | (2006.01) |
| *A61K 31/437* | (2006.01) |
| *A61K 31/4375* | (2006.01) |
| *A61P 17/06* | (2006.01) |
| *A61P 1/16* | (2006.01) |
| *A61P 37/06* | (2006.01) |
| *A61P 19/02* | (2006.01) |
| *A61K 31/496* | (2006.01) |
| *A61K 31/519* | (2006.01) |
| *A61K 31/5377* | (2006.01) |
| *A61K 31/541* | (2006.01) |
| *A61K 45/06* | (2006.01) |

(52) U.S. Cl.
CPC .......... *C07D 471/04* (2013.01); *A61K 31/437* (2013.01); *A61K 31/4375* (2013.01); *A61K 31/496* (2013.01); *A61K 31/519* (2013.01); *A61K 31/5377* (2013.01); *A61K 31/541* (2013.01); *A61K 45/06* (2013.01); *A61P 1/16* (2018.01); *A61P 17/06* (2018.01); *A61P 19/02* (2018.01); *A61P 37/06* (2018.01)

(58) Field of Classification Search
CPC ..... C07D 471/04; A61P 17/06; A61K 31/437; A61K 31/4375
USPC ......................................................... 546/119
See application file for complete search history.

(56) References Cited

FOREIGN PATENT DOCUMENTS

| | | | |
|---|---|---|---|
| WO | 200212242 A2 | 2/2002 | |
| WO | 2004080457 A1 | 9/2004 | |
| WO | 2006049880 A1 | 5/2006 | |
| WO | WO2007/022280 A1 | 2/2007 | |
| WO | WO-2007022280 A1 * | 2/2007 | ........... C07D 401/04 |
| WO | 2007123953 A2 | 11/2007 | |
| WO | 2008137436 A1 | 11/2008 | |
| WO | 2011022509 A2 | 2/2011 | |
| WO | 2011115804 A1 | 9/2011 | |
| WO | 2012068450 A1 | 5/2012 | |
| WO | 2012154608 A1 | 11/2012 | |
| WO | 2013003383 A1 | 1/2013 | |
| WO | WO2013/117615 A1 | 8/2013 | |
| WO | 2014034719 A1 | 3/2014 | |
| WO | 2014056953 A1 | 4/2014 | |
| WO | 2014111496 A1 | 7/2014 | |
| WO | 2014159802 A1 | 10/2014 | |
| WO | 2014177977 A1 | 11/2014 | |
| WO | 201523958 A1 | 2/2015 | |

(Continued)

OTHER PUBLICATIONS

Akbar Mohammad Hosseini et al. Toll-Like receptors in the Pathogenesis of Autoimmune Diseases. (Year: 2015).*

*Primary Examiner* — Rita J Desai
(74) *Attorney, Agent, or Firm* — Francine F. Li

(57) ABSTRACT

The invention disclosed herein relates to 4,5,6,7-tetrahydro-1H-pyrazolo[4,3-c]pyridinyl compounds and 4,5,6,7-tetrahydro-2H-pyrazolo[4,3-c]pyridinyl compounds of Formula (A), pharmaceutical compositions comprising such compounds and the use of such compounds in the treatment of autoimmune diseases.

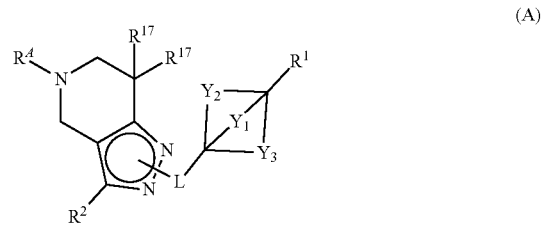

(A)

30 Claims, No Drawings

(56) References Cited

FOREIGN PATENT DOCUMENTS

| | | |
|---|---|---|
| WO | 2015024011 A2 | 2/2015 |
| WO | 2015024120 A1 | 2/2015 |
| WO | 2015025025 A1 | 2/2015 |
| WO | 2015036044 A1 | 3/2015 |
| WO | 2015057655 A1 | 4/2015 |
| WO | 2016023511 A1 | 2/2016 |
| WO | 2016109663 A2 | 7/2016 |
| WO | 2016109684 A2 | 7/2016 |
| WO | 2016109689 A2 | 7/2016 |
| WO | 2016128908 A1 | 8/2016 |
| WO | 2016142867 A1 | 9/2016 |
| WO | 2017161028 A1 | 9/2017 |
| WO | 2018047081 A1 | 3/2018 |

\* cited by examiner

US 10,954,233 B2

COMPOUNDS AND COMPOSITIONS AS INHIBITORS OF ENDOSOMAL TOLL-LIKE RECEPTORS

CROSS-REFERENCE TO RELATED APPLICATIONS

This application is a 35 U.S.C. 371 U.S. National Phase Application of International Application Serial No. PCT/IB2017/055375 filed 6 Sep. 2017 and claims the benefit of U.S. Provisional Application No. 62/385,726, filed 9 Sep. 2016, the disclosures of which are herein incorporated by reference in their entirety and for all purposes.

FIELD OF THE INVENTION

The invention provides 4,5,6,7-tetrahydro-1H-pyrazolo[4,3-c]pyridine compounds and 4,5,6,7-tetrahydro-2H-pyrazolo[4,3-c]pyridine compounds, the use thereof for inhibiting an endosomal Toll-like receptor (e.g. TLR7, TLR8 or TLR9) and any combinations thereof (including, but not limited to, TLR7/8, TLR7/8/9, TLR7/9, and TLR8/9), the use thereof for inhibiting an endosomal Toll-like receptor (e.g. TLR7, TLR8 or TLR9) pathway, and any combinations thereof, and methods of treating autoimmune diseases using such compounds.

BACKGROUND OF THE INVENTION

Early detection of specific classes of pathogens is accomplished by the innate immune system with the help of pattern recognition receptors (PRRs). Toll-like receptors (TLRs) are pattern recognition receptors which play an essential role in the innate immunity, by recognizing invasion of microbial pathogens and initiating intracellular signal transduction pathways to trigger expression of genes, the products of which can control innate immune responses. There are 10 TLRs in the human genome, where TLR1, TLR2, TLR4, TLR5, and TLR6 respond to extracellular stimuli, while TLR3, TLR7, TLR8, and TLR9 respond to intracytoplasmic pathogen associated molecular patterns (PAMPs), being associated with the endolysosomal compartment.

Toll-like receptors recognize pathogens associated molecular patterns present in molecules that are broadly shared by pathogens but are structurally distinct from host molecules. The ligands for these receptors are highly conserved microbial molecules such as lipopolysaccharides (LPS) (recognized by TLR4), lipopeptides (TLR2 in combination with TLR1 or TLR6), flagellin (TLR5), single-stranded RNA (TLR7 and TLR8), double-stranded RNA (TLR3), CpG motif-containing DNA (recognized by TLR9), and profilin present on uropathogenic bacteria (TLR 11). Thus cell-surface TLR dimers including TLR4-MD-2, TLR1-TLR2, and TLR6-TLR2 recognize microbial membrane lipids, whereas the endosomal Toll-like receptors TLR3, TLR7, TLR8, and TLR9 reside in intracellular organelles and recognize microbial nucleic acids.

TLR7, TLR8, and TLR9 belong to a subfamily of TLRs based on their genomic structure, sequence similarities, and homology. TLR7, TLR8, and TLR9 are located in intracellular endolysosomal compartments and show a unique pattern of cell type-specific expression that is thought to be responsible for different pathogen response profiles.

In addition to recognizing foreign material, TLRs can mistakenly respond to self products and cause autoimmune diseases. TLR7 and 9, innate immune sensors for microbial RNA or DNA, respectively, have been implicated in autoimmune diseases such as psoriasis (see Lande et al., "Plasmacytoid dendritic cells sense self-DNA coupled with antimicrobial peptide", Nature 449, pp 564-569, 2007), arthritis (see Asagiri et al., "Cathepsin K-dependent toll-like receptor 9 signaling revealed in experimental arthritis", Science 319, pp 624-627, 2008), and systemic lupus erythematosus (SLE) (see Pisitkun, P. et al. "Autoreactive B cell responses to RNA-related antigens due to TLR7 gene duplication", Science 312, pp 1669-72, 2006; Deane, J. A. et al., "Control of toll-like receptor 7 expression is essential to restrict autoimmunity and dendritic cell proliferation", Immunity, 27, pp 801-10, 2007; Christensen, S. R. et al. "Toll-like receptor 7 and TLR9 dictate autoantibody specificity and have opposing inflammatory and regulatory roles in a murine model of lupus", Immunity 25, pp 417-428, 2006; Ehlers, M., et al. "TLR9/MyD88 signaling is required for class switching to pathogenic IgG2a and 2b autoantibodies in SLE", J. Exp. Med. 203, pp 553-561, 2006; Deane, J. A., and Bolland S. "Nucleic acid-sensing TLRs as modifiers of autoimmunity", J. Immunol., 117, pp 6573-8, 2006; and Marshak-Rothstein, A., and Rifkin, I. R., "Immunologically active autoantigens: the role of toll-like receptors in the development of chronic inflammatory disease", Annu. Rev. Immunol., 25, pp 419-441, 2007).

It has been shown that autoimmunity is exacerbated by the aberrant trafficking of self nucleic acids to endolysosomes (see Lande et al., 2007; Marshak-Rothstein and Rifkin, 2007; and Leadbetter et al., "Chromatin-IgG complexes activate B cells by dual engagement of IgM and Toll-like receptors", Nature, 416, pp 603-607, 2002). In autoimmune diseases like SLE, self-RNA and self-DNA are complexed with autoantibodies against the nucleic acid or nucleoproteins, delivered into endosomal compartments via FcgRII-mediated endocytosis, leading to dendritic cell (DC) activation and production of type I interferon (IFN) (Barrat et al., "Nucleic acids of mammalian origin can act as endogenous ligands for Toll-like receptors and may promote systemic lupus erythematosus", J. Exp. Med. 202, pp 1131-1139, 2005). While in psoriasis, self-DNA and -RNA form complexes with the cationic antimicrobial peptide LL37, gain access to TLR7 and 9 in endolysosomes of DCs, and induce aberrant production of IFN-a (Ganguly et al., "Self-RNA-antimicrobial peptide complexes activate human dendritic cells through TLR7 and TLR8", J. Exp. Med. 206, pp 1983-1994, 2009; and Lande et al., 2007). In rheumatoid arthritis (RA) the synovial membrane is infiltrated by activated immune cells, predominantly macrophages and T cells, resulting in the chronic production of proinflammatory cytokines and matrix metalloproteinases. TNF plays a central role in RA and the inhibition of TLR8 has been shown to inhibit TNF production (see Sandra M. Sacre et al. "Inhibitors of TLR8 Reduce TNF Production from Human Rheumatoid Synovial Membrane Cultures", J. Immun., 81, pp 8002-8009, 2008).

Because of their association with autoimmune diseases, it has been suggested that TLR7, TLR8 and TLR9 are important therapeutic targets for the treatment of systemic lupus erythematosus, rheumatoid arthritis, psoriasis and other autoimmune diseases.

SUMMARY OF THE INVENTION

There remains a need for new treatments and therapies for autoimmune diseases, in particular autoimmune diseases associated with TLR7, TLR8 and/or TLR9 activity. The invention provides compounds, pharmaceutically acceptable salts thereof, pharmaceutical compositions thereof, which may inhibit an endosomal Toll-like receptor (e.g. TLR7, TLR8 or TLR9) and any combinations thereof (including, but not limited to, TLR7/8, TLR7/8/9, TLR7/9, and TLR8/9). Additionally, the compounds of the invention may inhibit an endosomal Toll-like receptor (e.g. TLR7, TLR8 or TLR9) pathway, and any combinations thereof. The invention further provides methods of treating, preventing, or ameliorating autoimmune diseases associated with the activity of an endosomal Toll-like receptor (e.g. TLR7, TLR8 or TLR9), or any combinations thereof (including, but not limited to, TLR7/8, TLR7/8/9, TLR7/9, and TLR8/9), comprising administering to a subject in need thereof an effective amount of a compound of the invention. Various embodiments of the invention are described herein.

In one aspect of the invention are compounds having the structure of Formula (A), and the pharmaceutically acceptable salts thereof, which may inhibit an endosomal Toll-like receptor (e.g. TLR7, TLR8 or TLR9) and any combinations thereof (including, but not limited to, TLR7/8, TLR7/8/9, TLR7/9, and TLR8/9). Additionally, the compounds of Formula (A) may inhibit an endosomal Toll-like receptor (e.g. TLR7, TLR8 or TLR9) pathway, and any combinations thereof:

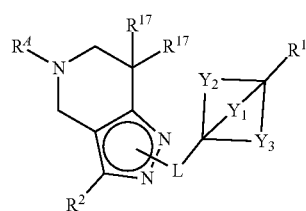

Formula (A)

wherein:
$R^A$ is

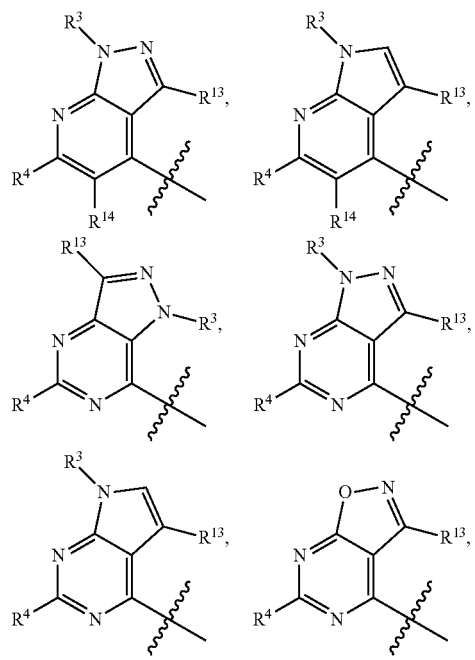

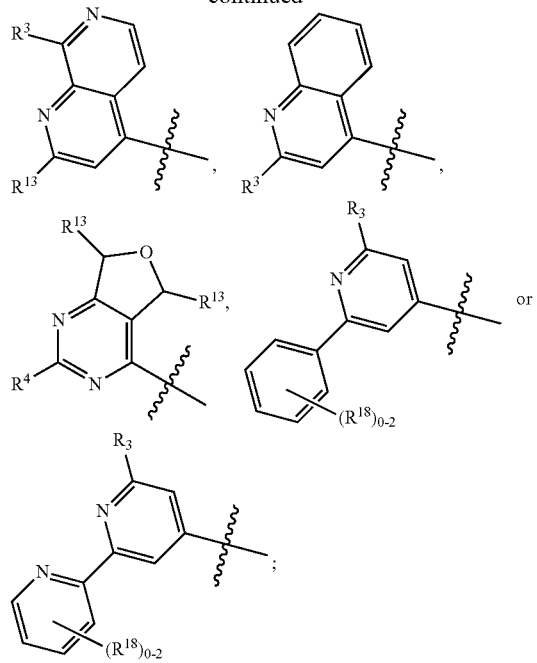

L is —CH$_2$— or —CH$_2$CH$_2$—;
Y$_1$ is —CH$_2$— or —CH$_2$CH$_2$—;
Y$_2$ is —CH$_2$— or —CH$_2$CH$_2$—;
Y$_3$ is —CH$_2$—, —XCH$_2$— or —CH$_2$X—;
X is —CH$_2$— or O;
$R^1$ is —NHC(=O)R$^6$, —NHC(=O)(CH$_2$)$_n$R$^6$, —NH(CH$_2$)$_n$C(=O)R$^6$, —NHC(=O)(CH$_2$)$_m$NHR$^5$, —NHC(=O)(CH$_2$)$_m$N(R$^5$)$_2$, —NHC(=O)(CHR$^9$)$_m$NHR$^5$, —NHC(=O)(CH$_2$)$_m$NH$_2$, —NHC(=O)(CH$_2$)$_n$OR$^9$, —NHC(=O)OR$^9$, —NH(CH$_2$)$_m$C(=O)N(R$^5$)$_2$, —NH(CHR$^9$)$_n$C(=O)R$^6$, NHC(=O)(CHR$^9$)$_n$R$^6$, —NHC(=O)(CHR$^9$)$_n$N(R$^8$)$_2$, —NHC(=O)(CHR$^9$)$_n$NHR$^8$, —NH(CHR$^9$)$_n$C(=O)N(R$^8$)$_2$, —NH(CHR$^9$)$_m$C(=O)R$^6$, —NHR$^6$, —NR$^5$R$^6$, —NH$_2$, —N(R$^5$)$_2$, —NHR$^5$, —NHR$^8$, —N(R$^6$R$^8$), —NH(C(R$^9$)$_2$)$_n$R$^{10}$, —NR$^9$C(=O)OR$^{11}$, —NH(CH$_2$)$_n$R$^6$, —NH(CHR$^9$)$_n$R$^6$, —N(R$^6$)$_2$, —NHC(=O)(CH$_2$)$_n$N(CD$_3$)$_2$, —NH(CHR$^9$)$_n$CH$_2$OR$^9$, —NHCH$_2$(CHR$^9$)$_n$OR$^9$, —NH(CHR$^9$)$_n$OR$^9$, —NR$^9$(CH$_2$)$_n$OR$^9$, —NHCH$_2$(C(R$^9$)$_2$)$_n$OR$^9$, —OR$^9$, —NR$^9$C(=O)R$^5$, —NR$^9$C(=O)(CH$_2$)$_n$R$^5$, —NR$^9$C(=O)OR$^5$, —NHS(=O)$_2$R$^5$, —NHC(=O)(CH$_2$)$_n$NR$^9$C(=O)R$^5$, —NHC(=O)(CH$_2$)$_n$NR$^9$S(=O)$_2$R$^5$,

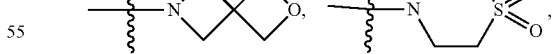

an 8-oxa-3-azabicyclo[3.2.1]octanyl, a 5-6 membered heteroaryl having 1 to 3 ring members independently selected from N, O and S, and a 4-6 membered heterocycloalkyl having 1 to 2 ring members independently selected from N, NH, NR$^{16}$ and O which is unsubstituted or is substituted with 1-2 R$^7$ groups;
$R^2$ is H, C$_1$-C$_6$alkyl, C$_1$-C$_6$haloalkyl or C$_1$-C$_6$alkyl substituted with 1-2 R$^{15}$ groups;
$R^3$ is H, C$_1$-C$_6$alkyl, —CD$_3$ or benzyl substituted with 1-2 R$^{10}$ groups;

$R^4$ is H, $NH_2$, $C_1$-$C_6$alkyl, halo or a phenyl substituted with 0-2 $R^{18}$ groups;

each $R^5$ is independently selected from $C_1$-$C_6$alkyl, —$CD_3$ and —$(CH_2)_nOR^9$;

$R^6$ is a $C_3$-$C_6$cycloalkyl, an oxa-3-azabicyclo[3.2.1]octane, or a 4-6 membered heterocycloalkyl having 1 to 2 ring members independently selected from N, NH, $NR^{16}$ and O which is unsubstituted or is substituted with 1-2 $R^{12}$ groups;

each $R^7$ is independently selected from $C_1$-$C_6$alkyl, halo, hydroxyl, oxo and a $C_1$-$C_6$alkyl substituted with 1 to 3 —OH;

each $R^8$ is independently selected from $C_1$-$C_6$haloalkyl, —$(C(R^9)_2)_nOR^9$ and a $C_1$-$C_6$alkyl substituted with 1 to 3 —OH;

each $R^9$ is independently selected from H and $C_1$-$C_6$alkyl;

$R^{10}$ is $C_1$-$C_6$alkoxy or $C_3$-$C_6$cycloalkyl;

$R^{11}$ is a $C_3$-$C_6$cycloalkyl which is unsubstituted or is substituted with 1 to 3 $C_1$-$C_6$alkyl groups;

each $R^{12}$ is independently selected from $C_1$-$C_6$alkyl, hydroxyl, halo and a $C_1$-$C_6$alkyl substituted with 1 to 3 —OH;

$R^{13}$ is H or $C_1$-$C_6$alkyl;

$R^{14}$ is H or $C_1$-$C_6$alkyl;

$R^{15}$ is —$NHC(=O)(CH_2)_mNHR^5$, —$NHC(=O)(CH_2)_mN(R^5)_2$, —$NHC(=O)(CH_2)_mNH_2$, —$NHC(=O)(CHR^9)_nR^6$, —$NHC(=O)(CHR^9)_nN(R^8)_2$, —$NHC(=O)(CHR^9)_nNHR^8$, —$NH(CHR^9)_nC(=O)N(R^8)_2$, —$NH(CHR^9)_nC(=O)R^6$, —$NHR^6$, —$NH_2$, —$N(R^5)_2$, —$NHR^8$, —$N(R^6R^8)$, —$NH(C(R^9)_2)_nR^{10}$, —$NR^9C(=O)OR^{11}$, —$NH(CHR^9)_nR^6$, —$N(R^6)_2$, —$N(CD_3)_2$, —$NH(CHR^9)_nOR^9$ or —$NHCH_2(C(R^9)_2)_nOR^9$;

each $R^{16}$ is $C_1$-$C_6$alkyl;

each $R^{17}$ is independently selected from H and $C_1$-$C_6$alkyl;

each $R^{18}$ is independently selected from halo, —CN, $C_1$-$C_6$alkoxy and $C_1$-$C_6$alkyl;

m is 1, 2, 3, 4, 5 or 6, and n is 1, 2, 3, 4, 5 or 6

In certain embodiments of such compounds of Formula (A) are compounds of Formula (I) and Formula (II):

Formula (I)

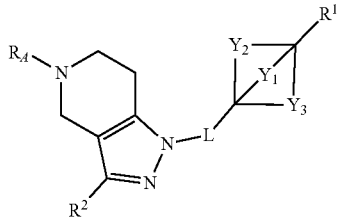

Formula (II)

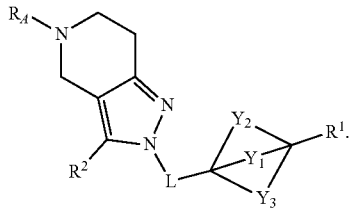

Another aspect of the invention is a pharmaceutical compositions that includes a therapeutically effective amount of a compound of Formula (A), Formula (I) or Formula (II) or subformulae thereof, or a pharmaceutically acceptable salt thereof, and a pharmaceutically acceptable carrier.

Another aspect of the invention is the use of a compound of Formula (A), Formula (I) or Formula (II), or subformulae thereof, or a pharmaceutically acceptable salt thereof, in the manufacture of a medicament for treating an autoimmune disease associated with the activity of an endosomal Toll-like receptor (e.g. TLR7, TLR8 or TLR9), or any combinations thereof (including, but not limited to, TLR7/8, TLR7/8/9, TLR7/9, and TLR8/9).

Another aspect of the invention is the use of a compound of Formula (A), Formula (I) or Formula (II), or subformulae thereof, or a pharmaceutically acceptable salt thereof, in the manufacture of a medicament for treating an autoimmune disease associated with i) TLR7 activity, or ii) TLR7 activity and TLR8 activity, or iii) TLR7 activity and TLR8 activity and TLR9 activity.

Another aspect of the invention is the use of a compound of Formula (A), Formula (I) or Formula (II), or subformulae thereof, or a pharmaceutically acceptable salt thereof, in the manufacture of a medicament for treating an autoimmune disease associated with the activity of an endosomal Toll-like receptor (e.g. TLR7, TLR8 or TLR9) pathway, and any combinations thereof.

Another aspect of the invention is the use of a compound of Formula (A), Formula (I) or Formula (II), or subformulae thereof, or a pharmaceutically acceptable salt thereof, in the manufacture of a medicament for treating an autoimmune disease.

Another aspect of the invention is the use of a compound of Formula (A), Formula (I) or Formula (II), or subformulae thereof, or a pharmaceutically acceptable salt thereof, in the manufacture of a medicament for treating an autoimmune disease is systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis. In an embodiment of this aspect the autoimmune disease is systemic lupus erythematosus, cutaneous lupus, discoid lupus, Sjögren's syndrome or psoriasis.

Another aspect of the invention is a method for treating an autoimmune disease associated with the activity of an endosomal Toll-like receptor (e.g. TLR7, TLR8 or TLR9), or any combinations thereof (including, but not limited to, TLR7/8, TLR7/8/9, TLR7/9, and TLR8/9), wherein the method includes administering to a subject in need of such treatment an effective amount of a compound of Formula (A), Formula (I) or Formula (II), or subformulae thereof, or pharmaceutically acceptable salt thereof, thereby treating the disease.

Another aspect of the invention is a method for treating an autoimmune disease associated with:

i) TLR7 activity, or ii) TLR7 activity and TLR8 activity, or iii) TLR7 activity and TLR8 activity and TLR9 activity, wherein the method includes administering to a subject in need of such treatment an effective amount of a compound of Formula (A), Formula (I) or Formula (II), or subformulae thereof, or pharmaceutically acceptable salt thereof, thereby treating the disease.

Another aspect of the invention is a method for treating an autoimmune disease associated with the activity of with the activity of an endosomal Toll-like receptor (e.g. TLR7, TLR8 or TLR9) pathway, and any combinations thereof, wherein the method includes administering to a subject in need of such treatment an effective amount of a compound of Formula (A), Formula (I) or Formula (II), or subformulae thereof, or pharmaceutically acceptable salt thereof, thereby treating the disease.

Another aspect of the invention is a method for treating an autoimmune disease associated with TLR7 activity, wherein the method includes administering to a subject in need of such treatment an effective amount of a compound of Formula (A), Formula (I) or Formula (II), or subformulae thereof, or pharmaceutically acceptable salt thereof, thereby treating the disease.

Another aspect of the invention is a method for treating an autoimmune disease associated with TLR7 and TLR8 activity, wherein the method includes administering to a subject in need of such treatment an effective amount of a compound of Formula (A), Formula (I) or Formula (II), or subformulae thereof, or pharmaceutically acceptable salt thereof, thereby treating the disease.

Another aspect of the invention is a method for treating an autoimmune disease associated with TLR7, TLR8 and TLR9 activity, wherein the method includes administering to a subject in need of such treatment an effective amount of a compound of Formula (A), Formula (I) or Formula (II), or subformulae thereof, or pharmaceutically acceptable salt thereof, thereby treating the disease.

In certain embodiments of such methods of treatment the autoimmune disease is systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis. In another embodiment the autoimmune disease is systemic lupus erythematosus, cutaneous lupus, discoid lupus, Sjögren's syndrome or psoriasis.

Another aspect of the invention is a compound of Formula (A), Formula (I) or Formula (II), or subformulae thereof, or pharmaceutically acceptable salt thereof, for use in treating an autoimmune disease is systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis. In an embodiment of this aspect the autoimmune disease is systemic lupus erythematosus, cutaneous lupus, discoid lupus, Sjögren's syndrome or psoriasis.

Another aspect of the invention is a combination comprising a therapeutically effect amount of a compound of Formula (A), Formula (I) or Formula (II), or subformulae thereof, or pharmaceutically acceptable salt thereof, and one or more additional therapeutically agents and optionally further comprising a pharmaceutically acceptable carrier, wherein the additional therapeutically agent is independently selected from anti-inflammatory agents, immunomodulatory agents, immunosuppressive agents, cytokines, nonsteroidal anti-inflammatory drugs (NSAIDs), antimalarial compounds, anti-rheumatic compounds, inhibitors of B-cell activating factor (BAFF), inhibitors of B-lymphocyte stimulator (BLyS), and steroid hormones.

DETAILED DESCRIPTION OF THE INVENTION

Various enumerated embodiments of the invention are described herein. It will be recognized that features specified in each embodiment may be combined with other specified features to provide further embodiments of the present invention.

Definitions

The term "$C_1$-$C_6$alkyl", as used herein, refers to a fully saturated branched or straight chain hydrocarbon containing 1 to 6 carbon atoms. Non-limiting examples of "$C_1$-$C_6$alkyl" groups include methyl, ethyl, n-propyl, isopropyl, n-butyl, isobutyl, sec-butyl, tert-butyl, n-pentyl, isopentyl and hexyl.

The term "$C_1$-$C_6$alkoxy", as used herein, refers to the group —O—$C_1$-$C_6$alkyl, wherein the "$C_1$-$C_6$alkyl" group is as defined herein. Non-limiting examples of "$C_1$-$C_6$alkoxy" groups include methoxy, ethoxy, n-propoxy, isopropoxy, n-butoxy, isobutoxy, sec-butoxy, tert-butoxy, n-pentyloxy, isopentyloxy and hexyloxy.

The term "cycloalkyl," as used herein, refers to a saturated, monocyclic, fused bicyclic, fused tricyclic or bridged polycyclic ring system. Non-limiting examples of fused bicyclic or bridged polycyclic ring systems include bicyclo[1.1.1]pentane, bicyclo[2.1.1]hexane, bicyclo[2.2.1]heptane, bicyclo[3.1.1]heptane, bicyclo[3.2.1]octane, bicyclo[2.2.2]octane and adamantanyl. As used herein, the term "$C_3$-$C_6$cycloalkyl", refers to a saturated monocyclic group having at least 3, and at most 6, carbon atoms. Non-limiting examples of such "$C_3$-$C_6$cycloalkyl" groups include cyclopropyl, cyclobutyl, cyclopentyl and cyclohexyl groups.

The term "$C_1$-$C_6$haloalkyl", as used herein, refer to the respective "$C_1$-$C_6$alkyl", as defined herein, wherein at least one of the hydrogen atoms of the "$C_1$-$C_6$alkyl" is replaced by a halo atom. The $C_1$-$C_6$haloalkyl groups can be mono$C_1$-$C_6$haloalkyl, wherein such $C_1$-$C_6$haloalkyl groups have one iodo, one bromo, one chloro or one fluoro. Additionally, the $C_1$-$C_6$haloalkyl groups can be di$C_1$-$C_6$haloalkyl wherein such $C_1$-$C_6$haloalkyl groups can have two halo atoms independently selected from iodo, bromo, chloro or fluoro. Furthermore, the $C_1$-$C_6$haloalkyl groups can be poly$C_1$-$C_6$haloalkyl wherein such $C_1$-$C_6$haloalkyl groups can have two or more of the same halo atoms or a combination of two or more different halo atoms. Such poly$C_1$-$C_6$haloalkyl can be perhalo$C_1$-$C_6$haloalkyl where all the hydrogen atoms of the respective $C_1$-$C_6$alkyl have been replaced with halo atoms and the halo atoms can be the same or a combination of different halo atoms. Non-limiting examples of $C_1$-$C_6$haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, trifluoroethyl, difluoropropyl, dichloroethyl and dichloropropyl.

The terms "halo" or "halogen" as used herein, refer to fluoro, chloro, bromo and iodo.

The term "5-6 membered heteroaryl," as used herein, refers to a monocyclic aromatic ring structure having 5 or 6 ring members, wherein 1 to 3 ring members are independently selected from the heteroatoms N, O and S. Non-limiting examples of 5-6 membered heteroaryls include 2- or 3-furyl; 2- or 3-thienyl; 1-, 2- or 3-pyrrolyl; 2-, 4-, or 5-oxazolyl; 2-, 4-, or 5-thiazolyl; 1-, 2-, 4-, or 5-imidazolyl; 1-, 3-, 4-, or 5-pyrazolyl; 3-, 4-, or 5-isoxazolyl; 3-, 4-, or 5-isothiazolyl; 4- or 5-1,2,3-oxadiazolyl; 4- or 5-1,2,3-triazolyl; 2- or 5-1,3,4-thiadiazolyl; 2-, 3-, or 4-pyridyl; 3-, 4-, 5- or 6-pyridazinyl; 2-, 4-, 5- or 6-pyrimidinyl, and 2- or 3-pyrazinyl.

The term "heteroatoms" as used herein, refers to nitrogen (N), oxygen (O) or sulfur (S) atoms.

The term "4-6 membered heterocycloalkyl," as used herein refers to a monocyclic ring structure having 4 to 6 ring members, wherein one to two of the ring members are independently selected from N, NH, $NR^{16}$, O or —S—, wherein $R^{16}$ is $C_1$-$C_6$alkyl. In preferred embodiments a 4-6 membered heterocycloalkyl is a monocyclic ring structure having 4 to 6 ring members wherein one to two of the ring members are independently selected from N, NH, $NR^{16}$ and O, wherein $R^{16}$ is $C_1$-$C_6$alkyl. Non-limiting examples of 4-6 membered heterocycloalkyl groups, as used herein, include azetadinyl, azetadin-1-yl, azetadin-2-yl, azetadin-3-yl, oxetanyl, oxetan-2-yl, oxetan-3-yl, oxetan-4-yl, thietanyl, thietan-2-yl, thietan-3-yl, thietan-4-yl, pyrrolidinyl, pyrrolidin-1-yl, pyrrolidin-2-yl, pyrrolidin-3-yl, pyrrolidin-4-yl, pyrrolidin-5-yl, tetrahydrofuranyl, tetrahydrofuran-2-yl, tetrahydrofuran-3-yl, tetrahydrofuran-4-yl, tetrahydrofuran-5-yl, tetrahydrothienyl, tetrahydrothien-2-yl, tetrahydrothien-3-yl, tetrahydrothien-4-yl, tetrahydrothien-5-yl, piperidinyl, piperidin-1-yl, piperidin-2-yl, piperidin-3-yl, piperidin-4-yl, piperidin-5-yl, piperidin-6-yl, tetrahydropyranyl, tetrahydropyran-2-yl, tetrahydropyran-3-yl, tetrahydropyran-4-yl, tetrahydropyran-5-yl, tetrahydropyran-6-yl, tetrahydrothiopyranyl, tetrahydrothiopyran-2-yl, tetrahydrothiopyran-3-yl, tetrahydrothiopyran-4-yl, tetrahydrothiopyran-5-yl, tetrahydrothiopyran-6-yl, piperazinyl, piperazin-1-yl, piperazin-2-yl, piperazin-3-yl, piperazin-4-yl, piperazin-5-yl, piperazin-6-yl, morpholinyl, morpholin-2-yl, morpholin-3-yl, morpholin-4-yl, morpholin-5-yl, morpholin-6-yl, thiomorpholinyl, thiomorpholin-2-yl, thiomorpholin-3-yl, thiomorpholin-4-yl, thiomorpholin-5-yl, thiomorpholin-6-yl, oxathianyl, oxathian-2-yl, oxathian-3-yl, oxathian-5-yl, oxathian-6-yl, dithianyl, dithian-2-yl, dithian-3-yl, dithian-5-yl, dithian-6-yl, dioxolanyl, dioxolan-2-yl, dioxolan-4-yl, dioxolan-5-yl, thioxanyl, thioxan-2-yl, thioxan-3-yl, thioxan-4-yl, thioxan-5-yl, dithiolanyl, dithiolan-2-yl, dithiolan-4-yl, dithiolan-5-yl, pyrazolidinyl, pyrazolidin-1-yl, pyrazolidin-2-yl, pyrazolidin-3-yl, pyrazolidin-4-yl and pyrazolidin-5-yl.

The term "hydroxyl" as used herein, refers to a —OH group.

The term "oxo" as used herein, refers to a =O group.

The term "autoimmune disease," or "autoimmune disorder," as used herein, refers diseases wherein cells uncontrollably attack the body's own tissues and organs (autoimmunity), producing inflammatory reactions and other serious symptoms and diseases. Non-limiting examples of autoimmune diseases include idiopathic thrombocytopenic purpura, hemolytic anemia, systemic lupus erythematosus, cutaneous lupus, discoid lupus, rheumatoid arthritis (RA), multiple sclerosis (MS), systemic sclerosis, immune-mediated or type 1 diabetes mellitus, immune mediated glomerulonephritis, scleroderma, pernicious anemia, alopecia, pemphigus, pemphigus vulgaris, myasthenia gravis, inflammatory bowel diseases, Crohn's disease, Graves' disease, psoriasis, autoimmune thyroid diseases, Hashimoto's disease, Hashimoto's thyroiditis, polymyositis, dermatomyositis, CREST syndrome, Goodpasture's syndrome, mixed connective tissue disease myasthenia gravis pseudoparalytica, ophtalmia sympatica, phakogene uveitis, chronical aggressive hepatitis, primary billiary cirrhosis, autoimmune hemolytic anemy, Werlof disease, vitiligo vulgaris, Behcet's disease, collagen disease, uveitis, Sjögren's syndrome, autoimmune myocarditis, autoimmune hepatic diseases, autoimmune gastritis, pemphigus, Guillain-Barre syndrome, atherosclerosis, inflammatory bowel disease, ankylosing spondylitis, idiopathic thrombocytopenia, polyarteritis nodosa, primary biliary sclerosis, sarcoidosis, sclerosing cholangitis, Takayasu's arteritis, temporal arteritis, Wegener's granulomatosis and HTLV-1-associated myelopathy.

The terms "combination" or "pharmaceutical combination," as used herein mean a product that results from the mixing or combining of more than one active ingredient and includes both fixed and non-fixed combinations of the active ingredients. The term "fixed combination" means that the active ingredients, by way of example, a compound of the invention and one or more additional therapeutic agent, are administered to a subject simultaneously in the form of a single entity or dosage. The term "non-fixed combination" means that the active ingredients, by way of example, a compound of the invention and one or more additional therapeutic agent, are administered to a subject as separate entities either simultaneously, concurrently or sequentially with no specific time limits, wherein such administration provides therapeutically effective levels of the active ingredients in the body of the subject. The latter also applies to cocktail therapy, e.g. the administration of 3 or more active ingredients.

The terms "composition" or "pharmaceutical composition," as used herein, refers to a mixture of a compound of the invention with at least one and optionally more than one other pharmaceutically acceptable chemical components, such as carriers, stabilizers, diluents, dispersing agents, suspending agents, thickening agents, and/or excipients.

As used herein, the term "inhibit", "inhibition" or "inhibiting" refers to the reduction or suppression of a given condition, symptom, or disorder, or disease, or a significant decrease in the baseline activity of a biological activity or process.

The term "an optical isomer" or "a stereoisomer", as used herein, refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)— or (S)—.

The term "pharmaceutically acceptable carrier", as used herein, includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "pharmaceutically acceptable salt," as used herein, refers to a salt which does not abrogate the biological activity and properties of the compounds of the invention, and does not cause significant irritation to a subject to which it is administered.

The term "subject", as used herein, encompasses mammals and non-mammals. Examples of mammals include, but are not limited to, humans, chimpanzees, apes, monkeys, cattle, horses, sheep, goats, swine, rabbits, dogs, cats, rats, mice, guinea pigs, and the like. Examples of non-mammals include, but are not limited to, birds, fish and the like. Frequently the subject is a human, and may be a human who has been diagnosed as in need of treatment for a disease or disorder associated with the activity of an endosomal Toll-like receptor (e.g. TLR7, TLR8 or TLR9) and any combinations thereof (including, but not limited to, TLR7/8, TLR7/8/9, TLR7/9, and TLR8/9), or associated with an endosomal Toll-like receptor (e.g. TLR7, TLR8 or TLR9) pathway, and any combinations.

The term "a subject in need of such treatment", refers to a subject which would benefit biologically, medically or in quality of life from such treatment.

The term "therapeutically effective amount," as used herein, refers to an amount of a compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by an endosomal Toll-like receptor (e.g. TLR7, TLR8 or TLR9) and any combinations thereof (including, but not limited to, TLR7/8, TLR7/8/9, TLR7/9, and TLR8/9), or mediated by an endosomal Toll-like receptor (e.g. TLR7, TLR8 or TLR9) pathway, and any combinations thereof or (ii) associated with an endosomal Toll-like receptor (e.g. TLR7, TLR8 or TLR9) and any combinations thereof (including, but not limited to, TLR7/8, TLR7/8/9, TLR7/9, and TLR8/9), or associated with an endosomal Toll-like receptor (e.g. TLR7, TLR8 or TLR9) pathway, and any combinations thereof, or (iii) characterized by activity (normal or abnormal) of an endosomal Toll-like receptor (e.g. TLR7, TLR8 or TLR9) and any combinations thereof (including, but not limited to, TLR7/8, TLR7/8/9, TLR7/9, and TLR8/9); or (2) reduce or inhibit the activity of an endosomal Toll-like receptor (e.g. TLR7, TLR8 or TLR9) and any combinations thereof (including, but not limited to, TLR7/8, TLR7/8/9, TLR7/9, and TLR8/9); or (3) reduce or inhibit the expression of an endosomal Toll-like receptor (e.g. TLR7, TLR8 or TLR9) and any combinations thereof (including, but not limited to, TLR7/8, TLR7/8/9, TLR7/9, and TLR8/9). In another non-limiting embodiment, the term "a therapeutically effective amount" refers to the amount of the compound provided herein that, when administered to a cell, or a tissue, or a non-cellular biological material, or a medium, is effective to at least partially reducing or inhibiting the activity of an endosomal Toll-like receptor (e.g. TLR7, TLR8 or TLR9) and any combinations thereof (including, but not limited to, TLR7/8, TLR7/8/9, TLR7/9, and TLR8/9), or inhibiting the activity of an endosomal Toll-like receptor (e.g. TLR7, TLR8 or TLR9) pathway, and any combinations thereof.

The terms "TLR7 inhibitors", "TLR7 antagonist", "inhibitor of TLR7" or "inhibitors of TLR7", as used herein, refer to a compound of the invention which inhibits Toll-like Receptor 7 (TLR7). Compounds of the invention inhibit both type I Interferon and proinflammatory cytokines downstream of TLR7.

The terms "TLR8 inhibitors", "TLR8 antagonist", "inhibitor of TLR8" or "inhibitors of TLR8", as used herein, refer to a compound of the invention which inhibits Toll-like Receptor 8 (TLR8).

The terms "TLR7 and TLR8 inhibitors", "TLR7 and TLR8 antagonists", "inhibitor of TLR7 and TLR8" or "inhibitors of TLR7 and TLR8", as used herein, refer to a compound of the invention which inhibits Toll-like Receptor 7 (TLR7) and Toll-like Receptor 8 (TLR8). Compounds of the invention inhibit both type I Interferon downstream of TLR7 and proinflammatory cytokines downstream of NF-KB in TLR7 and TLR8 signaling. A "TLR7 and TLR8 inhibitor" or "TLR7 and TLR8 antagonist" can also be represented by the term "TLR7/8 anatgonist".

The terms "TLR7, TLR8 and TLR9 inhibitors", "TLR7, TLR8 and TLR9 antagonists", "inhibitor of TLR7, TLR8 and TLR9" or "inhibitors of TLR7, TLR8 and TLR9", as used herein, refer to a compound of the invention which inhibits Toll-like Receptor 7 (TLR7), Toll-like Receptor 8 (TLR8) and Toll-like Receptor 9 (TLR9). Compounds of the invention inhibit both type I Interferon downstream of TLR7 and proinflammatory cytokines downstream of NF-KB in TLR7 and TLR8 signaling. A "TLR7 and TLR8 and TLR9 inhibitor" or "TLR7 and TLR8 and TLR9 antagonist" can also be represented by the term "TLR7/8/9 anatgonist".

The terms "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

The compound names provided herein were obtained using ChemDraw Ultra version 12.0 (CambridgeSoft®) or JChem version 5.3.1 (ChemAxon).

Unless specified otherwise, the term "compounds of the present invention", "compounds of the invention" or "compounds provided herein" refers to compounds of formula (A), Formula (I), Formula (II) and subformulae thereof (such as compounds of Formula (Ia to Ip) and Formula (IIa to IIk), and pharmaceutically acceptable salts, stereoisomers (including diastereoisomers and enantiomers), rotamers, tautomers and isotopically labeled compounds (including deuterium substitutions), as well as inherently formed moieties.

As used herein, the term "a," "an," "the" and similar terms used in the context of the present invention (especially in the context of the claims) are to be construed to cover both the singular and plural unless otherwise indicated herein or clearly contradicted by the context.

Compounds of the Invention

The compounds of the invention are compounds having the structure of Formula (A), or a pharmaceutically acceptable salt thereof:

Formula (A)

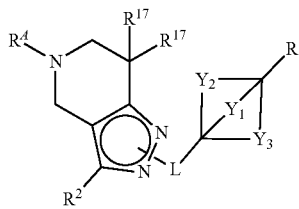

wherein:
R$^A$ is

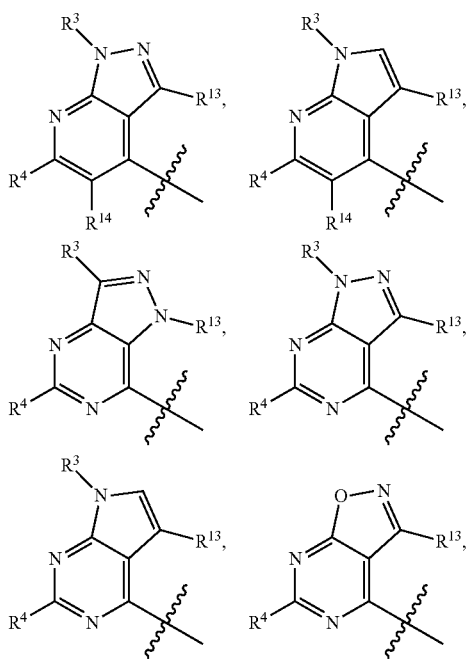

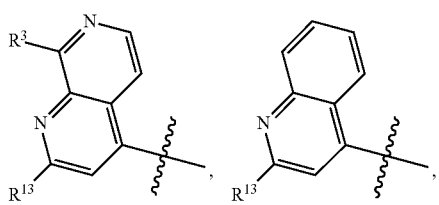

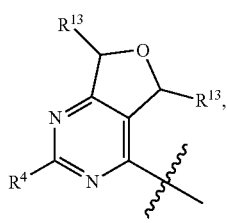

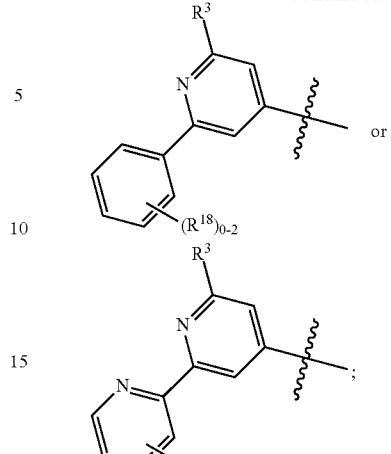

L is —CH$_2$— or —CH$_2$CH$_2$—;
Y$_1$ is —CH$_2$— or —CH$_2$CH$_2$—;
Y$_2$ is —CH$_2$— or —CH$_2$CH$_2$—;
Y$_3$ is —CH$_2$—, —XCH$_2$— or —CH$_2$X—;
X is —CH$_2$— or O;
R$^1$ is —NHC(=O)R$^6$, —NHC(=O)(CH$_2$)$_n$R$^6$, —NH(CH$_2$)$_n$C(=O)R$^6$, —NHC(=O)(CH$_2$)$_m$NHR$^5$, —NHC(=O)(CH$_2$)$_m$N(R$^5$)$_2$, —NHC(=O)(CHR$^9$)$_m$NHR$^5$, —NHC(=O)(CH$_2$)$_m$NH$_2$, —NHC(=O)(CH$_2$)$_n$OR$^9$, —NHC(=O)OR$^9$, —NH(CH$_2$)$_m$C(=O)N(R$^5$)$_2$, —NH(CHR$^9$)$_n$C(=O)R$^6$, NHC(=O)(CHR$^9$)$_n$R$^6$, —NHC(=O)(CHR$^9$)$_n$N(R$^8$)$_2$, —NHC(=O)(CHR$^9$)$_n$NHR$^8$, —NH(CHR$^9$)$_n$C(=O)N(R$^8$)$_2$, —NH(CHR$^9$)$_m$C(=O)R$^6$, —NHR$^6$, —NR$^5$R$^6$, —NH$_2$, —N(R$^5$)$_2$, —NHR$^5$, —NHR$^8$, —N(R$^6$R$^8$), —NH(C(R$^9$)$_2$)$_n$R$^{10}$, —NR$^9$C(=O)OR$^{11}$, —NH(CH$_2$)$_n$R$^6$, —NH(CHR$^9$)$_n$R$^6$, —N(R$^6$)$_2$, —NHC(=O)(CH$_2$)$_n$N(CD$_3$)$_2$, —NH(CHR$^9$)$_n$CH$_2$OR$^9$, —NHCH$_2$(CHR$^9$)$_n$OR$^9$, —NH(CHR$^9$)$_n$OR$^9$, —NR$^9$(CH$_2$)$_n$OR$^9$, —NHCH$_2$(C(R$^9$)$_2$)$_n$OR$^9$, —OR$^9$, —NR$^9$C(=O)R$^5$, —NR$^9$C(=O)(CH$_2$)$_n$R$^5$, —NR$^9$C(=O)OR$^5$, —NHS(=O)$_2$R$^5$, —NHC(=O)(CH$_2$)$_n$NR$^9$C(=O)R$^5$, —NHC(=O)(CH$_2$)$_n$NR$^9$S(=O)$_2$R$^5$,

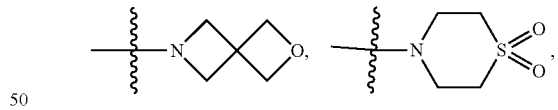

an 8-oxa-3-azabicyclo[3.2.1]octanyl, a 5-6 membered heteroaryl having 1 to 3 ring members independently selected from N, O and S, and a 4-6 membered heterocycloalkyl having 1 to 2 ring members independently selected from N, NH, NR$^{16}$ and O which is unsubstituted or is substituted with 1-2 R$^7$ groups;
R$^2$ is H, C$_1$-C$_6$alkyl, C$_1$-C$_6$haloalkyl or C$_1$-C$_6$alkyl substituted with 1-2 R$^{15}$ groups;
R$^3$ is H, C$_1$-C$_6$alkyl, —CD$_3$ or benzyl substituted with 1-2 R$^{10}$ groups;
R$^4$ is H, NH$_2$, C$_1$-C$_6$alkyl, halo or a phenyl substituted with 0-2 R$^{18}$ groups;
each R$^5$ is independently selected from C$_1$-C$_6$alkyl, —CD$_3$ and —(CH$_2$)$_n$OR$^9$;
R$^6$ is a C$_3$-C$_6$cycloalkyl, an oxa-3-azabicyclo[3.2.1]octane or a 4-6 membered heterocycloalkyl having 1 to 2 ring members independently selected from N, NH, NR$^{16}$ and O which is unsubstituted or is substituted with 1-2 R$^{12}$ groups;

each R$^7$ is independently selected from C$_1$-C$_6$alkyl, halo, hydroxyl, oxo and a C$_1$-C$_6$alkyl substituted with 1 to 3 —OH;

each R$^8$ is independently selected from C$_1$-C$_6$haloalkyl, —(C(R$^9$)$_2$)$_n$OR$^9$ and a C$_1$-C$_6$alkyl substituted with 1 to 3 —OH;

each R$^9$ is independently selected from H and C$_1$-C$_6$alkyl;

R$^{10}$ is C$_1$-C$_6$alkoxy or C$_3$-C$_6$cycloalkyl;

R$^1$ is a C$_3$-C$_6$cycloalkyl which is unsubstituted or is substituted with 1 to 3 C$_1$-C$_6$alkyl groups;

each R$^{12}$ is independently selected from C$_1$-C$_6$alkyl, hydroxyl, halo and a C$_1$-C$_6$alkyl substituted with 1 to 3 —OH;

R$^{13}$ is H or C$_1$-C$_6$alkyl;

R$^{14}$ is H or C$_1$-C$_6$alkyl;

R$^{15}$ is —NHC(=O)(CH$_2$)$_m$NHR$^5$, —NHC(=O)(CH$_2$)$_m$N(R$^5$)$_2$, —NHC(=O)(CH$_2$)$_m$NH$_2$, —NHC(=O)(CHR$^9$)$_n$R$^6$, —NHC(=O)(CHR$^9$)$_n$N(R$^8$)$_2$, —NHC(=O)(CHR$^9$)$_n$NHR$^8$, —NH(CHR$^9$)$_n$C(=O)N(R$^8$)$_2$, —NH(CHR$^9$)$_n$C(=O)R$^6$, —NHR$^6$, —NH$_2$, —N(R$^5$)$_2$, —NHR$^8$, —N(R$^6$R$^8$), —NH(C(R$^9$)$_2$)$_n$R$^{10}$, —NR$^9$C(=O)OR$^{11}$, —NH(CHR$^9$)$_n$R$^6$, —N(R$^6$)$_2$, —N(CD$_3$)$_2$, —NH(CHR$^9$)$_n$OR$^9$ or —NHCH$_2$(C(R$^9$)$_2$)$_n$OR$^9$;

each R$^{16}$ is C$_1$-C$_6$alkyl;

each R$^{17}$ is independently selected from H and C$_1$-C$_6$alkyl;

each R$^{18}$ is independently selected from halo, —CN, C$_1$-C$_6$alkoxy and C$_1$-C$_6$alkyl;

m is 1, 2, 3, 4, 5 or 6, and n is 1, 2, 3, 4, 5 or 6

Certain aspects and examples of the compounds of the invention are provided in the following listing of additional, enumerated embodiments. It will be recognized that features specified in each embodiment may be combined with other specified features to provide further embodiments of the present invention.

Embodiment 1

The compound having the structure of Formula (A) is a compound having the structure of Formula (I) or Formula (II), or a pharmaceutically acceptable salt thereof:

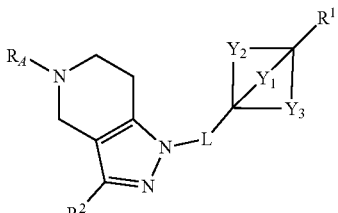

Formula (I)

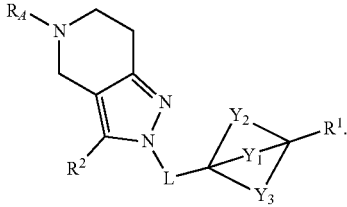

Formula (II)

wherein Y$_1$, Y$_2$, Y$_3$, L, R$^1$, R$^2$ and R$_A$ are as defined herein for compounds of Formula (A).

Embodiment 2

The compound having the structure of Formula (A) or Formula (I) is a compound having the structure of Formula (Ia), Formula (Ib), Formula (Ic), Formula (Id), Formula (Ie), Formula (If), Formula (Ig), Formula (Ih), Formula (Ii), Formula (Ij) or Formula (Ik), or a pharmaceutically acceptable salt thereof:

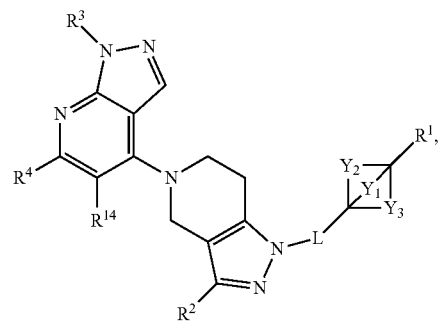

Formula (Ia)

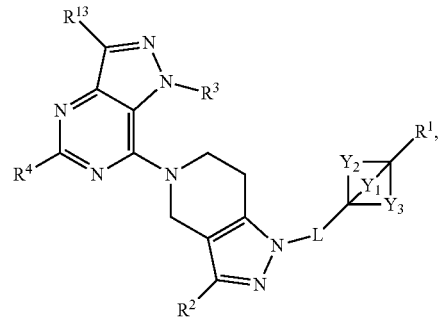

Formula (Ib)

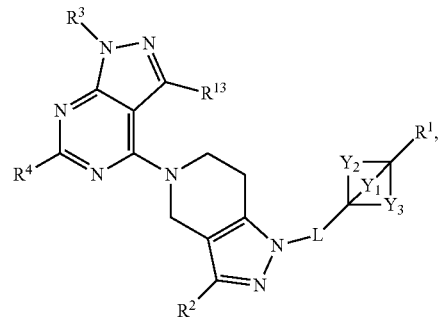

Formula (Ic)

Formula (Id)

Formula (Ie)

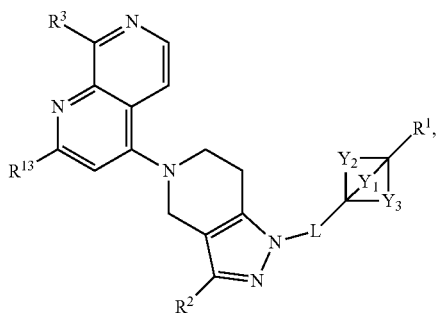

Formula (If)

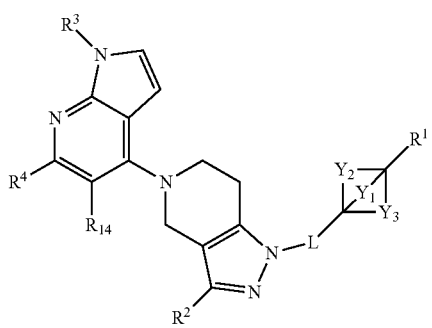

Formula (Ig)

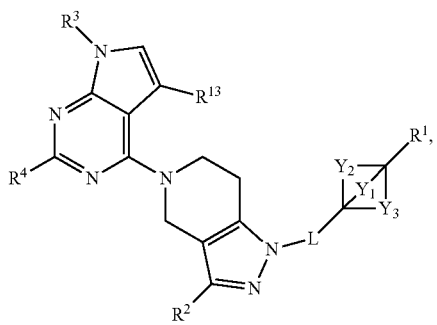

Formula (Ih)

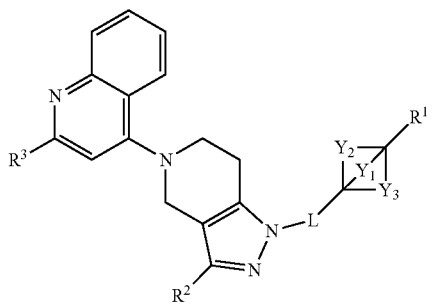

Formula (Ii)

Formula (Ij)

Formula (Ik)

wherein $Y_1$, $Y_2$, $Y_3$, L, $R^1$, $R^2$, $R^3$, $R^4$, $R^{13}$, $R^{14}$ and $R^{18}$ are as defined herein for compounds of Formula (A).

Embodiment 3

The compound having the structure of Formula (A) or Formula (I) is a compound having the structure of Formula (Ia) or Formula (Ig), or a pharmaceutically acceptable salt thereof:

Formula (Ia)

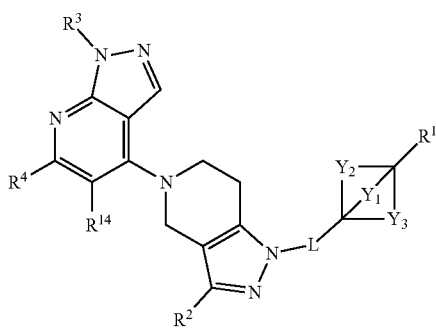

-continued

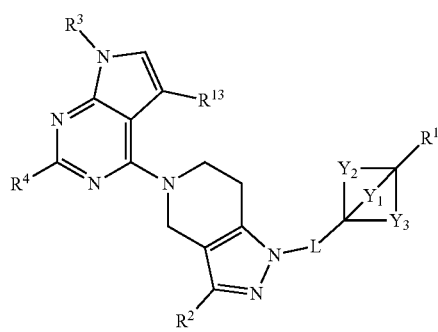

Formula (Ig)

wherein $Y_1$, $Y_2$, $Y_3$, L, $R^1$, $R^2$, $R^3$, $R^4$ and $R^{13}$ are as defined herein for compounds of Formula (A).

Embodiment 4

The compound having the structure of Formula (A) or Formula (I) is a compound having the structure of Formula (Ib), Formula (Ic) or Formula (Id), or a pharmaceutically acceptable salt thereof:

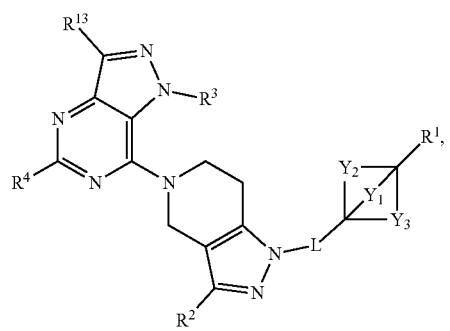

Formula (Ib)

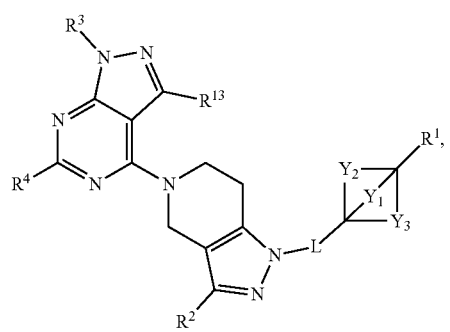

Formula (Ic)

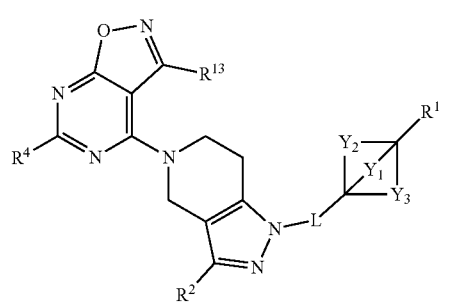

Formula (Id)

wherein $Y_1$, $Y_2$, $Y_3$, L, $R^1$, $R^2$, $R^3$, $R^4$ and $R^{13}$ are as defined herein for compounds of Formula (A).

Embodiment 5

The compound having the structure of Formula (A) or Formula (I) is a compound having the structure of Formula (Ie) or Formula (Ih), or a pharmaceutically acceptable salt thereof:

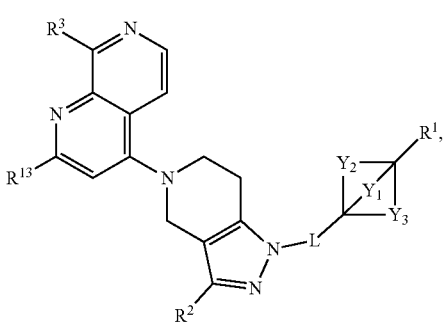

Formula (Ie)

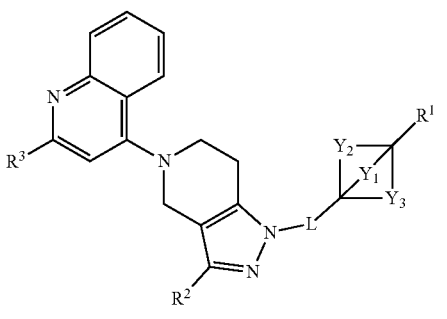

Formula (Ih)

wherein $Y_1$, $Y_2$, $Y_3$, L, $R^1$, $R^2$ and $R^3$ are as defined herein for compounds of Formula (A).

Embodiment 6

The compound having the structure of Formula (A) or Formula (I) is a compound having the structure of Formula (If), or a pharmaceutically acceptable salt thereof:

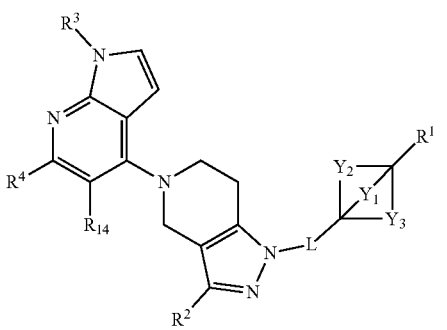

Formula (If)

wherein $Y_1$, $Y_2$, $Y_3$, L, $R^1$, $R^2$, $R^3$, $R^4$ and $R^{14}$ are as defined herein for compounds of Formula (A).

Embodiment 7

The compound having the structure of Formula (A) or Formula (I) is a compound having the structure of Formula (Ii), or a pharmaceutically acceptable salt thereof:

Formula (Ii)

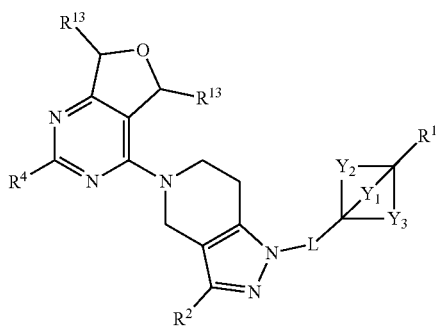

wherein $Y_1$, $Y_2$, $Y_3$, L, $R^1$, $R^2$, $R^4$ and each $R^{13}$ are as defined herein for compounds of Formula (A).

Embodiment 8

The compound having the structure of Formula (A) or Formula (I) is a compound having the structure of Formula (Ij) or Formula (Ik), or a pharmaceutically acceptable salt thereof:

Formula (Ij)

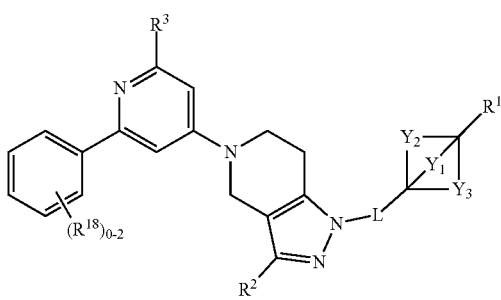

Formula (Ik)

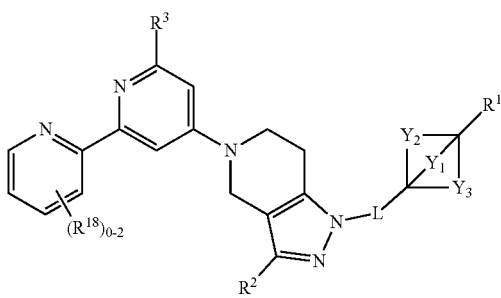

wherein $Y_1$, $Y_2$, $Y_3$, L, $R^1$, $R^2$, $R^3$ and $R^{18}$ are as defined herein for compounds of Formula (A).

Embodiment 9

The compound having the structure of Formula (A) or Formula (I) is a compound having the structure of Formula (Im), or a pharmaceutically acceptable salt thereof:

Formula (Im)

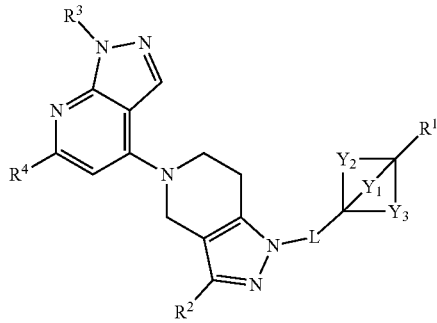

wherein $Y_1$, $Y_2$, $Y_3$, L, $R^1$, $R^2$, $R^3$ and $R^4$ are as defined herein for compounds of Formula (A).

Embodiment 10

The compound having the structure of Formula (A) or Formula (I) is a compound having the structure of Formula (In), or a pharmaceutically acceptable salt thereof:

Formula (In)

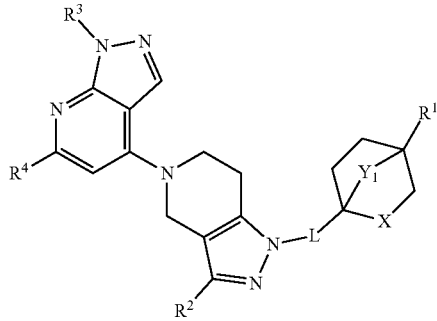

wherein $Y_1$, X, L, $R^1$, $R^2$, $R^3$ and $R^4$ are as defined herein for compounds of Formula (A).

Embodiment 11

The compound having the structure of Formula (A) or Formula (I) is a compound having the structure of Formula (Io), or a pharmaceutically acceptable salt thereof:

Formula (Io)

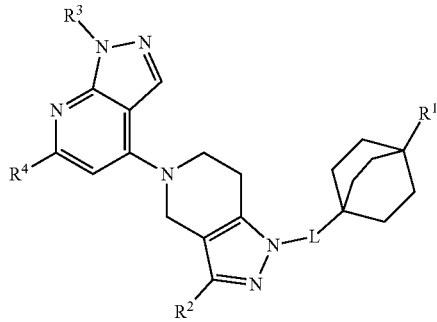

wherein L, $R^1$, $R^2$, $R^3$ and $R^4$ are as defined herein for compounds of Formula (A).

Embodiment 12

The compound having the structure of Formula (A) or Formula (I) is a compound having the structure of Formula (Ip), or a pharmaceutically acceptable salt thereof:

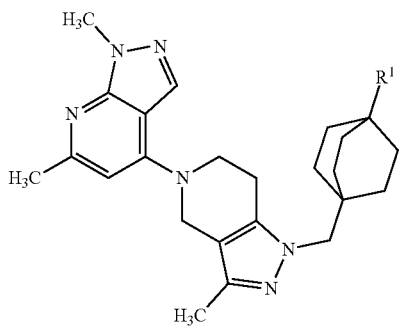

Formula (Ip)

wherein $R^1$ is as defined herein for compounds of Formula (A).

Embodiment 13

The compound having the structure of Formula (A) or Formula (ii) is a compound having the structure of Formula (IIa), Formula (IIb), Formula (IIc), Formula (IId), Formula (IIe), Formula (IIf), Formula (IIg), Formula (IIh), Formula (IIi), Formula (IIj) or Formula (IIk), or a pharmaceutically acceptable salt thereof:

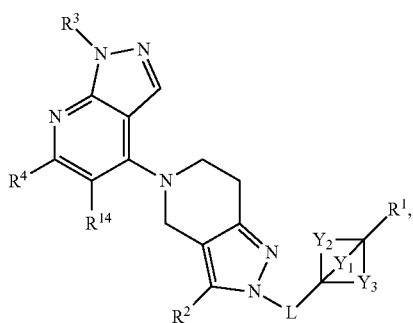

Formula (IIa)

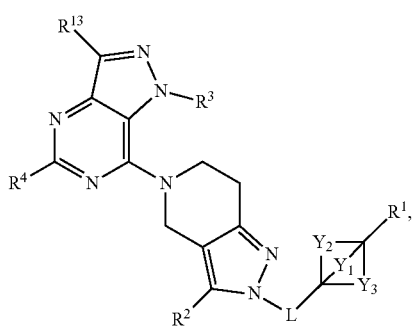

Formula (IIb)

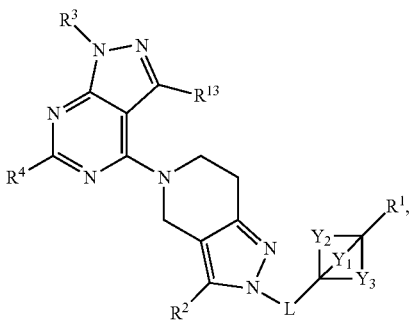

Formula (IIc)

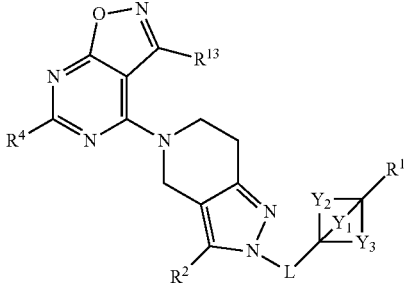

Formula (IId)

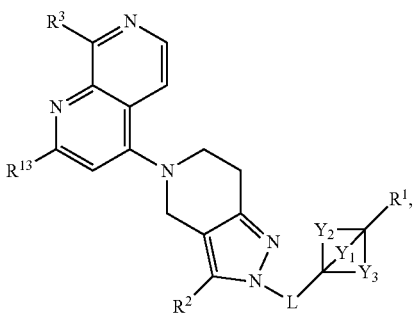

Formula (IIe)

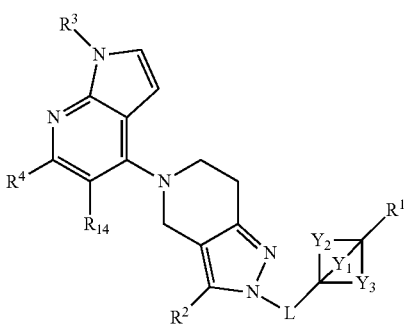

Formula (IIf)

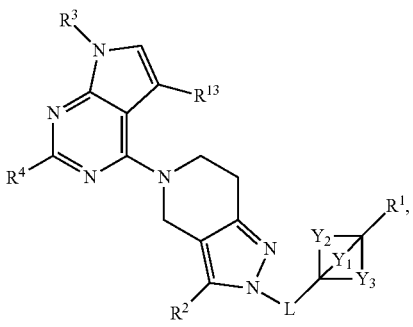

Formula (IIg)

-continued

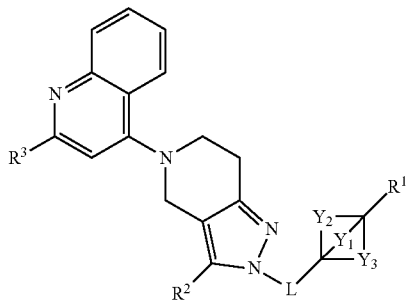

Formula (IIh)

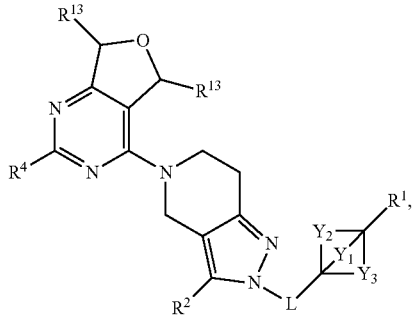

Formula (IIi)

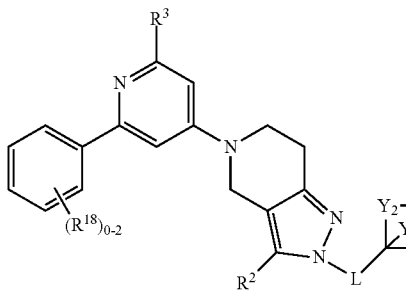

Formula (IIj)

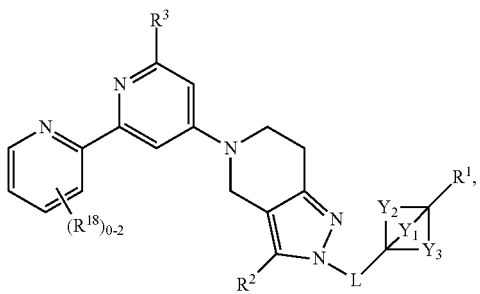

Formula (IIk)

wherein $Y_1$, $Y_2$, $Y_3$, L, $R^1$, $R^2$, $R^3$, $R^4$, $R^{13}$, $R^{14}$ and $R^{18}$ are as defined herein for compounds of Formula (A).

Embodiment 14

The compound having the structure of Formula (A) or Formula (II) is a compound having the structure of Formula (IIa) or Formula (IIg), or a pharmaceutically acceptable salt thereof:

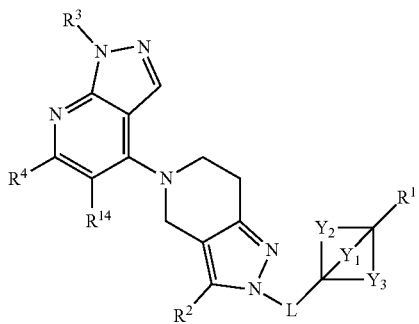

Formula (IIa)

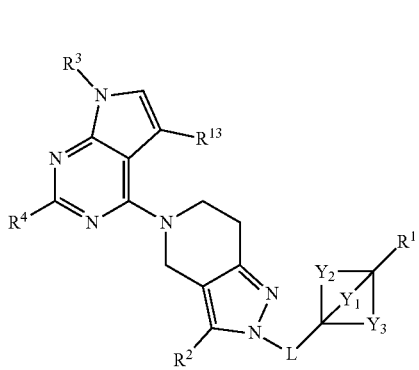

Formula (IIg)

wherein $Y_1$, $Y_2$, $Y_3$, L, $R^1$, $R^2$, $R^3$, $R^4$ and $R^{13}$ are as defined herein for compounds of Formula (A).

Embodiment 15

The compound having the structure of Formula (A) or Formula (II) is a compound having the structure of Formula (IIb), Formula (IIc) or Formula (IId), or a pharmaceutically acceptable salt thereof:

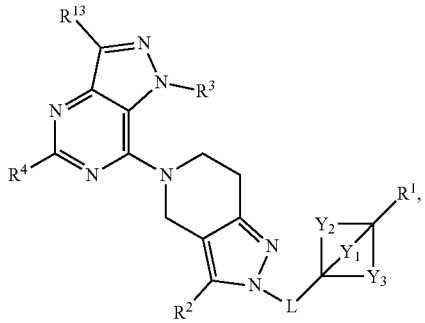

Formula (IIb)

-continued

Formula (IIc)

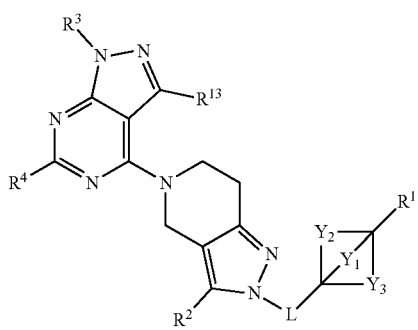

Formula (IId)

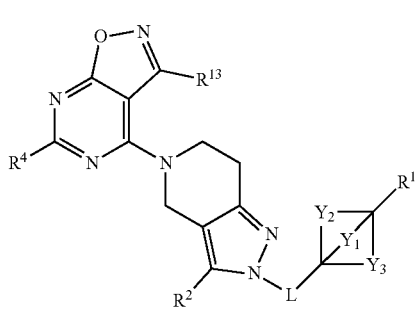

wherein $Y_1$, $Y_2$, $Y_3$, L, $R^1$, $R^2$, $R^3$, $R^4$ and $R^{13}$ are as defined herein for compounds of Formula (A).

Embodiment 16

The compound having the structure of Formula (A) or Formula (ii) is a compound having the structure of Formula (IIe) or Formula (IIh), or a pharmaceutically acceptable salt thereof:

Formula (IIe)

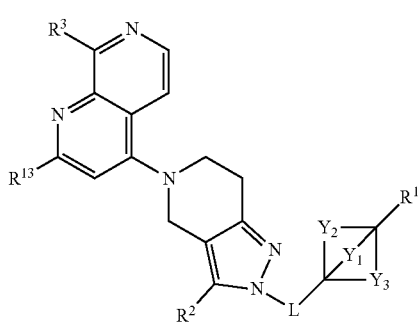

Formula (IIh)

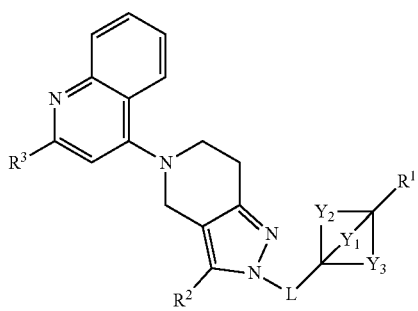

wherein $Y_1$, $Y_2$, $Y_3$, L, $R^1$, $R^2$ and $R^3$ are as defined herein for compounds of Formula (A).

Embodiment 17

The compound having the structure of Formula (A) or Formula (ii) is a compound having the structure of Formula (IIf), or a pharmaceutically acceptable salt thereof:

Formula (IIf)

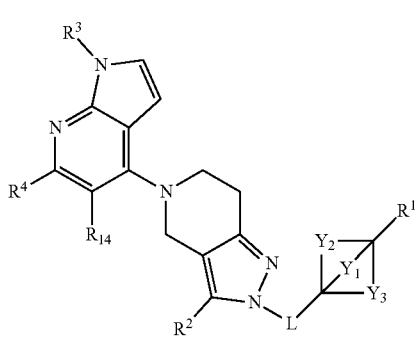

wherein $Y_1$, $Y_2$, $Y_3$, L, $R^1$, $R^2$, $R^3$, $R^4$ and $R^{14}$ are as defined herein for compounds of Formula (A).

Embodiment 18

The compound having the structure of Formula (A) or Formula (II) is a compound having the structure of Formula (IIi), or a pharmaceutically acceptable salt thereof:

Formula (IIi)

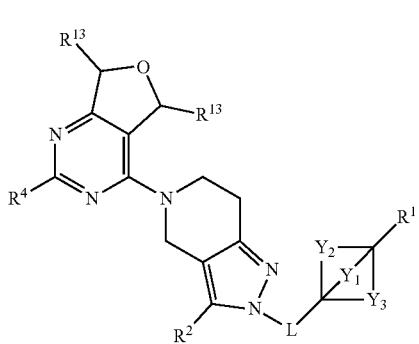

wherein $Y_1$, $Y_2$, $Y_3$, L, $R^1$, $R^2$, $R^4$ and each $R^{13}$ are as defined herein for compounds of Formula (A).

Embodiment 19

The compound having the structure of Formula (A) or Formula (II) is a compound having the structure of Formula (IIj) or Formula (IIk), or a pharmaceutically acceptable salt thereof:

Formula (IIj)

Formula (IIk)

wherein $Y_1$, $Y_2$, $Y_3$, L, $R^1$, $R^2$, $R^3$ and $R^{18}$ are as defined herein for compounds of Formula (A).

Embodiment 20

The compounds of Formula (A), Formula (I), Formula (II), Formula (Ia to Ip) and Formula (IIa to IIk) wherein,
L is —CH$_2$— or —CH$_2$CH$_2$—;
$Y_1$ is —CH$_2$— or —CH$_2$CH$_2$—;
$Y_2$ is —CH$_2$— or —CH$_2$CH$_2$—;
$Y_3$ is —CH$_2$— or —XCH$_2$—;
X is —CH$_2$— or O;
$R^1$ is —NHC(=O)R$^6$, —NHC(=O)(CH$_2$)$_n$R$^6$, —NHC(=O)(CH$_2$)$_m$NHR$^5$, —NHC(=O)(CH$_2$)$_m$N(R$^5$)$_2$, —NHC(=O)(CHR$^9$)$_m$NHR$^5$, —NHC(=O)(CH$_2$)$_m$NH$_2$, —NHC(=O)(CH$_2$)$_n$OR$^9$, —NHC(=O)OR$^9$, —NHC(=O)(CHR$^9$)$_n$R$^6$, —NHC(=O)(CHR$^9$)$_n$N(R$^8$)$_2$, —NHC(=O)(CHR$^9$)$_n$NHR$^8$, —NR$^9$C(=O)OR$^{11}$, —NHC(=O)(CH$_2$)$_n$N(CD$_3$)$_2$, —NR$^9$C(=O)R$^5$, —NR$^9$C(=O)(CH$_2$)$_n$R$^5$, —NR$^9$C(=O)OR$^5$, —NHS(=O)$_2$R$^5$, —NHC(=O)(CH$_2$)$_n$NR$^9$C(=O)R$^5$ or —NHC(=O)(CH$_2$)$_n$NR$^9$S(=O)$_2$R$^5$;
$R^2$ is H, C$_1$-C$_6$alkyl or C$_1$-C$_6$haloalkyl;
$R^3$ is H, C$_1$-C$_6$alkyl or —CD$_3$;
$R^4$ is H, NH$_2$, C$_1$-C$_6$alkyl or halo;
each $R^5$ is independently selected from C$_1$-C$_6$alkyl, —CD$_3$ and —(CH$_2$)$_n$OR$^9$;
$R^6$ is a C$_3$-C$_6$cycloalkyl or a 4-6 membered heterocycloalkyl having 1 to 2 ring members independently selected from N, NH, NR$^{16}$ and O which is unsubstituted or is substituted with 1-2 R$^{12}$ groups;
each $R^8$ is independently selected from C$_1$-C$_6$haloalkyl, —(C(R$^9$)$_2$)$_n$OR$^9$ and a C$_1$-C$_6$alkyl substituted with 1 to 3 —OH;
each $R^9$ is independently selected from H and C$_1$-C$_6$alkyl;
$R^{11}$ is a C$_3$-C$_6$cycloalkyl which is unsubstituted or is substituted with 1 to 3 C$_1$-C$_6$alkyl groups;
each $R^{12}$ is independently selected from C$_1$-C$_6$alkyl, hydroxyl, halo and a C$_1$-C$_6$alkyl substituted with 1 to 3 —OH;
$R^{13}$ is H or C$_1$-C$_6$alkyl;
$R^{14}$ is H or C$_1$-C$_6$alkyl;
each $R^{16}$ is C$_1$-C$_6$alkyl;
each $R^{17}$ is independently selected from H and C$_1$-C$_6$alkyl;
each $R^{18}$ is independently selected from halo, —CN, C$_1$-C$_6$alkoxy and C$_1$-C$_6$alkyl; m is 1, 2, 3, 4, 5 or 6, and n is 1, 2, 3, 4, 5 or 6.

Embodiment 21

The compounds of Formula (A), Formula (I), Formula (II), Formula (Ia to Ip) and Formula (IIa to IIk) wherein,
L is —CH$_2$— or —CH$_2$CH$_2$—;
$Y_1$ is —CH$_2$— or —CH$_2$CH$_2$—;
$Y_2$ is —CH$_2$— or —CH$_2$CH$_2$—;
$Y_3$ is —CH$_2$— or —XCH$_2$—;
X is —CH$_2$— or O;
$R^1$ is —NH(CH$_2$)$_n$C(=O)R$^6$, —NH(CH$_2$)$_m$C(=O)N(R$^5$)$_2$, —NH(CHR$^9$)$_n$C(=O)R$^6$, —NH(CHR$^9$)$_n$C(=O)N(R$^8$)$_2$, —NH(CHR$^9$)$_m$C(=O)R$^6$, —NH(C(R$^9$)$_2$)$_n$R$^{10}$, —NH(CH$_2$)$_n$R$^6$, —NH(CHR$^9$)$_n$R$^6$, —NH(CHR$^9$)CH$_2$OR$^9$, —NHCH$_2$(CHR$^9$)$_n$OR$^9$, —NH(CHR$^9$)$_n$OR$^9$, —NR$^9$(CH$_2$)$_n$OR$^9$, or —NHCH$_2$(C(R$^9$)$_2$)$_n$OR$^9$;
$R^2$ is H, C$_1$-C$_6$alkyl or C$_1$-C$_6$haloalkyl;
$R^3$ is H, C$_1$-C$_6$alkyl or —CD$_3$;
$R^4$ is H, NH$_2$, C$_1$-C$_6$alkyl or halo;
each $R^5$ is independently selected from C$_1$-C$_6$alkyl, —CD$_3$ and —(CH$_2$)$_n$OR$^9$;
$R^6$ is a C$_3$-C$_6$cycloalkyl or a 4-6 membered heterocycloalkyl having 1 to 2 ring members independently selected from N, NH, NR$^{16}$ and O which is unsubstituted or is substituted with 1-2 R$^{12}$ groups;
each $R^8$ is independently selected from C$_1$-C$_6$haloalkyl, —(C(R$^9$)$_2$)$_n$OR$^9$ and a C$_1$-C$_6$alkyl substituted with 1 to 3 —OH;
each $R^9$ is independently selected from H and C$_1$-C$_6$alkyl;
$R^{10}$ is C$_1$-C$_6$alkoxy or C$_3$-C$_6$cycloalkyl;
each $R^{12}$ is independently selected from C$_1$-C$_6$alkyl, hydroxyl, halo and a C$_1$-C$_6$alkyl substituted with 1 to 3 —OH;
$R^{13}$ is H or C$_1$-C$_6$alkyl;
$R^{14}$ is H or C$_1$-C$_6$alkyl;
each $R^{16}$ is C$_1$-C$_6$alkyl;
each $R^{17}$ is independently selected from H and C$_1$-C$_6$alkyl;
each $R^{18}$ is independently selected from halo, —CN, C$_1$-C$_6$alkoxy and C$_1$-C$_6$alkyl;
m is 1, 2, 3, 4, 5 or 6, and
n is 1, 2, 3, 4, 5 or 6.

Embodiment 22

The compounds of Formula (A), Formula (I), Formula (II), Formula (Ia to Ip) and Formula (IIa to IIk) wherein,
L is —CH$_2$— or —CH$_2$CH$_2$—;
$Y_1$ is —CH$_2$— or —CH$_2$CH$_2$—;
$Y_2$ is —CH$_2$— or —CH$_2$CH$_2$—;
$Y_3$ is —CH$_2$— or —XCH$_2$—;
X is —CH$_2$— or O;
$R^1$ is —NHR$^6$, —NR$^5$R$^6$, —NH$_2$, —N(R$^5$)$_2$, —NHR$^5$, —NHR$^8$, —N(R$^6$R$^8$) or —N(R$^6$)$_2$;
$R^2$ is H, C$_1$-C$_6$alkyl or C$_1$-C$_6$haloalkyl;
$R^3$ is H, C$_1$-C$_6$alkyl or —CD$_3$;
$R^4$ is H, NH$_2$, C$_1$-C$_6$alkyl or halo;
each $R^5$ is independently selected from C$_1$-C$_6$alkyl, —CD$_3$ and —(CH$_2$)$_n$OR$^9$;

$R^6$ is a $C_3$-$C_6$cycloalkyl or a 4-6 membered heterocycloalkyl having 1 to 2 ring members independently selected from N, NH, $NR^{16}$ and O which is unsubstituted or is substituted with 1-2 $R^{12}$ groups;

each $R^8$ is independently selected from $C_1$-$C_6$haloalkyl, —$(C(R^9)_2)_nOR^9$ and a $C_1$-$C_6$alkyl substituted with 1 to 3 —OH;

each $R^{12}$ is independently selected from $C_1$-$C_6$alkyl, hydroxyl, halo and a $C_1$-$C_6$alkyl substituted with 1 to 3 —OH;

$R^{13}$ is H or $C_1$-$C_6$alkyl;

$R^{14}$ is H or $C_1$-$C_6$alkyl;

each $R^{16}$ is $C_1$-$C_6$alkyl;

each $R^{17}$ is independently selected from H and $C_1$-$C_6$alkyl;

each $R^{18}$ is independently selected from halo, —CN, $C_1$-$C_6$alkoxy and $C_1$-$C_6$alkyl;

m is 1, 2, 3, 4, 5 or 6, and n is 1, 2, 3, 4, 5 or 6.

Embodiment 23

The compounds of Formula (A), Formula (I), Formula (II), Formula (Ia to Ip) and Formula (IIa to IIk) wherein,
$R^1$ is —NHC(=O)$R^6$, —NHC(=O)(CH$_2$)$_n$$R^6$, —NH(CH$_2$)$_n$C(=O)$R^6$, —NHC(=O)(CH$_2$)$_m$NHR$^5$, —NHC(=O)(CH$_2$)$_m$N(R$^5$)$_2$, —NHC(=O)(CHR$^9$)$_m$NHR$^5$, —NHC(=O)(CH$_2$)$_m$NH$_2$, —NHC(=O)(CH$_2$)$_n$OR$^9$, —NHC(=O)OR$^9$, —NH(CH$_2$)$_m$C(=O)N(R$^5$)$_2$, —NH(CHR$^9$)$_m$C(=O)$R^6$, NHC(=O)(CHR$^9$)$_n$$R^6$, —NHC(=O)(CHR$^9$)$_n$N(R$^8$)$_2$, —NHC(=O)(CHR$^9$)$_n$NHR$^8$, —NH(CHR$^9$)$_n$C(=O)N(R$^8$)$_2$, —NH(CHR$^9$)$_m$C(=O)$R^6$, —NHR$^6$, —NR$^5$R$^6$, —NH$_2$, —N(R$^5$)$_2$, —NHR$^5$, —NHR$^8$, —N(R$^6$R$^8$), —NH(C(R$^9$)$_2$)$_n$R$^{10}$, —NR$^9$C(=O)OR$^{11}$, —NH(CH$_2$)$_n$$R^6$, —NH(CHR$^9$)$_n$$R^6$, —N(R$^6$)$_2$, —NHC(=O)(CH$_2$)$_n$N(CD$_3$)$_2$, —NH(CHR$^9$)$_n$CH$_2$OR$^9$, —NHCH$_2$(CHR$^9$)$_n$OR$^9$, —NH(CHR$^9$)$_n$OR$^9$, —NR$^9$(CH$_2$)$_n$OR$^9$, —NHCH$_2$(C(R$^9$)$_2$)$_n$OR$^9$, —OR$^9$, —NR$^9$C(=O)R$^5$, —NR$^9$C(=O)(CH$_2$)$_n$R$^5$, —NR$^9$C(=O)OR$^5$, —NHS(=O)$_2$R$^5$, —NHC(=O)(CH$_2$)$_n$NR$^9$C(=O)R$^5$, or —NHC(=O)(CH$_2$)$_n$NR$^9$S(=O)$_2$R$^5$.

Embodiment 24

The compounds of Formula (A), Formula (I), Formula (II), Formula (Ia to Ip) and Formula (IIa to IIk) wherein,
$R^1$ is —NHC(=O)$R^6$, —NHC(=O)(CH$_2$)$_n$$R^6$, —NH(CH$_2$)$_n$C(=O)$R^6$, —NHC(=O)(CH$_2$)$_m$NHR$^5$, —NHC(=O)(CH$_2$)$_m$N(R$^5$)$_2$, —NHC(=O)(CHR$^9$)$_m$NHR$^5$, —NHC(=O)(CH$_2$)$_m$NH$_2$, —NHC(=O)(CH$_2$)$_n$OR$^9$, —NHC(=O)OR$^9$, —NH(CH$_2$)$_m$C(=O)N(R$^5$)$_2$, —NH(CHR$^9$)$_m$C(=O)$R^6$, —NHR$^6$, —NR$^5$R$^6$, —NH$_2$, —N(R$^5$)$_2$, —NHR$^5$, —NHR$^8$, —NR$^9$C(=O)OR$^{11}$, —NH(CH$_2$)$_n$R$^6$, —N(R$^6$)$_2$, —NHC(=O)(CH$_2$)$_n$N(CD$_3$)$_2$, —NH(CHR$^9$)$_n$CH$_2$OR$^9$, —NHCH$_2$(CHR$^9$)$_n$OR$^9$, —NH(CHR$^9$)$_n$OR$^9$, —NR$^9$(CH$_2$)$_n$OR$^9$, —NHCH$_2$(C(R$^9$)$_2$)$_n$OR$^9$, —OR$^9$, —NR$^9$C(=O)R$^5$, —NR$^9$C(=O)OR$^5$, —NHS(=O)$_2$R$^5$, —NHC(=O)(CH$_2$)$_n$NR$^9$C(=O)R$^5$, or —NHC(=O)(CH$_2$)$_n$NR$^9$S(=O)$_2$R$^5$.

Embodiment 25

The compounds of Formula (A), Formula (I), Formula (II), Formula (Ia to Ip) and Formula (IIa to IIk) wherein,
$R^1$ is —NHC(=O)$R^6$, —NHC(=O)(CH$_2$)$_n$$R^6$, —NHC(=O)(CH$_2$)$_m$NHR$^5$, —NHC(=O)(CH$_2$)$_m$N(R$^5$)$_2$, —NHC(=O)(CHR$^9$)$_m$NHR$^5$, —NHC(=O)(CH$_2$)$_m$NH$_2$, —NHC(=O)(CH$_2$)$_n$OR$^9$, —NHC(=O)OR$^9$, —NHC(=O)(CHR$^9$)$_n$R$^6$, —NHC(=O)(CHR$^9$)$_n$N(R$^8$)$_2$, —NHC(=O)(CHR$^9$)$_n$NHR$^8$, —NR$^9$C(=O)OR$^{11}$, —NHC(=O)(CH$_2$)$_n$N(CD$_3$)$_2$, —NR$^9$C(=O)R$^5$, —NR$^9$C(=O)(CH$_2$)$_n$R$^5$, —NR$^9$C(=O)OR$^5$, —NHS(=O)$_2$R$^5$, —NHC(=O)(CH$_2$)$_n$NR$^9$C(=O)R$^5$ or —NHC(=O)(CH$_2$)$_n$NR$^9$S(=O)$_2$R$^5$.

Embodiment 26

The compounds of Formula (A), Formula (I), Formula (II), Formula (Ia to Ip) and Formula (IIa to IIk) wherein,
$R^1$ is —NHC(=O)$R^6$, —NHC(=O)(CH$_2$)$_n$$R^6$, —NH(CH$_2$)$_n$C(=O)$R^6$, —NHC(=O)(CH$_2$)$_m$NHR$^5$, —NHC(=O)(CH$_2$)$_m$N(R$^5$)$_2$, —NHC(=O)(CHR$^9$)$_m$NHR$^5$, —NHC(=O)(CH$_2$)$_m$NH$_2$, —NH(CH$_2$)$_m$C(=O)N(R$^5$)$_2$, —NH(CHR$^9$)$_n$C(=O)$R^6$, —NHR$^6$, —NH$_2$, —N(R$^5$)$_2$, —NHR$^5$, —NHR$^8$, —NH(CHR$^9$)$_n$OR$^9$ or —NHCH$_2$(C(R$^9$)$_2$)$_n$OR$^9$.

Embodiment 27

The compounds of Formula (A), Formula (I), Formula (II), Formula (Ia to Ip) and Formula (IIa to IIk) wherein,
$R^1$ is —NHC(=O)$R^6$, —NHC(=O)(CH$_2$)$_m$N(R$^5$)$_2$, —NHC(=O)(CH$_2$)$_m$NHR$^5$, —NHC(=O)(CH$_2$)$_m$NH$_2$, —NHC(=O)(CHR$^9$)$_n$$R^6$, —NHC(=O)(CHR$^9$)$_n$NHR$^8$, —NH(CHR$^9$)$_n$C(=O)N(R$^8$)$_2$, —NH(CHR$^9$)$_n$C(=O)$R^6$, —NHR$^6$, —NH$_2$, —N(R$^5$)$_2$, or —NHR$^8$.

Embodiment 28

The compounds of Formula (A), Formula (I), Formula (II), Formula (Ia to Ip) and Formula (IIa to IIk) wherein,
$R^1$ is —NHC(=O)$R^6$, —NHC(=O)(CH$_2$)$_n$$R^6$, —NHC(=O)(CH$_2$)$_m$NHR$^5$, —NHC(=O)(CH$_2$)$_m$N(R$^5$)$_2$, —NHC(=O)(CHR$^9$)$_m$NHR$^5$, —NHC(=O)(CH$_2$)$_m$NH$_2$, —NHR$^6$, —NH$_2$, —N(R$^5$)$_2$, —NHR$^5$, or —NHR$^8$.

Embodiment 29

The compounds of Formula (A), Formula (I), Formula (II), Formula (Ia to Ip) and Formula (IIa to IIk) wherein,
$R^1$ is —NH(CH$_2$)$_n$C(=O)$R^6$, —NH(CH$_2$)$_m$C(=O)N(R$^5$)$_2$, —NH(CHR$^9$)$_n$C(=O)$R^6$, —NH(CHR$^9$)$_n$OR$^9$ or —NHCH$_2$(C(R$^9$)$_2$)$_n$OR$^9$.

Embodiment 30

The compounds of Formula (A), Formula (I), Formula (II), Formula (Ia to Ip) and Formula (IIa to IIk) wherein, $R^1$ is —NHC(=O)$R^6$, —NHC(=O)(CH$_2$)$_m$N(R$^5$)$_2$, —NHR$^6$ or —NH$_2$.

Embodiment 31

The compounds of Formula (A), Formula (I), Formula (II), Formula (Ia to Ip) and Formula (IIa to IIk) wherein, $R^1$ is —NHC(=O)$R^6$, —NHC(=O)(CHR$^9$)$_n$$R^6$, —NH(CHR$^9$)$_n$C(=O)$R^6$ or —NHR$^6$;

Embodiment 32

The compounds of Formula (A), Formula (I), Formula (II), Formula (Ia to Ip) and Formula (IIa to IIk) wherein, R¹ is —NH(CH₂)ₙC(=O)R⁶, —NH(CH₂)ₘC(=O)N(R⁵)₂, —NH(CHR⁹)ₙC(=O)R⁶, —NH(CHR⁹)ₙC(=O)N(R⁸)₂, —NH(CHR⁹)ₘC(=O)R⁶, —NH(C(R⁹)₂)ₙR¹⁰, —NH(CH₂)ₙR⁶, —NH(CHR⁹)ₙR⁶, —NH(CHR⁹)ₙCH₂OR⁹, —NHCH₂(CHR⁹)ₙOR⁹, —NH(CHR⁹)ₙOR⁹, —NR⁹(CH₂)ₙOR⁹, or —NHCH₂(C(R⁹)₂)ₙOR⁹.

Embodiment 33

The compounds of Formula (A), Formula (I), Formula (II), Formula (Ia to Ip) and Formula (IIa to IIk) wherein, R¹ is —NHR⁶, —NR⁵R⁶, —NH₂, —N(R⁵)₂, —NHR⁵, —NHR⁸, —N(R⁶R⁸) or —N(R⁶)₂.

Embodiment 34

The compounds of Formula (A), Formula (I), Formula (II), Formula (Ia to Ip) and Formula (IIa to IIk) wherein, R¹ is —NHC(=O)R⁶, —NHC(=O)(CH₂)ₘN(R⁵)₂, —NHC(=O)(CH₂)ₘNHR⁵, —NHC(=O)(CH₂)ₘNH₂, —NHC(=O)(CHR⁹)ₙR⁶, —NHC(=O)(CHR⁹)ₙNHR⁸, —NH(CHR⁹)ₙC(=O)N(R⁸)₂, —NH(CHR⁹)ₙC(=O)R⁶, —NHR⁶, —NH₂, —N(R⁵)₂, —NHR⁸, an 8-oxa-3-azabicyclo[3.2.1]octanyl,

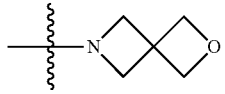

or a 4-6 membered heterocycloalkyl having 1 to 2 ring members independently selected from N, NH, NR¹⁶ or O which is unsubstituted or is substituted with 1-2 R⁷ groups.

Embodiment 35

The compounds of Formula (A), Formula (I), Formula (II), Formula (Ia to Ip) and Formula (IIa to IIk) wherein, R¹ is —NHC(=O)R⁶, —NHC(=O)(CH₂)ₙR⁶, —NH(CH₂)ₙC(=O)R⁶, —NHC(=O)(CH₂)ₘNHR⁵, —NHC(=O)(CH₂)ₘN(R⁵)₂, —NHC(=O)(CHR⁹)ₘNHR⁵, —NHC(=O)(CH₂)ₘNH₂, —NH(CH₂)ₘC(=O)N(R⁵)₂, —NH(CHR⁹)ₙC(=O)R⁶, —NHR⁶, —NH₂, —N(R⁵)₂, —NHR⁵, —NHR⁸, —NH(CHR⁹)ₙOR⁹, —NHCH₂(C(R⁹)₂)ₙOR⁹, an 8-oxa-3-azabicyclo[3.2.1]octanyl,

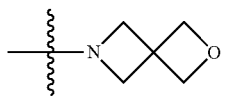 [SMILES: *N1CC2(COC2)C1]

or a 4-6 membered heterocycloalkyl having 1 to 2 ring members independently selected from N, NH, NR¹⁶ or O which is unsubstituted or is substituted with 1-2 R⁷ groups.

Embodiment 36

The compounds of Formula (A), Formula (I), Formula (II), Formula (Ia to Ip) and Formula (IIa to IIk) wherein,
L is —CH₂— or —CH₂CH₂—;
Y₁ is —CH₂— or —CH₂CH₂—;
Y₂ is —CH₂— or —CH₂CH₂—;
Y₃ is —CH₂— or —XCH₂—;
X is —CH₂— or O;
R¹ is

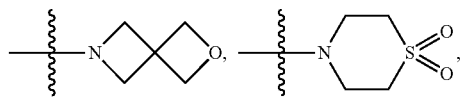

—OR⁹, an 8-oxa-3-azabicyclo[3.2.1]octanyl, a 5-6 membered heteroaryl having 1 to 3 ring members independently selected from N, O and S, or a 4-6 membered heterocycloalkyl having 1 to 2 ring members independently selected from N, NH, NR¹⁶ or O which is unsubstituted or is substituted with 1-2 R⁷ groups;
R² is H, C₁-C₆alkyl or C₁-C₆haloalkyl;
R³ is H, C₁-C₆alkyl or —CD₃;
R⁴ is H, NH₂, C₁-C₆alkyl or halo;
each R⁷ is independently selected from C₁-C₆alkyl, halo, hydroxyl, oxo and a C₁-C₆alkyl substituted with 1 to 3 —OH;
each R⁹ is independently selected from H and C₁-C₆alkyl;
R¹³ is H or C₁-C₆alkyl;
R¹⁴ is H or C₁-C₆alkyl;
each R¹⁶ is C₁-C₆alkyl;
each R¹⁷ is independently selected from H and C₁-C₆alkyl;
each R¹⁸ is independently selected from halo, —CN, C₁-C₆alkoxy and C₁-C₆alkyl;
m is 1, 2, 3, 4, 5 or 6, and
n is 1, 2, 3, 4, 5 or 6.

Embodiment 37

The compounds of Formula (A), Formula (I), Formula (II), Formula (Ia to Ip) and Formula (IIa to IIk) wherein, R¹ is 8-oxa-3-azabicyclo[3.2.1]octanyl,

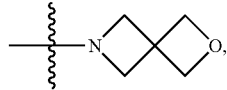

an unsubstituted 4-6 membered heterocycloalkyl having 1 to 2 ring members independently selected from N, NH, NR¹⁶ and O, or a 4-6 membered heterocycloalkyl having 1 to 2 ring members independently selected from N, NH, NR¹⁶ or O substituted with 1-2 R⁷ groups wherein each R⁷ is independently selected from C₁-C₆alkyl, hydroxyl and oxo.

Embodiment 38

The compounds of Formula (A), Formula (I), Formula (II), Formula (Ia to Ip) and Formula (IIa to IIk) wherein,
R¹ is an unsubstituted 4-6 membered heterocycloalkyl having 1 to 2 ring members independently selected from N, NH, NR¹⁶ and O, or a 4-6 membered heterocycloalkyl having 1 to 2 ring members independently selected from N, NH, NR¹⁶ or O substituted with 1-2 R⁷ groups wherein each R⁷ is independently selected from C₁-C₆alkyl, hydroxyl and oxo.

Embodiment 39

The compounds of Formula (A), Formula (I), Formula (II), Formula (Ia to Ip) and Formula (IIa to IIk) wherein, R$^1$ is azetadinyl, pyrrolidinyl, morpholinyl, piperidinyl, piperazinyl, or imidazolyl, or R$^1$ is azetadinyl, pyrrolidinyl, morpholinyl, piperidinyl, piperazinyl or imidazolyl substituted with 1-2 R$^7$ groups, wherein and each R$^7$ is independently selected from C$_1$-C$_6$alkyl, hydroxyl and oxo.

Embodiment 40

The compounds of Formula (A), Formula (I), Formula (II), Formula (Ia to Ip) and Formula (IIa to IIk) wherein,
R$^1$ is an unsubstituted 4-6 membered heterocycloalkyl having 1 to 2 ring members independently selected from N, NH, NR$^{16}$ and O, an 8-oxa-3-azabicyclo[3.2.1]octanyl,

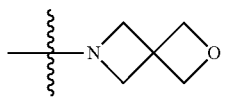 [SMILES: *N1CC2(COC2)C1]

or a 4-6 membered heterocycloalkyl having 1 to 2 ring members independently selected from N, NH, NR$^{16}$ or O substituted with 1-2 R$^7$ groups.

Embodiment 41

The compounds of Formula (A), Formula (I), Formula (II), Formula (Ia to Ip) and Formula (IIa to IIk) wherein,
R$^1$ is a 4-6 membered heterocycloalkyl having 1 to 2 ring members independently selected from N, NH, NR$^{16}$ or O which is unsubstituted or is substituted with 1-2 R$^7$ group.

Embodiment 42

The compounds of Formula (A), Formula (I), Formula (II), Formula (Ia to Ip) and Formula (IIa to IIk) wherein, R$^1$ is azetadinyl, pyrrolidinyl, morpholinyl, piperidinyl or piperazinyl.

Embodiment 43

The compounds of Formula (A), Formula (I), Formula (II), Formula (Ia to Ip) and Formula (IIa to IIk) wherein, R$^1$ is azetadinyl, pyrrolidinyl, morpholinyl, piperidinyl or piperazinyl, each of which is substituted with 1-2 R$^7$ groups.

Embodiment 44

The compounds of Formula (A), Formula (I), Formula (II), Formula (Ia to Ip) and Formula (IIa to IIk) wherein, R$^1$ is an 8-oxa-3-azabicyclo[3.2.1]octanyl, or

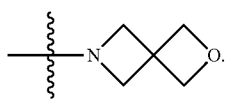 [SMILES: *N1CC2(COC2)C1]

Embodiment 45

The compounds of Formula (A), Formula (I), Formula (II), Formula (Ia to Ip) and Formula (IIa to IIk) wherein, R$^6$ is a C$_3$-C$_6$cycloalkyl or an unsubstituted 4-6 membered heterocycloalkyl having 1 to 2 ring members independently selected from N, NH and O.

Embodiment 46

The compounds of Formula (A), Formula (I), Formula (II), Formula (Ia to Ip) and Formula (IIa to IIk) wherein, R$^6$ is a 4-6 membered heterocycloalkyl having 1 to 2 ring members independently selected from N, NH and O.

Embodiment 47

The compounds of Formula (A), Formula (I), Formula (II), Formula (Ia to Ip) and Formula (IIa to IIk) wherein, R$^6$ is an unsubstituted 4-6 membered heterocycloalkyl having 1 to 2 ring members independently selected from N, NH, NR$^{16}$ and O.

Embodiment 48

The compounds of Formula (A), Formula (I), Formula (II), Formula (Ia to Ip) and Formula (IIa to IIk) wherein,
R$^6$ is a 4-6 membered heterocycloalkyl having 1 to 2 ring members independently selected from N, NH and O substituted with 1-2 R$^{12}$ groups, wherein each R$^{12}$ is independently selected from C$_1$-C$_6$alkyl, hydroxyl and a C$_1$-C$_6$alkyl substituted with 1 to 3 —OH.

Embodiment 49

The compounds of Formula (A), Formula (I), Formula (II), Formula (Ia to Ip) and Formula (IIa to IIk) wherein,
R$^6$ is a 4-6 membered heterocycloalkyl having 1 to 2 ring members independently selected from N, NH, NR$^{16}$ and O substituted with 1-2 R$^{12}$ groups, wherein each R$^{12}$ is independently selected from C$_1$-C$_6$alkyl, hydroxyl and a C$_1$-C$_6$alkyl substituted with 1 to 3 —OH.

Embodiment 50

The compounds of Formula (A), Formula (I), Formula (II), Formula (Ia to Ip) and Formula (IIa to IIk) wherein, R$^6$ is a C$_3$-C$_6$cycloalkyl.

Embodiment 51

The compounds of Formula (A), Formula (I), Formula (II), Formula (Ia to Ip) and Formula (IIa to IIk) wherein, R$^6$ is cyclobutyl, oxetanyl, piperidinyl, pyrrolidinyl, morpholinyl or azetadinyl.

Embodiment 52

The compounds of Formula (A), Formula (I), Formula (II), Formula (Ia to Ip) and Formula (IIa to IIk) wherein,
R$^6$ is cyclobutyl, oxetanyl, piperidinyl, pyrrolidinyl, morpholinyl or azetadinyl each of which is substituted with 1-2 R$^{12}$ groups, wherein each R$^{12}$ is independently selected from C$_1$-C$_6$alkyl, hydroxyl and a C$_1$-C$_6$alkyl substituted with 1 to 3 —OH.

Embodiment 53

The compounds of Formula (A), Formula (I), Formula (II), Formula (Ia to Ip) and Formula (IIa to IIk) wherein, $R^6$ is oxetanyl, piperidinyl, pyrrolidinyl, morpholinyl or azetadinyl.

Embodiment 54

The compounds of Formula (A), Formula (I), Formula (II), Formula (Ia to Ip) and Formula (IIa to IIk) wherein, $R^6$ is cyclobutyl.

Embodiment 55

The compounds of Formula (A), Formula (I), Formula (II), Formula (Ia to Ip) and Formula (IIa to IIk) wherein,
L is —$CH_2$—; $Y_1$ is —$CH_2CH_2$—; $Y_2$ is —$CH_2CH_2$—; $Y_3$ is —$XCH_2$—; and X is —$CH_2$— or O.

Embodiment 56

The compounds of Formula (A), Formula (I), Formula (II), Formula (Ia to Ip) and Formula (IIa to IIk) wherein,
L is —$CH_2$—; $Y_1$ is —$CH_2CH_2$—; $Y_2$ is —$CH_2CH_2$—; $Y_3$ is —$XCH_2$—; and X is —$CH_2$—.

Embodiment 57

The compounds of Formula (A), Formula (I), Formula (II), Formula (Ia to Ip) and Formula (IIa to IIk) wherein,
L is —$CH_2$— or —$CH_2CH_2$—; $Y_1$ is —$CH_2$— or —$CH_2CH_2$—; $Y_2$ is —$CH_2$— or —$CH_2CH_2$—; $Y_3$ is —$CH_2$— or —$XCH_2$—; and X is —$CH_2$— or O.

Embodiment 58

The compounds of Formula (A), Formula (I), Formula (II), Formula (Ia to Ip) and Formula (IIa to IIk) wherein,
L is —$CH_2$—; $Y_1$ is —$CH_2$—; $Y_2$ is —$CH_2$—; $Y_3$ is —$CH_2$—; and X is —$CH_2$—.

Embodiment 59

The compounds of Formula (A), Formula (I), Formula (II), Formula (Ia to Ip) and Formula (IIa to IIk) wherein,
L is —$CH_2$—; $Y_1$ is —$CH_2$—; $Y_2$ is —$CH_2CH_2$—; $Y_3$ is —$XCH_2$—; and X is —$CH_2$— or O.

Embodiment 60

The compounds of Formula (A), Formula (I), Formula (II), Formula (Ia to Ip) and Formula (IIa to IIk) wherein,
L is —$CH_2$—; $Y_1$ is —$CH_2$—; $Y_2$ is —$CH_2CH_2$—; $Y_3$ is —$XCH_2$—; and X is —$CH_2$—.

Embodiment 61

The compounds of Formula (A), Formula (I), Formula (II), Formula (Ia to Ip) and Formula (IIa to IIk) wherein, $R^2$ is $C_1$-$C_6$alkyl; $R^3$ is $C_1$-$C_6$alkyl, and $R^4$ is $C_1$-$C_6$alkyl.

Embodiment 62

The compounds of Formula (A), Formula (I), Formula (II), Formula (Ia to Ip) and Formula (IIa to IIk) wherein, $R^2$ is methyl; $R^3$ is methyl, and $R^4$ is methyl.

Embodiment 63

The compounds of Formula (A), Formula (I), Formula (II), Formula (Ia to Ip) and Formula (IIa to IIk) wherein, $R^2$ is H, $C_1$-$C_6$alkyl or $C_1$-$C_6$haloalkyl Embodiment 64. The compounds of Formula (A), Formula (I), Formula (II), Formula (Ia to Ip) and Formula (IIa to IIk) wherein, $R^2$ is H or $C_1$-$C_6$alkyl.

Embodiment 65

The compounds of Formula (A), Formula (I), Formula (II), Formula (Ia to Ip) and Formula (IIa to IIk) wherein, $R^3$ is H, $C_1$-$C_6$alkyl or —$CD_3$.

Embodiment 66

The compounds of Formula (A), Formula (I), Formula (II), Formula (Ia to Ip) and Formula (IIa to IIk) wherein, $R^3$ is H or $C_1$-$C_6$alkyl.

Embodiment 67

The compounds of Formula (A), Formula (I), Formula (II), Formula (Ia to Ip) and Formula (IIa to IIk) wherein, $R^4$ is H, $NH_2$, $C_1$-$C_6$alkyl or halo.

Embodiment 68

The compounds of Formula (A), Formula (I), Formula (II), Formula (Ia to Ip) and Formula (IIa to IIk) wherein, $R^4$ is H, $NH_2$ or $C_1$-$C_6$alkyl.

Embodiment 69

The compounds of Formula (A), Formula (I), Formula (II), Formula (Ia to Ip) and Formula (IIa to IIk) wherein, $R^4$ is H or $C_1$-$C_6$alkyl.

Embodiment 70

The compounds of Formula (A), Formula (I), Formula (II), Formula (Ia to Ip) and Formula (IIa to IIk) wherein, each $R^5$ is independently selected from $C_1$-$C_6$alkyl and —$(CH_2)_nOR^9$.

Embodiment 71

The compounds of Formula (A), Formula (I), Formula (II), Formula (Ia to Ip) and Formula (IIa to IIk) wherein, each $R^5$ is independently selected from $C_1$-$C_6$alkyl and —$CD_3$.

Embodiment 72

The compounds of Formula (A), Formula (I), Formula (II), Formula (Ia to Ip) and Formula (IIa to IIk) wherein, each $R^5$ is independently selected from methyl, ethyl, isopropyl, tert-butyl, —$CD_3$, —$CH_2CH_2OCH_2CH_3$ and —$CH_2CH_2OCH_3$.

Embodiment 73

The compounds of Formula (A), Formula (I), Formula (II), Formula (Ia to Ip) and Formula (IIa to IIk) wherein, each $R^7$ is independently selected from methyl, ethyl and oxo.

Embodiment 74

The compound of Formula (I), Formula (Ia), Formula (Ib) and Formula (Ic), wherein, each $R^8$ is independently selected from $C_1$-$C_6$haloalkyl, —$(C(R^9)_2)_nOR^9$ and a $C_1$-$C_6$alkyl substituted with 1 to 3 —OH.

Embodiment 75

The compounds of Formula (A), Formula (I), Formula (II), Formula (Ia to Ip) and Formula (IIa to IIk) wherein, each $R^8$ is independently selected from —$CH_2CHF_2$, —$CH_2CF_3$, —$CH(CH_3)CH_2OH$, —$CH_2C(CH_3)_2OCH_3$, —$CH_2CH_2OCH_3$, $CH_2CH_2OCH_2CH_3$ and —$CH_2C(CH_3)_2OH$.

Embodiment 76

The compounds of Formula (A), Formula (I), Formula (II), Formula (Ia to Ip) and Formula (IIa to IIk) wherein, each $R^9$ is independently selected from H and $C_1$-$C_6$alkyl.

Embodiment 77

The compounds of Formula (A), Formula (I), Formula (II), Formula (Ia to Ip) and Formula (IIa to IIk) wherein, each $R^9$ is independently selected from H, methyl and ethyl.

Embodiment 78

The compounds of Formula (A), Formula (I), Formula (II), Formula (Ia to Ip) and Formula (IIa to IIk) wherein, $R^{13}$ is H.

Embodiment 79

The compounds of Formula (A), Formula (I), Formula (II), Formula (Ia to Ip) and Formula (IIa to IIk) wherein, $R^{13}$ is $C_1$-$C_6$alkyl.

Embodiment 80

The compounds of Formula (A), Formula (I), Formula (II), Formula (Ia to Ip) and Formula (IIa to IIk) wherein, $R^{14}$ is H.

Embodiment 81

The compounds of Formula (A), Formula (I), Formula (II), Formula (Ia to Ip) and Formula (IIa to IIk) wherein, $R^{13}$ is H and $R^{14}$ is H.

Embodiment 82

The compounds of Formula (A), Formula (I), Formula (II), Formula (Ia to Ip) and Formula (IIa to IIk) wherein, m is 1, 2 or 3 and n is 1, 2, 3 or 4.

Embodiment 83

The compounds of Formula (A), Formula (I), Formula (II), Formula (Ia to Ip) and Formula (IIa to IIk) wherein, m is 1, 2 or 3.

Embodiment 84

The compounds of Formula (A), Formula (I), Formula (II), Formula (Ia to Ip) and Formula (IIa to IIk) wherein, n is 1, 2, 3 or 4.

Embodiment 85

The compounds of Formula (A), Formula (I), Formula (II), Formula (Ia to Ip) and Formula (IIa to IIk) wherein,
$R^1$ is —$NHC(=O)R^6$, —$NHC(=O)(CH_2)_nR^6$, —$NH(CH_2)_nC(=O)R^6$, —$NHC(=O)(CH_2)_mNHR^5$, —$NHC(=O)(CH_2)_mN(R^5)_2$, —$NHC(=O)(CHR^9)_mNHR^5$, —$NHC(=O)(CH_2)_mNH_2$, —$NH(CH_2)_mC(=O)N(R^5)_2$, —$NH(CHR^9)_nC(=O)R^6$, —$NHR^6$, —$NH_2$, —$N(R^5)_2$, —$NHR^5$, —$NHR^8$, —$NH(CHR^9)_nOR^9$, —$NHCH_2(C(R^9)_2)_nOR^9$, an 8-oxa-3-azabicyclo[3.2.1]octanyl,

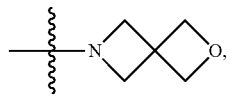

or a 4-6 membered heterocycloalkyl having 1 to 2 ring members independently selected from N, NH, $NR^{16}$ or O which is unsubstituted or is substituted with 1-2 $R^7$ groups;
each $R^5$ is independently selected from $C_1$-$C_6$alkyl and —$(CH_2)_nOR^9$;
$R^6$ is an unsubstituted 4-6 membered heterocycloalkyl having 1 to 2 ring members independently selected from N, NH and O, or a $C_3$-$C_6$cycloalkyl;
each $R^7$ is independently selected from $C_1$-$C_6$alkyl, hydroxyl and oxo;
each $R^8$ is independently selected from $C_1$-$C_6$haloalkyl, and —$(C(R^9)_2)_nOR^9$;
each $R^9$ is independently selected from H and $C_1$-$C_6$alkyl;
$R^{16}$ is $C_1$-$C_6$alkyl;
m is 1, 2, 3, 4, 5 or 6
and
n is 1, 2, 3, 4, 5 or 6.

Embodiment 86

The compounds of Formula (A), Formula (I), Formula (II), Formula (Ia to Ip) and Formula (IIa to IIk) wherein,
$R^1$ is —$NHC(=O)R^6$, —$NHC(=O)(CH_2)_mN(R^5)_2$, —$NHC(=O)(CH_2)_mNHR^5$, —$NHC(=O)(CH_2)_mNH_2$, —$NHC(=O)(CHR^9)_nR^6$, —$NHC(=O)(CHR^9)_nNHR^8$, —$NH(CHR^9)_nC(=O)N(R^8)_2$, —$NH(CHR^9)_nC(=O)R^6$, —$NHR^6$, —$NH_2$, —$N(R^5)_2$, —$NHR^8$, an 8-oxa-3-azabicyclo[3.2.1]octanyl,

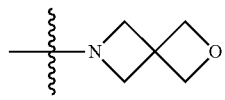

or a 4-6 membered heterocycloalkyl having 1 to 2 ring members independently selected from N, NH, $NR^{16}$ or O which is unsubstituted or is substituted with 1-2 $R^7$ groups;
each $R^5$ is independently selected from $C_1$-$C_6$alkyl and —$(CH_2)_nOR^9$;

$R^6$ is a 4-6 membered heterocycloalkyl having 1 to 2 ring members independently selected from N, NH, $NR^{16}$ and O, or a $C_3$-$C_6$cycloalkyl;

each $R^7$ is independently selected from $C_1$-$C_6$alkyl, hydroxyl and oxo;

each $R^8$ is independently selected from $C_1$-$C_6$alkyl, $C_1$-$C_6$haloalkyl, and —$(C(R^9)_2)_n OR^9$;

each $R^9$ is independently selected from H and $C_1$-$C_6$alkyl;

m is 1, 2, 3, 4, 5 or 6, and n is 1, 2, 3, 4, 5 or 6.

Embodiment 87

The compounds of Formula (A), Formula (I), Formula (II), Formula (Ia to Ip) and Formula (IIa to IIk) wherein,
$R^1$ is —NHC(=O)$R^6$, —NHC(=O)$(CH_2)_m N(R^5)_2$, —NHC(=O)$(CH_2)_m NHR^5$, —NHC(=O)$(CH_2)_m NH_2$, —NHC(=O)$(CHR^9)_n R^6$, —NHC(=O)$(CHR^9)_n NHR^8$, —NH$(CHR^9)_n C$(=O)$N(R^8)_2$, —NH$(CHR^9)_n C$(=O)$R^6$, —$NHR^6$, —$NH_2$, —$N(R^5)_2$, or —$NHR^8$;

each $R^5$ is independently selected from $C_1$-$C_6$alkyl and —$(CH_2)_n OR^9$;

$R^6$ is an unsubstituted 4-6 membered heterocycloalkyl having 1 to 2 ring members independently selected from N, NH, $NR^{16}$ and O, or a $C_3$-$C_6$cycloalkyl;

each $R^8$ is independently selected from $C_1$-$C_6$alkyl, $C_1$-$C_6$haloalkyl, —$(C(R^9)_2)_n OR^9$ and a $C_1$-$C_6$alkyl substituted with 1 to 3 —OH;

each $R^9$ is independently selected from H and $C_1$-$C_6$alkyl;

m is 1, 2, 3, 4, 5 or 6, and n is 1, 2, 3, 4, 5 or 6.

Embodiment 88

The compounds of Formula (A), Formula (I), Formula (II), Formula (Ia to Ip) and Formula (IIa to IIk) wherein,
$R^1$ is —NHC(=O)$(CH_2)_m N(R^5)_2$, —NHC(=O)$(CH_2)_m NHR^5$, —NHC(=O)$(CH_2)_m NH_2$, —NHC(=O)$(CHR^9)_n NHR^8$, —NH$(CHR^9)_n C$(=O)$N(R^8)_2$, —$NH_2$, —$N(R^5)_2$, or —$NHR^8$;

each $R^5$ is independently selected from $C_1$-$C_6$alkyl and —$(CH_2)_n OR^9$;

each $R^8$ is independently selected from $C_1$-$C_6$alkyl, $C_1$-$C_6$haloalkyl, —$(C(R^9)_2)_n OR^9$ and a $C_1$-$C_6$alkyl substituted with 1 to 3 —OH;

each $R^9$ is independently selected from H and $C_1$-$C_6$alkyl;

m is 1, 2, 3, 4, 5 or 6, and n is 1, 2, 3, 4, 5 or 6.

Embodiment 89

The compounds of Formula (A), Formula (I), Formula (II), Formula (Ia to Ip) and Formula (IIa to IIk) wherein,
$R^1$ is —NHC(=O)$R^6$, —NHC(=O)$(CHR^9)_n R^6$, —NH$(CHR^9)_n C$(=O)$R^6$ or —$NHR^6$;

$R^6$ is an unsubstituted 4-6 membered heterocycloalkyl having 1 to 2 ring members independently selected from N, NH, $NR^{16}$ and O, or a $C_3$-$C_6$cycloalkyl;

each $R^9$ is independently selected from H and $C_1$-$C_6$alkyl;

m is 1, 2, 3, 4, 5 or 6, and n is 1, 2, 3, 4, 5 or 6.

Embodiment 90

The compounds of Formula (A), Formula (I), Formula (II), Formula (Ia to Ip) and Formula (IIa to IIk) wherein,
L is —$CH_2$—;

$Y_1$ is —$CH_2CH_2$—;

$Y_2$ is —$CH_2CH_2$—;

$Y_3$ is —$XCH_2$—;

X is —$CH_2$—;

$R^1$ is —NHC(=O)$R^6$;

$R^2$ is $C_1$-$C_6$alkyl;

$R^3$ is $C_1$-$C_6$alkyl;

$R^4$ is $C_1$-$C_6$alkyl;

$R^6$ is an unsubstituted 4-6 membered heterocycloalkyl having 1 to 2 ring members independently selected from N, NH, and O;

$R^{13}$ is H;

$R^{14}$ is H; and each $R^{17}$ is H.

Embodiment 91

The compound of Formula (A), Formula (I), Formula (II), Formula (Ia to Ip) and Formula (IIa to IIk), or a pharmaceutically acceptable salt thereof, selected from:

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine;

4-((3-methyl-5-(6-methyl-1H-pyrazolo[3,4-b]pyridin-4-yl)-4,5,6,7-tetrahydro-1H-pyrazolo[4,3-c]pyridin-1-yl)methyl)bicyclo[2.2.2]octan-1-amine;

4-((3-methyl-5-(2-methyl-1,7-naphthyridin-4-yl)-4,5,6,7-tetrahydro-1H-pyrazolo[4,3-c]pyridin-1-yl)methyl)bicyclo[2.2.2]octan-1-amine;

4-((3-methyl-5-(2-methyl-7H-pyrrolo[2,3-d]pyrimidin-4-yl)-4,5,6,7-tetrahydro-1H-pyrazolo[4,3-c]pyridin-1-yl)methyl)bicyclo[2.2.2]octan-1-amine;

4-((5-(1,6-dimethyl-1H-pyrrolo[2,3-b]pyridin-4-yl)-3-methyl-4,5,6,7-tetrahydro-1H-pyrazolo[4,3-c]pyridin-1-yl)methyl)bicyclo[2.2.2]octan-1-amine;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)oxetan-3-amine;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(dimethylamino)acetamide (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide;

(R)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide;

6-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)-2-oxa-6-azaspiro[3.3]heptane;

4-(1-((4-aminobicyclo[2.2.2]octan-1-yl)methyl)-6,7-dihydro-1H-pyrazolo[4,3-c]pyridin-5(4H)-yl)-1-methyl-1H-pyrazolo[3,4-d]pyrimidin-6-amine;

4-(2-((4-aminobicyclo[2.2.2]octan-1-yl)methyl)-6,7-dihydro-2H-pyrazolo[4,3-c]pyridin-5(4H)-yl)-1-methyl-1H-pyrazolo[3,4-d]pyrimidin-6-amine;

4-(1-((4-aminobicyclo[2.2.2]octan-1-yl)methyl)-3-methyl-6,7-dihydro-1H-pyrazolo[4,3-c]pyridin-5(4H)-yl)-1-methyl-1H-pyrazolo[3,4-d]pyrimidin-6-amine;

4-(2-((4-aminobicyclo[2.2.2]octan-1-yl)methyl)-3-methyl-6,7-dihydro-2H-pyrazolo[4,3-c]pyridin-5(4H)-yl)-1-methyl-1H-pyrazolo[3,4-d]pyrimidin-6-amine;

4-((5-(5-chloro-1-methyl-1H-pyrazolo[4,3-d]pyrimidin-7-yl)-3-methyl-4,5,6,7-tetrahydro-1H-pyrazolo[4,3-c]pyridin-1-yl)methyl)bicyclo[2.2.2]octan-1-amine;

1,6-dimethyl-4-(3-methyl-1-((4-(pyrrolidin-1-yl)bicyclo[2.2.2]octan-1-yl)methyl)-6,7-dihydro-1H-pyrazolo[4,3-c]pyridin-5(4H)-yl)-1H-pyrazolo[3,4-d]pyrimidine;

1,3,5-trimethyl-7-(3-methyl-1-((4-(pyrrolidin-1-yl)bicyclo[2.2.2]octan-1-yl)methyl)-6,7-dihydro-1H-pyrazolo[4,3-c]pyridin-5(4H)-yl)-1H-pyrazolo[4,3-d]pyrimidine;

N-(2-methoxyethyl)-4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-amine;

4-(4-((5-(1,6-dimethyl-1H-pyrazolo[3,4-d]pyrimidin-4-yl)-3-methyl-4,5,6,7-tetrahydro-1H-pyrazolo[4,3-c]pyridin-1-yl)methyl)bicyclo[2.2.2]octan-1-yl)morpholine;

2-(ethylamino)-N-(4-((3-methyl-5-(6-methyl-1H-pyrazolo[3,4-d]pyrimidin-4-yl)-4,5,6,7-tetrahydro-1H-pyrazolo[4,3-c]pyridin-1-yl)methyl)bicyclo[2.2.2]octan-1-yl)acetamide;

4-(4-((3-methyl-5-(6-methyl-1H-pyrazolo[3,4-d]pyrimidin-4-yl)-4,5,6,7-tetrahydro-1H-pyrazolo[4,3-c]pyridin-1-yl)methyl)bicyclo[2.2.2]octan-1-yl)morpholine;

2-(ethylamino)-N-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)acetamide;

4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)-N-(oxetan-3-ylmethyl)bicyclo[2.2.2]octan-1-amine;

3-(dimethylamino)-N-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)propanamide;

4-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)morpholine;

4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-amine;

N-cyclobutyl-4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-amine;

N,N-dicyclobutyl-4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-amine;

6-methyl-4-(3-methyl-1-((4-(piperidin-1-yl)bicyclo[2.2.2]octan-1-yl)methyl)-6,7-dihydro-1H-pyrazolo[4,3-c]pyridin-5(4H)-yl)-1H-pyrazolo[3,4-d]pyrimidine;

6-methyl-4-(3-methyl-1-((4-(pyrrolidin-1-yl)bicyclo[2.2.2]octan-1-yl)methyl)-6,7-dihydro-1H-pyrazolo[4,3-c]pyridin-5(4H)-yl)-1H-pyrazolo[3,4-d]pyrimidine;

(3-(((4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)amino)methyl)oxetan-3-yl)methanol;

N-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)azetidine-3-carboxamide;

(S)—N-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)morpholine-3-carboxamide;

(S)—N-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)morpholine-2-carboxamide;

(R)—N-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)morpholine-3-carboxamide;

(R)—N-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)morpholine-2-carboxamide;

3,6-dimethyl-4-(3-methyl-1-((4-morpholinobicyclo[2.2.2]octan-1-yl)methyl)-6,7-dihydro-1H-pyrazolo[4,3-c]pyridin-5(4H)-yl)isoxazolo[5,4-d]pyrimidine;

1,3,5-trimethyl-7-(3-methyl-1-((4-(piperidin-1-yl)bicyclo[2.2.2]octan-1-yl)methyl)-6,7-dihydro-1H-pyrazolo[4,3-c]pyridin-5(4H)-yl)-1H-pyrazolo[4,3-d]pyrimidine;

1,6-dimethyl-4-(3-methyl-1-((4-(piperidin-1-yl)bicyclo[2.2.2]octan-1-yl)methyl)-6,7-dihydro-1H-pyrazolo[4,3-c]pyridin-5(4H)-yl)-1H-pyrazolo[3,4-d]pyrimidine;

4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)-N,N-bis(trideuteromethyl)bicyclo[2.2.2]octan-1-amine;

4-((3-methyl-5-(1H-pyrazolo[3,4-b]pyridin-4-yl)-4,5,6,7-tetrahydro-1H-pyrazolo[4,3-c]pyridin-1-yl)methyl)bicyclo[2.2.2]octan-1-amine;

4-((3-methyl-5-(1H-pyrazolo[3,4-b]pyridin-4-yl)-4,5,6,7-tetrahydro-2H-pyrazolo[4,3-c]pyridin-2-yl)methyl)bicyclo[2.2.2]octan-1-amine;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N,N-dimethylbicyclo[2.2.2]octan-1-amine;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.1]heptan-1-amine;

4-((5-(1,6-dimethyl-1H-pyrazolo[3,4-b]pyridin-4-yl)-3-(trifluoromethyl)-4,5,6,7-tetrahydro-1H-pyrazolo[4,3-c]pyridin-1-yl)methyl)bicyclo[2.2.2]octan-1-amine;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-ol;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)acetamide;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)methanesulfonamide;

tert-butyl (4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)(methyl)carbamate;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-methylbicyclo[2.2.2]octan-1-amine;

1-methylcyclopropyl (4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)carbamate;

3-((5-(1,6-dimethyl-1H-pyrazolo[3,4-b]pyridin-4-yl)-3-methyl-4,5,6,7-tetrahydro-2H-pyrazolo[4,3-c]pyridin-2-yl)methyl)bicyclo[1.1.1]pentan-1-amine;

4-((5-(1-(4-methoxybenzyl)-6-methyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine;

N-cyclobutyl-4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-isopropylbicyclo[2.2.2]octan-1-amine;

2-((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)propan-1-ol;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-ethylbicyclo[2.2.2]octan-1-amine;

5-(1,6-dimethyl-1H-pyrazolo[3,4-b]pyridin-4-yl)-3-methyl-1-((4-(pyrrolidin-1-yl)bicyclo[2.2.2]octan-1-yl)methyl)-4,5,6,7-tetrahydro-1H-pyrazolo[4,3-c]pyridine;

4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine;

4-((5-(1,6-dimethyl-1H-pyrazolo[3,4-b]pyridin-4-yl)-7,7-dimethyl-4,5,6,7-tetrahydro-1H-pyrazolo[4,3-c]pyridin-1-yl)methyl)bicyclo[2.2.2]octan-1-amine;

N-(2,2-difluoroethyl)-4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine;

-((3-methyl-5-(2-methylquinolin-4-yl)-4,5,6,7-tetrahydro-1H-pyrazolo[4,3-c]pyridin-1-yl)methyl)bicyclo[2.2.2]octan-1-amine;

4-((3-methyl-5-(2-phenylpyridin-4-yl)-4,5,6,7-tetrahydro-1H-pyrazolo[4,3-c]pyridin-1-yl)methyl)bicyclo[2.2.2]octan-1-amine;

1-((4-(azetidin-1-yl)bicyclo[2.2.2]octan-1-yl)methyl)-5-(1,6-dimethyl-1H-pyrazolo[3,4-b]pyridin-4-yl)-3-methyl-4,5,6,7-tetrahydro-1H-pyrazolo[4,3-c]pyridine;

4-((5-(1,6-dimethyl-1H-pyrazolo[3,4-b]pyridin-4-yl)-7,7-dimethyl-4,5,6,7-tetrahydro-2H-pyrazolo[4,3-c]pyridin-2-yl)methyl)bicyclo[2.2.2]octan-1-amine;

4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)thiomorpholine 1,1-dioxide;

5-(1,6-dimethyl-1H-pyrazolo[3,4-b]pyridin-4-yl)-3-methyl-1-((4-(piperidin-1-yl)bicyclo[2.2.2]octan-1-yl)methyl)-4,5,6,7-tetrahydro-1H-pyrazolo[4,3-c]pyridine;

1-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)azetidin-3-ol;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(2-methoxyethyl)bicyclo[2.2.2]octan-1-amine;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N,N-bis(2-methoxyethyl)bicyclo[2.2.2]octan-1-amine;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(2-ethoxyethyl)bicyclo[2.2.2]octan-1-amine;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N,N-bis(2-ethoxyethyl)bicyclo[2.2.2]octan-1-amine;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(2-methoxyethyl)-N-methylbicyclo[2.2.2]octan-1-amine;

(3S,4R)-1-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)pyrrolidine-3,4-diol;

(S)-1-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)pyrrolidin-3-ol;

2-((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)-N,N-dimethylacetamide;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-N-methyloxetan-3-amine;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-isopropyl-N-methylbicyclo[2.2.2]octan-1-amine;

N-cyclobutyl-4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-methylbicyclo[2.2.2]octan-1-amine;

(3S,4S)-1-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)pyrrolidine-3,4-diol;

1-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-2-oxabicyclo[2.2.2]octan-4-amine;

5-(1,6-dimethyl-1H-pyrazolo[3,4-b]pyridin-4-yl)-3-methyl-1-((4-(pyrrolidin-1-yl)-2-oxabicyclo[2.2.2]octan-1-yl)methyl)-4,5,6,7-tetrahydro-1H-pyrazolo[4,3-c]pyridine;

4-((5-(6-(4-fluorophenyl)-1-methyl-1H-pyrazolo[3,4-d]pyrimidin-4-yl)-3-methyl-4,5,6,7-tetrahydro-1H-pyrazolo[4,3-c]pyridin-1-yl)methyl)bicyclo[2.2.2]octan-1-amine;

4-(4-(1-((4-aminobicyclo[2.2.2]octan-1-yl)methyl)-3-methyl-6,7-dihydro-1H-pyrazolo[4,3-c]pyridin-5(4H)-yl)pyridin-2-yl)benzonitrile;

3-methyl-5-(2-phenylpyridin-4-yl)-1-((4-(pyrrolidin-1-yl)bicyclo[2.2.2]octan-1-yl)methyl)-4,5,6,7-tetrahydro-1H-pyrazolo[4,3-c]pyridine;

2-methyl-4-(3-methyl-1-((4-(pyrrolidin-1-yl)bicyclo[2.2.2]octan-1-yl)methyl)-6,7-dihydro-1H-pyrazolo[4,3-c]pyridin-5(4H)-yl)-1,7-naphthyridine;

4-((5-(2-(4-fluorophenyl)pyridin-4-yl)-3-methyl-4,5,6,7-tetrahydro-1H-pyrazolo[4,3-c]pyridin-1-yl)methyl)bicyclo[2.2.2]octan-1-amine;

4-((5-(2-(2-fluoro-4-methylphenyl)pyridin-4-yl)-3-methyl-4,5,6,7-tetrahydro-1H-pyrazolo[4,3-c]pyridin-1-yl)methyl)bicyclo[2.2.2]octan-1-amine;

4-((5-(2-(4-methoxyphenyl)pyridin-4-yl)-3-methyl-4,5,6,7-tetrahydro-1H-pyrazolo[4,3-c]pyridin-1-yl)methyl)bicyclo[2.2.2]octan-1-amine;

4-((3-methyl-5-(2-(p-tolyl)pyridin-4-yl)-4,5,6,7-tetrahydro-1H-pyrazolo[4,3-c]pyridin-1-yl)methyl)bicyclo[2.2.2]octan-1-amine;

4-(2-(5-(1,6-dimethyl-1H-pyrazolo[3,4-b]pyridin-4-yl)-3-methyl-4,5,6,7-tetrahydro-1H-pyrazolo[4,3-c]pyridin-1-yl)ethyl)bicyclo[2.2.2]octan-1-amine;

4-((5-(2,8-dimethyl-1,7-naphthyridin-4-yl)-3-methyl-4,5,6,7-tetrahydro-1H-pyrazolo[4,3-c]pyridin-1-yl)methyl)bicyclo[2.2.2]octan-1-amine;

4-((3-methyl-5-(2-methyl-6-phenylpyridin-4-yl)-4,5,6,7-tetrahydro-1H-pyrazolo[4,3-c]pyridin-1-yl)methyl)bicyclo[2.2.2]octan-1-amine;

4-((5-([2,2'-bipyridin]-4-yl)-3-methyl-4,5,6,7-tetrahydro-1H-pyrazolo[4,3-c]pyridin-1-yl)methyl)bicyclo[2.2.2]octan-1-amine;

5-(1,6-dimethyl-1H-pyrazolo[3,4-b]pyridin-4-yl)-3-methyl-1-((4-(piperidin-1-yl)-2-oxabicyclo[2.2.2]octan-1-yl)methyl)-4,5,6,7-tetrahydro-1H-pyrazolo[4,3-c]pyridine;

4-(5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(1-methoxypropan-2-yl)bicyclo[2.2.2]octan-1-amine;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-ethyl-N-methylbicyclo[2.2.2]octan-1-amine;

1-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N,N-dimethyl-2-oxabicyclo[2.2.2]octan-4-amine;

2-((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)-1-(piperidin-1-yl)ethanone;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(pyrrolidin-1-yl)acetamide;

4-(5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(2-methoxy-2-methylpropyl)bicyclo[2.2.2]octan-1-amine;

1-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(2-methoxyethyl)-2-oxabicyclo[2.2.2]octan-4-amine;

4-((5-(2-chloro-5,7-dihydrofuro[3,4-d]pyrimidin-4-yl)-3-methyl-4,5,6,7-tetrahydro-1H-pyrazolo[4,3-c]pyridin-1-yl)methyl)bicyclo[2.2.2]octan-1-amine;

4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-1-methylpiperazin-2-one;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-3-(dimethylamino)propanamide;

2-((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)-1-(pyrrolidin-1-yl)ethanone;

(R)-4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-methyl morpholine;

1-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-4-methylpiperazin-2-one;

(S)-4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-methylmorpholine;

(2S,6R)-4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2,6-dimethylmorpholine;

(2S,6S)-4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2,6-dimethylmorpholine;

N-(cyclobutylmethyl)-1-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-2-oxabicyclo[2.2.2]octan-4-amine;

(2R,6R)-4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2,6-dimethylmorpholine;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(ethylamino)acetamide;

3-amino-N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)propanamide;

6-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-oxa-6-azaspiro[3.3]heptane;

(R)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(methylamino)propanamide;

(S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(methylamino)propanamide;

1-((4-(1H-imidazol-1-yl)bicyclo[2.2.2]octan-1-yl)methyl)-5-(1,6-dimethyl-1H-pyrazolo[3,4-b]pyridin-4-yl)-3-methyl-4,5,6,7-tetrahydro-1H-pyrazolo[4,3-c]pyridine;

(1R,5S)-3-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-8-oxa-3-azabicyclo[3.2.1]octane;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(methylamino)acetamide;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-4-methylmorpholine-3-carboxamide;

1-((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)-2-methylpropan-2-ol;

2-(ethylamino)-N-(4-((3-methyl-5-(5-methyl-1H-pyrazolo[4,3-b]pyridin-7-yl)-4,5,6,7-tetrahydro-1H-pyrazolo[4,3-c]pyridin-1-yl)methyl)bicyclo[2.2.2]octan-1-yl)acetamide;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-2-carboxamide;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-3-(ethylamino)propanamide;

N-ethyl-4-((3-methyl-5-(2-phenylpyridin-4-yl)-4,5,6,7-tetrahydro-1H-pyrazolo[4,3-c]pyridin-1-yl)methyl)bicyclo[2.2.2]octan-1-amine;

(S)-4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-3-methylmorpholine;

(R)-4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-3-methylmorpholine;

N-(2-methoxyethyl)-4-((3-methyl-5-(2-phenylpyridin-4-yl)-4,5,6,7-tetrahydro-1H-pyrazolo[4,3-c]pyridin-1-yl)methyl)bicyclo[2.2.2]octan-1-amine;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)azetidine-3-carboxamide;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(ethyl(methyl)amino)acetamide;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(3-fluoroazetidin-1-yl)acetamide;

2-(bis(trideuteromethyl)amino)-N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)acetamide;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-hydroxyacetamide;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(3-hydroxyazetidin-1-yl)acetamide;

(3-(((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)methyl)oxetan-3-yl)methanol;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(N-methylmethylsulfonamido)acetamide;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(N-methylacetamido)acetamide 4-((3-methyl-5-(6-methyl-1-(trideuteromethyl)-1H-pyrazolo[3,4-b]pyridin-4-yl)-4,5,6,7-tetrahydro-1H-pyrazolo[4,3-c]pyridin-1-yl)methyl)bicyclo[2.2.2]octan-1-amine;

(S)—N-(4-((5-(1-ethyl-6-methyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-3-(methylamino)propanamide;

N-cyclobutyl-1-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-2-oxabicyclo[2.2.2]octan-4-amine;

N-cyclobutyl-4-((3-methyl-5-(2-phenylpyridin-4-yl)-4,5,6,7-tetrahydro-1H-pyrazolo[4,3-c]pyridin-1-yl)methyl)bicyclo[2.2.2]octan-1-amine;

tert-butyl (4-((5-(1-ethyl-6-methyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)carbamate;

tert-butyl (4-((3-methyl-5-(2-methyl-7H-pyrrolo[2,3-d]pyrimidin-4-yl)-4,5,6,7-tetrahydro-1H-pyrazolo[4,3-c]pyridin-1-yl)methyl)bicyclo[2.2.2]octan-1-yl)carbamate;

tert-butyl (4-((3-methyl-5-(2-methyl-1,7-naphthyridin-4-yl)-4,5,6,7-tetrahydro-1H-pyrazolo[4,3-c]pyridin-1-yl)methyl)bicyclo[2.2.2]octan-1-yl)carbamate;

tert-butyl (4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.1]heptan-1-yl)carbamate;

4-((5-(1,6-dimethyl-1H-pyrazolo[3,4-d]pyrimidin-4-yl)-3-methyl-4,5,6,7-tetrahydro-1H-pyrazolo[4,3-c]pyridin-1-yl)methyl)bicyclo[2.2.2]octan-1-amine, and 4-((5-(1-ethyl-6-methyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine.

Embodiment 92

The compound of Formula (A), Formula (I), Formula (II), Formula (Ia to Ip) and Formula (IIa to IIk), or a pharmaceutically acceptable salt thereof, selected from:

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)oxetan-3-amine;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(dimethylamino)acetamide;

(S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide;

(R)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide, and 6-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)-2-oxa-6-azaspiro[3.3]heptane.

Depending on the choice of the starting materials and procedures, certain embodiments of the compounds of the present invention are present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

In certain embodiments, compounds of Formula (A), Formula (I), Formula (II), Formula (Ia to Ip) and Formula (IIa to IIk) are prepared as a pharmaceutically acceptable acid addition salt by reacting the free base form of a compound of Formula (A), Formula (I), Formula (II), Formula (Ia to Ip) or Formula (IIa to IIk), with a stoichiometric amount of an appropriate pharmaceutically acceptable organic acid or inorganic acid or a suitable anion exchange reagent. Certain compounds of the present invention are capable of forming acid addition salts by virtue of the presence of amino groups or groups similar thereto. Alternatively, the salt forms of compounds of Formula (A), Formula (I), Formula (II), Formula (Ia to Ip) and Formula (IIa to IIk) are prepared using salts of the starting materials or intermediates.

Pharmaceutically acceptable acid addition salts can be formed with inorganic acids and organic acids. The organic acid or inorganic acids used to form certain pharmaceutically acceptable acid addition salts of compounds of Formula (A), Formula (I), Formula (II), Formula (Ia to Ip) and Formula (IIa to IIk) include, but are not limited to, acetic acid, adipic acid, ascorbic acid, aspartic acid, benzoic acid, benzenesulfonic acid, carbonic acid, camphor sulfonic acid, capric acid, chlorotheophyllinate, citric acid, ethanedisulfonic acid, fumaric acid, D-glycero-D-gulo-Heptonicacid, galactaric aid, galactaric acid/mucic acid, gluceptic acid, glucoheptonoic acid, gluconic acid, glucuronic acid, glutamatic acid, glutaric acid, glycolic acid, hippuric acid, hydrobromic acid, hydrochloric acid, hydroiodic acid, isethionic acid, lactic acid, lactobionic acid, lauryl sulfuric acid, malic acid, maleic acid, malonic acid, mandelic acid, mesylic acid, methanesulfonic acid, mucic acid, naphthoic acid, 1-hydroxy-2-naphthoic acid, naphthalenesulfonic acid, 2-naphthalenesulfonic acid, nicotinic acid, nitric acid, octadecanoic acid, oleaic acid, oxalic acid, palmitic acid, pamoic acid, phosphoric acid, polygalacturonic acid, propionic acid, sebacic acid, stearic acid, succinic acid, sulfosalicylic acid, sulfuric acid, tartaric acid, p-toluenesulfonic acid, trifluoroacetic acid and triphenylacetic acid.

Lists of additional suitable acid addition salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002.

Salt forms of the compounds of the invention can be converted into the free compounds by treatment with a suitable basic agent.

Pharmaceutically acceptable acid addition salts of compounds of Formula (A), Formula (I), Formula (II), Formula (Ia to Ip) and Formula (IIa to IIk) include, but are not limited to, a acetate, adipate, ascorbate, aspartate, benzoate, besylatye, benzenesulfonate, bicarbonate/carbonate, bisulfate/sulfate, bromide/hydrobromide, camphor sulfonate, camsylate, caprate, chloride/hydrochloride, chlorotheophyllinate, citrate, edisylate, ethanedisulfonate, fumarate, gluceptate, glucoheptonate, gluconate, glucuronate, glutamate, glutarate, glycolate, hippurate, hydroiodide/iodide, isethionate, lactate, lactobionate, laurylsulphate, malate, maleate, malonate, mandelate, mesylate, methanesulfonate, methylsulfate, mucate, naphthoate, napsylate, 2-napsylate, naphthalenesulfonate, 2-naphthalenesulfonate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, p-toluenesulfonate, trifluoroacetate, trifenatate, triphenylacetete and xinafoate salt forms.

In one embodiment, the present invention provides N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)oxetan-3-amine in an acetate, adipate, ascorbate, aspartate, benzoate, besylatye, benzenesulfonate, bicarbonate/carbonate, bisulfate/sulfate, bromide/hydrobromide, camphor sulfonate, camsylate, caprate, chloride/hydrochloride, chlortheophyllonate, citrate, edisylate, ethanedisulfonate, fumarate, gluceptate, glucoheptonate, gluconate, glucuronate, glutamate, glutarate, glycolate, hippurate, hydroiodide/iodide, isethionate, lactate, lactobionate, laurylsulphate, malate, maleate, malonate, mandelate, mesylate, methanesulfonate, methylsulfate, mucate, naphthoate, napsylate, 2-napsylate, naphthalenesulfonate, 2-naphthalenesulfonate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, p-toluenesulfonate, trifluoroacetate, trifenatate, triphenylacetete or xinafoate salt form.

In one embodiment, the present invention provides N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(dimethylamino)acetamide in an acetate, adipate, ascorbate, aspartate, benzoate, besylatye, benzenesulfonate, bicarbonate/carbonate, bisulfate/sulfate, bromide/hydrobromide, camphor sulfonate, camsylate, caprate, chloride/hydrochloride, chlortheophyllonate, citrate, edisylate, ethanedisulfonate, fumarate, gluceptate, glucoheptonate, gluconate, glucuronate, glutamate, glutarate, glycolate, hippurate, hydroiodide/iodide, isethionate, lactate, lactobionate, laurylsulphate, malate, maleate, malonate, mandelate, mesylate, methanesulfonate, methylsulfate, mucate, naphthoate, napsylate, 2-napsylate, naphthalenesulfonate, 2-naphthalenesulfonate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, p-toluenesulfonate, trifluoroacetate, trifenatate, triphenylacetete or xinafoate salt form.

In one embodiment, the present invention provides (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide in an acetate, adipate, ascorbate, aspartate, benzoate, besylatye, benzenesulfonate, bicarbonate/carbonate, bisulfate/sulfate, bromide/hydrobromide, camphor sulfonate, camsylate, caprate, chloride/hydrochloride, chlortheophyllonate, citrate, edisylate, ethanedisulfonate, fumarate, gluceptate, glucoheptonate, gluconate, glucuronate, glutamate, glutarate, glycolate, hippurate, hydroiodide/iodide, isethionate, lactate, lactobionate, laurylsulphate, malate, maleate, malonate, mandelate, mesylate, methanesulfonate, methylsulfate, mucate, naphthoate, napsylate, 2-napsylate, naphthalenesulfonate, 2-naphthalenesulfonate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, p-toluenesulfonate, trifluoroacetate, trifenatate, triphenylacetete or xinafoate salt form.

In one embodiment, the present invention provides (R)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide in an acetate, adipate, ascorbate, aspartate, benzoate, besylatye, benzenesulfonate, bicarbonate/carbonate, bisulfate/sulfate, bromide/hydrobromide, camphor sulfonate, camsylate, caprate, chloride/hydrochloride, chlortheophyllonate, citrate, edisylate, ethanedisulfonate, fumarate, gluceptate, glucoheptonate, gluconate, glucuronate, glutamate, glutarate, glycolate, hippurate, hydroiodide/iodide, isethionate, lactate, lactobionate, laurylsulphate, malate, maleate, malonate, mandelate, mesylate, methanesulfonate, methylsulfate, mucate, naphthoate, napsylate, 2-napsylate, naphthalenesulfonate, 2-naphthalenesulfonate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, p-toluenesulfonate, trifluoroacetate, trifenatate, triphenylacetete or xinafoate salt form.

In one embodiment, the present invention provides 6-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)-2-oxa-6-azaspiro[3.3]heptane in an acetate, adipate, ascorbate, aspartate, benzoate, besylatye, benzenesulfonate, bicarbonate/carbonate, bisulfate/sulfate, bromide/hydrobromide, camphor sulfonate, camsylate, caprate, chloride/hydrochloride, chlortheophyllonate, citrate, edisylate, ethanedisulfonate, fumarate, gluceptate, glucoheptonate, gluconate, glucuronate, glutamate, glutarate, glycolate, hippurate, hydroiodide/iodide, isethionate, lactate, lactobionate, laurylsulphate, malate, maleate, malonate, mandelate, mesylate, methanesulfonate, methylsulfate, mucate, naphthoate, napsylate, 2-napsylate, naphthalenesulfonate, 2-naphthalenesulfonate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, p-toluenesulfonate, trifluoroacetate, trifenatate, triphenylacetete or xinafoate salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{123}$I, $^{124}$I, $^{125}$I respectively. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention that contain groups capable of acting as donors and/or acceptors for hydrogen bonds may be capable of forming co-crystals with suitable co-crystal formers. These co-crystals may be prepared from compounds of the invention by known co-crystal forming procedures. Such procedures include grinding, heating, co-subliming, co-melting, or contacting in solution compounds of the invention with the co-crystal former under crystallization conditions and isolating co-crystals thereby formed. Suitable co-crystal formers include those described in WO 2004/078163. Hence the invention further provides co-crystals comprising a compound of Formula (A), Formula (I), Formula (II), Formula (Ia to Ip) and Formula (IIa to IIk).

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization. Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Processes for Making Compounds of Formula (A) and Subformulae Thereof

General procedures for preparing compounds of Formula (A), Formula (I), Formula (II), Formula (Ia to Ip) and Formula (IIa to IIk) are described herein. In the reactions described, reactive functional groups, for example hydroxy, amino, imino, thio or carboxy groups, where these are desired in the final product, may be protected to avoid their unwanted participation in the reactions. Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosäuren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide und Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Compounds of Formula (A), Formula (I), Formula (II), Formula (Ia to Ip) or Formula (IIa to IIk) are made by processes described herein and as illustrated in the Examples. Non-limiting examples of synthetic schemes used to make compounds of the invention are illustrated in Scheme 1 and Scheme 2.

Scheme 1 illustrates one embodiment for making compounds of Formula (A), Formula (I) and Formula (II) using Buchwald-Hartwig Amination, where Pd catalyzed cross-coupling of protected amine intermediate (Int-A) or protected amine intermediate (Int-B) with a heteroaryl halide intermediate (Int-1) followed by deprotection gives a compound of Formula (Ia) or Formula (IIa), respectively, where $R^1$ is $NH_2$. Further alkylation or acylation results in compounds of Formula (Ia) or Formula (IIa), where $R^1$ is as further defined herein.

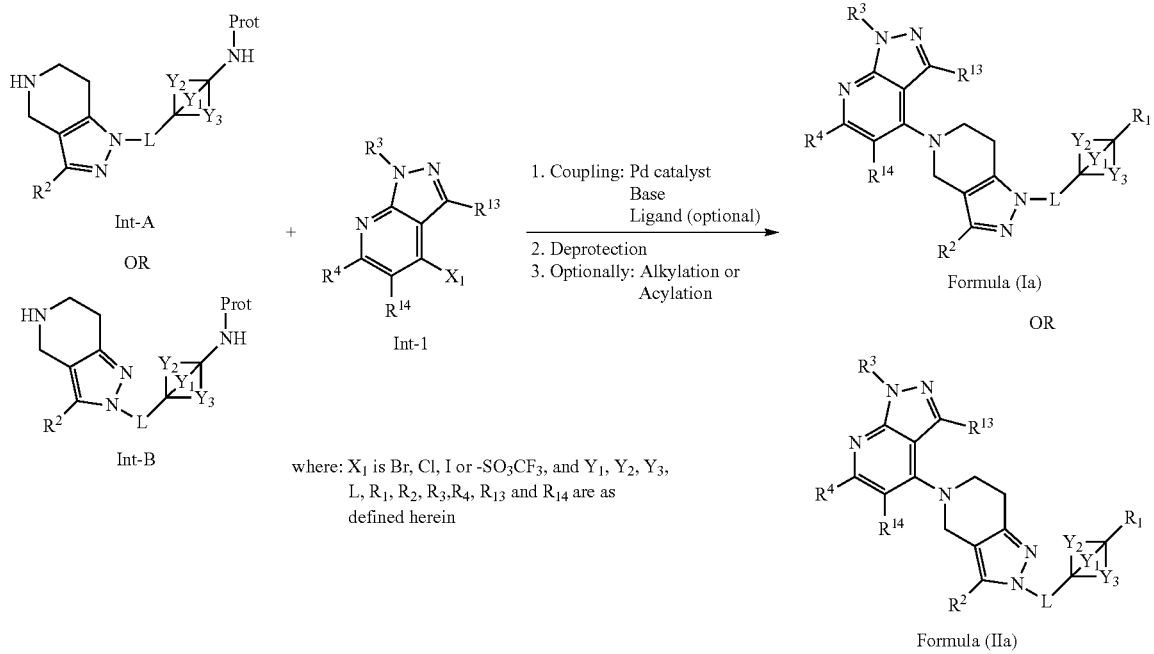

In additional embodiments, compounds of Formula (A), Formula (I) and Formula (II) can be obtained by replacing intermediate (Int-1) with either intermediates Int-2, Int-3, Int-4, Int-5, Int-6, Int-7, Int-8, Int-9, Int-10 or Int-11, resulting compounds of Formula (Ic), Formula (Ib), Formula (If), Formula (Ig), Formula (Id), Formula (Ie), Formula (Ij), Formula (Ii), Formula (Ik), Formula (Ih), Formula (IIc), Formula (IIb), Formula (IIf), Formula (IIg), Formula (IId), Formula (IIe), Formula (IIj), Formula (IIi), Formula (IIk), and Formula (IIh), respectively. Table 1 shows the alternative intermediates and the respective products, where $TG_A$ is

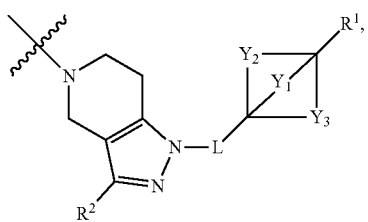

$TG_B$ is

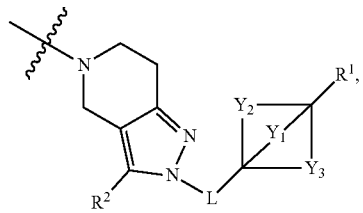

$X_1$ is Br, Cl, I or —SO$_3$CF$_3$, and $Y_1$, $Y_2$, $Y_3$, L, $R^1$, $R^2$, $R^3$, $R^4$, $R^{13}$ and $R^{14}$ are as defined herein.

TABLE 1

| Alternative to Int-1 | Product with Int-A after Deprotection and Optional Alkylation or Acylation | Product with Int-B after Deprotection and Optional Alkylation or Acylation |
|---|---|---|
| Int-2 | Formula (Ic) | Formula (IIc) |
| Int-3 | Formula (Ib) | Formula (IIb) |
| Int-4 | Formula (If) | Formula (IIf) |
| Int-5 | Formula (Ig) | Formula (IIg) |

TABLE 1-continued

| Alternative to Int-1 | Product with Int-A after Deprotection and Optional Alkylation or Acylation | Product with Int-B after Deprotection and Optional Alkylation or Acylation |
|---|---|---|
| Int-6 | Formula (Id) | Formula (IId) |
| Int-7 | Formula (Ie) | Formula (IIe) |
| Int-8 | Formula (Ij) | Formula (IIj) |
| Int-9 | Formula (Ii) | Formula (IIi) |
| Int-10 | Formula (Ik) | Formula (IIk) |
| Int-11 | Formula (Ih) | Formula (IIh) |

The Pd catalyst used in the coupling reactions of Scheme 1 is selected from Pd(II) catalysts, for example, bis(tri-o-tolylphosphine)palladium(II)dichloride, bis(tri-o-tolylphosphine)Pd(dba)₂, bis(tri-o-tolylphosphine)Pd₂(dba)₃, PdCl₂ (dppf), (tri-o-tolylphosphine)Pd(OAc)₂, Pd(OAc)₂ and a palladacycle.

The optional ligand of Scheme 1 is selected from diphenylphospinobinaphthyl (BINAP), diphenylphospinoferrocene (DPPF), tri-o-tolylphosphine (P(o-tol)₃), triphenylphosphine (PPh₃), tri-tert-butylphosphine (P(t-Bu)₃), 2-(dicyclohexylphosphino)3,6-dimethoxy-2',4',6'-triisopropyl-1,1'-biphenyl (BrettPhos), 2-(di-tert-butylphosphino)-2',4',6'-triisopropyl-3,6-dimethoxy-1,1'-biphenyl (t-BuBrettPhos), 2-dicyclohexylphosphino-2',4',6'-triisopropylbiphenyl (XPhos), 2-di-tert-butylphosphino-2',4',6'-triisopropylbiphenyl (t-BuXPhos), 2-Dicyclohexylphosphino-2',6'-dimethoxybiphenyl (SPhos), 2-Dicyclohexylphosphino-2',6'-diisopropoxybiphenyl (RuPhos), 2-dicyclohexylphosphino-2'-(N,N-dimethylamino)biphenyl (DavePhos), 2'-(di-tert-butylphosphino)-N,N-dimethylbiphenyl-2-amine, 2-di-tert-butylphosphino-2'-(N,N-dimethylamino)biphenyl (t-BuDavePhos), 2-diphenylphosphino-2',6'-bis(dimethylamino)-1,1'-biphenyl (PhCPhos), 2-Di(tert-butyl)phosphino-2',4',6'-triisopropyl-3-methoxy-6-methylbiphenyl (RockPhos), 2-(di-adamantanylphosphino)-2',4',6'-triisopropyl-3,6-dimethoxy-1,1'-biphenyl (AdBrettPhos), di-tert-butyl(2',4',6'-tricyclohexyl-3,6-dimethoxy-[1,1'-biphenyl]-2-yl)phosphine, di-tert-butyl(2',4',6'-triisopropyl-3,4,5,6-tetramethyl-[1,1'-biphenyl]-2-yl)phosphine, 4,5-Bis(diphenylphosphino)-9,9-dimethylxanthene (Xantphos), 2-(2-dicyclohexylphosphanylphenyl)-N1,N1,N3,N3-tetramethyl-benzene-1,3-diamine (CPhos), 2'-(Diphenylphosphino)-N,N'-dimethyl-(1,1'-biphenyl)-2-amine (PhDavePhos), 2-{Bis[3,5-bis(trifluoromethyl)phenyl]phosphino}-3,6-dimethoxy-2',4',6'-triisopropyl-1,1'-biphenyl (JackiePhos), (2-Biphenyl)di-tert-butylphosphine (JohnPhos), (2-Biphenyl)dicyclohexylphosphine (CyJohnPhos), 2-Dicyclohexylphosphino-2'-methylbiphenyl (MePhos), 2-Di-t-butylphosphino-2'-methyl)-1,1'-biphenyl (t-BuMePhos), 2-Dicyclohexylphosphino-2',6'-dimethoxybiphenyl (SPhos), Sodium 2'-dicyclohexylphosphino-2,6-dimethoxy-1,1'-biphenyl-3-sulfonate hydrate (sSPhos), rac-2-(Di-tert-butylphosphino)-1,1'-binaphthyl (TrixiePhos), 2-di-tert-butylphosphino-3,4,5,6-tetramethyl-2',4',6'-triisopropylbiphenyl (Me₄ t-BuXPhos), 2'-Dicyclohexylphosphino-2,6-di-1-propyl-4-sulfonato-1,1'-biphenyl hydrate sodium salt (XPhos-SO₃Na), di-tert-butyl(2',4',6'-triisopropyl-4,5-dimethoxy-3,6-dimethyl-[1,1'-biphenyl]-2-yl)phosphine and 2'-(dicyclohexylphosphino)-N,N-dimethyl-[1,1'-biphenyl]-4-amine and Tricyclohexylphosphine (P(Cy)3).

The bases used in such coupling reactions of Scheme 1 include, KOAc, NaOAc, K₂CO₃, Na₂CO₃, NaOEt, KOtBu, NaOtBu, LiHMDS, Cs₂CO₃, K₃PO₄, NaOH, KOH, tBuOH and NEt₃. Such coupling reactions are stirred at temperatures in the range of approximately 100-180° C., or are conducted in a microwave oven. In addition, solvents, for example benzene, toluene, 1,2-dimethoxyethane, acetonitrile, DCM, DMF, THF, dioxane and N-methyl-2-pyrrolidone are used. The reaction may be carried out under an inert gas such as nitrogen or argon.

Scheme 2 illustrates another embodiment for making compounds of Formula (A), Formula (I) and Formula (II) using base catalyzed cross-coupling of protected amine intermediate (Int-A) or protected amine intermediate (Int-B) with a heteroaryl halide intermediate (Int-1) followed by deprotection gives a compound of Formula (Ia) or Formula (IIa), respectively, where R¹ is NH₂. Further alkylation or acylation results in compounds of Formula (Ia) or Formula (IIa), where R¹ is as further defined herein.

Scheme 2: Base catalyzed cross-coupling

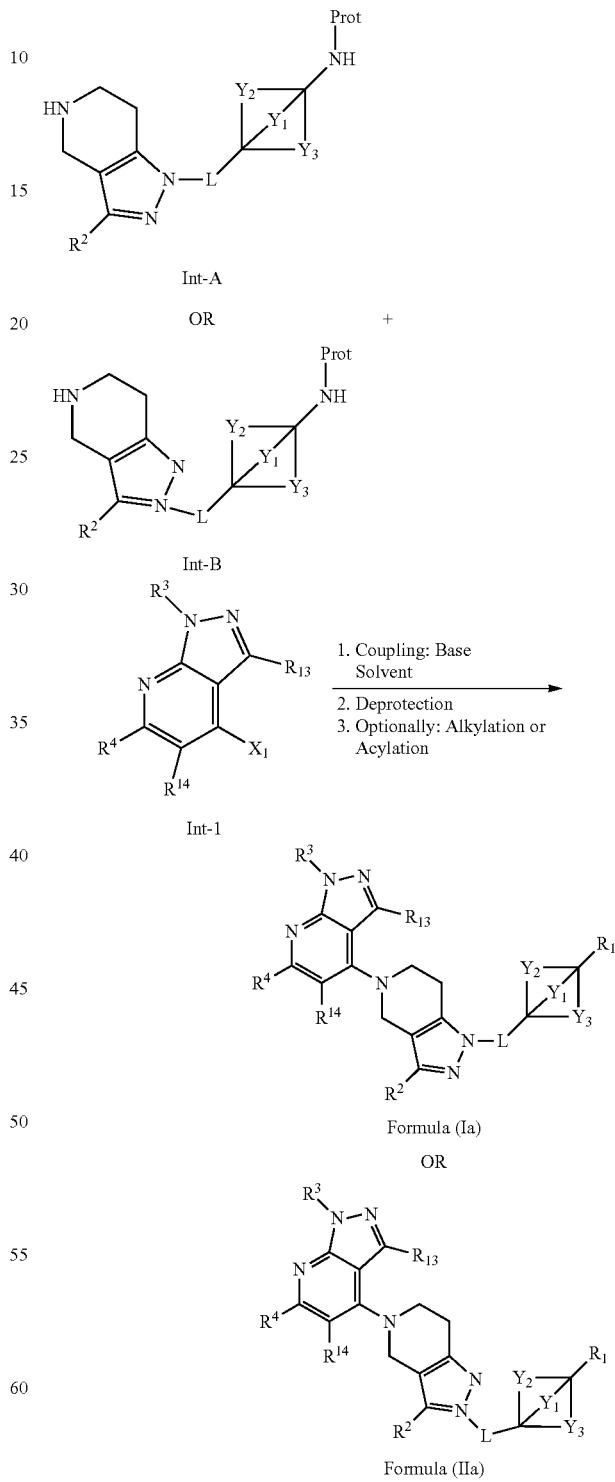

where: X₁ is Br, Cl, I or —SO₃CF₃, and Y₁, Y₂, Y₃, L, R₁, R₂, R₃, R₄, R₁₃ and R₁₄ are as defined herein In additional embodiments, compounds of Formula (A), Formula (I) and Formula (II) can be obtained by replacing intermediate (Int-1) with either intermediates Int-2, Int-3, Int-4, Int-5, Int-6, Int-7, Int-8, Int-9, Int-10 or Int-11, resulting compounds of Formula (Ic), Formula (Ib), Formula (If), Formula (Ig), Formula (Id), Formula (Ie), Formula (Ij), Formula (Ii), Formula (Ik), Formula (Ih), Formula (IIc), Formula (Ib), Formula (IIf), Formula (IIg), Formula (IId), Formula (IIe), Formula (IIj), Formula (IIi), Formula (IIk), and Formula (IIh), respectively. Table 2 shows the alternative intermediates and the respective products, where $TG_A$ is

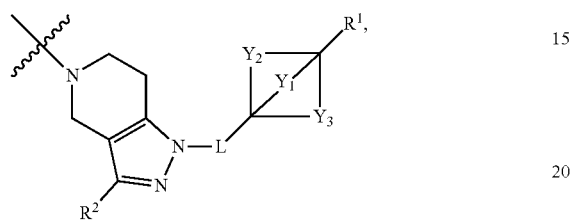

$TG_B$ is

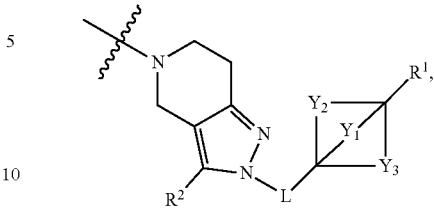

$X_1$ is Br, Cl, I or $—SO_3CF_3$, and $Y_1$, $Y_2$, $Y_3$, L, $R^1$, $R^2$, $R^3$, $R^4$, $R^{13}$ and $R^{14}$ are as defined herein.

TABLE 2

| Alternative for Int-1 | Product with Int-A after Deprotection and Optional Alkylation or Acylation | Product with Int-B after Deprotection and Optional Alkylation or Acylation |
| --- | --- | --- |
| Int-2 | Formula (Ic) | Formula (IIc) |
| Int-3 | Formula (Ib) | Formula (IIb) |
| Int-4 | Formula (If) | Formula (IIf) |

TABLE 2-continued

| Alternative for Int-1 | Product with Int-A after Deprotection and Optional Alkylation or Acylation | Product with Int-B after Deprotection and Optional Alkylation or Acylation |
|---|---|---|
| Int-5 | Formula (Ig) | Formula (IIg) |
| Int-6 | Formula (Id) | Formula (IId) |
| Int-7 | Formula (Ie) | Formula (IIe) |
| Int-8 | Formula (Ij) | Formula (IIj) |
| Int-9 | Formula (Ii) | Formula (IIi) |
| Int-10 | Formula (Ik) | Formula (IIk) |

TABLE 2-continued

| Alternative for Int-1 | Product with Int-A after Deprotection and Optional Alkylation or Acylation | Product with Int-B after Deprotection and Optional Alkylation or Acylation |
|---|---|---|
| 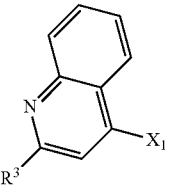 Int-11 | 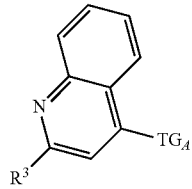 Formula (Ih) | 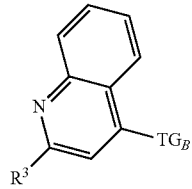 Formula (IIh) |

The bases used in such coupling reactions of Scheme 2 include, DIPEA, $Cs_2CO_3$, 1,8-diazabicycloundec-7-ene (DBU), $NEt_3$, $K_2CO_3$, $CaCO_3$, $Na_2CO_3$, $K_3PO_4$, KF, KOAc, NaOEt, KOtBu and NaOH. Such coupling reactions are stirred at temperatures in the range of approximately 80-180° C., or are conducted in a microwave oven. The solvent used in such coupling reactions of Scheme (VII) and Scheme (VIII), include $H_2O$, 2-methyl-THF, 2-methyl-THF/$H_2O$ (1:1), THF, MeOH, butanol, t-butanol, EtOAc, CAN, ACN, DMSO, NMP, toluene dimethylacetamide and DMF. The reaction may be carried out under an inert gas such as nitrogen or argon.

Intermediates Int-A and Int-B

Scheme 3 illustrates an embodiment for making intermediates Int-A and Int-B.

Scheme 4 illustrates an embodiment for making intermediates Int-A and Int-B.

Scheme 4

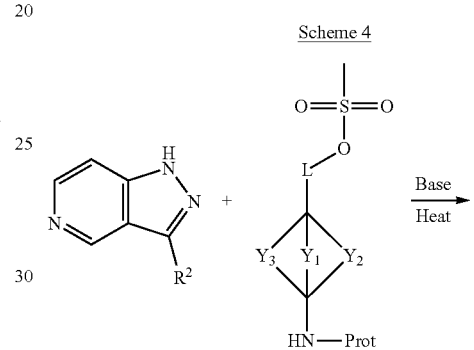

Scheme 3

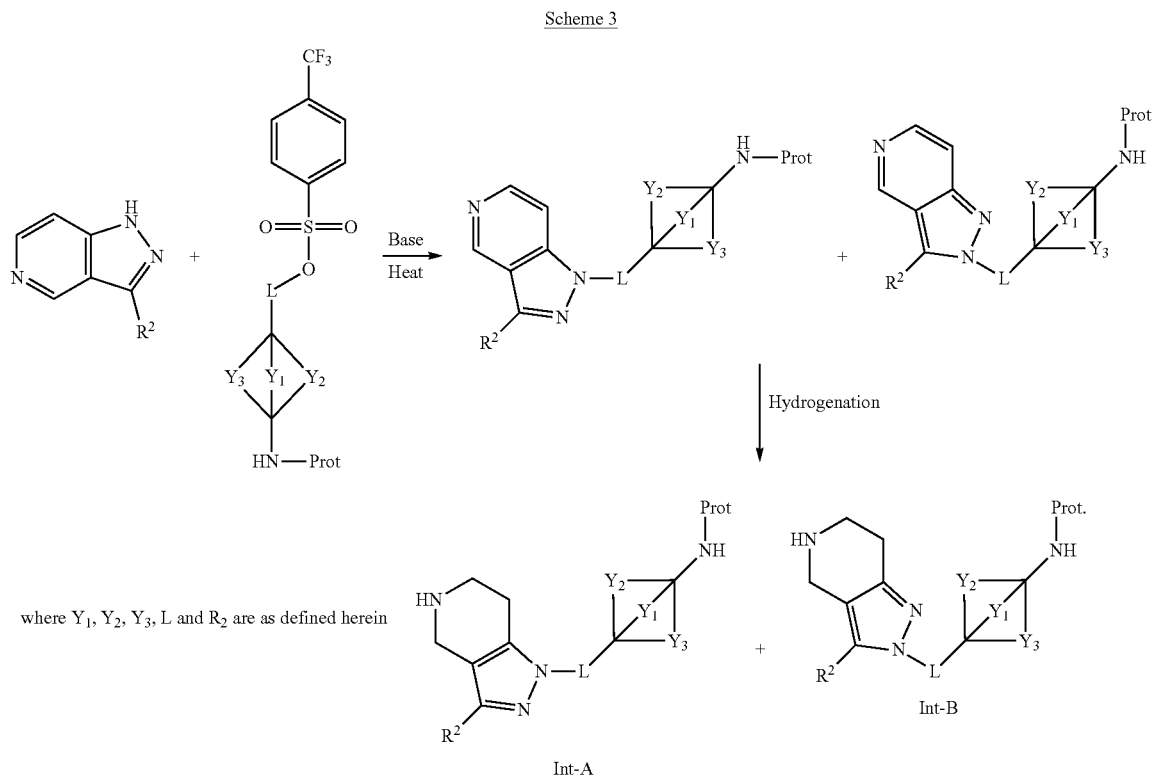

where $Y_1$, $Y_2$, $Y_3$, L and $R_2$ are as defined herein

-continued

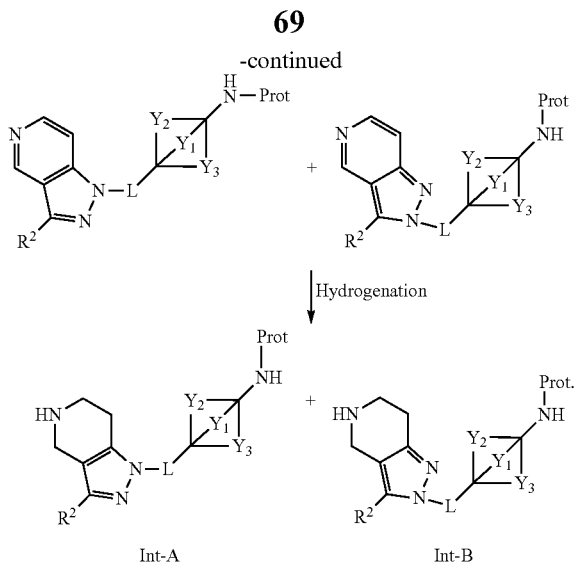

where $Y_1, Y_2, Y_3, L$ and $R_2$ are as defined herein

The amine protecting group (Prot) in Schemes 1 to 4 is selected from methyl carbamate, 9-Fluorenylmethyl carbamate (Fmoc), 2,2,2-Trichlorethyl carbamate (Troc), t-butyl carbamate Boc), 2-(Trimethylsilyl)ethyl carbamate (Teoc), allyl carbamate (Alloc), benzyl carbamate (Cbz), benzylideneamine, p-toluenesulfonamide, trifluoroacetamide, acetamide, phthalimide, benzylamine, 4-methoxybenzyl amine (PMB), allyl amine and tritylamine.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

EXAMPLES

The compounds of the present invention can be produced as shown in the following examples. The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art or can be produced by organic synthesis methods as described herein.

Abbreviations

BH$_3$-DMS borane dimethyl sulfide
brine concentrated aqueous sodium chloride solution
CPME cyclopentyl methyl ether
d doublet
dd doublet of doublets
DCM dichloromethane
DMA dimethylacetamide
DMAP 4-Dimethylaminopyridine
DME 1,2-dimethoxyethane
DMF N,N-dimethylformamide
DMSO dimethylsulfoxide
DIPEA diisopropylethylamine
ESI electrospray ionization
ESIMS electrospray ionization mass spectrometry
EtOAc ethyl acetate
EtOH ethanol
eq equivalent
HPLC high pressure liquid chromatography
hr hour
hrs hours
IPA isopropyl alcohol
LC-MS or LC/MS liquid chromatography and mass spectrometry
MeOH methanol
MS mass spectrometry
m multiplet
mg milligram
min minutes
mL milliliter
mm millimeter
mmol millimol
m/z mass to charge ratio
nm nanometer
nM nanomolar
NMR nuclear magnetic resonance
RT retention time
rt room temperature
s singlet
t triplet
TFA trifluoroacetic acid
THF tetrahydrofuran
UV ultra violet
µm micrometer
Instrumentation
LC-MS Methods
Method 1: The instrument was comprised of an Agilent LC/MS system with a 1200sl HPLC pump and 6100 series single quadrupole mass spectrometer with electrospray (ESI) ionization. The sample was injected onto a Waters Acquity®HSS T3 column C18 1.81 µm 2.1×50 mm at 60° C. The gradient pump method used a flow rate of 0.9 mL/min throughout the 2.25 min run, with mobile phase A: 0.05% TFA in H2O and mobile phase B: 0.035% TFA in acetonitrile, 10% B-100% B in 1.36 min.
Method 2: 3.5MIN_10TO100B: The instrument was comprised of an Agilent LC/MS system with a 1200 sl HPLC pump and 6100 series single quadrupole mass spectrometer with electrospray (ESI) ionization. The sample was injected onto a Waters Acquity®HSS T3 column C18 1.81 µm 2.1×50 mm at 60° C. The gradient pump method used a flow rate of 0.9 mL/min throughout the 2.25 min run, with mobile phase A: 0.05% TFA in H$_2$O and mobile phase B: 0.035% TFA in acetonitrile, 10% B-100% B in 1.36 min.
Tail Groups
The Tail Group intermediates used to obtain compounds of the invention are shown below and in Table 4, with their respective synthesis also described below. Unless purchased, the synthesis of certain reagents used to obtain these intermediates is also described below.

Purchased Reagents

| Reagent No. | Reagent Structure | Reagent Name |
| --- | --- | --- |
| i-A0 | | 4,5,6,7-tetrahydro-1H-pyrazolo[4,3-c]pyridine |
| i-A1 | | 3-methyl-1H-pyrazolo[4,3-c]pyridine |
| i-A2 | | 1H-pyrazolo[4,3-c]pyridine |
| i-A3 | | tert-butyl 7,7-dimethyl-1,4,6,7-tetrahydro-5H-pyrazolo[4,3-c]pyridine-5-carboxylate |
| i-A4 | | 3-methyl-4,5,6,7-tetrahydro-1H-pyrazolo[4,3-c]pyridine |
| i-A6 | | 3-(trifluoromethyl)-1H-pyrazolo[4,3-c]pyridine |
| i-A7 | | tert-butyl 3-(trifluoromethyl)-6,7-dihydro-1H-pyrazolo[4,3-c]pyridine-5(4H)-carboxylate |

Synthesis of Certain Intermediates Used in the Synthesis of Various Tail Groups

Synthesis of 4-((tert-butoxycarbonyl)amino)bicyclo[2.2.2]octan-1-yl)methyl 4-(trifluoromethyl)benzenesulfonate (i-B1)

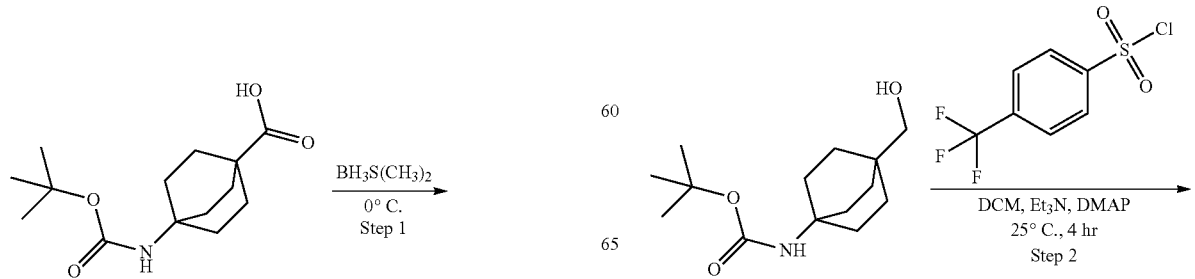

-continued

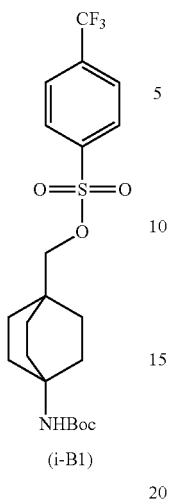

(i-B1)

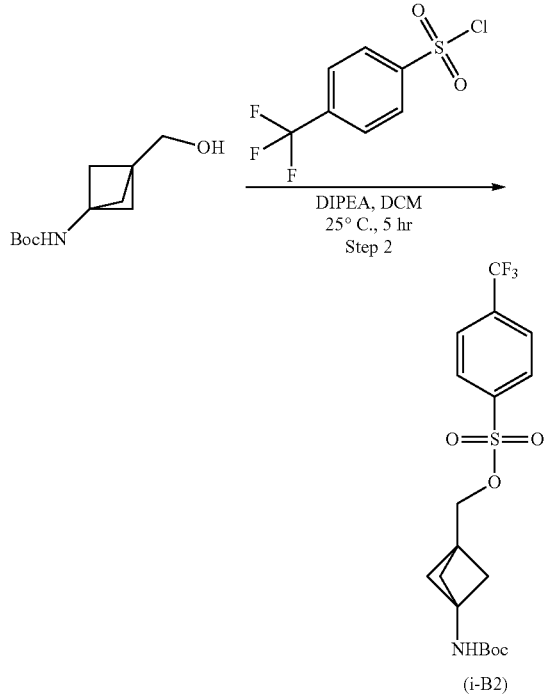

(i-B2)

Step 1: To a solution of 4-((tert-butoxycarbonyl)amino)bicyclo[2.2.2]octane-1-carboxylic acid (4.565 g, 16.9 mmol) in THF (30 mL) was added BH$_3$-DMS (5.15 mL, 3.0 eq) at 00° C. After addition, the reaction was further stirred overnight at rt. LC/MS indicated that the reaction was complete. The reaction was then treated with dropwise addition of 10% citric acid. Aqueous work up followed by ISCO purification (hexane/EtOAc) afforded tert-butyl (4-(hydroxymethyl)bicyclo[2.2.2]octan-1-yl)carbamate as a white solid. $^1$H NMR (400 MHz, DMSO-d6) δ 6.31 (s, 1H), 4.31 (t, J=5.4 Hz, 1H), 2.99 (d, J=5.4 Hz, 2H), 1.75-1.61 (m, 6H), 1.41-1.27 (m, 15H). ESIMS (M+H$^+$) 256.20.

Step 2: To a mixture of tert-butyl (4-(hydroxymethyl)bicyclo[2.2.2]octan-1-yl)carbamate (1.021 g, 4.0 mmol) and 4-(trifluoromethyl)benzenesulfonyl chloride (1.566 g, 6.4 mmol, 1.6 eq) and DCM (10 mL) was added Et$_3$N (1.12 mL, 2.0 eq) and DMAP (49 mg, 0.1 eq) at rt. After addition, the resulting mixture was further stirred at rt for 4 hrs. LC/MS indicated the reaction was complete: mainly two peaks, product peak with m/z 408 (M+H$^+$-56) and intermediate peak with m/z 331. Aqueous work up followed by ISCO purification (hexane/EtOAc) to get the product (i-B1) as a white solid. $^1$H NMR (400 MHz, DMSO-d6) δ 8.12 (d, J=8.4 Hz, 2H), 8.06 (d, J=8.4 Hz, 2H), 6.39 (s, 1H), 3.74 (s, 2H), 1.75-1.57 (m, 6H), 1.42-1.26 (m, 15H). ESIMS calcd. for C$_{21}$H$_{28}$F$_3$NO$_5$S (M+H$^+$) 464.17, found 408.00 (M+H$^+$-56).

Step 1: LiAlH$_4$ (83 mg, 2.188 mmol) was dissolved in THF (20 mL) at 0° C. Starting material methyl 3-((tert-butoxycarbonyl)amino)bicyclo[1.1.1]pentane-1-carboxylate (240 mg, 0.995 mmol) was dissolved in 5 mL THF, then was added to the LiAlH$_4$ solution at 0° C. After completion of the reaction, the reaction mixture was warmed up to rt and stirred for 2 hrs. Sat. Na$_2$SO$_4$ solution was then added to quench the reaction. After filtering the solvent was removed to obtain tert-butyl (3-(hydroxymethyl)bicyclo[1.1.1]pentan-1-yl)carbamate for use in the next step.

Step 2: tert-Butyl (3-(hydroxymethyl)bicyclo[1.1.1]pentan-1-yl)carbamate (180 mg, 0.844 mmol), 4-(trifluoromethyl)benzenesulfonyl chloride (206 mg, 0.844 mmol) and DIPEA (0.295 mL, 1.688 mmol) were mixed in DCM (5 mL) and the reaction mixture was stirred at 25° C. for 5 hrs. After working-up and prep LC-MS, (3-((tert-butoxycarbonyl)amino)bicyclo[1.1.1]pentan-1-yl)methyl 4-(trifluoromethyl)benzenesulfonate (i-B2) was obtained for use in the next step. ESIMS (M+H$^+$) 422.1.

Synthesis of 2-(4-((tert-butoxycarbonyl)amino)bicyclo[2.2.2]octan-1-yl)ethyl methanesulfonate (i-B3)

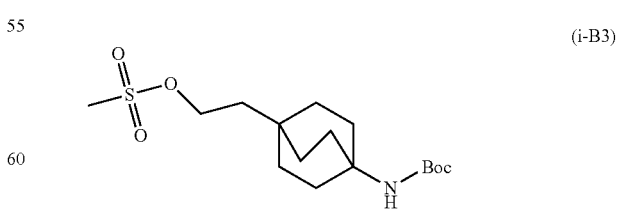

(i-B3)

Synthesis of (3-((tert-butoxycarbonyl)amino)bicyclo[1.1.1]pentan-1-yl)methyl 4-(trifluoromethyl)benzenesulfonate (i-B2)

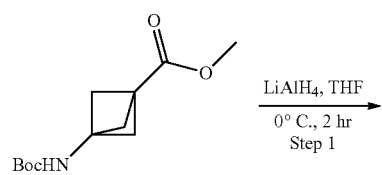

2-(4-((tert-butoxycarbonyl)amino)bicyclo[2.2.2]octan-1-yl)ethyl methanesulfonate (i-B3) was synthesized by mixing (287 mg, 1.065 mmol) of tert-butyl (4-(2-hydroxyethyl)bicyclo[2.2.2]octan-1-yl)carbamate and triethylamine (216 mg, 2.131 mmol) in DCM (10.700 ml). To this solution was added methanesulfonyl chloride (159 mg, 1.385 mmol) at 0° C. After addition, the resulting mixture was further stirred at 25° C. for 18 hrs. LC-MS indicated the reaction was completed. After workup (water addition and extraction in DCM), the organic layer was dried over MgSO4, filtered and concentrated in vacuo. The residue was used without further purification. 1H NMR (400 MHz, Chloroform-d) δ 4.23 (d, J=6.0 Hz, 1H), 4.15 (t, J=7.3 Hz, 2H), 2.92 (s, 3H), 1.78-1.71 (m, 6H), 1.55-1.50 (m, 2H), 1.50-1.42 (m, 6H), 1.35 (s, 9H). ESIMS (M+H$^+$) 348.2.

Synthesis of (4-((tert-butoxycarbonyl)amino)bicyclo[2.2.1]heptan-1-yl)methyl 4-(trifluoromethyl)benzenesulfonate (i-B4)

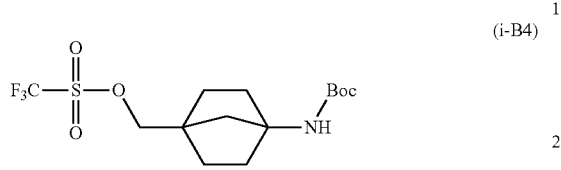

(i-B4)

(4-((tert-butoxycarbonyl)amino)bicyclo[2.2.1]heptan-1-yl)methyl trifluoromethanesulfonate (i-B4) was made by following the synthetic method for 2-(4-((tert-butoxycarbonyl)amino)bicyclo[2.2.2]octan-1-yl)ethyl methanesulfonate (i-B3), except methyl 4-((tert-butoxycarbonyl)amino)bicyclo[2.2.1]heptane-1-carboxylate was used in place of tert-butyl (4-(2-hydroxyethyl)bicyclo[2.2.2]octan-1-yl)carbamate. 4-((tert-butoxycarbonyl)amino)bicyclo[2.2.1]heptan-1-yl)methyl trifluoromethanesulfonate (i-B4) was typically used as crude.

Synthesis of (4-((tert-butoxycarbonyl)amino)bicyclo[2.2.1]heptan-1-yl)methyl methanesulfonate (i-B5)

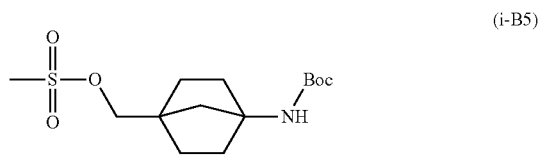 [SMILES: CC(C)(C)OC(=O)NC12CCC(COS(C)(=O)=O)(CC1)C2]

(i-B5)

(4-((tert-butoxycarbonyl)amino)bicyclo[2.2.1]heptan-1-yl)methyl methanesulfonate (i-B5) was made by following the synthetic method for 2-(4-((tert-butoxycarbonyl)amino)bicyclo[2.2.2]octan-1-yl)ethyl methanesulfonate (i-B3), except tert-butyl (4-(2-hydroxyethyl)bicyclo[2.2.1]heptan-1-yl)carbamate was used in place of tert-butyl (4-(2-hydroxyethyl)bicyclo[2.2.2]octan-1-yl)carbamate. (4-((tert-butoxycarbonyl)amino)bicyclo[2.2.1]heptan-1-yl)methyl methanesulfonate (i-B5) was typically used as crude.

Synthesis of (4-((tert-butoxycarbonyl)amino)-2-oxabicyclo[2.2.2]octan-1-yl)methyl 4-(trifluoromethyl)benzenesulfonate i-B6)

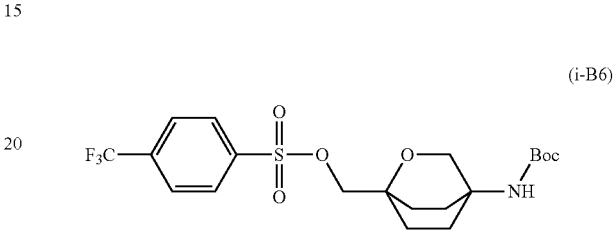

(i-B6)

(4-((tert-butoxycarbonyl)amino)-2-oxabicyclo[2.2.2]octan-1-yl)methyl 4-(trifluoromethyl)benzenesulfonate (i-B6) was made by following the synthetic method for (3-((tert-butoxycarbonyl)amino)bicyclo[1.1.1]pentan-1-yl)methyl 4-(trifluoromethyl)benzenesulfonate (i-B2), except methyl 4-((tert-butoxycarbonyl)amino)-2-oxabicyclo[2.2.2]octane-1-carboxylate was used in place of methyl 3-((tert-butoxycarbonyl)amino)bicyclo[1.1.1]pentane-1-carboxylate. RT (method 1): 1.84 min. ESIMS calcd. for C$_{20}$H$_{26}$F$_3$NO$_6$S (M+H$^+$) 465.5, found 488.5 (M+Na)

Synthesis of Tail Groups

Synthesis of tert-butyl (4-((4,5,6,7-tetrahydro-1H-pyrazolo[4,3-c]pyridin-1-yl)methyl)bicyclo[2.2.2]octan-1-yl)carbamate (TG1) and tert-butyl (4-((4,5,6,7-tetrahydro-2H-pyrazolo[4,3-c]pyridin-2-yl)methyl)bicyclo[2.2.2]octan-1-yl)carbamate (TG2)

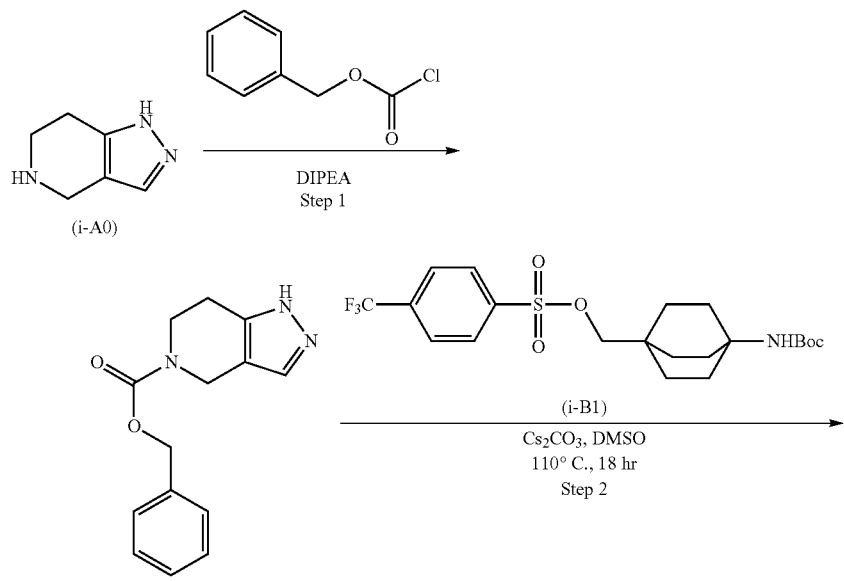

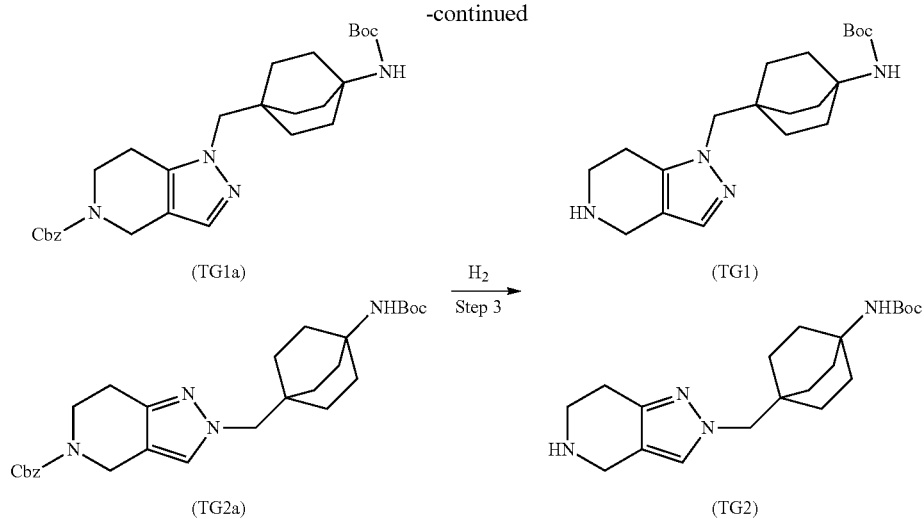

Step 1: A solution of 4,5,6,7-tetrahydro-1H-pyrazolo[4,3-c]pyridine (i-A0) (165 mg, 0.64 mmol) in methanol (13.5 ml) was treated with DIPEA (2.91 ml, 16.66 mmol), followed by dropwise addition of benzyl chloroformate (0.837 ml, 5.95 mmol). The whole mixture was stirred for 18 hrs. LCMS showed a completed reaction and the reaction mixture was concentrated in vacuo. The residue was loaded on a 24 g silica gel column using 10% methanol in DCM to afford benzyl 1,4,6,7-tetrahydro-5H-pyrazolo[4,3-c]pyridine-5-carboxylate (MS calculated for $C_{14}H_{15}N_3O_2$ (M+H$^+$) 258.1, found 258.1).

Step 2: To a 20 mL scintillation vial containing benzyl 1,4,6,7-tetrahydro-5H-pyrazolo[4,3-c]pyridine-5-carboxylate (165 mg, 0.641 mmol), was added 4-((tert-butoxycarbonyl)amino)bicyclo[2.2.2]octan-1-yl)methyl 4-(trifluoromethyl)benzenesulfonate (i-B1) (446 mg, 0.962 mmol), cesium carbonate (418 mg, 1.28 mmol) and anhydrous DMSO (3.2 mL). The mixture was heated to 110° C. for 18 hr, before diluted in ethyl acetate and water. Citric acid was added as solid to neutrilize pH. After partition, the aqueous layer was re-extracted with ethyl acetate three times. All the organic layers were combined, dried over magnesium sulfate and concentrated in vacuo. The residue was purified on a 40 g silica gel column using 0-10% methanol in DCM to afford a mixture of the two desired regioisomers (MS calculated for $C_{20}H_{32}N_4O_2$ (M+H$^+$) 361.3, found 361.3.

Step 3: To a mixture of (TG1a) and (TG2a) (102 mg, 0.21 mmol), was added palladium on carbon (0.0220 g, 0.0207 mmol) and ethanol (1 ml). The mixture was stirred with hydrogen (65 psi) for 18 hr; LCMS showed 90% conversion. The mixture was filtered, washed with methanol and concentrated in vacuo. The residue was loaded on a 40 g silica gel column using 0-80% isopropanol in DCM with 2% ammonia as modifier to afford the pure product directly used in the separation step (below).
Regioisomer Separation 56 mg (0.16 mmol) of TG1 and TG2 from step two were separated using SFC chromatography on a 21×250 mm Cyano column (phase: 3 μM 4.6×50 mm, cyano, solvents mixture: CO$_2$: 85%; 1/1 v/v IPA:MeOH+10 mM NH$_4$OAc– 15%; prep conditions: 80 g/min, 88/6/6 CO$_2$/IPA/MeOH+ mM NH4OAc, ~115 bar, 2 min stacked injections, 5.25 min elution time) to afford tert-butyl (4-((4,5,6,7-tetrahydro-1H-pyrazolo[4,3-c]pyridin-1-yl)methyl)bicyclo[2.2.2]octan-1-yl)carbamate (TG1; peak 2, RT 2.1 min., ESIMS calcd. for $C_{21}H_{34}N_4O_2$ (M+H+) 361.3, found 361.3) and tert-butyl (4-((4,5,6,7-tetrahydro-2H-pyrazolo[4,3-c]pyridin-2-yl)methyl)bicyclo[2.2.2]octan-1-yl)carbamate (TG2; peak 1, RT 1.71 min. ESIMS calcd. for $C_{20}H_{32}N_4O_2$ (M+H+) 361.3, found 361.3.

Synthesis of tert-butyl (4-((3-methyl-4,5,6,7-tetrahydro-1H-pyrazolo[4,3-c]pyridin-1-yl)methyl)bicyclo[2.2.2]octan-1-yl)carbamate (TG3) and tert-butyl (4-((3-methyl-4,5,6,7-tetrahydro-2H-pyrazolo[4,3-c]pyridin-2-yl)methyl)bicyclo[2.2.2]octan-1-yl)carbamate (TG4)

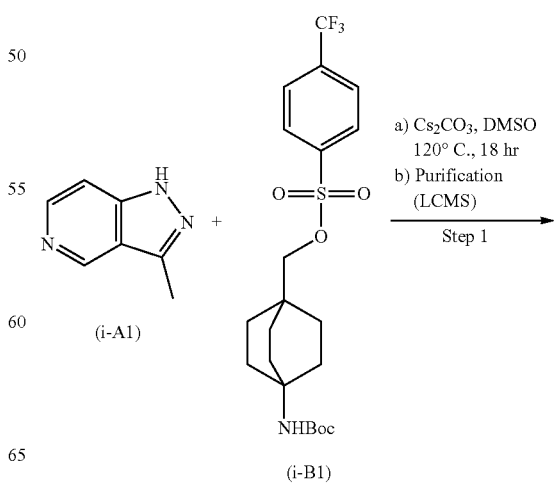

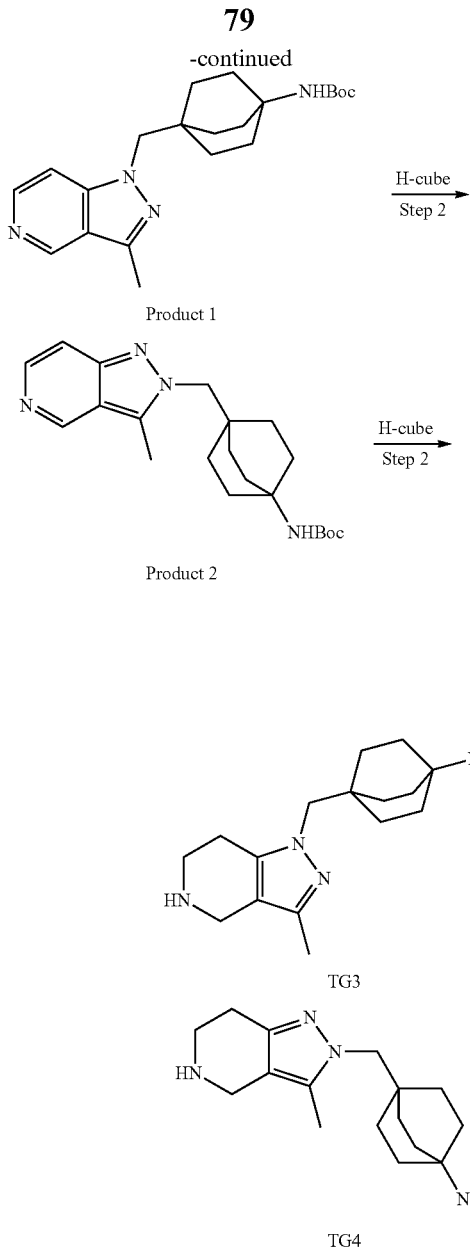

Product 1

Product 2

TG3

TG4

Step 1: A suspension of 3-methyl-1H-pyrazolo[4,3-c]pyridine (i-A1) (2.66 g, 19.98 mmol), in DMSO (80 ml) was treated with (4-(((tert-butoxycarbonyl)amino)bicyclo[2.2.2]octan-1-yl)methyl 4-(trifluoromethyl)benzenesulfonate (i-B1) (9.26 g, 19.98 mmol) and cesium carbonate (13.02 g, 40.0 mmol). The mixture was heated to 120° C. for 18 hr to complete, before being cooled to rt and diluted in ethyl acetate and water. After partitioning, the organic layer was dried over magnesium sulfate and concentrated in vacuo. The residue was purified on a 120 g silica gel column using 0-80% ethyl acetate in hexane and extended to 80% ethyl acetae in hexane to afford the desired products tert-butyl (4-((3-methyl-1H-pyrazolo[4,3-c]pyridin-1-yl)methyl)bicyclo[2.2.2]octan-1-yl)carbamate (product 1). The gradient was extended 100% ethyl acetate to elute the by-product tert-butyl (4-((3-methyl-2H-pyrazolo[4,3-c]pyridin-2-yl)methyl)bicyclo[2.2.2]octan-1-yl)carbamate (product 2).

Product 1: RT (LCMS Method 1): 1.510 min (mass −M+1-371.2), $^1$H NMR (400 MHz, Methanol-$d_4$) δ 9.07 (s, 1H), 8.37 (d, J=6.1 Hz, 1H), 7.60 (d, J=6.2 Hz, 1H), 6.18 (broad s, 1H), 4.17 (s, 2H), 2.71 (s, 3H), 1.87 (dd, J=10.0, 5.9 Hz, 6H), 1.66 (dd, J=10.0, 5.9 Hz, 6H), 1.47 (s, 9H). ESIMS calcd. for $C_{21}H_{30}N_4O_2$ (M+H+) 371.5, found 371.5.

Product 2: RT (LCMS Method 1): 1.47 min. ESIMS calcd. for $C_{21}H_{30}N_4O_2$ (M+H+) 371.5, found 371.5.

Step 2: Hydrogenation of Product 1 tert-butyl (4-((3-methyl-1H-pyrazolo[4,3-c]pyridin-1-yl)methyl)bicyclo[2.2.2]octan-1-yl)carbamate (product 1) (3.6267 g, 9.79 mmol) was hydrogenated using a H-cube system. Once complete, the reaction solution was concentrated and loaded on a 120 g silica gel column using 0-100% IPA in DCM with 1% ammonia as modifier and then extended to 100% IPA with 1% ammonia as modifier to elute tert-butyl (4-((3-methyl-4,5,6,7-tetrahydro-1H-pyrazolo[4,3-c]pyridin-1-yl)methyl)bicyclo[2.2.2]octan-1-yl)carbamate (TG3): $^1$H NMR (400 MHz, CD$_3$OD) δ 3.73 (s, 2H), 3.65 (s, 2H), 3.04 (t, J=5.8 Hz, 2H), 2.65 (t, J=5.9 Hz, 2H), 2.12 (s, 3H), 1.87-1.74 (m, 6H), 1.61-1.47 (m, 6H), 1.39 (s, 9H); ESIMS calcd. for $C_{21}H_{34}N_4O_2$ (M+H+) 375.5, found 375.5.

Step 2: Hydrogenation of Product 2 tert-butyl (4-((3-methyl-2H-pyrazolo[4,3-c]pyridin-2-yl)methyl)bicyclo[2.2.2]octan-1-yl)carbamate (1.011 g, 2.73 mmol) was hydrogenated using a H-cube system. Once complete, the reaction solution was concentrated and loaded on a 24 g silica gel column using 0-100% IPA in DCM with 3% NH$_3$ as modifier to yield tert-butyl (4-((3-methyl-4,5,6,7-tetrahydro-2H-pyrazolo[4,3-c]pyridin-2-yl)methyl)bicyclo[2.2.2]octan-1-yl)carbamate (TG4). $^1$H NMR (400 MHz, Methanol-d4) δ 4.89 (d, J=1.4 Hz, 1H), 3.75 (m 4H), 3.09 (t, J=5.9 Hz, 2H), 2.72 (m, 2H), 2.15 (s, 3H), 1.79 (m, 6H), 1.54 (m, 6H), 1.40 (s, 9H). ESIMS calcd. for $C_{21}H_{34}N_4O_2$ (M+H$^+$) 375.5, found 375.5.

Synthesis of tert-butyl (4-((3-methyl-4,5,6,7-tetrahydro-1H-pyrazolo[4,3-c]pyridin-1-yl)methyl)bicyclo[2.2.1]heptan-1-yl)carbamate (TG5)

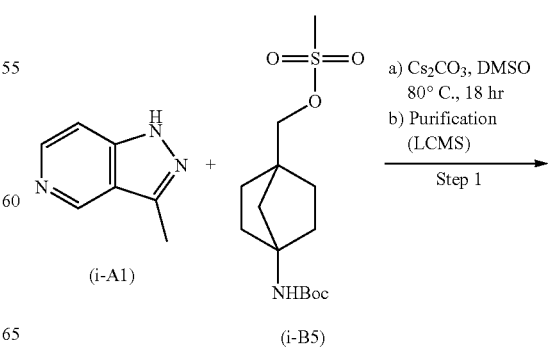

-continued

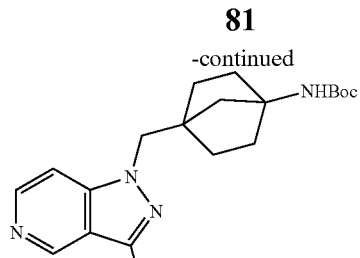

Product 1

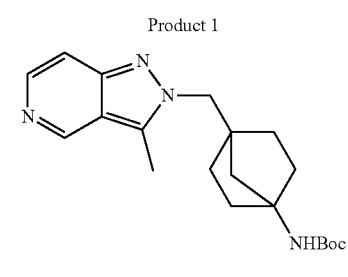

Product 2

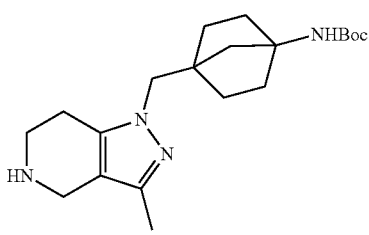

TG5

Step 1. A mixture of 3-methyl-1H-pyrazolo[4,3-c]pyridine (i-A1) (133 mg, 1.0 mmol), (4-((tert-butoxycarbonyl)amino)bicyclo[2.2.1]heptan-1-yl)methyl methanesulfonate (i-B5) (351 mg, 1.1 mmol) and Cs$_2$CO$_3$ in DMSO (2 mL) was stirred at 80° C. overnight. LC-MS showed completion of the reaction. The reaction mixture was then cooled down to rt and diluted with EtOAc/water. The layers were separated and the organic layer was dried over Na$_2$SO$_4$ then concentrated. The crude product was added (solid loading) to a 40 g silica gel column and was eluted with 0-100% EtOAc in hexanes. Collected fractions and concentrated to give product 1, tert-butyl (4-((3-methyl-1H-pyrazolo[4,3-c]pyridin-1-yl)methyl)bicyclo[2.2.1]heptan-1-yl)carbamate, and product 2, tert-butyl (4-((3-methyl-2H-pyrazolo[4,3-c]pyridin-2-yl)methyl)bicyclo[2.2.1]heptan-1-yl)carbamate.

Step 2. 220 mg (0.617 mmol) of, tert-butyl (4-((3-methyl-1H-pyrazolo[4,3-c]pyridin-1-yl)methyl)bicyclo[2.2.1]heptan-1-yl)carbamate was transformed to the desired product, tert-butyl (4-((3-methyl-4,5,6,7-tetrahydro-1H-pyrazolo[4,3-c]pyridin-1-yl)methyl)bicyclo[2.2.1]heptan-1-yl)carbamate (TG5) using H-Cube: 90° C., 20 bar H$_2$, 10% Pd/C, 1 mL/min flow rate. RT (LCMS Method 2) 1.92 min. MS calculated for C$_{20}$H$_{32}$N$_4$O$_2$ (M+H$^+$) 361.5, found 361.5. Note: Product 2 was not hydrogenated.

Synthesis of tert-butyl 1-((4-((tert-butoxycarbonyl)amino)bicyclo[2.2.2]octan-1-yl)methyl)-7,7-dimethyl-6,7-dihydro-1H-pyrazolo[4,3-c]pyridine-5(4H)-carboxylate (TG6a) and tert-butyl 2-((4-((tert-butoxycarbonyl)amino)bicyclo[2.2.2]octan-1-yl)methyl)-7,7-dimethyl-6,7-dihydro-2H-pyrazolo[4,3-c]pyridine-5(4H)-carboxylate (TG7a)

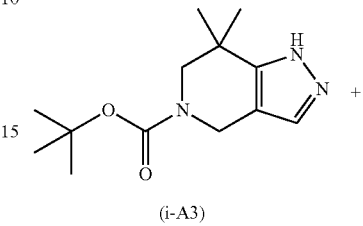

(i-A3)

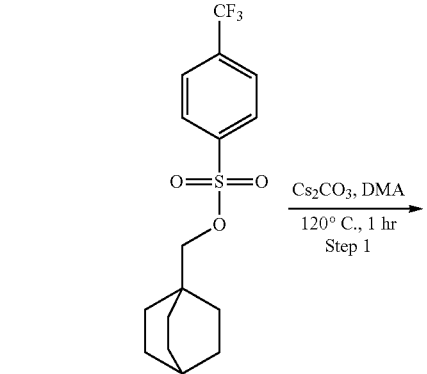

(i-B1)

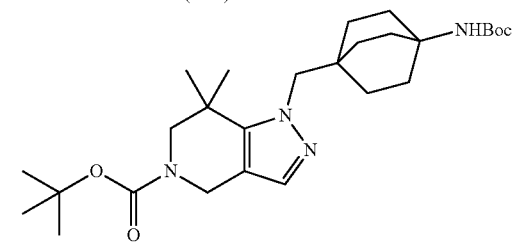

(TG6a)

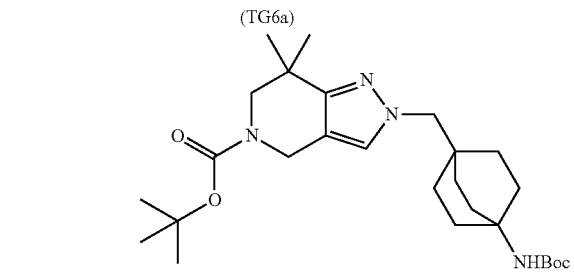

(TG7a)

tert-butyl 7,7-dimethyl-1,4,6,7-tetrahydro-5H-pyrazolo[4,3-c]pyridine-5-carboxylate (iA3) (120 mg, 0.477 mmol), (4-((tert-butoxycarbonyl)amino)bicyclo[2.2.2]octan-1-yl)methyl 4-(trifluoromethyl)benzenesulfonate (i-B1) (220 mg, 0.477 mmol) and Cs2CO3 (156 mg, 0.477 mmol) were mixed in DMA (10 mL) and stirred at 120° C. for 1 hr. After working-up and prep LC-MS, tert-butyl 1-((4-((tert-butoxycarbonyl)amino)bicyclo[2.2.2]octan-1-yl)methyl)-7,7-dimethyl-6,7-dihydro-1H-pyrazolo[4,3-c]pyridine-5(4H)-carboxylate (TG6a) and tert-butyl 2-((4-((tert-butoxycarbonyl)amino)bicyclo[2.2.2]octan-1-yl)methyl)-7,7-dimethyl-6,7-dihydro-2H-pyrazolo[4,3-c]pyridine-5(4H)-carboxylate TG7a) were obtained.

Synthesis of 4-((7,7-dimethyl-4,5,6,7-tetrahydro-1H-pyrazolo[4,3-c]pyridin-1-yl)methyl)bicyclo[2.2.2]octan-1-amine (TG6)

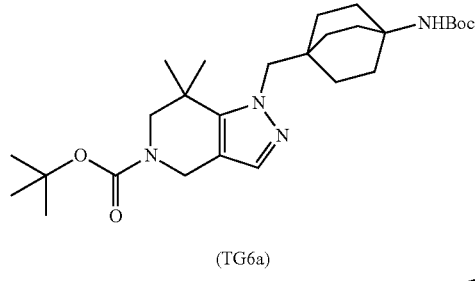

(TG6a)

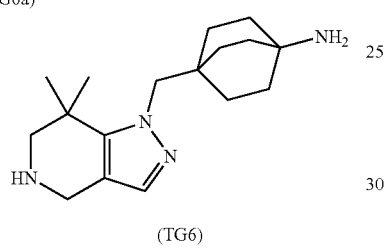

(TG6)

tert-butyl 1-((4-((tert-butoxycarbonyl)amino)bicyclo[2.2.2]octan-1-yl)methyl)-7,7-dimethyl-6,7-dihydro-1H-pyrazolo[4,3-c]pyridine-5(4H)-carboxylate (TG6a) (70 mg, 0.143 mmol) and HCl in dioxane (4N) (0.433 mL, 14.27 mmol) were mixed in MeOH (1 mL) and stirred at 50° C. for 5 hrs. After working-up and prep LC-MS 4-((7,7-dimethyl-4,5,6,7-tetrahydro-1H-pyrazolo[4,3-c]pyridin-1-yl)methyl)bicyclo[2.2.2]octan-1-amine (TG6) was obtained.

Synthesis of 4-((7,7-dimethyl-4,5,6,7-tetrahydro-2H-pyrazolo[4,3-c]pyridin-2-yl)methyl)bicyclo[2.2.2]octan-1-amine (TG7)

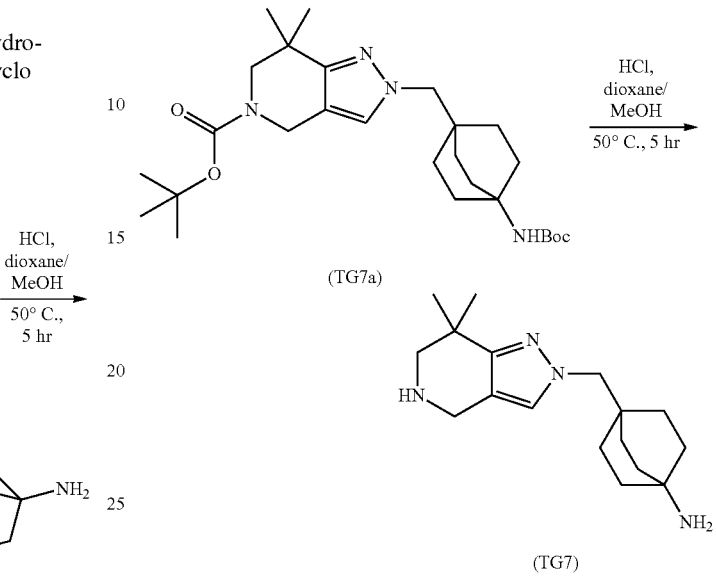

(TG7a)

(TG7)

tert-butyl 2-((4-((tert-butoxycarbonyl)amino)bicyclo[2.2.2]octan-1-yl)methyl)-7,7-dimethyl-6,7-dihydro-2H-pyrazolo[4,3-c]pyridine-5(4H)-carboxylate (TG7a) (70 mg, 0.143 mmol) and HCl in dioxane (4N) (0.433 mL, 14.27 mmol) were mixed in MeOH (1 mL) and stirred at 50° C. for 5 hrs. After working-up and prep LC-MS 4-((7,7-dimethyl-4,5,6,7-tetrahydro-2H-pyrazolo[4,3-c]pyridin-2-yl)methyl)bicyclo[2.2.2]octan-1-amine (TG7) was obtained.

Synthesis of 4-((3-(trifluoromethyl)-4,5,6,7-tetrahydro-1H-pyrazolo[4,3-c]pyridin-1-yl)methyl)bicyclo[2.2.2]octan-1-amine (TG8)

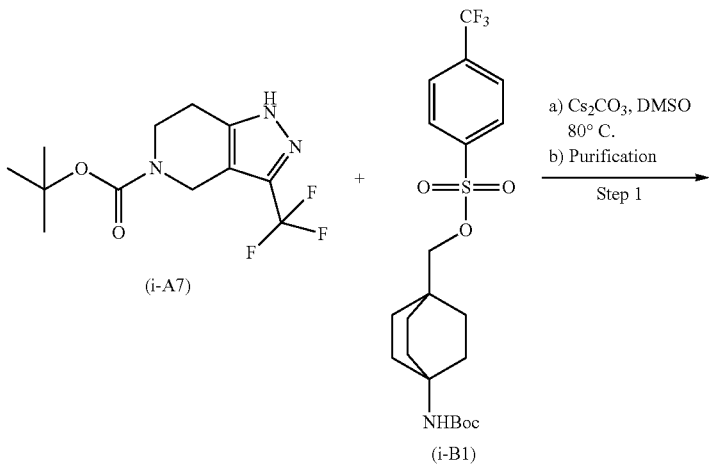

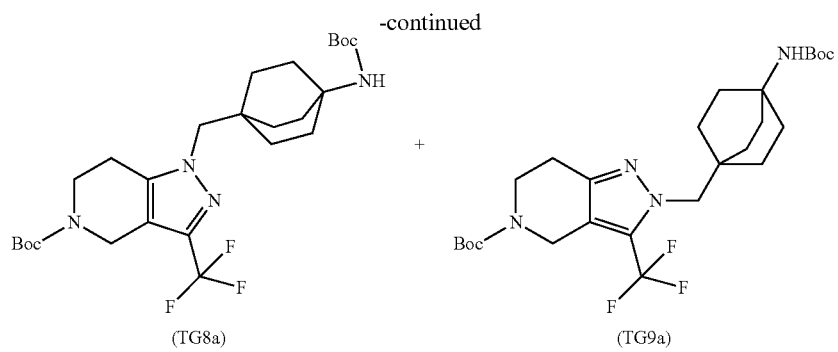

(TG8a)  +  (TG9a)

Step 2 | HCl
MeOH/dioxane

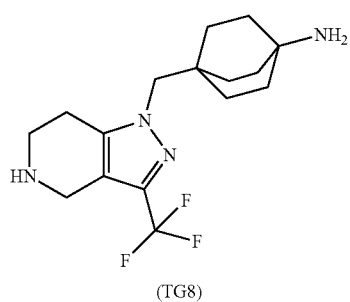

(TG8)

Step 1. A mixture of 291 mg (1 mmol) of tert-butyl 3-(trifluoromethyl)-6,7-dihydro-1H-pyrazolo[4,3-c]pyridine-5(4H)-carboxylate (i-A7), 510 mg (1.1 mmol) of (4-((tert-butoxycarbonyl)amino)bicyclo[2.2.1]heptan-1-yl)methyl methanesulfo(4-((tert-butoxycarbonyl)amino) bicyclo[2.2.2]octan-1-yl)methyl methanesulfonate and cesium carbonate (652 mg, 2.0 mmol) in DMSO (5 mL) was stirred at 80° C. overnight. After cooling to rt the mixture was diluted with EtOAc/water. The layers were separated and the aqueous layer was extracted with EtOAc. The combined organic layers were dried over Na$_2$SO$_4$ then concentrated to give the crude product. The crude product was added (solid loading) to a 40 g silica gel column and was eluted with 0-50% EtOAc in hexanes. Collected fractions and concentrated to give the desired product, tert-butyl 1-((4-((tert-butoxycarbonyl)amino)bicyclo[2.2.2]octan-1-yl)methyl)-3-(trifluoromethyl)-6,7-dihydro-1H-pyrazolo[4,3-c]pyridine-5(4H)-carboxylate (TG8a) and a trace amount of tert-butyl 2-((4-((tert-butoxycarbonyl)amino)bicyclo[2.2.2]octan-1-yl)methyl)-3-(trifluoromethyl)-2,4,6,7-tetrahydro-5H-pyrazolo[4,3-c]pyridine-5-carboxylate (TG9a). TG8a: 1H NMR (500 MHz, Methylene Chloride-d2) δ 4.51-4.46 (m, 2H), 4.36 (s, 1H), 3.84 (s, 2H), 3.65 (t, J=5.8 Hz, 2H), 2.70 (t, J=5.9 Hz, 2H), 1.82-1.73 (m, 6H), 1.59-1.52 (m, 6H), 1.46 (s, 9H), 1.38 (s, 9H). MS (ES+): 529.4 (M+1)+. TG9a: Method 1 (RT: 2.07 min), MS (ES+): 529.4 (M+1)+.

Step 2: To a solution of 66 mg (0.125 mmol) of tert-butyl 1-((4-((tert-butoxycarbonyl)amino)bicyclo[2.2.2]octan-1-yl)methyl)-3-(trifluoromethyl)-6,7-dihydro-1H-pyrazolo[4,3-c]pyridine-5(4H)-carboxylate (TG8a) in dioxane/MeOH (0.5 mL/0.3 mL) was added HCl (4M solution in dioxane, 0.5 mL). The resulting mixture was stirred at rt for 2 hrs. The reaction mixture was concentrated and lyophilized to give the final product, 4-((3-(trifluoromethyl)-4,5,6,7-tetrahydro-1H-pyrazolo[4,3-c]pyridin-1-yl)methyl)bicyclo[2.2.2]octan-1-amine (TG8), as HCl salt. Method 1 (RT=0.9 min), MS (ES+): 329.2 (M+1)+.

Synthesis of tert-butyl methyl(4-((3-methyl-4,5,6,7-tetrahydro-1H-pyrazolo[4,3-c]pyridin-1-yl)methyl) bicyclo[2.2.2]octan-1-yl)carbamate (TG10)

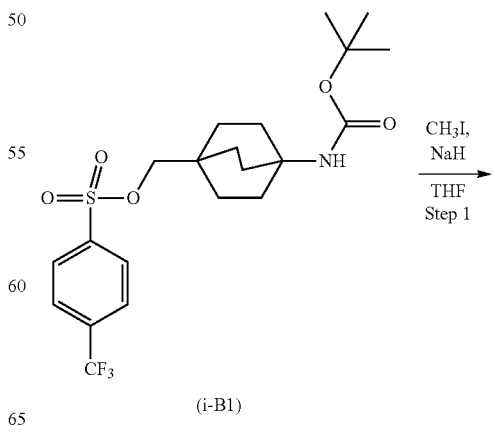

(i-B1)

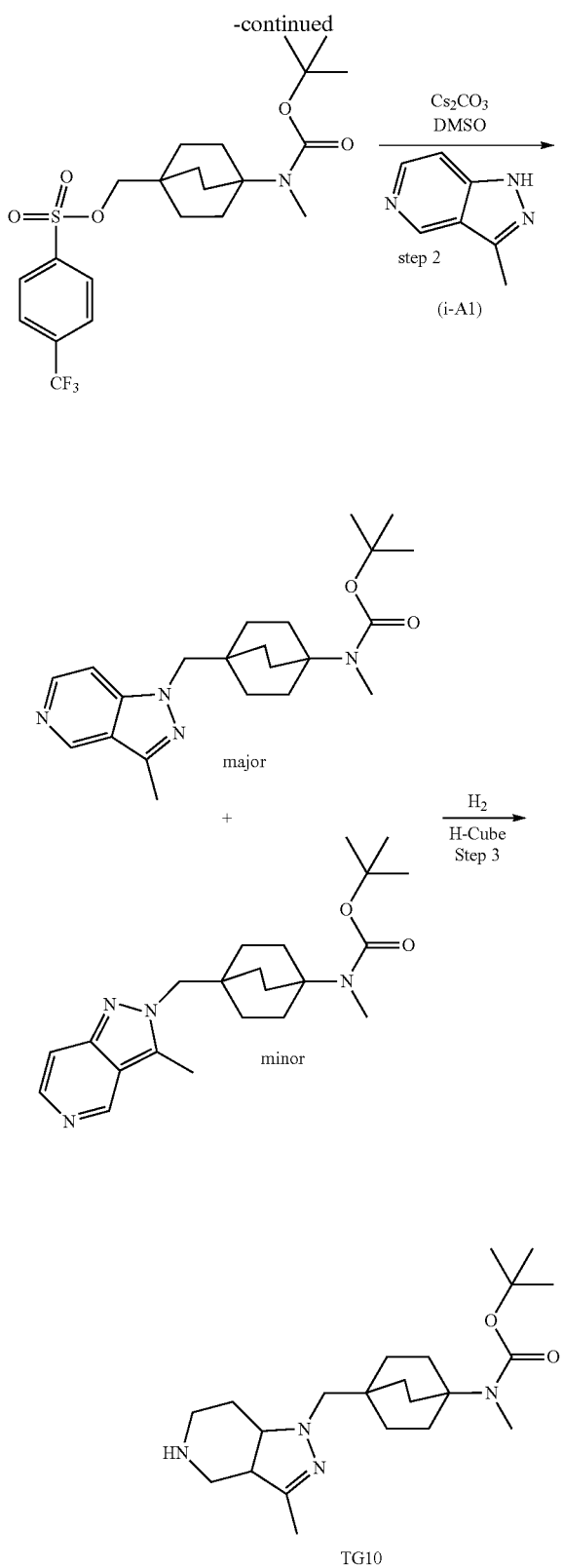

cooled back to 0° C. before CH₃I (2.84 g, 20.0 mmol) was added dropwise. The resulting mixture was slowly warmed up to rt and stirred overnight. LC-MS showed desired product but the reaction was not complete. Additional NaH (1.0 eq.) and CH₃I (5.0 eq.) were added and the reaction mixture was stirred at rt overnight. The reaction was quenched at 0° C. by dropwise adding 2.0 mL of 2-propanol, then 3.0 mL of cold water. The mixture was then partitioned between EtOAc and water. The layers were separated and the aqueous layer was extracted with EtOAc. The combined organic layers were dried over Na₂SO₄ then concentrated. The crude product was added to a 80 g silica gel column and was eluted with 0-30% EtOAc in hexanes. Collected fractions and concentrated to give (4-((tert-butoxycarbonyl)(methyl)amino)bicyclo[2.2.2]octan-1-yl)methyl 4-(trifluoromethyl)benzenesulfonate. RT: 3.1 min (method 2). 1H NMR (400 MHz, Methanol-d4) δ 8.11 (d, J=8.2 Hz, 2H), 7.98 (d, J=8.2 Hz, 2H), 3.73 (d, J=1.9 Hz, 2H), 2.82 (s, 3H), 2.04-1.95 (m, 6H), 1.53-1.42 (m, 15H).

Step 2. A mixture of 133 mg (1.0 mmol) of 3-methyl-1H-pyrazolo[4,3-c]pyridine, 525 mg (1.1 mmol) of (4-((tert-butoxycarbonyl)(methyl)amino)bicyclo[2.2.2]octan-1-yl) methyl 4-(trifluoromethyl)benzenesulfonate and 652 mg (2.0 mmol) of Cs₂CO₃ in DMSO was stirred at 80° C. overnight. After cooling to rt, the mixture was diluted with EtOAc/water. The layers were separated and the organic layer was dried over Na₂SO₄, then concentrated. The crude product was added (solid loading) to a 40 g silica gel column and was eluted with 0-100% EtOAc in hexanes. Collected fractions and concentrated to give tert-butyl methyl(4-((3-methyl-1H-pyrazolo[4,3-c]pyridin-1-yl)methyl)bicyclo[2.2.2]octan-1-yl)carbamate as the major product (eluting first), and tert-butyl methyl(4-((3-methyl-2H-pyrazolo[4,3-c]pyridin-2-yl)methyl)bicyclo[2.2.2]octan-1-yl)carbamate as the minor by-product (eluting second). Major product (tert-butyl methyl(4-((3-methyl-1H-pyrazolo[4,3-c]pyridin-1-yl)methyl)bicyclo[2.2.2]octan-1-yl)carbamate): ¹H NMR (400 MHz, Methanol-d4) δ 8.99 (d, J=1.1 Hz, 1H), 8.29 (d, J=6.2 Hz, 1H), 7.52 (dd, J=6.2, 1.2 Hz, 1H), 4.10-4.07 (m, 2H), 2.80 (s, 3H), 2.63 (s, 3H), 2.01-1.94 (m, 6H), 1.63-1.56 (m, 6H), 1.43 (s, 9H). MS (ES+): 385.2 (M+1)+. Minor product (tert-butyl methyl(4-((3-methyl-2H-pyrazolo[4,3-c]pyridin-2-yl)methyl)bicyclo[2.2.2]octan-1-yl)carbamate): 1H NMR (400 MHz, Methanol-d4) δ 9.08 (d, J=1.3 Hz, 1H), 8.14 (d, J=6.4 Hz, 1H), 7.48 (dd, J=6.3, 1.2 Hz, 1H), 4.19 (s, 2H), 2.81 (s, 3H), 2.77 (s, 3H), 2.07-1.97 (m, 6H), 1.70-1.62 (m, 6H), 1.43 (s, 9H). MS (ES+): 385.2 (M+1)+.

Step 3. tert-butyl methyl(4-((3-methyl-2H-pyrazolo[4,3-c]pyridin-2-yl)methyl)bicyclo[2.2.2]octan-1-yl)carbamate (233 mg, 0.606 mmol) was transformed to the desired product, tert-butyl methyl(4-((3-methyl-4,5,6,7-tetrahydro-1H-pyrazolo[4,3-c]pyridin-1-yl)methyl)bicyclo[2.2.2]octan-1-yl)carbamate (TG10) using H-Cube: 100° C., 15 bar H₂, 10% Pd/C, 1 mL/min flow rate. The product was used directly without purification. RT (method 2): 1.7 min, MS (ES+): 389.3 (M+1)+.

Step 1. To a solution of 1.85 g (4.0 mmol) of (4-((tert-butoxycarbonyl)amino)bicyclo[2.2.2]octan-1-yl)methyl 4-(trifluoromethyl)benzenesulfonate (i-B1) in THF was added 208 mg (5.2 mmol) of NaH at 0° C. under N₂. The mixture was warmed up to rt and stirred for 30 min then

TABLE 4

Additional Tail Groups

| Tail Group Code | Tail Group | Characterization | Synthesis Method |
|---|---|---|---|
| TG11 | 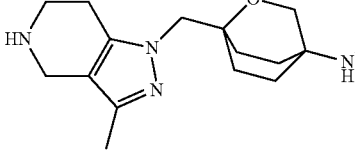<br>tert-butyl (1-((3-methyl-4,5,6,7-tetrahydro-1H-pyrazolo[4,3-c]pyridin-1-yl)methyl)-2-oxabicyclo[2.2.2]octan-4-yl)carbamate | Method 1 (RT = 1.17 min), MS (ES+): 378.3 (M + 1) | See Synthesis of TG3 Use (i-B6) in place of (i-B1) |
| TG12 | 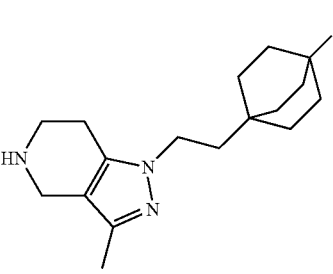<br>tert-butyl (4-(2-(3-methyl-4,5,6,7-tetrahydro-1H-pyrazolo[4,3-c]pyridin-1-yl)ethyl)bicyclo[2.2.2]octan-1-yl)carbamate | Method 1 (RT = 1.25 min.), MS (ES+): 390.2 (M + 1) | See Synthesis of TG3 Use (i-B3) in place of (i-B1) |
| TG13 | 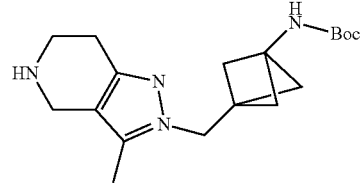<br>tert-butyl (3-((3-methyl-4,5,6,7-tetrahydro-2H-pyrazolo[4,3-c]pyridin-2-yl)methyl)bicyclo[1.1.1]pentan-1-yl)carbamate | Method 1 (RT = 1.09 min.), MS (ES+): 334.2 (M + 1) | See Synthesis of TG4 Use (i-B2) in place of (i-B1) |
| TG14 | 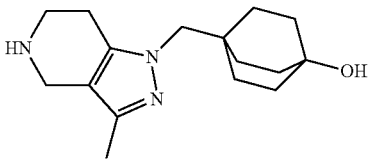<br>4-((3-methyl-4,5,6,7-tetrahydro-1H-pyrazolo[4,3-c]pyridin-1-yl)methyl)bicyclo[2.2.2]octan-1-ol | | See Synthesis of TG3. Use 4-hydroxybicyclo[2.2.2]octane-1-carboxylic acid as staring material instead of 4-((tert-butoxycarbonyl)amino)bicyclo[2.2.2]octane-1-carboxylic acid |

Head Groups

The Head Group intermediates used to obtain compounds of the invention are shown in Table 5 and their synthesis is described below. Unless purchased, the synthesis of certain reagents used to obtain these intermediates is also described below.

TABLE 5

Head Groups

| Head Group Code | Head Group | Head Group Name | Synthesis Method or Purchase |
|---|---|---|---|
| HG1 | (structure) | 4-bromo-1,6-dimethyl-1H-pyrazolo[3,4-b]pyridine | Purchased |
| HG2 | (structure) | 4-chloro-1-methyl-1H-pyrazolo[3,4-d]pyrimidin-6-amine | Purchased |
| HG2a | (structure) | tert-butyl (4-chloro-1-methyl-1H-pyrazolo[3,4-d]pyrimidin-6-yl)carbamate | Boc Protected HG2 |
| HG3 | (structure) | 5,7-dichloro-1-methyl-1H-pyrazolo[4,3-d]pyrimidine | Purchased |
| HG4 | (structure) | 7-chloro-1,3,5-trimethyl-1H-pyrazolo[4,3-d]pyrimidine | Purchased |
| HG5 | (structure) | 4-chloro-3,6-dimethylisoxazolo[5,4-d]pyrimidine | Purchased |
| HG6 | (structure) | 4-chloro-1H-pyrazolo[3,4-b]pyridine | Purchased |

TABLE 5-continued

Head Groups

| Head Group Code | Head Group | Head Group Name | Synthesis Method or Purchase |
|---|---|---|---|
| HG7 | | 1-(4-methoxybenzyl)-6-methyl-1H-pyrazolo[3,4-b]pyridin-4-yl trifluoromethanesulfonate | See Below |
| HG8 | | 4-chloro-2-methylquinoline | Purchased |
| HG9 | | 4-chloro-2-methyl-1,7-naphthyridine | Purchased |
| HG10 | | 4-chloro-2,8-dimethyl-1,7-naphthyridine | See below |
| HG11 | | 2,4-dichloro-5,7-dihydrofuro[3,4-d]pyrimidine | Purchased |
| HG12 | | 7-chloro-5-methyl-1H-pyrazolo[4,3-b]pyridine | Purchased |

TABLE 5-continued

Head Groups

| Head Group Code | Head Group | Head Group Name | Synthesis Method or Purchase |
|---|---|---|---|
| HG13 | 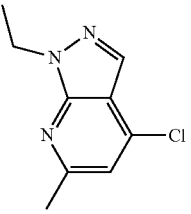 | 4-chloro-1-ethyl-6-methyl-1H-pyrazolo[3,4-b]pyridine | See below |
| HG14 | 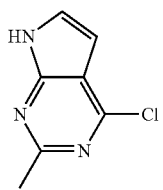 | 4-chloro-2-methyl-7H-pyrrolo[2,3-d]pyrimidine | Purchased |
| HG15 | 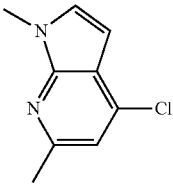 | 4-chloro-1,6-dimethyl-1H-pyrrolo[2,3-b]pyridine | Purchased |
| HG16 | 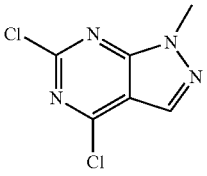 | 4,6-dichloro-1-methyl-1H-pyrazolo[3,4-d]pyrimidine | Purchased |
| HG17 | 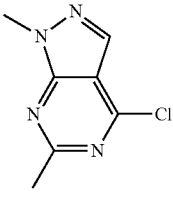 | 4-chloro-1,6-dimethyl-1H-pyrazolo[3,4-d]pyrimidine | Purchased |
| HG18 |  | 4-chloro-6-methyl-1H-pyrazolo[3,4-d]pyrimidine | Purchased |

Synthesis of 1-(4-methoxybenzyl)-6-methyl-1H-pyrazolo[3,4-b]pyridin-4-yl trifluoromethanesulfonate (HG7)

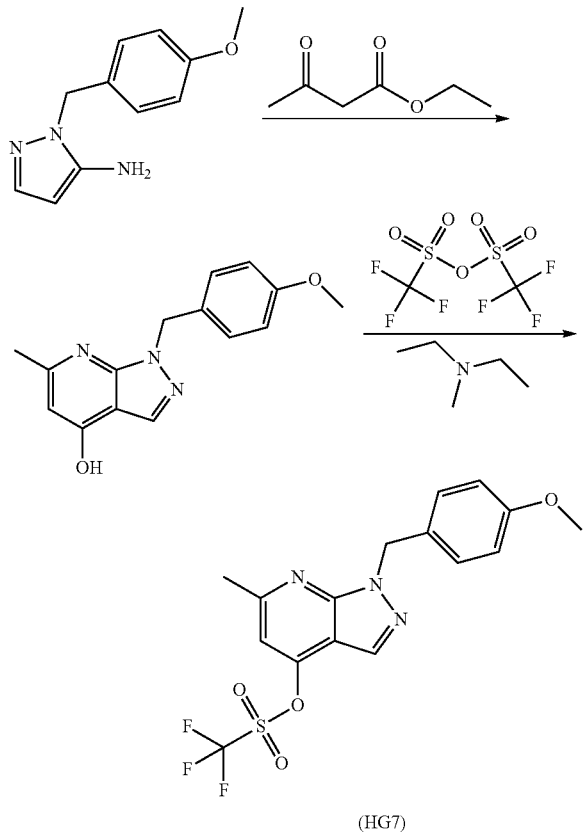

(HG7)

Step 1: A solution of 1-(4-methoxybenzyl)-1H-pyrazol-5-amine and ethyl acetoacetate in acetic acid was stirred at rt overnight. The reaction was concentrated in vacuo and then taken up in DOWThermA and heated in a sealed vessel to 230° C. The reaction was maintained at this temperature for 40 min and then cooled to rt. The reaction was purified by column chromatography (SiO$_2$, ISCO, 0-15% MeOH in dichloromethane) to afford the desired phenol directly used in the next step.

Step 2: To the solution of 1-(4-methoxybenzyl)-6-methyl-1H-pyrazolo[3,4-b]pyridin-4-ol (1.895 g, 7.04 mmol) in mix solvent of DCM (100 mL, 3.33 parts) and THF (30 mL, 1 part) at 0° C. was added triethylamine (7.36 mL, 52.8 mmol) followed by triflicAnhydride (2.97 mL, 17.59 mmol). The reaction was gradually warmed up to rt in 3 hrs. The reaction was quenched with saturated sodium bicarbonate solution and extracted with DCM. The organic phase was washed with brine and dried. The crude product was purified by silica gel chromatography, eluted with 10% to 50% ethyl acetate in hexane to give 1-(4-methoxybenzyl)-6-methyl-1H-pyrazolo[3,4-b]pyridin-4-yl trifluoromethanesulfonate (HG7). RT (LC/MS method 2): 2.79 min. ESIMS calcd. for C$_{16}$H$_{14}$F$_3$N$_3$O$_4$(M+H+) 402.9, found 402.9.

Synthesis of 4-chloro-2,8-dimethyl-1,7-naphthyridine (HG10)

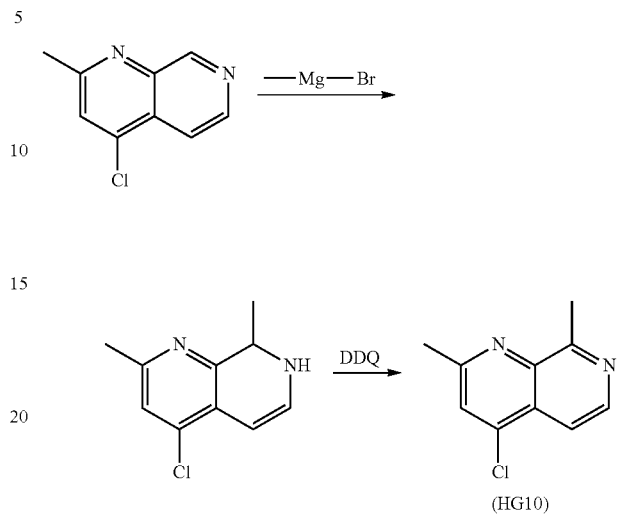

(HG10)

To a solution of 4-chloro-2-methyl-1,7-naphthyridine (405 mg, 2.267 mmol) in THF (10 mL) was intermittently added methylmagnesium bromide (4.53 mL, 13.60 mmol, 3M in diether ether) over 30 min at rt. The reaction changed from a light brown to a dark green suspension. After stirring overnight, the reaction was stopped and then quenched by addition of saturated NH$_4$Cl (10 mL), extracted with EtOAc (3×25 mL). EtOAc was washed with brine (5 mL), dried over Na$_2$SO$_4$ and evaporated to give the crude desired product 4-chloro-2,8-dimethyl-7,8-dihydro-1,7-naphthyridine. MS 195.1 (M+1), RT (LC/MS method 1) 0.94 min. Contained byproduct MS 193.1 (M+1), RT (LC/MS method 1) 0.85 min. The crude was used w/o purification in next step.

The crude 4-chloro-2,8-dimethyl-7,8-dihydro-1,7-naphthyridine (440 mg, 2.260 mmol) from above was dissolved in DCM (20 mL). DDQ (513 mg, 2.260 mmol) was added. The mixture was sonicated for 2 min. LCMS showed completion of the reaction. The mixture was diluted with EtOAc (50 mL), filtered through Celite filter cake. The filter cake was washed with EtOAc (50 mL). The organic was evaporated to give a dark residue. The crude was purified by flash chromatography (EtOAc:hex/0-100%) giving 4-chloro-2,8-dimethyl-1,7-naphthyridine (HG10): MS 193.1 (M+1), RT 0.82 min. (method 1).

Synthesis of 4-chloro-1-ethyl-6-methyl-1H-pyrazolo[3,4-b]pyridine (HG13)

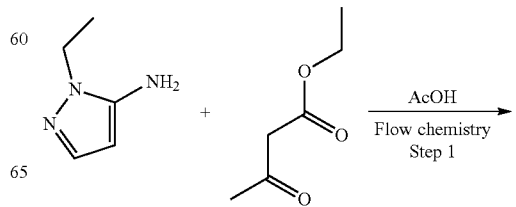

-continued

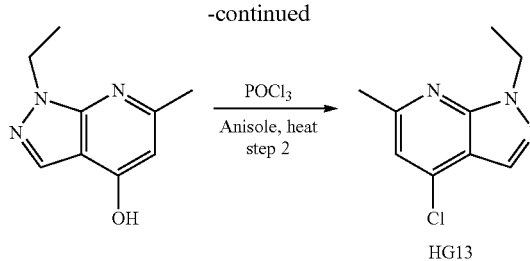

Step 1. A mixture of 2.5 g of 1-ethyl-1H-pyrazol-5-amine (22.5 mmol), 23.4 g (180 mmol) of ethyl 3-oxobutanoate and 1.35 g (22.5 mmol) of AcOH was reacted in flow using a Vapourtec R2C+/R4 (trip pressure set to 40 bar; SS tube reactor; solution pressure set by 250 psi BPR) in dioxane at a flow rate of 0.2 mL/min at 250° C. The reaction was quenched using MeOH (flow rate 0.25 mL/min). The resulting solution was concentrated and triturated in EtOAc to afford 1-ethyl-6-methyl-1H-pyrazolo[3,4-b]pyridin-4-ol as an off-white solid. RT 0.95 min (method 2). MS (M+1): 178.2

Step 2.

A sealed vessel charged with 1-ethyl-6-methyl-1H-pyrazolo[3,4-b]pyridin-4-ol (Ig, 5.64 mmol) and $POCl_3$ (0.631 mL, 6.77 mmol) in anisole (8 mL) was heated at 130° C. for 2 hrs. The reaction was cooled down and the solvent was removed in vacuo and dried to afford 4-chloro-1-ethyl-6-methyl-1H-pyrazolo[3,4-b]pyridine (HG13). RT 0.52 min (LC/MS method 2). MS (M+1): 196.6.

Synthesis of Exemplary Compounds

Example 1

Synthesis of 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 1)

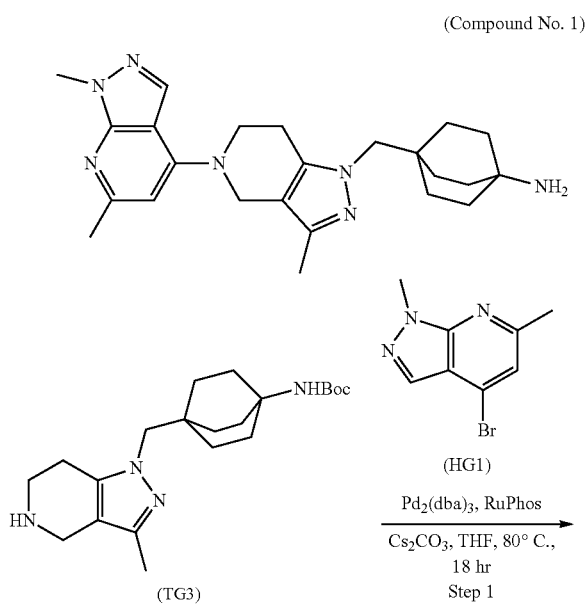

-continued

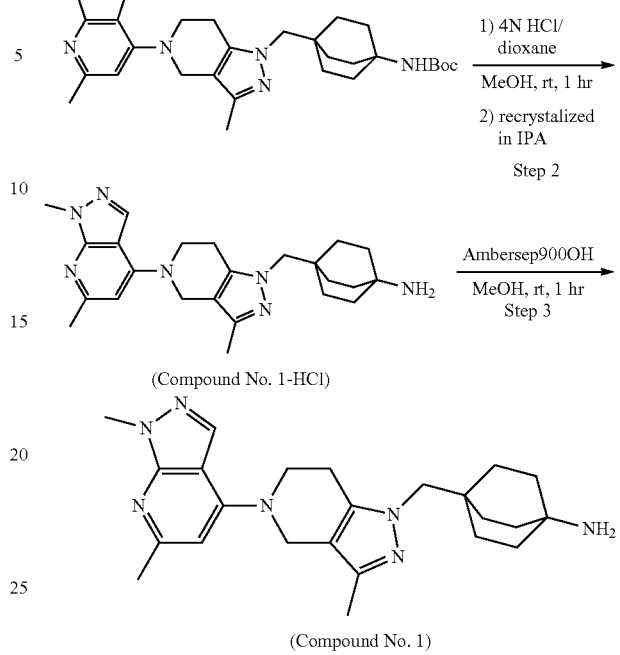

Step 1:

To a pressure flask containing tert-butyl (4-((3-methyl-4,5,6,7-tetrahydro-1H-pyrazolo[4,3-c]pyridin-1-yl)methyl)bicyclo[2.2.2]octan-1-yl)carbamate (TG3) (0.565 g, 42.5 mmol) was added 4-bromo-1,6-dimethyl-1H-pyrazolo[3,4-b]pyridine (HG1) (0.94 g, 2.5 mmol), cesium carbonate (1.63 g, 5.0 mmol), $Pd_2(dba)_3$ (0.057 g, 0.062 mmol), RuPhos (0.14 g, 0.3 mmol) and THF (25 mL). The mixture was heated at 80° C. for 18 hrs to complete, then cooled to rt. The mixture was diluted in ethyl acetate and water. After partition, the aqueous layer was extracted with ethyl acetate once more. Both organic layers were combined, dried over $MgSO_4$, filtered and concentrated in vacuo. The residue was purified via flash chromatography using 0-100% B/A (A=heptane; B=25% ethanol in ethyl acetate) to elute tert-butyl (4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)carbamate: $^1$H NMR (400 MHz, CDCl3) δ 7.98 (s, 1H), 6.27 (s, 1H), 4.49 (s, 2H), 4.38-4.25 (m, 1H), 4.11 (s, 3H), 3.94 (t, J=5.5 Hz, 2H), 3.70 (s, 2H), 2.87 (t, J=5.6 Hz, 2H), 2.62 (s, 3H), 2.25 (s, 3H), 1.89-1.75 (m, 6H), 1.58 (m, 6H), 1.42 (s, 9H); MS calculated for $C_{29}H_{72}N_7O_2$(M+H$^+$) 520.34, found 520.4.

Step 2.

To a 500 mL round bottom flask containing tert-butyl (4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)carbamate (1.5 g, 1.45 mmol) was added methanol (6 mL), then 4N HCl in dioxane (7.2 mL, 28.9 mmol). The mixture was stirred at rt for 18 hr then concentrated in vacuo. The residue was treated with isopropanol portionwise at 70° C. to get all solid dissolved. The solution was cooled naturally to rt and aged for 18 hrs. Then the solid was filtered and the filtrate was concentrated and the crystallization process repeated. Both batches were combined and dried under vacuum at 40° C. for 18 hrs to afford of 4-((5-(1,6-dimethyl-1H-pyrazolo[3,4-b]pyridin-4-yl)-3-methyl-4,5,6,7-tetrahydro-1H-pyrazolo[4,3-c]pyridin- 1-yl)methyl)bicyclo[2.2.2]octan-1-amine as HCl salt (Compound No. 1-HCl): ¹H NMR (400 MHz, CD₃OD) δ 8.51 (s, 1H), 6.88 (s, 1H), 5.06-4.92 (m, 2H), 4.24 (s, 2H), 4.11 (s, 3H), 3.97 (s, 2H), 3.10 (t, J=5.6 Hz, 2H), 2.69 (s, 3H), 2.38 (s, 3H), 1.88-1.59 (m, 12H); MS (M+H⁺) found 420.3.

Step 3.

Ambersep 900OH (17 ml, 0.8 meq/mL, prewashed with 60 mL of MeOH) was added into a solution of 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine as HCl salt (Compound No. 1-HCl) (1.53 g, 2.7 mmol) in MeOH (100 mL). The mixture was stirred at rt for 1 hr then filtered, washed with 50 mL of MeOH and concentrated. The crude product was added (by solid loading) to a 12 g silica gel column and was eluted with 2-9% MeOH (containing small amount of ammonia) in DCM. Collected fractions and concentrated to give the product, 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine, as the free base (Compound No. 1): ¹H NMR (400 MHz, CD₃OD) δ 8.15 (s, 1H), 6.45 (s, 1H), 4.54 (s, 2H), 4.00 (s, 3H), 3.97 (t, J=5.6 Hz, 2H), 3.73 (s, 2H), 2.90 (t, J=5.6 Hz, 2H), 2.55 (s, 3H), 2.23 (s, 3H), 1.55 (s, 12H); MS (M+H⁺) 420.3.

Example 2

Synthesis of 4-((3-methyl-5-(6-methyl-1H-pyrazolo[3,4-b]pyridin-4-yl)-4,5,6,7-tetrahydro-1H-pyrazolo[4,3-c]pyridin-1-yl)methyl)bicyclo[2.2.2]octan-1-amine (Compound No. 2) and 4-((5-(1-(4-methoxybenzyl)-6-methyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 53)

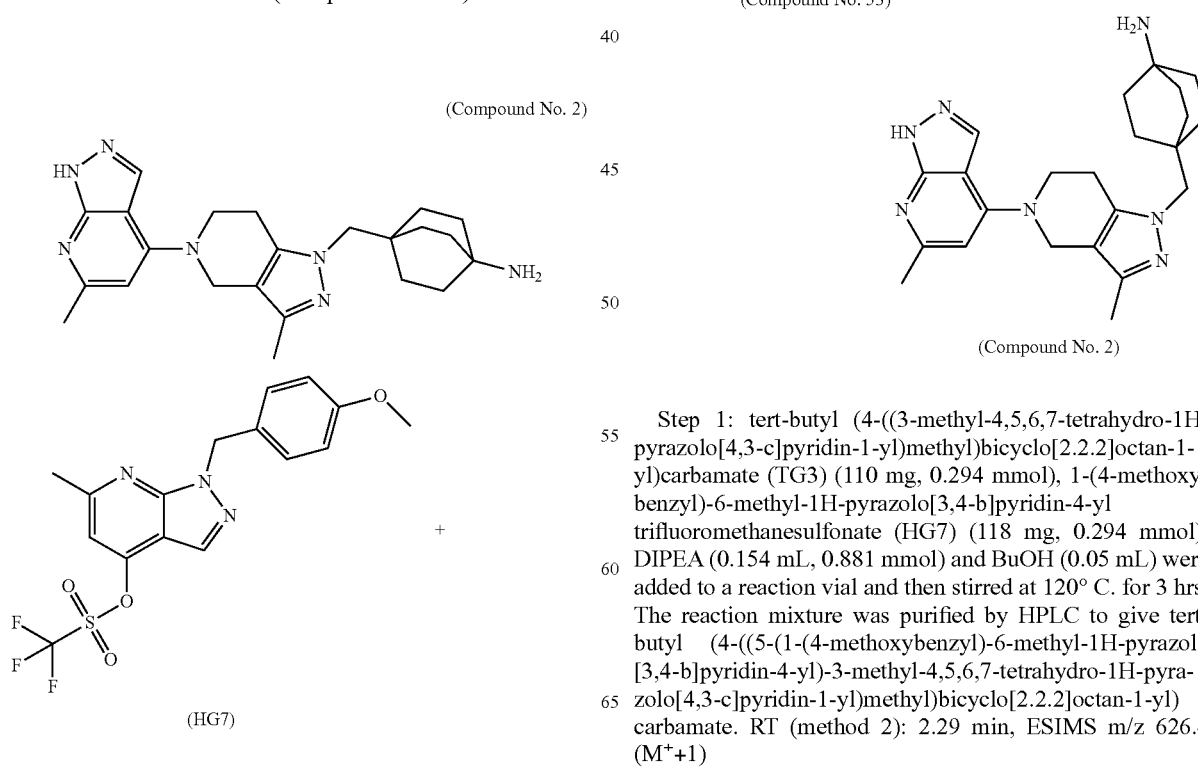

Step 1: tert-butyl (4-((3-methyl-4,5,6,7-tetrahydro-1H-pyrazolo[4,3-c]pyridin-1-yl)methyl)bicyclo[2.2.2]octan-1-yl)carbamate (TG3) (110 mg, 0.294 mmol), 1-(4-methoxybenzyl)-6-methyl-1H-pyrazolo[3,4-b]pyridin-4-yl trifluoromethanesulfonate (HG7) (118 mg, 0.294 mmol), DIPEA (0.154 mL, 0.881 mmol) and BuOH (0.05 mL) were added to a reaction vial and then stirred at 120° C. for 3 hrs. The reaction mixture was purified by HPLC to give tert-butyl (4-((5-(1-(4-methoxybenzyl)-6-methyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)carbamate. RT (method 2): 2.29 min, ESIMS m/z 626.4 (M⁺+1)

Step 2: To the solution of tert-butyl (4-((5-(1-(4-methoxybenzyl)-6-methyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)carbamate (110 mg, 0.176 mmol) in MeOH (1 mL) was added hydrochloric acid (0.879 mL, 5.27 mmol). The reaction was stirred for 16 hr at 25° C. and then dried to give 4-((5-(1-(4-methoxybenzyl)-6-methyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 53) as HCl salt. RT (method 1): 1.28 min, ESIMS m/z 526.3 (M$^+$+1)

Step 3: To a 20 mL pressure tube was added 4-((5-(1-(4-methoxybenzyl)-6-methyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 53) (80 mg, 0.152 mmol), cysteine (36.9 mg, 0.304 mmol) and TFA (2 mL). The mixture was heated at 75° C. for 2 hr and then cooled to rt and concentrated in vacuo. The residue was purified by HPLC to give 4-((3-methyl-5-(6-methyl-1H-pyrazolo[3,4-b]pyridin-4-yl)-4,5,6,7-tetrahydro-1H-pyrazolo[4,3-c]pyridin-1-yl)methyl)bicyclo[2.2.2]octan-1-amine (Compound No. 2). ESIMS m/z 406.2 (M$^+$+1); $^1$H NMR (400 MHz, Methanol-d$_4$) δ 8.09 (s, 1H), 6.34 (s, 1H), 4.44 (s, 2H), 3.88 (t, J=5.6 Hz, 2H), 3.63 (s, 2H), 3.56 (s, 4H), 2.80 (t, J=5.6 Hz, 2H), 2.41 (s, 3H), 2.13 (s, 3H), 1.44 (s, 12H).

Example 3

Synthesis of 4-((3-methyl-5-(2-methyl-1,7-naphthyridin-4-yl)-4,5,6,7-tetrahydro-1H-pyrazolo[4,3-c]pyridin-1-yl)methyl)bicyclo[2.2.2]octan-1-amine (Compound No. 3) and tert-butyl (4-((3-methyl-5-(2-methyl-1,7-naphthyridin-4-yl)-4,5,6,7-tetrahydro-1H-pyrazolo[4,3-c]pyridin-1-yl)methyl)bicyclo[2.2.2]octan-1-yl)carbamate (Compound No. 147)

(Compound No. 3)

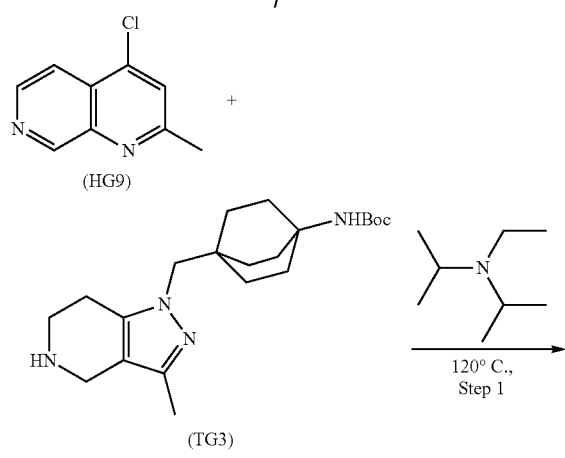

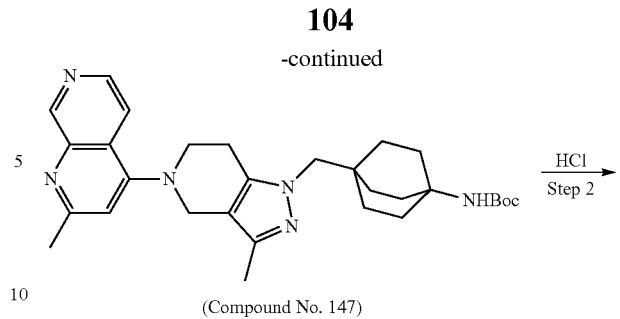

(Compound No. 147)

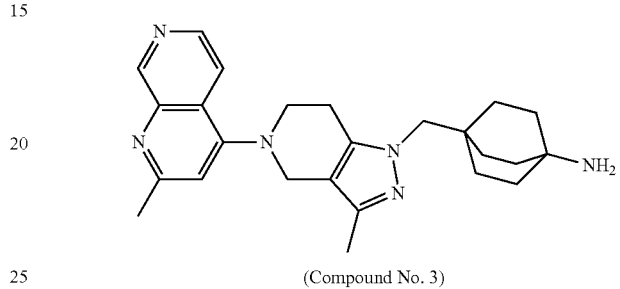

(Compound No. 3)

Step 1: To the reaction vial were added tert-butyl (4-((3-methyl-4,5,6,7-tetrahydro-1H-pyrazolo[4,3-c]pyridin-1-yl)methyl)bicyclo[2.2.2]octan-1-yl)carbamate (TG3) (105 mg, 0.280 mmol), 4-chloro-2-methyl-1,7-naphthyridine (HG9) (50 mg, 0.280 mmol), DIPEA (0.147 mL, 0.840 mmol) and BuOH (0.1 mL). The reaction was stirred at 120° C. for 3 hr, diluted with methanol and purified by HPLC. The fractions were pooled, neutralized with Na$_2$CO$_3$ and then extracted with ethyl acetate to give tert-butyl (4-((3-methyl-5-(2-methyl-1,7-naphthyridin-4-yl)-4,5,6,7-tetrahydro-1H-pyrazolo[4,3-c]pyridin-1-yl)methyl)bicyclo[2.2.2]octan-1-yl)carbamate (Compound No. 147)$^1$H NMR (400 MHz, DMSO-d$_6$) δ 9.53 (s, 1H), 8.73 (d, J=5.9 Hz, 1H), 8.34-7.92 (m, 2H), 7.39 (s, 1H), 4.68 (s, 2H), 4.03 (t, J=5.2 Hz, 2H), 3.72 (s, 2H), 3.08 (s, 2H), 2.78 (s, 3H), 2.51 (s, 9H), 2.12 (s, 3H), 1.80-1.45 (m, 12H). ESIMS m/z 518.0 (M$^+$+1).

Step 2: To a solution of tert-butyl (4-((3-methyl-5-(2-methyl-1,7-naphthyridin-4-yl)-4,5,6,7-tetrahydro-1H-pyrazolo[4,3-c]pyridin-1-yl)methyl)bicyclo[2.2.2]octan-1-yl)carbamate (124 mg, 0.240 mmol) in MeOH (1 mL) was added hydrochloric acid (1.200 mL, 7.20 mmol). The reaction was stirred for 16 hr at 25° C. The reaction was dried to give 4-((3-methyl-5-(2-methyl-1,7-naphthyridin-4-yl)-4,5,6,7-tetrahydro-1H-pyrazolo[4,3-c]pyridin-1-yl)methyl)bicyclo[2.2.2]octan-1-amine (Compound No. 3) as an HCl salt. ESIMS m/z 417.2 (M+1); $^1$H NMR (400 MHz, DMSO-d$_6$) δ 9.53 (s, 1H), 8.73 (d, J=5.9 Hz, 1H), 8.16-8.05 (m, 4H), 7.39 (s, 1H), 4.70 (s, 2H), 4.03 (t, J=5.6 Hz, 2H), 3.72 (s, 2H), 3.13-3.03 (m, 2H), 2.78 (s, 3H), 2.12 (s, 3H), 1.75-1.63 (m, 6H), 1.60-1.49 (m, 6H).

Example 4

Synthesis of 4-((3-methyl-5-(2-methyl-7H-pyrrolo[2,3-d]pyrimidin-4-yl)-4,5,6,7-tetrahydro-1H-pyrazolo[4,3-c]pyridin-1-yl)methyl)bicyclo[2.2.2]octan-1-amine (Compound No. 4) and tert-butyl (4-((3-methyl-5-(2-methyl-7H-pyrrolo[2,3-d]pyrimidin-4-yl)-4,5,6,7-tetrahydro-1H-pyrazolo[4,3-c]pyridin-1-yl)methyl)bicyclo[2.2.2]octan-1-yl)carbamate (Compound No. 146)

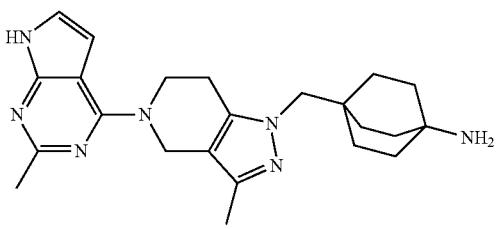
(Compound No. 4)

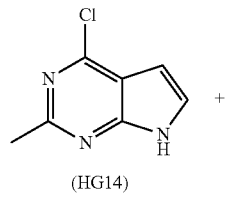
(HG14)

+

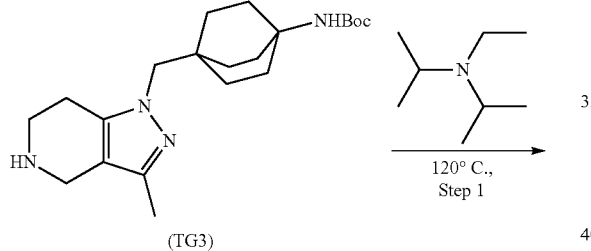
(TG3)

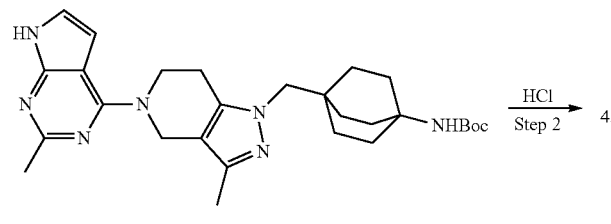
(Compound No. 146)

(Compound No. 4)

Step 1: To a reaction vial were added tert-butyl (4-((3-methyl-4,5,6,7-tetrahydro-1H-pyrazolo[4,3-c]pyridin-1-yl)methyl)bicyclo[2.2.2]octan-1-yl)carbamate (TG3) (67.0 mg, 0.179 mmol), 4-chloro-2-methyl-7H-pyrrolo[2,3-d]pyrimidine (HG14) (30 mg, 0.179 mmol), DIPEA (0.094 mL, 0.537 mmol) and BuOH (0.1 mL). The reaction was stirred at 120° C. for 3 hr and then diluted with methanol and purified by HPLC to give tert-butyl (4-((3-methyl-5-(2-methyl-7H-pyrrolo[2,3-d]pyrimidin-4-yl)-4,5,6,7-tetrahydro-1H-pyrazolo[4,3-c]pyridin-1-yl)methyl)bicyclo[2.2.2]octan-1-yl)carbamate (Compound No. 146). RT (method 2): 2.11 min. MS (ES+): 507.3 (M+1)+.

Step 2: To a solution of tert-butyl (4-((3-methyl-5-(2-methyl-7H-pyrrolo[2,3-d]pyrimidin-4-yl)-4,5,6,7-tetrahydro-1H-pyrazolo[4,3-c]pyridin-1-yl)methyl)bicyclo[2.2.2]octan-1-yl)carbamate (35 mg, 0.075 mmol) in MeOH (1 mL) was added hydrochloric acid (0.445 mL, 2.67 mmol). The reaction was stirred for 16 hr at 25° C. and then dried to give 4-((3-methyl-5-(2-methyl-7H-pyrrolo[2,3-d]pyrimidin-4-yl)-4,5,6,7-tetrahydro-1H-pyrazolo[4,3-c]pyridin-1-yl)methyl)bicyclo[2.2.2]octan-1-amine (Compound No. 4) as an HCl salt. ESIMS m/z 406.2 (M$^+$+1); $^1$H NMR (400 MHz, Methanol-$d_4$) δ 7.36 (d, J=3.5 Hz, 1H), 7.08 (d, J=3.6 Hz, 1H), 5.18 (s, 2H), 4.47 (t, J=5.3 Hz, 2H), 4.17 (s, 2H), 3.16 (t, J=5.3 Hz, 2H), 2.71 (s, 3H), 2.52 (s, 3H), 1.90-1.66 (m, 12H).

Example 5

Synthesis of 4-((5-(1,6-dimethyl-1H-pyrrolo[2,3-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 5)

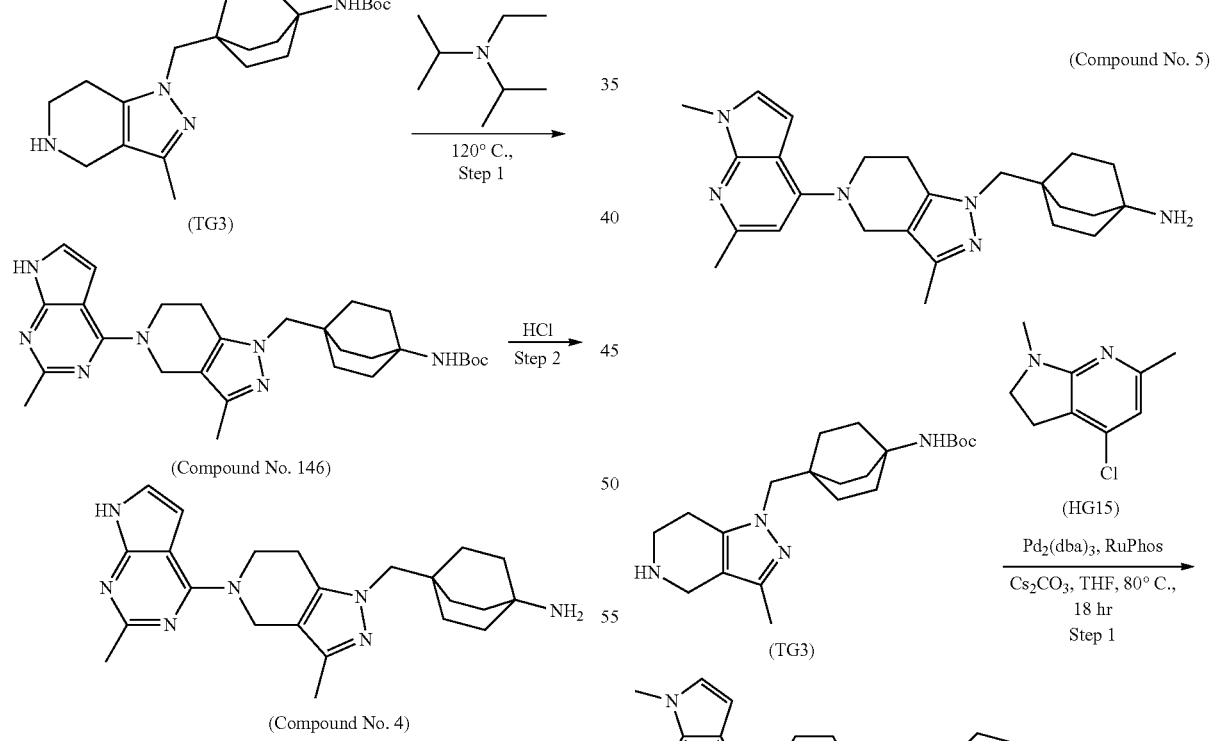
(Compound No. 5)

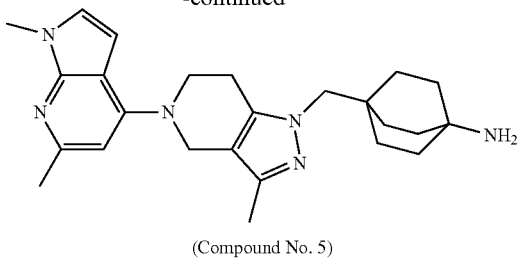

(Compound No. 5)

Step 1: To the reaction vial were added tert-butyl (4-((3-methyl-4,5,6,7-tetrahydro-1H-pyrazolo[4,3-c]pyridin-1-yl)methyl)bicyclo[2.2.2]octan-1-yl)carbamate (TG3) (62.2 mg, 0.166 mmol), 4-chloro-1,6-dimethyl-1H-pyrrolo[2,3-b]pyridine (HG15) (30 mg, 0.166 mmol), RuPhos (9.30 mg, 0.020 mmol), tris(dibenzylideneacetone)dipalladium(0) (7.60 mg, 8.30 μmol), Cs$_2$CO$_3$ (108 mg, 0.332 mmol) and THF (2 mL). The reaction was stirred @75° C. for 18 hrs. Reaction completed. The reaction was diluted with ethyl acetate and filtered through celite to remove salt. The filtrate was dried and the crude product was directly used in the next step.

Step 2: To a solution of tert-butyl (4-((5-(1,6-dimethyl-1H-pyrrolo[2,3-b]pyridin-4-yl)-3-methyl-4,5,6,7-tetrahydro-1H-pyrazolo[4,3-c]pyridin-1-yl)methyl)bicyclo[2.2.2]octan-1-yl)carbamate (30 mg, 0.046 mmol) in MeOH (1 mL) was added hydrochloric acid (0.231 mL, 1.388 mmol). The reaction was stirred for 16 hr at 25° C., then was dried and purified by HPLC to give -((5-(1,6-dimethyl-1H-pyrrolo[2,3-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 5): ESIMS m/z 419.2 (M$^+$+1);

$^1$H NMR (400 MHz, Methanol-d$_4$) δ 7.14 (d, J=3.6 Hz, 1H), 6.80 (d, J=3.6 Hz, 1H), 6.66 (s, 1H), 4.67 (s, 2H), 4.03 (t, J=5.6 Hz, 2H), 3.79 (s, 3H), 3.69 (s, 2H), 2.86 (t, J=5.6 Hz, 2H), 2.55 (s, 3H), 2.13 (s, 3H), 1.66 (dd, J=10.9, 4.6 Hz, 6H), 1.56 (dd, J=10.8, 4.7 Hz, 6H).

Example 6

Synthesis of N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)oxetan-3-amine (Compound No. 6)

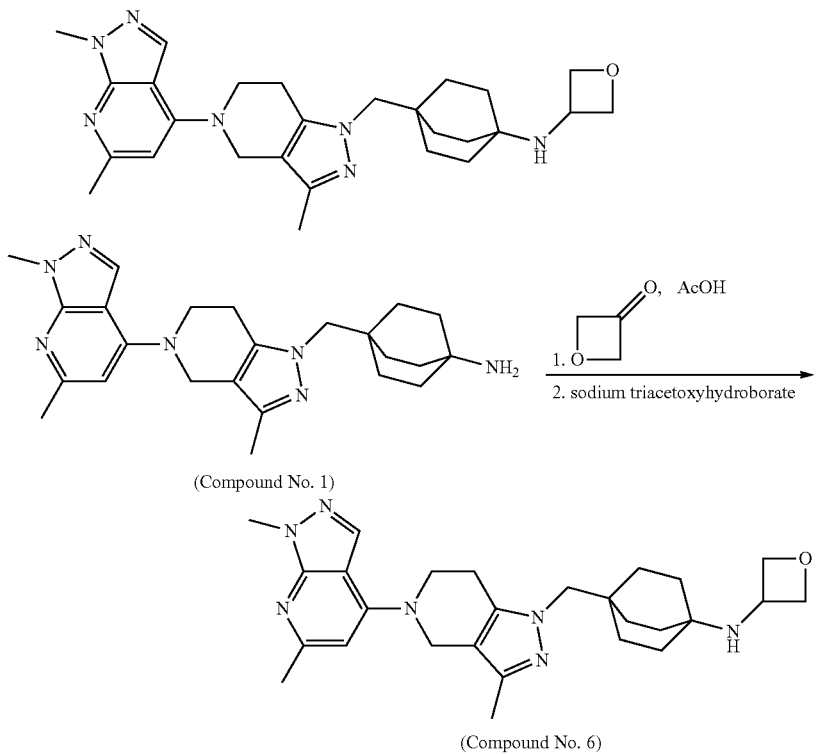

To a solution of 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 1 from Example 1, 1.68 g, 4.0 mmol) in DCE (40 mL) was added acetic acid (0.229 mL, 1.0 eq.) and oxetan-3-one (2.94 g, 10 eq.). The mixture was stirred at sodium triacetoxyhydroborate (2.62 g, 3.0 eq.) was added. The mixture was then stirred at rt overnight. More oxetan-3-one (1.47 g, 5 eq.), sodium triacetoxyhydroborate (1.3 g, 1.5 eq.) and 20 mL of DCE were added and the mixture was stirred at rt for additional 5 hrs then treated with 40 mL of 1N NaOH. The layers were separated and the aqueous layer was extracted with DCM/MeOH (5:1 v/v, 100 mL×3). The combined organic layers were dried over Na$_2$SO$_4$, filtered and concentrated to give the crude product. The crude product was added to a 40 g gold silica gel column and was eluted with 0-50% (over 25 min) IPA (containing 0.02 M ammonia) in DCM. Collected fractions and concentrated to give N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)oxetan-3-amine (Compound No. 6): 1H NMR (400 MHz, Methanol-d4) δ 8.05 (s, 1H), 6.35 (s, 1H), 4.60 (t, J=6.8 Hz, 2H), 4.43 (s, 2H), 4.34 (t, J=6.6 Hz, 2H), 4.04 (p, J=7.2 Hz, 1H), 3.90 (s, 3H), 3.87 (t, J=5.6 Hz, 2H), 3.61 (s, 2H), 2.79 (t, J=5.6 Hz, 2H), 2.44 (s, 3H), 2.12 (s, 3H), 1.47-1.33 (m, 12H). MS (ES+): 476.3 (M+1)+.

Example 7

Synthesis of N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(dimethylamino)acetamide (Compound No. 7)

pound No. 1 from Example 1, 2.52 g, 6.0 mmol) and 2-(dimethylamino)acetic acid (0.742 g, 1.2 eq.) in DCM (60 mL) was added DIPEA (2.1 mL, 2.0 eq.) then HATU (2.74 g, 1.2 eq.). The resulting mixture was stirred at rt for 1 hr then washed with 30 mL of water. The aqueous layer was extracted with DCM (100 mL×3) and the combined organic layers were dried over Na$_2$SO$_4$, filtered and concentrated to give the crude product. The crude product was added to a 80 g gold silica gel column and was eluted with 0-50% (over 30 min) IPA (containing 0.02 M of ammonia) in DCM. Collected fractions and concentrated to give N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(dimethylamino)acetamide (Compound No. 7): 1H NMR (600 MHz, Methanol-d4) δ 8.17 (s, 1H), 6.47 (s, 1H), 4.56 (s, 2H), 4.02 (s, 3H), 3.99 (dd, J=6.1, 5.1 Hz, 2H), 3.74 (s, 2H), 2.94-2.91 (m, 2H), 2.90

(Compound No. 7)

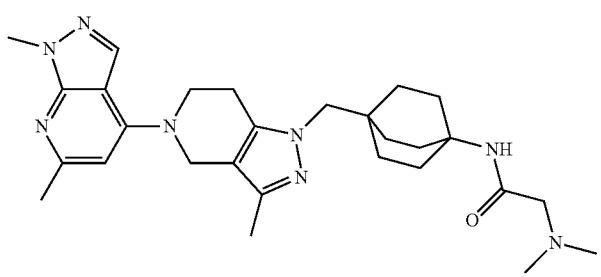

(Compound No. 1)

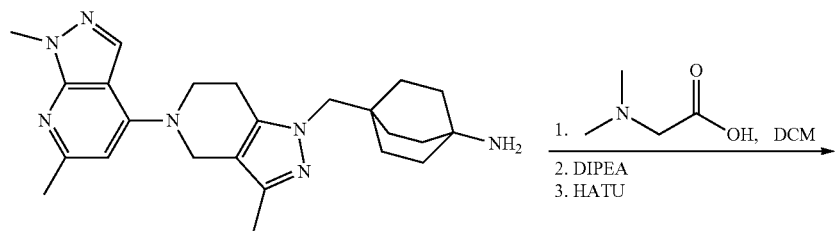

(Compound No. 7)

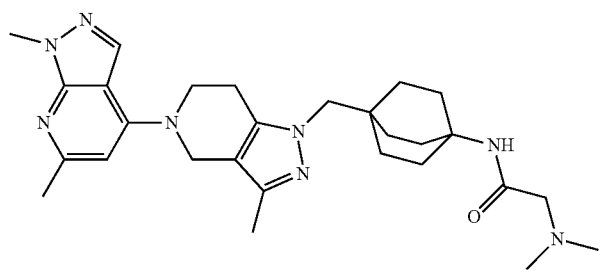

To a mixture of 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine (Com- (s, 2H), 2.56 (s, 3H), 2.36 (s, 1H), 2.30 (s, 6H), 2.25 (s, 3H), 1.94-1.87 (m, 6H), 1.63-1.57 (m, 6H). MS (ES+): 505.4 (M+1)+.

Example 8

Synthesis of (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide (Compound No. 8)

(Compound No. 8)

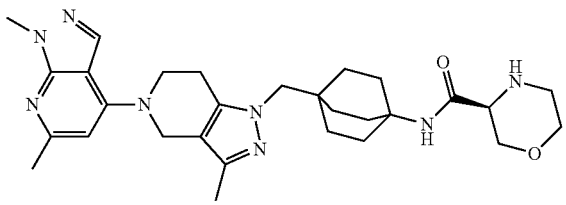

A mixture of 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 1 from Example 1) (42 mg, 0.1 mmol), (S)-4-(tert-butoxycarbonyl)morpholine-3-carboxylic acid (25.4 mg, 0.11 mmol) and DIPEA (0.035 mL, 0.2 mmol) in 1.0 mL of DMF was added HATU (45.6 mg, 0.12 mmol) then stirred at rt for 30 min. LC-MS confirmed completion of the reaction. The intermediate was purified by mass-triggered HPLC (10-90% ACN in H$_2$O over 3.5 min). The collected fractions were concentrated and the residue was dissolved in MeOH/1,4-dioxane (1.5 mL, 1:2 v/v). 4M HCl in 1,4-dioxane (1.0 mL) was added and the mixture was stirred at rt for 1 hr then concentrated and lyophilized to give (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide (Compound No. 8), as an HCl salt. 1H NMR (400 MHz, Methanol-d4) δ 8.52 (s, 1H), 7.92 (s, 1H), 6.88 (s, 1H), 5.06-4.91 (m, 2H), 4.25 (s, 2H), 4.19-4.09 (m, 4H), 4.03-3.89 (m, 4H), 3.78-3.56 (m, 4H), 3.22 (ddd, J=12.9, 11.2, 3.7 Hz, 1H), 3.17-3.05 (m, 2H), 2.70 (s, 3H), 2.41 (s, 3H), 1.93 (dd, J=8.9, 5.0 Hz, 6H), 1.72-1.54 (m, 6H). MS (ES+): 533.3 (M+1)+.

Example 9

Synthesis of (R)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide (Compound No. 9)

(Compound No. 9)

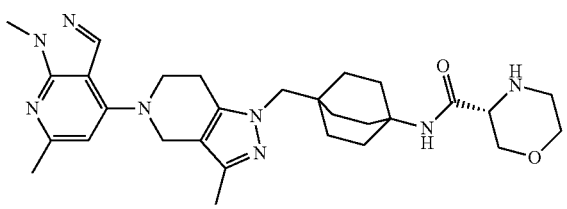

A mixture of 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 1 from Example 1) (42 mg, 0.1 mmol), (R)-4-(tert-butoxycarbonyl)morpholine-3-carboxylic acid (25.4 mg, 0.11 mmol) and DIPEA (0.035 mL, 0.2 mmol) in 1.0 mL of DMF was added HATU (45.6 mg, 0.12 mmol) then stirred at rt for 30 min. LC-MS confirmed completion of the reaction. The intermediate was purified by mass-triggered HPLC (10-90% ACN in H$_2$O over 3.5 min). Collectioned fractions were concentrated and the residue was dissolved in MeOH/1,4-dioxane (1.5 mL, 1:2 v/v). 4M HCl in 1,4-dioxane (1.0 mL) was added and the mixture was stirred at rt for 1 hr then concentrated and lyophilized to give (R)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide (Compound No. 9), as HCl salt. 1H NMR (400 MHz, Methanol-d4) δ 8.51 (s, 1H), 7.92 (s, 1H), 6.88 (s, 1H), 5.03-4.92 (m, 1H), 4.32-4.18 (m, 2H), 4.20-4.09 (m, 4H), 4.03-3.89 (m, 4H), 3.78-3.54 (m, 4H), 3.22 (ddd, J=13.0, 11.2, 3.8 Hz, 1H), 3.15-3.05 (m, 2H), 2.69 (s, 3H), 2.39 (s, 3H), 1.98-1.85 (m, 6H), 1.62 (dd, J=10.3, 5.9 Hz, 6H). MS (ES+): 533.3 (M+1)+.

Example 10

Synthesis of 6-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)-2-oxa-6-azaspiro[3.3]heptane (Compound No. 10) and 4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-amine (Compound No. 26)

(Compound No. 10)

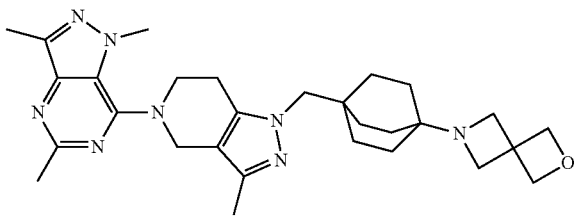

(Compound No. 26)

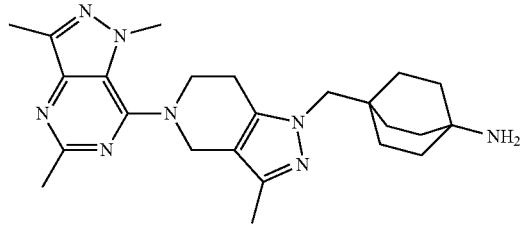

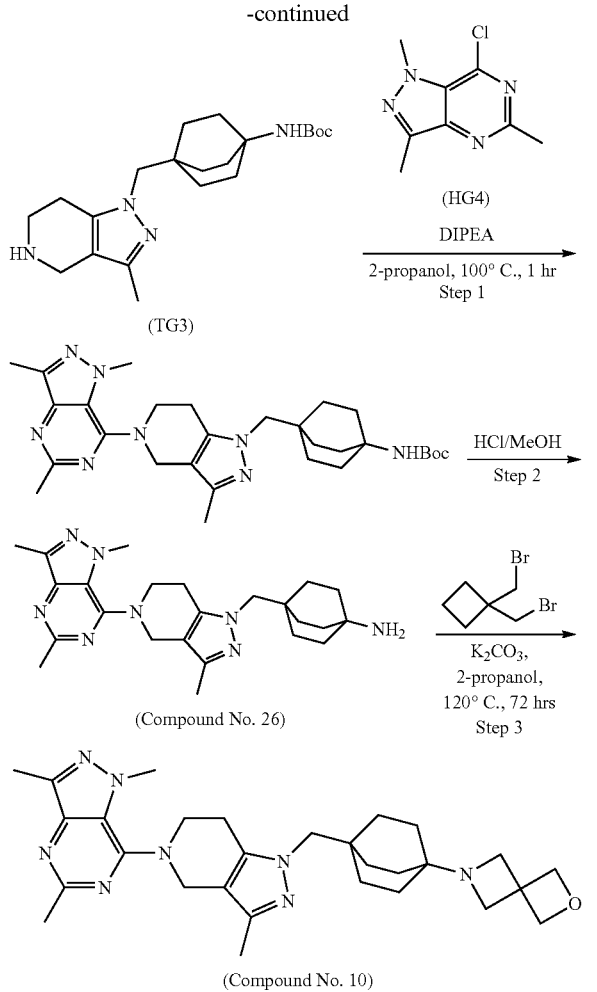

(TG3)

(HG4)

DIPEA
2-propanol, 100° C., 1 hr
Step 1

HCl/MeOH
Step 2

(Compound No. 26)

K$_2$CO$_3$,
2-propanol,
120° C., 72 hrs
Step 3

(Compound No. 10)

Step 1. A mixture of 7-chloro-1,3,5-trimethyl-1H-pyrazolo[4,3-d]pyrimidine (HG4) (263 mg, 1.335 mmol), tert-butyl (4-((3-methyl-4,5,6,7-tetrahydro-1H-pyrazolo[4,3-c]pyridin-1-yl)methyl)bicyclo[2.2.2]octan-1-yl)carbamate (TG3) (500 mg, 1.335 mmol) and DIPEA (0.233 mL, 1.335 mmol) in 2-propanol (30 mL) was heated to 100° C. for 1 hr. After working-up and column chromatography (eluent: 2:1 EtOAc:hexane), tert-butyl (4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)carbamate was obtained. LC-MS: MS (ES+): 535.4; RT: 1.171 min (method 1)

Step 2. tert-butyl (4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl) carbamate was subjected to the same conditions described in step 2 of Example 4 to yield 4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-amine (Compound No. 26). $^1$H NMR (400 MHz, Methanol-d$_4$) δ 4.96 (s, 2H), 4.31 (t, J=5.6 Hz, 2H), 4.24 (s, 3H), 3.77 (s, 2H), 3.04-2.98 (m, 2H), 2.71 (s, 3H), 2.53 (s, 3H), 2.21 (s, 3H), 1.80-1.62 (m, 12H). MS (ES+): 435.4 (M+1)+.

Step 3. A mixture of (60 mg, 0.138 mmol) of 4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl) methyl)bicyclo[2.2.2]octan-1-amine (Compound No. 26), 101 mg (0.414 mmol) of 1,1-bis(bromomethyl)cyclobutane and K$_2$CO$_3$ (95 mg, 0.690 mmol) in 2-propanol (10 mL) was heated to 120° C. for 72 hrs. After cooling to rt, the 2-propanol was evaporated, water was added and the mixture was extracted with EtOAc. The organic layers were combined, dried (Na$_2$SO$_3$) and concentrated. The residue was purified by preparative LC-MS to give 6-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)-2-oxa-6-azaspiro[3.3]heptane (Compound No. 10). $^1$H NMR (400 MHz, Methanol-d$_4$) δ 4.70 (s, 4H), 4.52 (s, 2H), 4.11 (s, 3H), 3.86 (t, J=5.7 Hz, 2H), 3.71 (s, 2H), 3.39 (s, 4H), 2.99 (t, J=5.5 Hz, 2H), 2.59 (s, 3H), 2.50 (s, 3H), 2.18 (s, 3H), 1.58-1.40 (m, 12H). MS (ES+): 517.3 (M+1)+.

Example 11

Synthesis of 4-((5-(6-(4-fluorophenyl)-1-methyl-1H-pyrazolo[3,4-d]pyrimidin-4-yl)-3-methyl-4,5,6,7-tetrahydro-1H-pyrazolo[4,3-c]pyridin-1-yl)methyl) bicyclo[2.2.2]octan-1-amine (Compound No. 83)

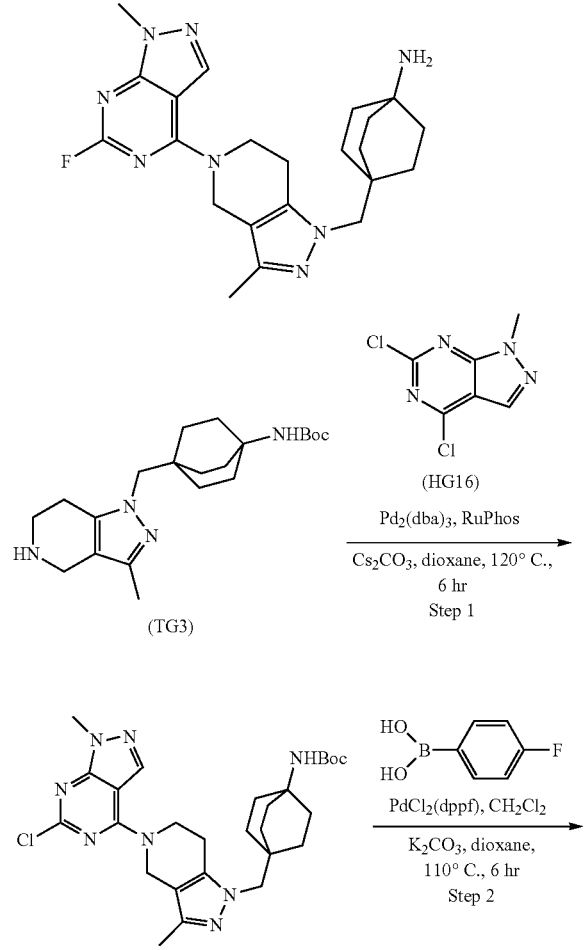

(Compound No. 83)

(TG3)

(HG16)

Pd$_2$(dba)$_3$, RuPhos
Cs$_2$CO$_3$, dioxane, 120° C.,
6 hr
Step 1

PdCl$_2$(dppf), CH$_2$Cl$_2$
K$_2$CO$_3$, dioxane,
110° C., 6 hr
Step 2

-continued

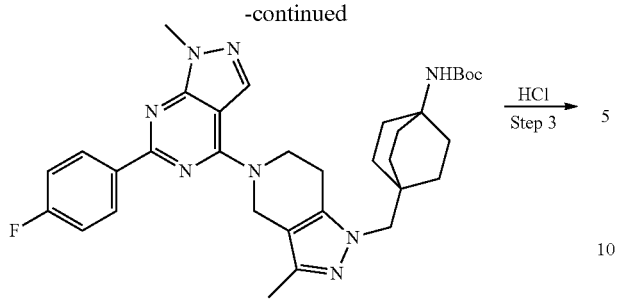

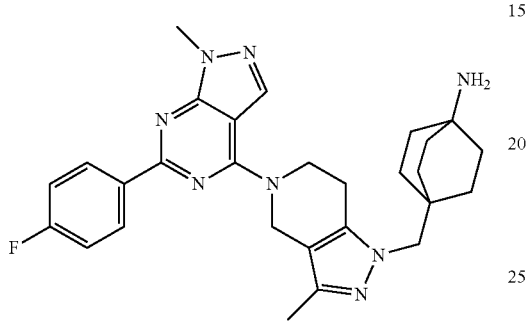

(Compound No. 83)

Step 1: 4,6-dichloro-1-methyl-1H-pyrazolo[3,4-d]pyrimidine (HG16) (40 mg, 0.197 mmol), tert-butyl (4-((3-methyl-4,5,6,7-tetrahydro-1H-pyrazolo[4,3-c]pyridin-1-yl)methyl)bicyclo[2.2.2]octan-1-yl)carbamate (TG3) (70 mg, 0.187 mmol), Pd2dba3 (10 mg, 10.92 µmol), RuPhos (10 mg, 0.021 mmol) and Cs2CO3 (65 mg, 0.199 mmol) were mixed in dioxane (5 mL) and stirred at 120° C. for 6 hrs. After working-up and prep LC-MS, tert-butyl (4-((5-(6-chloro-1-methyl-1H-pyrazolo[3,4-d]pyrimidin-4-yl)-3-methyl-4,5,6,7-tetrahydro-1H-pyrazolo[4,3-c]pyridin-1-yl)methyl)bicyclo[2.2.2]octan-1-yl)carbamate was obtained.

Step 2: tert-butyl (4-((5-(6-chloro-1-methyl-1H-pyrazolo[3,4-d]pyrimidin-4-yl)-3-methyl-4,5,6,7-tetrahydro-1H-pyrazolo[4,3-c]pyridin-1-yl)methyl)bicyclo[2.2.2]octan-1-yl)carbamate (20 mg, 0.037 mmol), (4-fluorophenyl)boronic acid (10 mg, 0.071 mmol), PdCl2(dppf).CH2Cl2 adduct (6 mg, 7.35 µmol) and K$_2$CO$_3$ (20 mg, 0.145 mmol) were mixed in dioxane (3 mL) and stirred at 110° C. for 6 hrs. After working-up and prep LC-MS, tert-butyl (4-((5-(6-(4-fluorophenyl)-1-methyl-1H-pyrazolo[3,4-d]pyrimidin-4-yl)-3-methyl-4,5,6,7-tetrahydro-1H-pyrazolo[4,3-c]pyridin-1-yl)methyl)bicyclo[2.2.2]octan-1-yl)carbamate was obtained.

Step 3: tert-butyl (4-((5-(6-(4-fluorophenyl)-1-methyl-1H-pyrazolo[3,4-d]pyrimidin-4-yl)-3-methyl-4,5,6,7-tetrahydro-1H-pyrazolo[4,3-c]pyridin-1-yl)methyl)bicyclo[2.2.2]octan-1-yl)carbamate (10 mg, 0.017 mmol) and 4N HCl (0.152 mL, 4.99 mmol) were mixed in MeOH (1 mL) and stirred at 50° C. for 5 hrs. After working-up and prep LC-MS, 4-((5-(6-(4-fluorophenyl)-1-methyl-1H-pyrazolo[3,4-d]pyrimidin-4-yl)-3-methyl-4,5,6,7-tetrahydro-1H-pyrazolo[4,3-c]pyridin-1-yl)methyl)bicyclo[2.2.2]octan-1-amine (Compound No. 83) was obtained. $^1$H NMR (400 MHz, Methanol-d$_4$) δ 8.55 (dd, J=8.7, 5.7 Hz, 2H), 8.27 (s, 1H), 7.21 (t, J=8.8 Hz, 2H), 4.97 (s, 2H), 4.38 (brs, 2H), 4.06 (s, 3H), 3.80 (s, 2H), 2.92 (t, J=5.4 Hz, 2H), 2.29 (s, 3H), 1.80-1.60 (m, 12H). MS (ES+): 501.3 (M+1)+.

Example 12

Synthesis of 4-(4-(1-((4-aminobicyclo[2.2.2]octan-1-yl)methyl)-3-methyl-6,7-dihydro-1H-pyrazolo[4,3-c]pyridin-5(4H)-yl)pyridin-2-yl)benzonitrile (Compound No. 84)

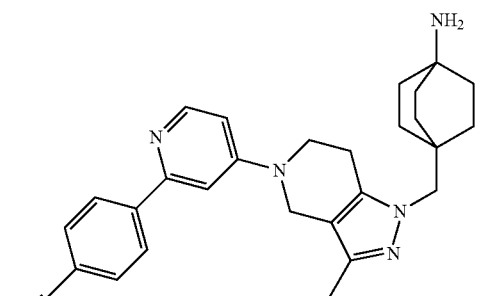

(Compound No. 84)

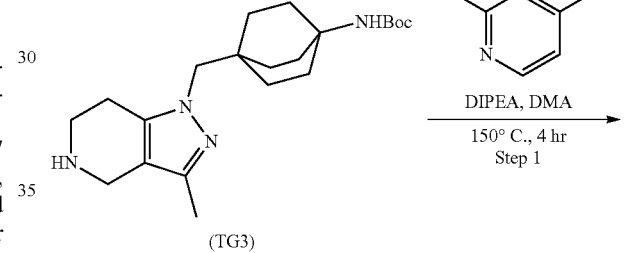

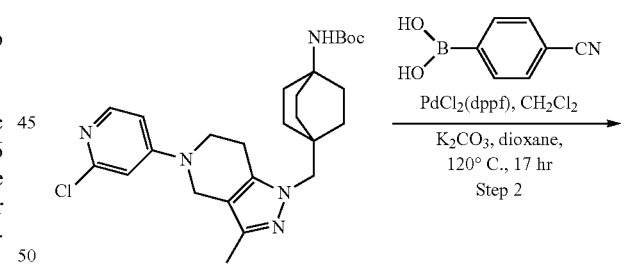

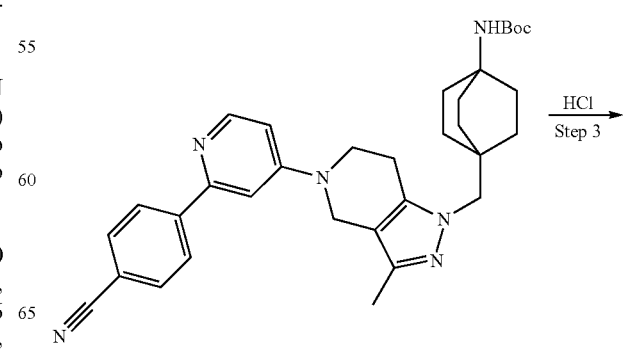

-continued

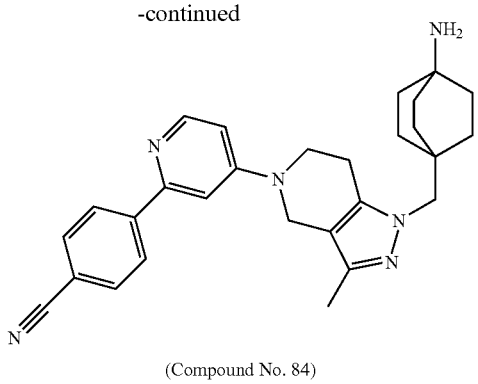

(Compound No. 84)

Step 1: 2-chloro-4-fluoropyridine (130 mg, 0.988 mmol), tert-butyl (4-((3-methyl-4,5,6,7-tetrahydro-1H-pyrazolo[4,3-c]pyridin-1-yl)methyl)bicyclo[2.2.2]octan-1-yl)carbamate (TG3) (370 mg, 0.988 mmol) and DIPEA (130 mg, 1.006 mmol) were mixed in DMA (5 mL) and stirred at 150° C. for 4 hrs. After working-up and column chromatography (2:1 EtOAc:hexane), tert-butyl (4-((5-(2-chloropyridin-4-yl)-3-methyl-4,5,6,7-tetrahydro-1H-pyrazolo[4,3-c]pyridin-1-yl)methyl)bicyclo[2.2.2]octan-1-yl)carbamate was obtained.

Step 2: tert-butyl (4-((5-(2-chloropyridin-4-yl)-3-methyl-4,5,6,7-tetrahydro-1H-pyrazolo[4,3-c]pyridin-1-yl)methyl)bicyclo[2.2.2]octan-1-yl)carbamate (25 mg, 0.051 mmol), (4-cyanophenyl)boronic acid (15 mg, 0.102 mmol), PdCl$_2$(dppf).CH$_2$Cl$_2$ adduct (5 mg, 6.12 µmol) and K$_2$CO$_3$ (25 mg, 0.181 mmol) were mixed in dioxane (3 mL) and stirred at 120° C. for 17 hrs. After working-up and prep LC-MS, tert-butyl (4-((5-(2-(4-cyanophenyl)pyridin-4-yl)-3-methyl-4,5,6,7-tetrahydro-1H-pyrazolo[4,3-c]pyridin-1-yl)methyl)bicyclo[2.2.2]octan-1-yl)carbamate was obtained.

Step 3: tert-Butyl (4-((5-(2-(4-cyanophenyl)pyridin-4-yl)-3-methyl-4,5,6,7-tetrahydro-1H-pyrazolo[4,3-c]pyridin-1-yl)methyl)bicyclo[2.2.2]octan-1-yl)carbamate (20 mg, 0.036 mmol) and 4N HCl (0.220 mL, 7.24 mmol) were mixed in MeOH (1 mL) and stirred at 50° C. for 3 hrs. After working-up and prep LC-MS, 4-(4-(1-((4-aminobicyclo[2.2.2]octan-1-yl)methyl)-3-methyl-6,7-dihydro-1H-pyrazolo[4,3-c]pyridin-5(4H)-yl)pyridin-2-yl)benzonitrile (Compound No. 84) was obtained. 1H NMR (400 MHz, Methanol-d4) δ 8.25 (d, J=7.4 Hz, 1H), 8.08-7.97 (m, 4H), 7.56 (brs, 1H), 7.36 (m, 1H), 4.71 (s, 2H), 4.09 (brs, 2H), 3.79 (s, 2H), 2.93 (t, J=5.4 Hz, 2H), 2.25 (s, 3H), 1.82-1.60 (m, 12H). MS (ES+): 453.3 (M+1)+

Example 13

Synthesis of 5-(1,6-dimethyl-1H-pyrazolo[3,4-b]pyridin-4-yl)-3-methyl-1-((4-(pyrrolidin-1-yl)bicyclo[2.2.2]octan-1-yl)methyl)-4,5,6,7-tetrahydro-1H-pyrazolo[4,3-c]pyridine (Compound No. 58)

(Compound No. 58)

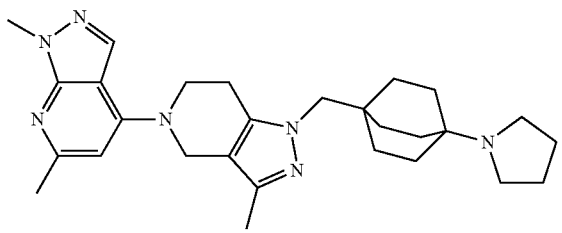

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 1 from Example 1) (23 mg, 0.055 mmol) was treated with potassium carbonate (22.73 mg, 0.164 mmol), 1,4-dibromobutane (59.2 mg, 0.274 mmol) and ethanol (548 µl). The mixture was heated to 120° C. for 30 min by microwave irradiation. The mixture was diluted with ethyl acetate and 1N NaOH. After extraction, the aqueous layer was re-extracted with ethyl acetate twice. The organic layers were combined, dried with MgSO$_4$ and concentrated in vacuo. The residue was loaded on a 4 g silica gel column using 0-50% IPA/DCM with 3% ammonia as modifier to obtain 5-(1,6-dimethyl-1H-pyrazolo[3,4-b]pyridin-4-yl)-3-methyl-1-((4-(pyrrolidin-1-yl)bicyclo[2.2.2]octan-1-yl)methyl)-4,5,6,7-tetrahydro-1H-pyrazolo[4,3-c]pyridine (Compound 58). 1H NMR (400 MHz, Methanol-d4) δ 8.06 (s, 1H), 6.36 (s, 1H), 4.45 (s, 2H), 3.99 (s, 3H), 3.89 (m, 2H), 3.64 (s, 2H), 2.81 (m, 2H), 2.64 (s, 4H), 2.45 (s, 3H), 2.13 (s, 3H), 1.68 (s, 4H), 1.63-1.35 (m, 12H). ESIMS (M+H+) 475.2.

Example 14

Synthesis of 4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine (Compound No. 59)

(Compound No. 59)

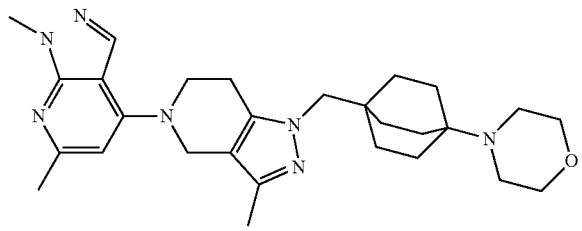

4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine was obtained using the method described in Example 13, except 1-bromo-2-(2-bromoethoxy)ethane (63.6 mg, 0.274 mmol) was used in place of 1,4-dibromobutane. 1H NMR (400 MHz, Methanol-d4) δ 8.16 (s, 1H), 6.46 (s, 1H), 4.55 (s, 2H), 3.99 (d, J=9.5 Hz, 5H), 3.73 (s, 2H), 3.68-3.51 (m, 4H), 2.91 (t, J=5.4 Hz, 2H), 2.23 (s, 3H), 1.57 (m, 12H). ESIMS (M+H+) 491.0.

Example 15

Synthesis of 1-((4-(1H-imidazol-1-yl)bicyclo[2.2.2]octan-1-yl)methyl)-5-(1,6-dimethyl-1H-pyrazolo[3,4-b]pyridin-4-yl)-3-methyl-4,5,6,7-tetrahydro-1H-pyrazolo[4,3-c]pyridine (Compound No. 119)

(Compound No. 119)

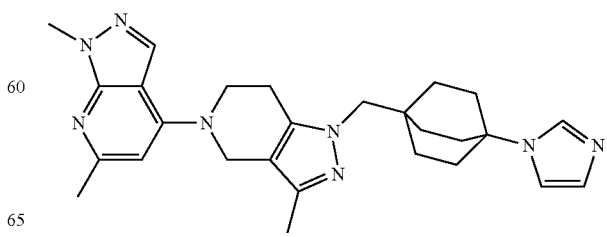

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 1 from Example 1) (55 mg, 0.131 mmol) was taken in water (807 µl) and 1 drop phosphorous acid was added (pH: ~1). Paraformaldehyde (4.72 mg, 0.157 mmol) and glyoxal (18.04 µl, 0.157 mmol) 40% in water were added and the resulting mixture was heated to 80° C. A solution of ammonium chloride (8.41 mg, 0.157 mmol) dissolved in water (202 µl) was added dropwise over 10 min and the resulting mixture was heated to 110° C. for 18 hr, LC-MS showed still ~50% unconverted starting material. An additional 47 mg of paraformaldehyde, glyoxal (18 mL) and NH$_4$Cl (84 mg) were added to the mixture (to get it to go to completion). The mixture was heated at 110° C. for 18 hrs. The reaction mixture was adjusted to pH 8-9 using aqueous Na$_2$CO$_3$, extracted twice with DCM. The organic layers were concentrated and loaded on a 4 g silica gel column using 0-50% IPA in DCM with 3% NH$_3$ as modifier to afford 1-((4-(1H-imidazol-1-yl)bicyclo[2.2.2]octan-1-yl)methyl)-5-(1,6-dimethyl-1H-pyrazolo[3,4-b]pyridin-4-yl)-3-methyl-4,5,6,7-tetrahydro-1H-pyrazolo[4,3-c]pyridine (Compound 119). 1H NMR (400 MHz, Methanol-d4) δ 8.16 (s, 1H), 6.46 (s, 1H), 4.55 (s, 2H), 4.01 (s, 3H), 3.91 (m, 2H), 3.73 (s, 2H), 3.68-3.51 (m, 4H), 2.91 (m, 2H), 2.55 (m, 4H), 2.52 (s, 3H), 2.23 (s, 3H), 1.57 (m, 12H). ESIMS (M+H$^+$) found 471.6.

Example 16

Synthesis of 4-((3-methyl-5-(6-methyl-1-(methyl-d3)-1H-pyrazolo[3,4-b]pyridin-4-yl)-4,5,6,7-tetrahydro-1H-pyrazolo[4,3-c]pyridin-1-yl)methyl)bicyclo[2.2.2]octan-1-amine (Compound No. 140)

(Compound No. 140)

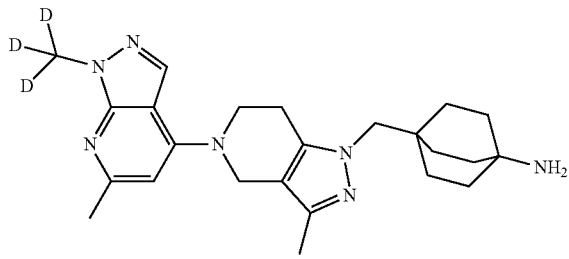

To a mixture of tert-butyl (4-((3-methyl-5-(6-methyl-1H-pyrazolo[3,4-b]pyridin-4-yl)-4,5,6,7-tetrahydro-1H-pyrazolo[4,3-c]pyridin-1-yl)methyl)bicyclo[2.2.2]octan-1-yl) carbamate and K$_2$CO$_3$ in a 20 mL round-bottomed flask containing 3 mL of DMF was added dropwise CD3I (0.1 mL of a solution of 27.7 µL CD$_3$I in 1 mL of DMF) at 0° C. The resulting mixture was slowly warmed up to rt and stirred overnight. The mixture was then concentrated then purified by ISCO (4 g silica gel column, 0-10% MeOH in DCM as eluent) to afford tert-butyl (4-((3-methyl-5-(6-methyl-1-(methyl-d3)-1H-pyrazolo[3,4-b]pyridin-4-yl)-4,5,6,7-tetrahydro-1H-pyrazolo[4,3-c]pyridin-1-yl)methyl)bicyclo[2.2.2]octan-1-yl)carbamate. RT=1.13 min (method 1), MS (ES+): 524.3 (M+1)+. To a solution of 11.5 mg (0.022 mmol) of tert-butyl (4-((3-methyl-5-(6-methyl-1-(methyl-d3)-1H-pyrazolo[3,4-b]pyridin-4-yl)-4,5,6,7-tetrahydro-1H-pyrazolo[4,3-c]pyridin-1-yl)methyl)bicyclo[2.2.2]octan-1-yl)carbamate in 1 mL of dioxane and 0.1 mL of MeOH was added 1 mL of 4M HCl in dioxane. The resulting mixture was stirred at rt for 1 hr then concentrated and lyophilized to give the desired product (Compound No. 140) as an HCl salt. 1H NMR (400 MHz, Methanol-d4) δ 8.51 (s, 1H), 6.88 (s, 1H), 5.04-4.94 (m, 2H), 4.25 (s, 2H), 3.98 (s, 2H), 3.78-3.56 (m, 2H), 3.11 (d, J=5.1 Hz, 2H), 2.70 (s, 3H), 2.39 (s, 3H), 1.85-1.66 (m, 12H). MS (ES+): 423.3 (M+1)+.

Example 17

Synthesis of 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N,N-dimethylbicyclo[2.2.2]octan-1-amine (Compound No. 43)

(Compound No. 43)

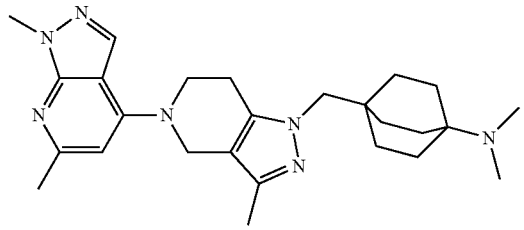

To a solution of 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 1 from Example 1) in THF/MeOH (5 mL/1.5 mL) in a 100 mL round-bottomed flask was added DIPEA (0.13 mL, 97 mg, 0.75 mmol). The mixture was stirred at rt for 10 min before formaldehyde (0.037 mL, 37 wt % in water) was added. The resulting mixture was stirred at rt for min before NaBH$_3$CN (157 mg, 2.5 mmol) was added. Then the mixture was then stirred at rt overnight, quenched by adding 2.0 mL of water then extracted with DCM. The combined organic layers were then dried over Na$_2$SO$_4$ then concentrated. The crude product was added to a 4 g silica gel column and was eluted with 0-8% MeOH (containing very small amount of ammonia) in DCM. Collected fractions and concentrated then lyophilized to give the desired product, 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N,N-dimethylbicyclo[2.2.2]octan-1-amine. 1H NMR (600 MHz, Methanol-d4) δ 8.07 (s, 1H), 6.39 (s, 1H), 4.47 (s, 3H), 3.86 (s, 5H), 3.63 (d, J=2.5 Hz, 2H), 2.78 (t, J=5.6 Hz, 2H), 2.58 (s, 6H), 2.41 (s, 3H), 2.07 (s, 3H), 1.71-1.65 (m, 6H), 1.55-1.49 (m, 6H). MS (ES+): 448.4 (M+1)+.

Example 18

Synthesis of N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)methanesulfonamide (Compound No. 48)

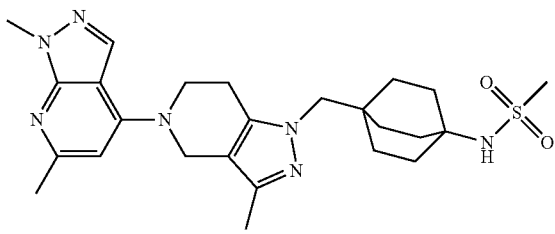

(Compound No. 48)

To a mixture of 57 mg (0.1 mmol) of 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 1) and 39 mg (0.052 mL, 0.3 mmol) of DIPEA in 2 mL of DCM was added 14.9 mg (10.1 µL, 0.13 mmol) of methanesulfonyl chloride at 0° C. The resulting mixture was slowly warmed up to rt and stirred for 2 hrs. The crude product was added (by solid loading) to a 4 g silica gel column and was eluted with 0-7% MeOH (containing very small amount of ammonia) in DCM, and further purified by mass-triggered HPLC. Collected fractions, 1.0 mL of 1N aqueous HCl was added then concentrated and lyophilized to give N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)methanesulfonamide (Compound No. 48), as HCl salt. 1H NMR (400 MHz, Methanol-d4) δ 8.53 (s, 1H), 6.89 (s, 1H), 5.06-4.94 (m, 2H), 4.25 (s, 2H), 4.12 (s, 3H), 3.98 (s, 2H), 3.18-3.06 (m, 2H), 2.94 (s, 3H), 2.70 (s, 3H), 2.43 (s, 3H), 1.96-1.85 (m, 6H), 1.67-1.57 (m, 6H). MS (ES+): 498.2 (M+1)+.

Example 19

Synthesis of 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-methylbicyclo[2.2.2]octan-1-amine (Compound No. 50) and tert-butyl (4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)(methyl)carbamate (Compound 49)

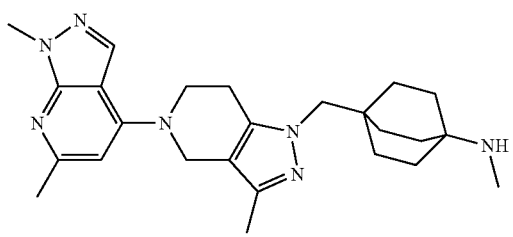

(Compound No. 50)

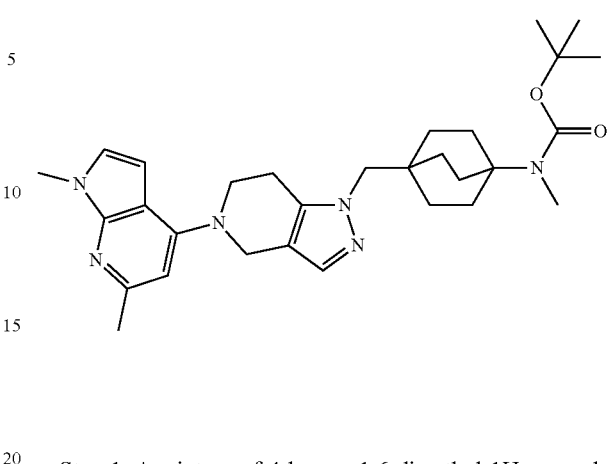

(Compound No. 49)

Step 1. A mixture of 4-bromo-1,6-dimethyl-1H-pyrazolo[3,4-b]pyridine (HG1) (67 mg, 0.295 mmol), tert-butyl methyl(4-((3-methyl-4,5,6,7-tetrahydro-1H-pyrazolo[4,3-c]pyridin-1-yl)methyl)bicyclo[2.2.2]octan-1-yl)carbamate (TG10) (115 mg, 0.295 mmol), Pd$_2$dba$_3$ (6.8 mg, 0.074 mmol), RuPhos (17 mg, 0.035 mmol) and Cs$_2$CO$_3$ (192 mg, 0.590 mmol) in THF was purged with argon before being heated to 75° C. for 15 hrs. The reaction mixture was cooled down to rt then diluted in ethyl acetate and water. The layers were separated and the aqueous layer was extracted with ethyl acetate. The combined organic layers were dried over Na$_2$SO$_4$, filtered and concentrated in vacuo. The crude product was added to a 12 g silica gel column and was eluted with 0-5% methanol in DCM. Collected fractions and concentrated to give tert-butyl (4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)(methyl)carbamate (Compound No. 49). 1H NMR (400 MHz, Methanol-d4) δ 8.16 (s, 1H), 6.46 (s, 1H), 4.54 (s, 2H), 4.00 (s, 5H), 3.72 (s, 2H), 2.90 (t, J=5.6 Hz, 2H), 2.80 (s, 3H), 2.55 (s, 3H), 2.23 (s, 3H), 2.04-1.91 (m, 6H), 1.60-1.52 (m, 6H), 1.43 (s, 9H). MS (ES+): 534.4 (M+1)+.

Step 2. To a solution of 90 mg (0.169 mmol) of tert-butyl (4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)(methyl)carbamate (Compound No. 49) in dioxane/MeOH (1 mL/1 mL) was added HCl (2 mL of a 4M solution in dioxane). The resulting mixture was stirred at rt for 2 hrs. LC-MS showed completion of the reaction. The reaction mixture was concentrated and the residue was dissolved in 2.0 mL of MeOH then Ambersep 900 OH (0.8 meq/mL, 5.0 eq., prewashed with 5.0 mL of MeOH) was added and the mixture was stirred at rt for 1 hour. Filtered and washed with 10 mL of MeOH then concentrated. The crude product was added to a 4 g silica gel column and was eluted with 2-9% MeOH (containing a small amount of ammonia) in DCM. Collected fractions and concentrated then lyophilized to give 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-methylbicyclo[2.2.2]octan-1-amine (Compound No. 50). 1H NMR (400 MHz, Methanol-d4) δ 8.05 (s, 1H), 6.36 (s, 1H), 4.44 (s, 2H), 3.90 (s, 3H), 3.88 (t, J=5.8 Hz, 2H), 3.64 (s, 2H), 2.80 (t, J=5.6 Hz, 2H), 2.44 (s, 3H), 2.17 (s, 3H), 2.13 (s, 3H), 1.49 (s, 12H). MS (ES+): 434.3 (M+1)+.

Example 20

Synthesis of 1-methylcyclopropyl (4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)carbamate (Compound No. 51)

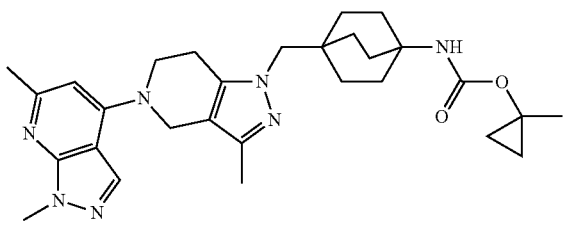

(Compound No. 51)

To a suspension of 57 mg (0.1 mmol) of 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 1) in 1 mL of DMA was added DIPEA (52 mg, 0.4 mmol) then 1-methylcyclopropyl (4-nitrophenyl) carbonate (24 mg, 0.1 mmol). The resulting mixture was heated under microwave irradiation at 150° C. for 2 hrs. The reaction mixture was diluted with water and extracted with EtOAc. The combined organic layers were washed with brine, dried over $Na_2SO_4$ and concentrated. The crude product was added to a 4 g silica gel column and was eluted with 0-8% MeOH in DCM. Collected fractions and concentrated then lyophilized to give 1-methylcyclopropyl (4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)carbamate (Compound No. 51). 1H NMR (400 MHz, Methanol-d4) δ 8.05 (s, 1H), 6.35 (s, 1H), 4.44 (s, 2H), 3.90 (s, 3H), 3.87 (t, J=5.6 Hz, 2H), 3.61 (s, 2H), 2.80 (t, J=5.6 Hz, 2H), 2.44 (s, 3H), 2.13 (s, 3H), 1.74-1.63 (m, 6H), 1.50-1.40 (m, 6H), 1.35 (s, 3H), 0.71-0.61 (m, 2H), 0.48-0.41 (m, 2H). MS (ES+): 518.3 (M+1)+.

Example 21

Synthesis of N-(2,2-difluoroethyl)-4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 61)

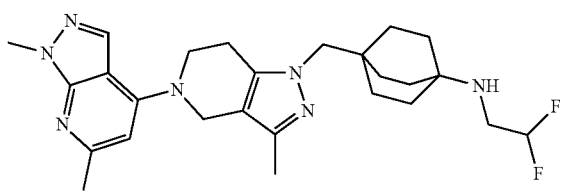

(Compound No. 61)

To a mixture of 29.4 mg (0.07 mmol) of 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 1) and 18.1 mg (0.024 mL, 0.14 mmol) of DIPEA in 1 mL of THF was added 2,2-difluoroethyl trifluoromethanesulfonate (16.5 mg (10.3 μL, 0.077 mmol). The resulting mixture was stirred at 85° C. for 2 hrs. LC-MS showed desired product and completion of the reaction. The crude product was directly added to a 4 g silica gel column and was eluted with 2-9% MeOH (containing a small amount of ammonia) in DCM. Collected fractions and concentrated then lyophilized to give N-(2,2-difluoroethyl)-4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 61). 1H NMR (400 MHz, Methanol-d4) δ 8.05 (s, 1H), 6.36 (s, 1H), 5.79 (tt, J=55.9, 4.1 Hz, 1H), 4.44 (s, 2H), 3.89 (m, 5H), 3.64 (s, 2H), 2.94-2.75 (m, 4H), 2.44 (s, 3H), 2.13 (s, 3H), 1.49 (s, 12H). MS (ES+): 484.2 (M+1)+.

Example 22

Synthesis of 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(2-methoxyethyl)bicyclo[2.2.2]octan-1-amine (Compound No. 69) and 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N,N-bis(2-methoxyethyl)bicyclo[2.2.2]octan-1-amine (Compound No. 70)

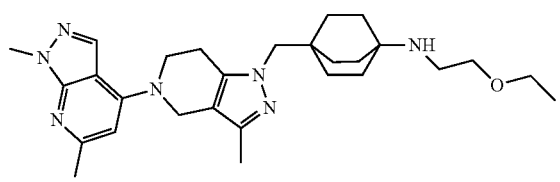

Compound No. 69

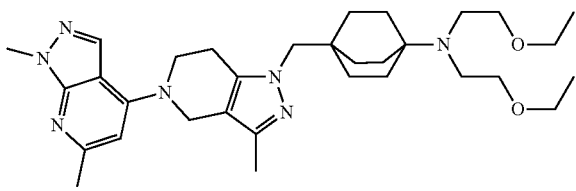

Compound No. 70

A mixture of 21 mg (0.05 mmol) of 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 1), 43 mg (0.031 mL, 0.250 mmol) of 1-bromo-2-ethoxyethane and 21 mg (0.150 mmol) of potassium carbonate in EtOH (1 mL) was heated under microwave irradiation at 120° C. for 30 min. LC-MS showed desired product 1 but the reaction was not complete. The solvent was changed to IPA and heated in an oil bath at 110° C. overnight. LC-MS showed two products. The crude product was added to a 12 g silica gel column and was eluted with 0-30% IPA (containing 1% of ammonia) in DCM. Collected fractions and concentrated then lyophilized to give 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(2-ethoxyethyl)bicyclo[2.2.2]octan-1-amine (Compound No. 69) and 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N,N-bis(2-ethoxyethyl)bicyclo[2.2.2]octan-1-amine (Compound No. 70). Compound No. 69: 1H NMR (400 MHz, Methanol-d4) δ 8.16 (s, 1H), 8.05 (d, J=8.2 Hz, 0H), 8.04 (s, 0H), 7.54 (d, J=8.1 Hz, 0H), 6.46 (s, 1H), 4.54 (s, 2H), 4.00 (s, 3H), 3.98 (t, J=5.7 Hz, 2H), 3.73 (s, 2H), 3.35 (s, 2H), 2.98 (s, 3H), 2.94 (s, 3H), 2.90 (t, J=5.6 Hz, 2H), 2.55 (s, 3H), 2.23 (s, 3H), 1.56 (s, 12H). MS (ES+): 505.4 (M+1)+.

Compound No. 70: 1H NMR (400 MHz, Methanol-d4) δ 8.15 (s, 1H), 6.45 (s, 1H), 4.54 (s, 2H), 4.00 (s, 3H), 3.97 (t, J=5.5 Hz, 2H), 3.69 (s, 2H), 3.31 (d, J=1.1 Hz, 6H), 2.90 (t, J=5.6 Hz, 2H), 2.75-2.65 (m, 4H), 2.55 (s, 3H), 2.23 (s, 3H), 1.64-1.47 (m, 12H). MS (ES+): 536.4 (M+1)+.

Example 23

Synthesis of 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(2-methoxyethyl)-N-methylbicyclo[2.2.2]octan-1-amine. (Compound No. 73)

Compound No. 73

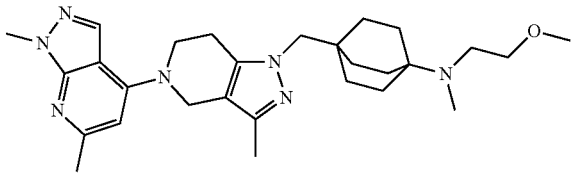

A mixture of 12 mg (0.028 mmol) of 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-methylbicyclo[2.2.2]octan-1-amine (Compound No. 50), 19 mg (0.013 mL, 0.138 mmol) of 1-bromo-2-methoxyethane and 11.5 mg (0.083 mmol) of K$_2$CO$_3$ in IPA was heated under microwave irradiation at 150° C. for 1 hr. The crude product was directly added to a 4 g silica gel column and was eluted with 0-30% IPA (containing 1% of ammonia) in DCM. Collected fractions and concentrated then lyophilized to give 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(2-methoxyethyl)-N-methylbicyclo[2.2.2]octan-1-amine (Compound No. 73). 1H NMR (400 MHz, Methanol-d4) δ 8.16 (s, 1H), 6.46 (s, 1H), 4.54 (s, 2H), 4.00 (s, 3H), 3.98 (t, J=5.7 Hz, 2H), 3.72 (s, 2H), 3.43 (t, J=5.8 Hz, 2H), 2.90 (t, J=5.6 Hz, 2H), 2.63 (s, 2H), 2.55 (s, 3H), 2.23 (s, 6H), 1.67-1.49 (m, 12H). MS (ES+): 492.4 (M+1)+.

Example 24

Synthesis of 2-((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)-N,N-dimethylacetamide (Compound No. 76)

Compound No. 76

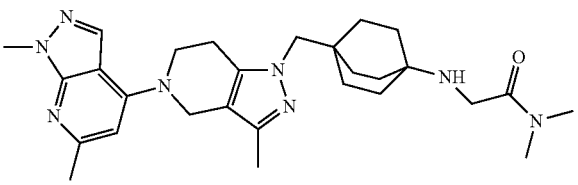

A mixture of 42.0 mg (0.1 mmol) of 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 1), 18.3 mg (0.11 mmol) of 2-bromo-N,N-dimethylacetamide and 65.2 mg (0.2 mmol) of cesium carbonate in 1 mL DMF was stirred at rt overnight. The crude product was added to a 4 g silica gel column and was eluted with 0-30% IPA (containing 1% of ammonia) in DCM. Collected fractions and concentrated then lyophilized to afford 2-((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)-N,N-dimethylacetamide (Compound No. 76). 1H NMR (400 MHz, Methanol-d4) δ 8.17 (d, J=1.8 Hz, 1H), 6.47 (s, 1H), 4.56 (s, 2H), 4.02 (s, 3H), 4.00 (t, J=5.7 Hz, 2H), 3.76 (m, 2H), 3.56 (m, 2H), 3.03-2.95 (m, 6H), 2.92 (t, J=5.6 Hz, 2H), 2.56 (s, 3H), 2.25 (s, 3H), 1.73-1.56 (m, 12H). MS (ES+): 505.4 (M+1)+.

Example 25

Synthesis of N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-N-methyloxetan-3-amine (Compound No. 77)

Compound No. 77

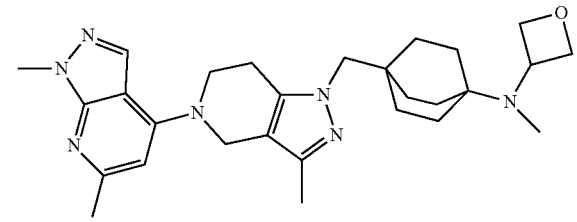

To a solution of 2.1 mg (4.4 μmol of N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)oxetan-3-amine (Compound No. 6) in THF (1 mL) was added acetic acid (1.33 mL (1.26 μL, 0.022 mmol) of and 10.9 mg (0.134 mmol) of formaldehyde. The mixture was stirred at rt for 1 hour before sodium cyanotrihydroborate was added. The resulting mixture was then stirred at rt overnight. The reaction was quenched by adding 0.1 mL of water then concentrated. The crude product was added to a 4 g silica gel column and was eluted with 0-50% IPA (containing 1% of ammonia) in DCM. Collected fractions and concentrated then lyophilized to afford N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-N-methyloxetan-3-amine (Compound No. 77). 1H NMR (400 MHz, Methanol-d4) δ 8.05 (s, 1H), 6.35 (s, 1H), 4.58 (t, J=6.9 Hz, 2H), 4.47 (t, J=7.0 Hz, 2H), 4.44 (s, 2H), 4.25 (q, J=7.3 Hz, 1H), 3.90 (s, 3H), 3.87 (t, J=5.5 Hz, 2H), 3.61 (s, 2H), 2.79 (t, J=5.6 Hz, 2H), 2.44 (s, 3H), 2.18 (s, 3H), 2.12 (s, 3H), 1.45 (s, 12H). MS (ES+): 490.4 (M+1)+.

Example 26

Synthesis of 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(2-methoxy-2-methylpropyl)bicyclo[2.2.2]octan-1-amine (Compound No. 101)

Compound No. 101

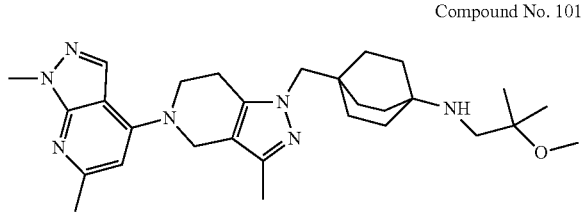

Step 1. To a solution of 14.2 mg (0.12 mmol) of 2-methoxy-2-methylpropanoic acid in DMF (2 mL) was added HATU (45.6 mg, 0.12 mmol) and DIPEA (0.035 mL, 25.8 mg, 0.2 mmol). The mixture was stirred at rt for 5 min before of 42.0 mg (0.1 mmol) 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 1) was added. The resulting mixture was then stirred at rt for 1 hour. LC-MS showed completion of the reaction. The mixture was partitioned between EtOAc and water. The layers were separated and the aqueous layer was extracted with EtOAc. The combined organic layer was dried over $Na_2SO_4$ then concentrated. The crude product was added to a 4 g silica gel column and was eluted with 0-50% IPA (containing 1% of ammonia) in DCM. Collected fractions and concentrated then lyophilized to afford N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-methoxy-2-methylpropanamide. 1H NMR (400 MHz, Methanol-d4) δ 8.19 (s, 1H), 6.77 (s, 1H), 6.51 (s, 1H), 4.58 (s, 2H), 3.96 (t, J=5.4 Hz, 2H), 3.94 (s, 3H), 3.64 (s, 2H), 3.12 (s, 3H), 2.84 (t, J=5.6 Hz, 2H), 2.49 (s, 3H), 2.14 (s, 3H), 1.83-1.73 (m, 6H), 1.53-1.43 (m, 6H), 1.17 (s, 6H). MS (ES+): 520.3 (M+1)+.

Step 2. To a stirred solution of 17 mg (0.033 mmol) of N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-methoxy-2-methylpropanamide in THF (1 mL) was added 6.5 mg (0.164 mmol) of $LiAlH_4$ at 0° C. The resulting mixture was then slowly warmed up to rt and stirred overnight. After cooling at 0° C. the reaction was quenched with IPA then water and concentrated. The crude product was added (by solid loading) to a 4 g silica gel column and was eluted with 0-30% IPA (containing 1% of ammonia) in DCM. Collected fractions and concentrated then further purified by mass-triggered HPLC to afford 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(2-methoxy-2-methylpropyl)bicyclo[2.2.2]octan-1-amine (Compound No. 101), which was neutralized using Ambersep 900 OH (Strong Base Anion Exchanger). 1H NMR (600 MHz, Methanol-d4) δ 8.05 (d, J=1.1 Hz, 1H), 6.35 (s, 1H), 4.44 (s, 2H), 3.90 (s, 3H), 3.90-3.85 (m, 2H), 3.64 (d, J=6.3 Hz, 2H), 3.07 (s, 2H), 2.83-2.77 (m, 2H), 2.44 (s, 3H), 2.13 (s, 3H), 1.57-1.46 (m, 12H), 1.07 (s, 6H). MS (ES+): 506.4 (M+1)+.

Example 27

Synthesis of 4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-1-methylpiperazin-2-one (Compound No. 104)

Compound No. 104

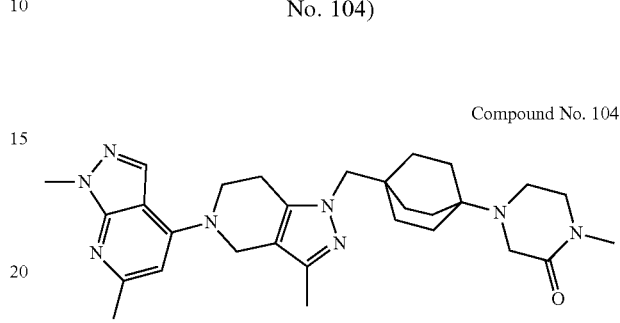

Step 1: To a solution of 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 1) (121 mg, 0.246 mmol) in CPME (12.3 mL) was added tert-butyl methyl(2-oxoethyl)carbamate (63.8 mg, 0.369 mmol). The mixture was stirred at 25° C. for 30 min before sodium triacetoxyborohydride (156 mg, 0.737 mmol) was added. Then the mixture was stirred at 25° C. for 3 hrs. The mixture was concentrated and purified on a 4 g silica gel column using 0-40% IPA in DCM with 2% $NH_3$ as modifier to elute 88.6 mg (0.154 mmol) of tert-butyl (2-((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)ethyl)(methyl)carbamate. RT (method 1): 1.26 min, MS (ES+): 577.4 (M+1)+.

Step 2: A mixture of 40 mg (0.069 mmol) of tert-butyl (2-((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)ethyl)(methyl)carbamate, 35.5 mg (0.024 mL, 0.208 mmol) of ethyl 2-bromoacetate and 10.5 mg (0.076 mmol) of potassium carbonate in EtOH (1 mL) was heated under microwave irradiation at 150° C. for 1 hour. LC-MS showed completion of the reaction. The reaction was cooled down to rt, 1N aqueous NaOH was added and the mixture was stirred at rt for 3 hrs. The reaction mixture was then diluted with 2 mL of water and the organic solvent was removed on the rotorvap, and washed with $Et_2O$ (3 mL). The aqueous layer was then acidified carefully with 1N aqueous HCl to ~pH 3. Extracted with EtOAc then DCM/MeOH but most product remained in the aqueous phase based on LC-MS. Both aqueous and organic phase were concentrated then purified by mass-triggered HPLC to afford 2-((2-((tert-butoxycarbonyl)(methyl)amino)ethyl)(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)acetic acid. RT (method 2): 1.72 min, MS (ES+): 634.8 (M+1)+.

Step 3. To a mixture of 27.0 mg (0.043 mmol) of 2-((2-((tert-butoxycarbonyl)(methyl)amino)ethyl)(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)acetic acid in 1 mL of 1,4- dioxane was added 0.3 mL of MeOH to get a clear solution. 4 M HCl in dioxane was added dropwise and the resulting mixture was stirred at rt for 1 hr. LC-MS showed completion of the reaction. The mixture was concentrated and the residue was dissolved in 2.0 mL of DMF and DIPEA (38 μL, 5 eq.) then added dropwise into a solution of HATU (21 mg, 1.3 eq.) in 3.0 mL of DMF at 0° C. The resulting mixture was stirred at 0° C. for 30 min. LC-MS showed completion of the reaction. The crude product was purified by mass-triggered HPLC (10-20% ACN in H2O over 3.5 min) then neutralized using basic resin to afford 4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-1-methylpiperazin-2-one (Compound No. 104). 1H NMR (400 MHz, Methanol-d4) δ 8.05 (s, 1H), 6.35 (s, 1H), 4.44 (s, 2H), 3.90 (s, 3H), 3.87 (t, J=5.5 Hz, 2H), 3.62 (s, 2H), 3.17 (dd, J=6.3, 4.5 Hz, 2H), 3.08 (s, 2H), 2.80 (m, 5H), 2.66 (dd, J=6.3, 4.5 Hz, 2H), 2.44 (s, 3H), 2.13 (s, 3H), 1.48 (tq, J=9.4, 6.4, 4.7 Hz, 12H). MS (ES+): 517.3 (M+1)+.

Example 28

Synthesis of 1-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-4-methylpiperazin-2-one (Compound No. 108)

Compond No. 108

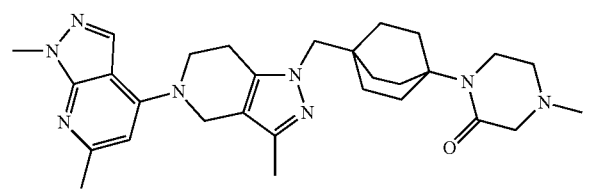

Step 1: To a mixture of 80 mg (0.139 mmol) of tert-butyl (2-((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)ethyl)(methyl) carbamate (Example 27, Step 1) and 36 mg (0.048 μL, 0.277 mmol) of DIPEA in 1.0 mL of DCM was added dropwise into a solution of 2-bromoacetyl bromide (0.062 mL, 0.694 mmol) in DCM (1.0 mL) at 0° C. The resulting mixture was slowly warmed up to rt and stirred for 1 hr. Then quenched the reaction by adding 0.1 mL of water and concentrated. The crude product was added to a 4 g silica gel column and was eluted with 0-30% IPA (containing 0.02 M ammnia) in DCM. Collected fractions and concentrated to afford tert-butyl (2-(2-bromo-N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl) acetamido)ethyl)(methyl)carbamate. RT (method 1): 1.45 min. MS (ES+): 701.2, 700.3 (M+1)+.

Step 2: To a mixture of 40.0 mg (0.057 mmol) of tert-butyl (2-(2-bromo-N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)acetamido)ethyl)(methyl)carbamate in 1 mL of 1,4-dioxane was added 0.5 mL of MeOH to get a clear solution. 4 M HCl in dioxane (0.5 mL, 2.0 mmol) was added dropwise and the resulting mixture was stirred at rt for 30 min. LC-MS showed completion of the reaction. The mixture was concentrated and to the residue were added 5.0 mL of DMF and cesium carbonate. The resulting mixture was stirred at rt for 1 hr and concentrated. The crude product was purified by mass-triggered HPLC (10-20% ACN in H2O over 3.5 min) then 1N aqueous HCl was added and lyophilized to afford 1-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-4-methylpiperazin-2-one, as HCl salt (Compound No. 108). 1H NMR (400 MHz, Methanol-d4) δ 8.05 (s, 1H), 6.35 (s, 1H), 4.44 (s, 2H), 3.90 (s, 3H), 3.87 (t, J=5.5 Hz, 2H), 3.62 (s, 2H), 2.80 (t, J=5.5 Hz, 2H), 2.45 (m, 5H), 2.17 (dd, J=7.9, 6.9 Hz, 2H), 2.14 (s, 6H), 2.13 (s, 3H), 1.80-1.73 (m, 6H), 1.50-1.43 (m, 6H). MS (ES+): 519.3 (M+1)+.

Example 29

Synthesis of N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(3-fluoroazetidin-1-yl)acetamide (Compound No. 133)

Compound No. 133

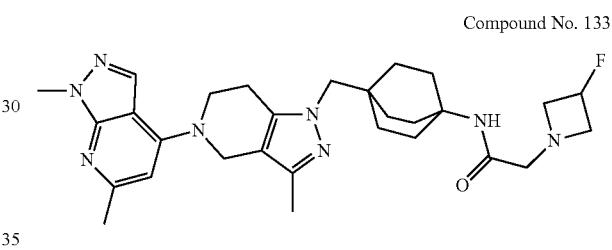

Step 1: To a mixture of 16.7 mg (0.120 mmol) of 2-bromoacetic acid and 42.0 mg (0.1 mmol) of 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 1) in DCM (1 mL) were added HATU (45.6 mg, 0.12 mmol) and DIPEA (25.8 mg, 0.035 mL, 0.2 mmol). The resulting mixture was stirred at rt for 1 hr. LC-MS confirmed the completion of the reaction and the mixture was concentrated. The crude product was added to a 4 g silica gel column and was eluted with 0-50% IPA (containing 0.02 M of ammonia) in DCM. Collected fractions and concentrated to afford 2-bromo-N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)acetamide. RT (method 1): 1.26 min. MS (ES+): 540.2 and 542.1 (M+1)+.

Step 2: A mixture of 27 mg (0.05 mmol) of 2-bromo-N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)acetamide, 7.3 mg (0.065 mmol) of 3-fluoroazetidine and 20.7 mg (0.15 mmol) of potassium carbonate in DMA (1 mL) was heated at 120° C. under microwave irradiation for 40 min. After concentration, the crude product was purified by mass-triggered HPLC (10-30% ACN in H$_2$O over 3.5 min) then 1N aqueous HCl was added and lyophilized to afford N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(3-fluoroazetidin-1-yl)acetamide (Compound No. 133), as HCl salt. RT (method 1): 1.04 min. MS (ES+): 535.3 (M+1)+.

Example 30

Synthesis of N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-hydroxyacetamide (Compound No. 135) and N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(3-hydroxyazetidin-1-yl)acetamide (Compound No. 136)

Compound No. 135

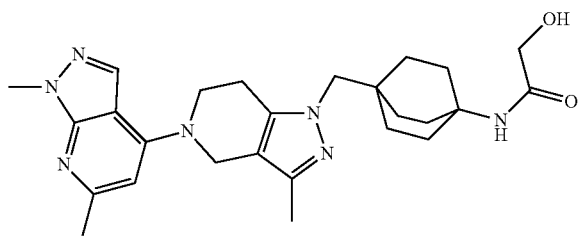

Compound No. 136

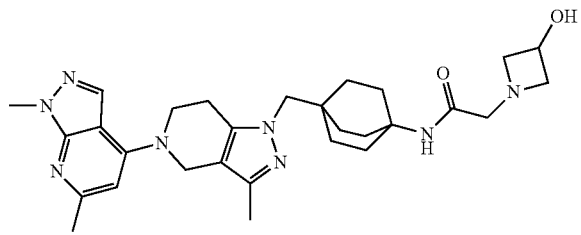

Step 1: To a mixture of 10.1 mg (0.11 mmol) of 2-oxoacetic acid and 42 mg (0.1 mmol) of 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine (Compound No. 1) in DCM was added HATU (41.8 mg, 0.11 mmol) and DIPEA (25.8 mg, 0.035 mL, 0.2 mmol). The resulting mixture was then stirred at rt for 1 hr then loaded to a 4 g silica gel column and was eluted with 0-50% IPA (containing 0.02 M of ammonia) in DCM. Collected fractions and concentrated. The residue was dissolved in 2 mL of DCE, azetidin-3-ol (HCl salt) was added and the mixture was stirred at rt for 30 min before sodium triacetoxyhydroborate was added. The mixture was then stirred at rt overnight. LC-MS showed some desired product 1 but mainly byproduct 2. The crude product was purified by mass-triggered HPLC (10-30% ACN in H2O over 3.5 min) then 1N aqueous HCl was added and lyophilized to give N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(3-hydroxyazetidin-1-yl)acetamide (Compound No. 136) [RT (method 1): 1.05 min. MS (ES+): 478.3 (M+1)+] and N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-hydroxyacetamide (Compound No. 135) [RT (method 1): 0.98 min. MS (ES+): 533.3 (M+1)+], both as HCl salt.

TABLE 6

Additional Exemplary Compounds

| Compound No. | Structure and Name | Characterization | Synthesis Method |
|---|---|---|---|
| 11 | 4-(1-((4-aminobicyclo[2.2.2]octan-1-yl)methyl)-6,7-dihydro-1H-pyrazolo[4,3-c]pyridin-5(4H)-yl)-1-methyl-1H-pyrazolo[3,4-d]pyrimidin-6-amine | | See Example 1 Replace (HG1) in step 1 with (HG2) and (TG3) with (TG1) |
| 12 | 4-(2-((4-aminobicyclo[2.2.2]octan-1-yl)methyl)-6,7-dihydro-2H-pyrazol[4,3-c]pyridin-5(4H)-yl)-1-methyl-1H-pyrazolo[3,4-d]pyrimidin-6-amine | | See Example 1 Replace (HG1) in step 1 with (HG2) and (TG3) with (TG2) |

TABLE 6-continued

Additional Exemplary Compounds

| Compound No. | Structure and Name | Characterization | Synthesis Method |
|---|---|---|---|
| 13 | 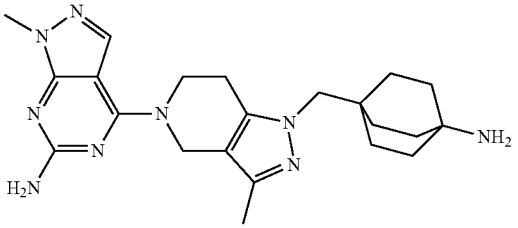4-(1-((4-aminobicyclo[2.2.2]octan-1-yl)methyl)-3-methyl-6,7-dihydro-1H-pyrazolo[4,3-c]pyridin-5(4H)-yl)-1-methyl-1H-pyrazolo[3,4-d]pyrimidin-6-amine | RT (method 2): 1.13 min. MS (ES+): 423.3 (M + 1)+. | See Example 1 Replace (HG1) in step 1 with (HG2) |
| 14 | 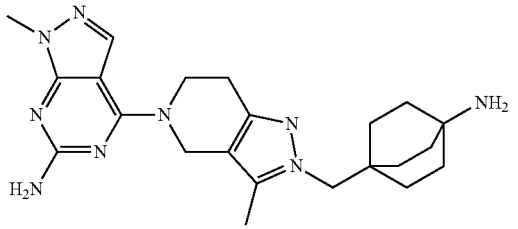4-(2-((4-aminobicyclo[2.2.2]octan-1-yl)methyl)-3-methyl-6,7-dihydro-2H-pyrazolo[4,3-c]pyridin-5(4H)-yl)-1-methyl-1H-pyrazolo[3,4-d]pyrimidin-6-amine | RT (method 2): 1.17 min. MS (ES+): 423.3 (M + 1)+. | See Example 1 Replace (HG1) in step 1 with (HG2) and (TG3) with (TG4) |
| 15 | 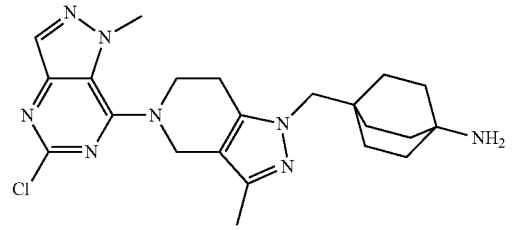4-((5-(5-chloro-1-methyl-1H-pyrazolo[4,3-c]pyrimidin-7-yl)-3-methyl-4,5,6,7-tetrahydro-1H-pyrazolo[4,3-c]pyridin-1-yl)methyl)bicyclo[2.2.2]octan-1-amine | $^1$H NMR (400 MHz, Methanol-$d_4$) δ 8.00 (s, 1H), 4.64 (s, 2H), 4.25 (s, 3H), 4.10-3.87 (m, 2H), 3.78 (s, 2H), 3.03 (t, J = 5.5 Hz, 2H), 2.19 (s, 3H), 1.96-1.40 (m, 12H). MS (ES+): 441.3 (M + 1)+. | See Example 1 Replace (HG1) in step 1 with (HG3) |
| 16 | 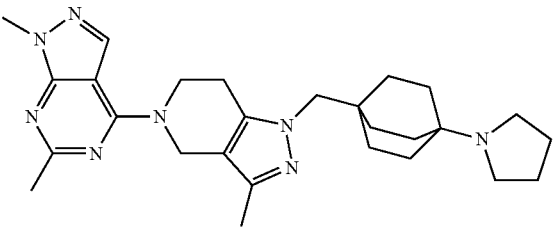1,6-dimethyl-4-(3-methyl-1-((4-(pyrrolidin-1-yl)bicyclo[2.2.2]octan-1-yl)methyl)-6,7-dihydro-1H-pyrazolo[4,3-c]pyridin-5(4H)-yl)-1H-pyrazolo[3,4-d]pyrimidine | $^1$H NMR (400 MHz, Methanol-$d_4$) δ 8.26 (s, 1H), 4.83 (s, 2H), 4.22 (brs, 2H), 3.91 (s, 3H), 4.10-3.87 (m, 2H), 3.69 (s, 2H), 3.09 (m, 2H), 2.82 (m, 2H), 2.52 (s, 3H), 2.15 (s, 3H), 1.98-1.52 (m, 16H). MS (ES+): 475.4 (M + 1)+. | See Example 13 Replace Compound No. 1 with Compound No. 149 |

TABLE 6-continued

Additional Exemplary Compounds

| Compound No. | Structure and Name | Characterization | Synthesis Method |
|---|---|---|---|
| 17 | 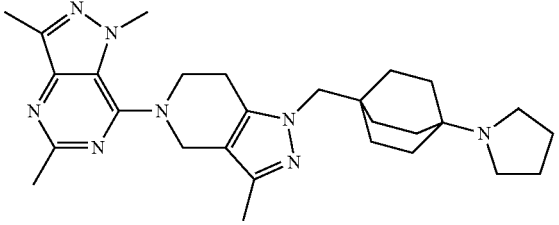<br>1,3,5-trimethyl-7-(3-methyl-1-((4-(pyrrolidin-1-yl)bicyclo[2.2.2]octan-1-yl)methyl)-6,7-dihydro-1H-pyrazolo[4,3-c]pyridin-5(4H)-yl)-1H-pyrazolo[4,3-d]pyrimidine | $^1$H NMR (400 MHz, Methanol-d$_4$) δ 4.96 (s, 2H), 4.27 (m, 2H), 4.24 (s, 3H), 3.77 (s, 2H), 3.63-3.55 (m, 2H), 3.38 (m, 2H), 3.21 (m, 2H), 3.06-2.98 (m, 2H), 2.71 (s, 3H), 2.53 (s, 3H), 2.21 (s, 3H), 2.08-1.92 (m, 4H), 1.91-1.83 (m, 6H), 1.72-1.60 (m, 6H). MS (ES+): 489.4 (M + 1)+. | See Example 13 Replace Compound No. 1 with Compound No. 26 |
| 18 | 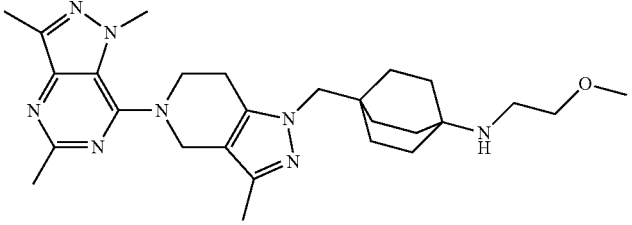<br>N-(2-methoxyethyl)-4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-amine | $^1$H NMR (400 MHz, Methanol-d$_4$) δ 4.95 (s, 2H), 4.31 (t, J = 6.6 Hz, 2H), 4.24 (s, 3H), 3.78 (s, 2H), 3.63-3.55 (m, 2H), 3.39 (s, 3H), 3.14-3.07 (m, 2H), 3.06-2.98 (m, 2H), 2.71 (s, 3H), 2.53 (s, 3H), 2.20 (s, 3H), 1.86-1.77 (m, 6H), 1.72-1.62 (m, 6H). MS (ES+): 493.4 (M + 1)+. | See Example 17 Replace Compound No. 1 with Compound No. 26 and replace formaldehyde with 2-methoxy-acetaldehyde |
| 19 | 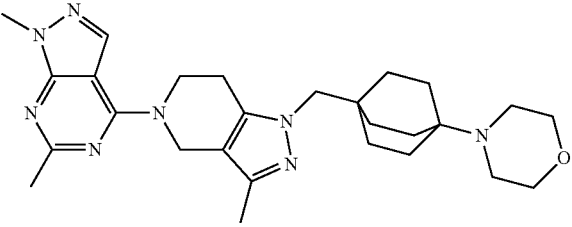<br>4-(4-((5-(1,6-dimethyl-1H-pyrazolo[3,4-d]pyridin-4-yl)-3-methyl-4,5,6,7-tetrahydro-1H-pyrazolo[4,3-c]pyridin-1-yl)methyl)bicyclo[2.2.2]octan-1-yl)morpholine | $^1$H NMR (400 MHz, Methanol-d$_4$) δ 8.22 (s, 1H), 4.87 (s, 2H), 4.26 (brs, 2H), 3.96 (s, 3H), 3.73 (s, 2H), 3.69 (m, 4H), 2.86 (t, J = 5.5 Hz, 2H), 2.68 (m, 4H), 2.55 (s, 3H), 2.24 (s, 3H), 1.68-1.50 (m, 12H). MS (ES+): 491.4 (M + 1)+. | See Example 14 Replace Compound No. 1 with Compound No. 149 |
| 20 | 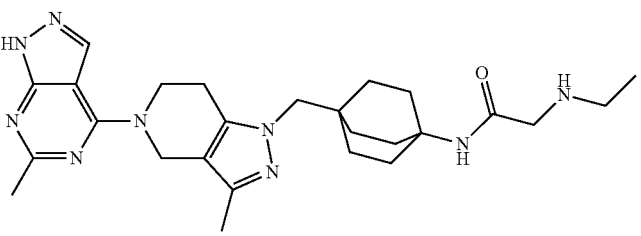<br>2-(ethylamino)-N-(4-((3-methyl-5-(6-methyl-1H-pyrazolo[3,4-d]pyrimidin-4-yl)-4,5,6,7-tetrahydro-1H-pyrazolo[4,3-c]pyridin-1-yl)methyl)bicyclo[2.2.2]octan-1-yl)acetamide | $^1$H NMR (400 MHz, Methanol-d$_4$) δ 8.98 (s, 1H), 5.02 (s, 2H), 4.55 (s, 2H), 3.73 (brs, 2H), 3.63 (s, 2H), 3.03 (q, J = 7.3 Hz, 2H), 2.93 (brs, 2H), 2.66 (s, 3H), 2.27 (s, 3H), 1.89 (dd, J = 9.8, 6.0 Hz, 6H), 1.58 (dd, J = 9.7, 6.1 Hz, 6H), 1.28 (t, J = 7.3 Hz, 3H). MS (ES+): 492.4 (M + 1)+. | See Example 7 Replace Compound No. 1 with Compound No. 58 and replace 2-(dimethyl-amino)acetic acid with ethylglycine |

TABLE 6-continued

Additional Exemplary Compounds

| Compound No. | Structure and Name | Characterization | Synthesis Method |
|---|---|---|---|
| 21 | 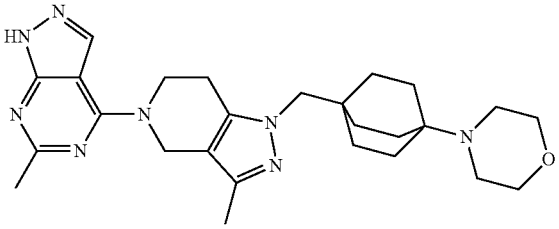<br>4-(4-((3-methyl-5-(6-methyl-1H-pyrazolo[3,4-d]pyrimidin-4-yl)-4,5,6,7-tetrahydro-1H-pyrazolo[4,3-c]pyridin-1-yl)methyl)bicyclo[2.2.2]octan-1-yl)morpholine | $^1$H NMR (400 MHz, Methanol-d$_4$) δ 8.99 (s, 1H), 5.01 (s, 2H), 4.56 (s, 2H), 4.06 (m, 2H), 3.84-3.68 (m, 4H), 3.41 (m, 2H), 3.14-2..90 (m, 4H), 2.66 (s, 3H), 2.26 (s, 3H), 1.88 (dd, J = 9.3, 5.6 Hz, 6H), 1.69 (dd, J = 9.4, 5.4 Hz, 6H). MS (ES+): 477.4 (M + 1)+. | See Example 14 and Example 1 Replace (HG1) in step 1 with (HG18) |
| 22 | 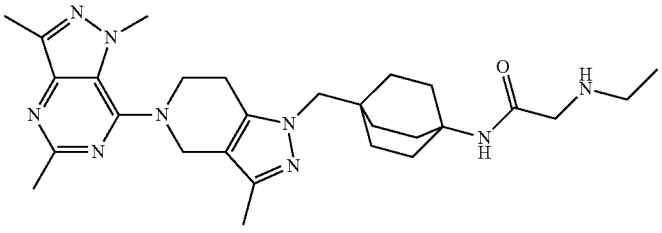<br>2-(ethylamino)-N-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)acetamide | $^1$H NMR (400 MHz, Methanol-d$_4$) δ 4.98 (s, 2H), 4.32 (m, 2H), 4.25 (s, 3H), 3.75 (s, 2H), 3.67 (s, 3H), 3.64 (s, 2H), 3.08-3.00 (m, 4H), 2.72 (s, 3H), 2.48 (s, 3H), 1.93-1.87 (m, 6H), 1.61-1.57 (m, 6H), 1.30 (m, 3H). MS (ES+): 520.4 (M + 1)+. | See Example 7 Replace Compound No. 1 with Compound No. 26 and replace 2-(dimethylamino)acetic acid with ethylglycine |
| 23 | 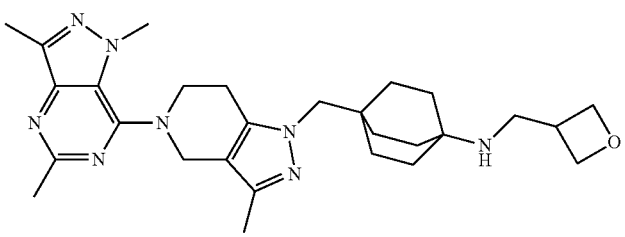<br>4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)-N-(oxetan-3-ylmethyl)bicyclo[2.2.2]octan-1-amine | $^1$H NMR (400 MHz, Methanol-d$_4$) δ 4.96 (s, 2H), 4.31 (t, J = 5.6 Hz, 2H), 4.24 (s, 3H), 3.78 (s, 2H), 3.72-3.45 (m, 4H), 3.12-2.98 (m, 4H), 2.71 (s, 3H), 2.53 (s, 3H), 2.21 (s, 3H), 2.06-1.97 (m, 1H), 1.88-1.72 (m, 6H), 1.72-1.63 (m, 6H). MS (ES+): 505.4 (M + 1)+. | See Example 17 Replace Compound No. 1 with Compoound No. 26 and replace formaldehyde with oxetane-3-carbaldehyde |
| 24 | 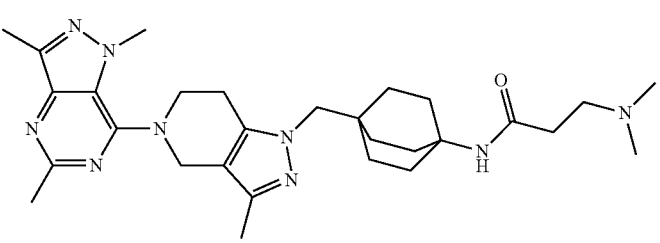<br>3-(dimethylamino)-N-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)propanamide | $^1$H NMR (400 MHz, Methanol-d$_4$) δ 4.97 (s, 2H), 4.31 (t, J = 5.7 Hz, 2H), 4.24 (s, 3H), 3.73 (s, 2H), 3.33 (m, 2H), 3.02 (t, J = 5.5 Hz, 2H), 2.86 (s, 6H), 2.71 (s, 3H), 2.61 (t, J = 6.6 Hz, 2H) 2.53 (s, 3H), 2.22 (s, 3H), 1.94-1.86 (m, 6H), 1.62-1.53 (m, 6H). MS (ES+): 534.4 (M + 1)+. | See Example 7 Replace Compound No. 1 with Compound No. 26 and replace 2-(dimethylamino)acetic acid with 3-(dimethylamino) propanoic acid |

TABLE 6-continued

Additional Exemplary Compounds

| Compound No. | Structure and Name | Characterization | Synthesis Method |
|---|---|---|---|
| 25 | 4-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)morpholine | $^1$H NMR (400 MHz, Methanol-d$_4$) δ 4.53 (s, 2H), 4.11 (s, 3H), 3.87 (t, J = 5.7 Hz, 2H), 3.76-3.64 (m, 6H), 3.01 (J = 5.6 Hz, 2H), 2.65 (brs, 4H), 2.60 (s, 3H), 2.60 (s, 3H), 2.18 (s, 3H), 1.70-1.50 (m, 12H). MS (ES+): 505.4 (M + 1)+. | See Example 14 Replace Compound No. 1 with Compound No. 26 |
| 26 | 4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-amine | $^1$H NMR (400 MHz, Methanol-d$_4$) δ 4.96 (s, 2H), 4.31 (t, J = 5.6 Hz, 2H), 4.24 (s, 3H), 3.77 (s, 2H), 3.04-2.98 (m, 2H), 2.71 (s, 3H), 2.53 (s, 3H), 2.21 (s, 3H), 1.80-1.62 (m, 12H). MS (ES+): 435.4 (M + 1)+. | See Example 10 |
| 27 | N-cyclobutyl-4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-amine | $^1$H NMR (400 MHz, Methanol-d$_4$) δ 4.96 (s, 2H), 4.31 (t, J = 5.6 Hz, 2H), 4.24 (s, 3H), 3.77 (s, 2H), 3.01 (t, J = 5.5 Hz, 2H), 2.79 (d, J = 7.4 Hz, 2H), 2.71 (s, 3H), 2.53 (s, 3H), 2.20 (s, 3H), 1.80-1.60 (m, 12H), 1.16-0.96 (m, 1H), 0.74-0.65 (m, 2H), 0.41-0.31 (m, 2H). MS (ES+): 489.4 (M + 1)+. | See example 6 Replace Compound No. 1 with Compound No. 26 and replace oxetan-3-one with 1-cyclobutanone |
| 28 | N,N-dicyclobutyl-4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-amine | $^1$H NMR (400 MHz, Methanol-d$_4$) δ 4.94 (s, 2H), 4.30 (t, J = 5.6 Hz, 2H), 4.24 (s, 3H), 3.76 (s, 2H), 3.21-2.98 (m, 6H), 2.69 (s, 3H), 2.53 (s, 3H), 2.20 (s, 3H), 1.96-1.86 (m, 6H), 1.72-1.62 (m, 6H), 1.26-1.18 (m, 2H), 0.84-0.75 (m, 4H), 0.54-0.38 (m, 4H). MS (ES+): 543.4 (M + 1)+. | See example 6 Replace Compound No. 1 with Compound No. 26 and replace oxetan-3-one with cyclobutanone |

TABLE 6-continued

Additional Exemplary Compounds

| Compound No. | Structure and Name | Characterization | Synthesis Method |
|---|---|---|---|
| 29 | 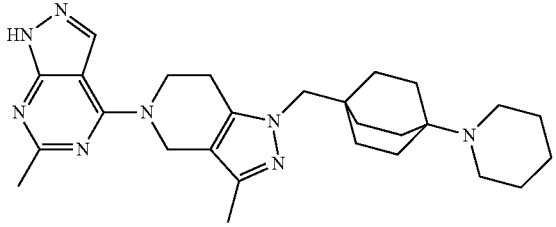<br>6-methyl-4-(3-methyl-1-((4-(piperidin-1-yl)bicyclo[2.2.2]octan-1-yl)methyl)-6,7-dihydro-1H-pyrazolo[4,3-c]pyridin-5(4H)-yl)-1H-pyrazolo[3,4-d]pyrimidine | $^1$H NMR (400 MHz, Methanol-$d_4$) δ 8.99 (s, 1H), 5.01 (s, 2H), 4.56 (brs, 2H), 3.81 (s, 2H), 3.58-3.50 (m, 2H), 3.06-2.88 (m, 2H), 2.86-2.76 (m, 2H), 2.66 (s, 3H), 2.26 (brs, 3H), 2.00-1.62 (m, 18H). MS (ES+): 475.3 (M + 1)+. | See Example 13 and Example 1 Replace (HG1) in step 1 with (HG18) and replace 1,4-dibromo-butane with 1,5-dibromo-pnetane |
| 30 | 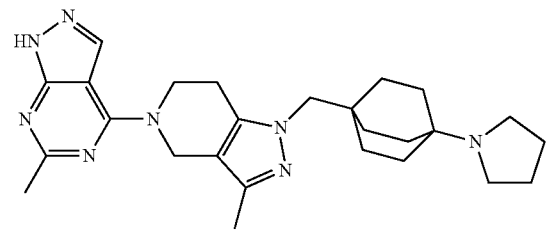<br>6-methyl-4-(3-methyl-1-((4-(pyrrolidin-1-yl)bicyclo[2.2.2]octan-1-yl)methyl)-6,7-dihydro-1H-pyrazolo[4,3-c]pyridin-5(4H)-yl)-1H-pyrazolo[3,4-d]pyrimidine | $^1$H NMR (400 MHz, Methanol-$d_4$) δ 8.85 (s, 1H), 4.92 (s, 2H), 4.43 (brs, 2H), 3.70 (s, 2H), 3.28-3.30 (m, 2H), 3.16-3.05 (m, 2H), 2.94-2.77 (m, 2H), 2.56 (s, 3H), 2.16 (brs, 3H), 1.98-1.52 (m, 16H). MS (ES+): 461.4 (M + 1)+. | See Example 13 and Example 1 Replace (HG1) in step 1 with (HG18) |
| 31 | 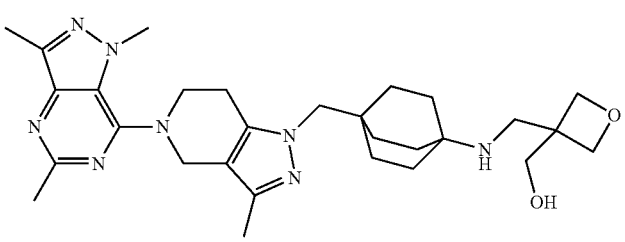<br>(3-(((4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)amino)methyl)oxetan-3-yl)methanol | $^1$H NMR (400 MHz, Methanol-$d_4$) δ 4.52 (s, 2H), 4.50 (s, 2H), 4.45-4.35 (m, 4H), 4.11 (s, 3H), 3.87 (t, J = 5.6 Hz, 2H), 3.75 (s, 2H), 3.01 (t, J = 5.5 Hz, 2H), 2.87 (s, 2H), 2.60 (s, 3H), 2.50 (s, 3H), 2.18 (s, 3H), 1.64-1.52 (m, 12H). MS (ES+): 535.4 (M + 1)+. | See Example 17 This is a by-product from example 17 |
| 32 | 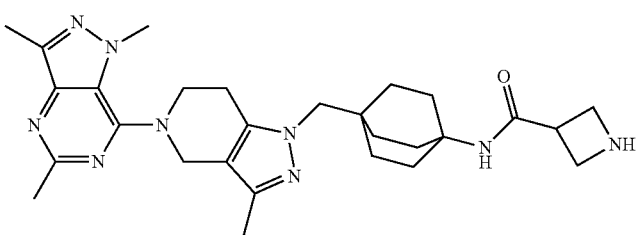<br>N-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)azetidine-3-carboxamide | $^1$H NMR (400 MHz, Methanol-$d_4$) δ 5.03 (s, 2H), 4.34 (t, J = 5.5 Hz, 2H), 4.25 (s, 3H), 4.15-4.10 (m, 4H), 3.87 (s, 2H), 3.62-3.56 (m, 1H), 3.09 (t, J = 5.5 Hz, 2H), 2.74 (s, 3H), 2.55 (s, 3H), 2.32 (s, 3H), 1.96-1.88 (m, 6H), 1.66-1.56 (m, 6H). MS (ES+): 518.4 (M + 1)+. | See Example 7 Replace Compound No. 1 with Compound No. 26 and replace 2-(dimethyl-amino)acetic acid with axzetidine-3-carboxylic acid |

TABLE 6-continued

Additional Exemplary Compounds

| Compound No. | Structure and Name | Characterization | Synthesis Method |
|---|---|---|---|
| 33 | (S)-N-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)morpholine-3-carboxamide | $^1$H NMR (400 MHz, Methanol-$d_4$) δ 4.53 (s, 2H), 4.11 (s, 3H), 3.90-3.78 (m, 3H), 3.72-3.66 (m, 3H), 3.50-3.38 (m, 3H), 3.00 (t, J = 5.5 Hz, 2H), 2.90-2.78 (m, 2H), 2.59 (s, 3H), 2.50 (s, 3H), 2.18 (s, 3H), 1.92-1.84 (m, 6H), 1.62-1.52 (m, 6H). MS (ES+): 548.4 (M + 1)+. | See Example 7 Replace Compound No. 1 with Compound No. 26 and replace 2-(dimethylamino)acetic acid with (S)-morpholine-3-carboxylic acid |
| 34 | (S)-N-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)morpholine-2-carboxamide | $^1$H NMR (400 MHz, Methanol-$d_4$) δ 4.52 (s, 2H), 4.11 (s, 3H), 3.95-3.76 (m, 4H), 3.72 (s, 2H), 3.66-3.56 (m, 1H), 3.15-3.09 (m, 1H), 3.00 (t, J = 5.5 Hz, 2H), 2.80-2.75 (m, 2H), 2.59 (s, 3H), 2.54 (m, 1H), 2.50 (s, 3H), 2.18 (s, 3H), 1.92-1.84 (m, 6H), 1.62-1.52 (m, 6H). MS (ES+): 548.4 (M + 1)+. | See Example 7 Replace Compound No. 1 with Compound No. 26 and replace 2-(dimethylamino)acetic acid with (S)-morpholine-2-carboxylic acid |
| 35 | (R)-N-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)morpholine-3-carboxamide | $^1$H NMR (400 MHz, Methanol-$d_4$) δ 4.53 (s, 2H), 4.11 (s, 3H), 3.90-3.80 (m, 3H), 3.74-3.67 (m, 3H), 3.50-3.38 (m, 3H), 3.00 (t, J = 5.5 Hz, 2H), 2.90-2.78 (m, 2H), 2.60 (s, 3H), 2.50 (s, 3H), 2.18 (s, 3H), 1.92-1.84 (m, 6H), 1.62-1.52 (m, 6H). MS (ES+): 548.4 (M + 1)+. | See Example 7 Replace Compound No. 1 with Compound No. 26 and replace 2-(dimethylamino)acetic acid with (R)-morpholine-3-carboxylic acid |
| 36 | (R)-N-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)morpholine-2-carboxamide | 1H NMR (400 MHz, Methanol-d4) δ 4.53 (s, 2H), 4.12 (s, 3H), 3.96-3.76 (m, 4H), 3.72 (s, 2H), 3.66-3.56 (m, 1H), 3.16-3.07 (m, 1H), 3.00 (t, J = 5.5 Hz, 2H), 2.82-2.75 (m, 2H), 2.59 (s, 3H), 2.54 (m, 1H), 2.50 (s, 3H), 2.18 (s, 3H), 1.92-1.84 (m, 6H), 1.62-1.52 (m, 6H). MS (ES+): 548.4 (M + 1)+. | See Example 7 Replace Compound No. 1 with Compound No. 26 and replace 2-(dimethylamino)acetic acid with (R)-morpholine-2-carboxylic acid |

TABLE 6-continued

Additional Exemplary Compounds

| Compound No. | Structure and Name | Characterization | Synthesis Method |
|---|---|---|---|
| 37 | 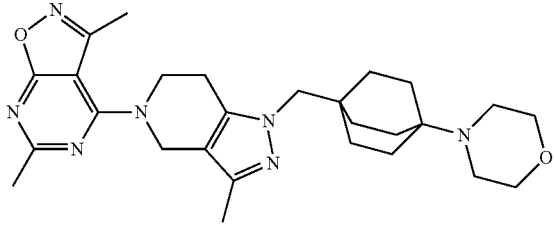<br>3,6-dimethyl-4-(3-methyl-1-((4-morpholinobicyclo[2.2.2]octan-1-yl)methyl)-6,7-dihydro-1H-pyrazolo[4,3-c]pyridin-5(4H)-yl)isoxazolo[5,4-d]pyrimidine | $^1$H NMR (400 MHz, Methanol-$d_4$) δ 4.76 (s, 2H), 4.18 (t, J = 5.6 Hz, 2H), 4.10-4.02 (m, 2H), 3.81 (s, 2H), 3.78-3.68 (m, 2H), 3.46-3.38 (m, 2H), 3.16-3.06 (m, 2H), 2.96-2.90 (m, 2H), 2.73 (s, 3H), 2.56 (s, 3H), 2.23 (s, 3H), 1.92-1.84 (m, 6H), 1.72-1.60 (m, 6H). MS (ES+): 492.4 (M + 1)+. | See Example 14 and See Example 1 Replace (HG1) in step 1 with (HG5) |
| 38 | 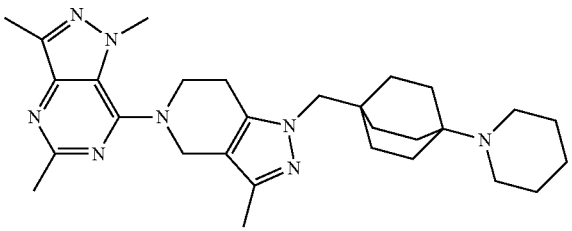<br>1,3,5-trimethyl-7-(3-methyl-1-((4-(piperidin-1-yl)bicyclo[2.2.2]octan-1-yl)methyl)-6,7-dihydro-1H-pyrazolo[4,3-c]pyridin-5(4H)-yl)-1H-pyrazolo[4,3-d]pyrimidine | $^1$H NMR (400 MHz, Methanol-$d_4$) δ 4.96 (s, 2H), 4.31 (t, J = 5.7 Hz, 2H), 4.24 (s, 3H), 3.78 (s, 2H), 3.58-3.52 (m, 2H), 3.02 (t, J = 5.3 Hz, 2H), 2.88-2.76 (m, 2H), 2.71 (s, 3H), 2.53 (s, 3H), 2.20 (s, 3H), 2.00-1.42 (m, 18H). MS (ES+): 503.4 (M + 1)+. | See Example 13 Replace Compound No. 1 with Compound No. 26 and replace 1,4-dibromobutane with 1,5-dibromopentane |
| 39 | 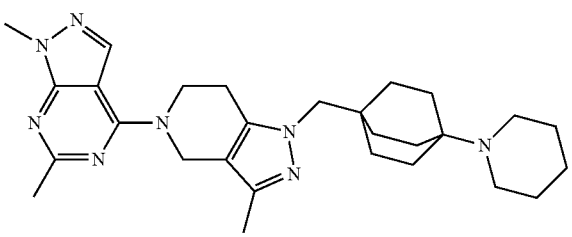<br>1,6-dimethyl-4-(3-methyl-1-((4-(piperidin-1-yl)bicyclo[2.2.2]octan-1-yl)methyl)-6,7-dihydro-1H-pyrazolo[4,3-c]pyridin-5(4H)-yl)-1H-pyrazolo[3,4-d]pyrimidine | $^1$H NMR (400 MHz, Methanol-$d_4$) δ 8.42 (s, 1H), 4.92 (s, 2H), 4.35 (brs, 2H), 4.04 (s, 3H), 3.82 (s, 2H), 3.58-3.50 (m, 2H), 2.98-2.90 (m, 2H), 2.86-2.76 (m, 2H), 2.66 (s, 3H), 2.26 (s, 3H), 2.00-1.62 (m, 18H). MS (ES+): 489.4 (M + 1)+. | See Example 13 Replace Compound No. 1 with Compound No. 149 and replace 1,4-dibromobutane with 1,5-dibromopentane |
| 40 | 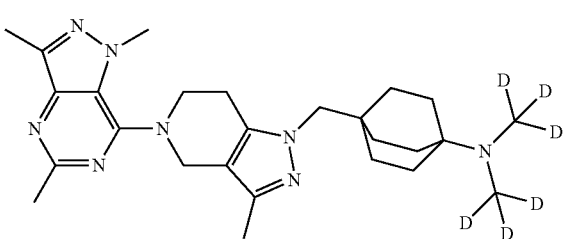<br>4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)-N,N-bis(trideuteromethyl)bicyclo[2.2.2]octan-1-amine | $^1$H NMR (400 MHz, Methanol-$d_4$) δ 4.95 (s, 2H), 4.31 (t, J = 5.6 Hz, 2H), 4.24 (s, 3H), 3.78 (s, 2H), 3.01 (t, J = 5.5 Hz, 2H), 2.78 (s, 3H), 2.53 (s, 3H), 2.20 (s, 3H), 1.90-1.80 (m, 6H), 1.72-1.62 (m, 6H). MS (ES+): 469.4 (M + 1)+. | See Example 17 Replace Compound No. 1 with Compound No. 26 and replace then treat with CD$_3$I |

TABLE 6-continued

Additional Exemplary Compounds

| Compound No. | Structure and Name | Characterization | Synthesis Method |
|---|---|---|---|
| 41 | 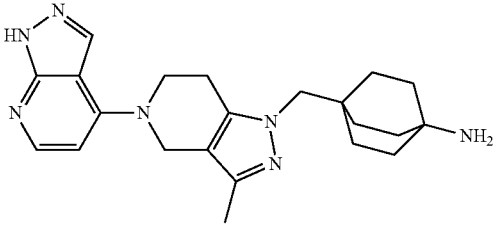<br>4-((3-methyl-5-(1H-pyrazolo[3,4-b]pyridin-4-yl)-4,5,6,7-tetrahydro-1H-pyrazolo[4,3-c]pyridin-1-yl)methyl)bicyclo[2.2.2]octan-1-amine | 1H NMR (400 MHz, DMSO-d6) δ 8.23 (s, 1H), 8.03 (s, 1H), 7.70 (s, 3H), 4.44 (s, 2H), 3.85 (s, 2H), 3.62 (s, 2H), 2.07 (s, 3H), 1.69-1.29 (m, 14H). MS (ES+): 393.2 (M + 1)+. | See Example 1 Replace (HG1) in step 1 with (HG6) |
| 42 | 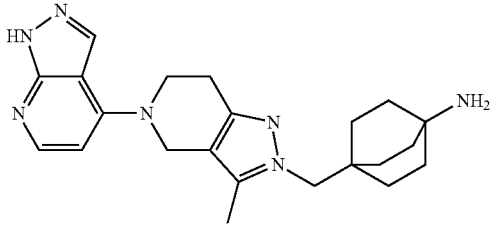<br>4-((3-methyl-5-(1H-pyrazolo[3,4-b]pyridin-4-yl)-4,5,6,7-tetrahydro-2H-pyrazolo[4,3-c]pyridin-2-yl)methyl)bicyclo[2.2.2]octan-1-amine | ¹H NMR (400 MHz, DMSO-d₆) δ 8.20 (s, 1H), 8.00 (d, J = 5.6 Hz, 1H), 6.39 (d, J = 5.7 Hz, 1H), 4.45 (s, 2H), 3.84 (t, J = 5.7 Hz, 2H), 3.61 (s, 2H), 2.72 (t, J = 5.7 Hz, 2H), 2.13 (s, 3H), 1.78 (s, 1H), 1.36 (q, J = 9.8 Hz, 12H). MS (ES+): 393.2 (M + 1)+. | See Example 1 Replace (HG1) in step 1 with (HG6) and (TG3) with (TG2) |
| 43 | 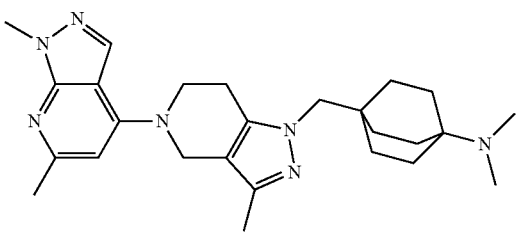<br>4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N,N-dimethylbicyclo[2.2.2]octan-1-amine | 1H NMR (600 MHz, Methanol-d4) δ 8.07 (s, 1H), 6.39 (s, 1H), 4.47 (s, 3H), 3.86 (s, 5H), 3.63 (d, J = 2.5 Hz, 2H), 2.78 (t, J = 5.6 Hz, 2H), 2.58 (s, 6H), 2.41 (s, 3H), 2.07 (s, 3H), 1.71-1.65 (m, 6H), 1.55-1.49 (m, 6H). MS (ES+): 448.4 (M + 1)+. | See example 17 |
| 44 | 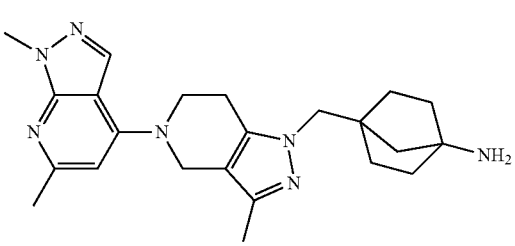<br>4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.1]heptan-1-amine | 1H NMR (600 MHz, Methanol-d4) δ 8.52 (s, 1H), 6.90 (s, 1H), 4.97 (s, 2H), 4.37 (s, 2H), 4.27 (d, J = 8.2 Hz, 2H), 4.12 (s, 3H), 3.13 (t, J = 5.5 Hz, 2H), 2.70 (s, 3H), 2.42 (s, 3H), 1.92-1.73 (m, 8H), 1.67-1.54 (m, 2H). MS (ES+): 406.3 (M + 1)+. | See Example 1 Replace (TG3) in step 1 with (TG5) |

TABLE 6-continued

Additional Exemplary Compounds

| Compound No. | Structure and Name | Characterization | Synthesis Method |
|---|---|---|---|
| 45 | 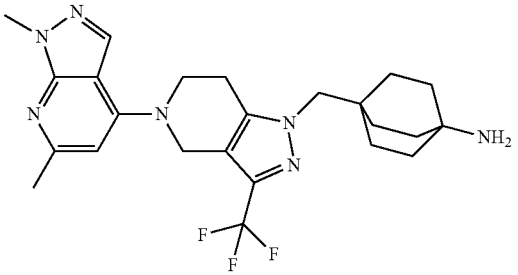<br>4-((5-(1,6-dimethyl-1H-pyrazolo[3,4-b]pyridin-4-yl)-3-(trifluoromethyl)-4,5,6,7-tetrahydro-1H-pyrazolo[4,3-c]pyridin-1-yl)methyl)bicyclo[2.2.2]octan-1-amine | 1H NMR (600 MHz, Methanol-d4) δ 8.37 (s, 1H), 6.83 (s, 1H), 5.08 (s, 2H), 4.36-4.16 (m, 2H), 4.11 (s, 3H), 4.02 (s, 2H), 3.08 (s, 2H), 2.69 (s, 3H), 1.82-1.68 (m, 12H). MS (ES+): 474.3 (M + 1)+. | See Example 1 Replace (TG3) in step 1 with (TG8) |
| 46 | 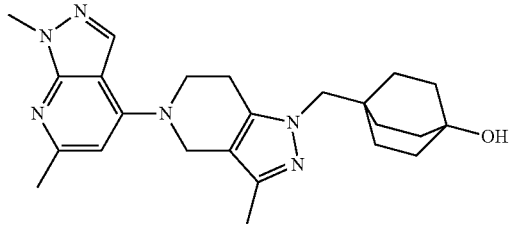<br>4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-ol | 1H NMR (400 MHz, Methanol-d4) δ 8.53 (s, 1H), 6.89 (s, 1H), 4.97 (d, J = 10.7 Hz, 2H), 4.24 (d, J = 11.9 Hz, 2H), 4.12 (s, 3H), 3.99 (s, 2H), 3.14 (td, J = 5.1, 4.6, 2.6 Hz, 2H), 2.70 (s, 3H), 2.45 (s, 3H), 1.64 (s, 12H). MS (ES+): 421.2 (M + 1)+. | See Example 1 Replace TG3 with TG14 |
| 47 | 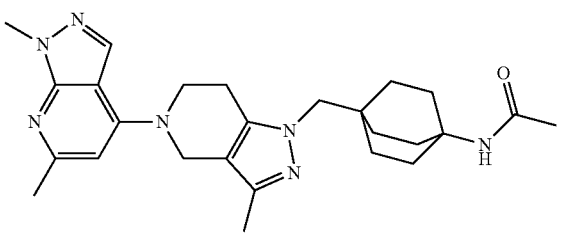<br>N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)acetamide | RT (method 1): 1.18 min. MS (ES+): 462.2 (M + 1)+. | See Example 7 Replace Compound No. 1 with Compound No. 26 and replace 2-(dimethylamino)acetic acid with acetic acid |
| 48 | 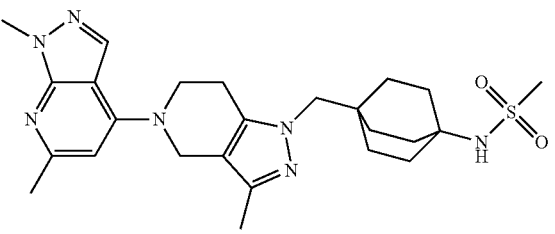<br>N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)methanesulfonamide | 1H NMR (400 MHz, Methanol-d4) δ 8.53 (s, 1H), 6.89 (s, 1H), 5.06-4.94 (m, 2H), 4.25 (s, 2H), 4.12 (s, 3H), 3.98 (s, 2H), 3.18-3.06 (m, 2H), 2.94 (s, 3H), 2.70 (s, 3H), 2.43 (s, 3H), 1.96-1.85 (m, 6H), 1.67-1.57 (m, 6H). MS (ES+): 498.2 (M + 1)+. | See Example 18 |

TABLE 6-continued

Additional Exemplary Compounds

| Compound No. | Structure and Name | Characterization | Synthesis Method |
|---|---|---|---|
| 49 | 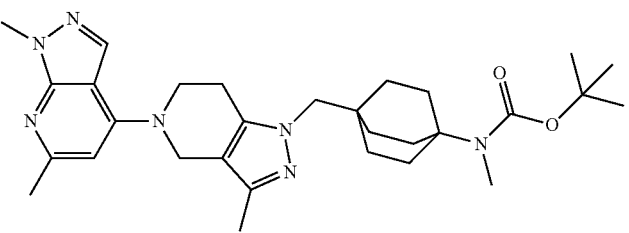<br>tert-butyl (4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)methyl)carbamate | 1H NMR (400 MHz, Methanol-d4) δ 8.16 (s, 1H), 6.46 (s, 1H), 4.54 (s, 2H), 4.00 (s, 5H), 3.72 (s, 2H), 2.90 (t, J = 5.6 Hz, 2H), 2.80 (s, 3H), 2.55 (s, 3H), 2.23 (s, 3H), 2.04-1.91 (m, 6H), 1.60-1.52 (m, 6H), 1.43 (s, 9H). MS (ES+): 534.4 (M + 1)+. | See Example 19 |
| 50 | 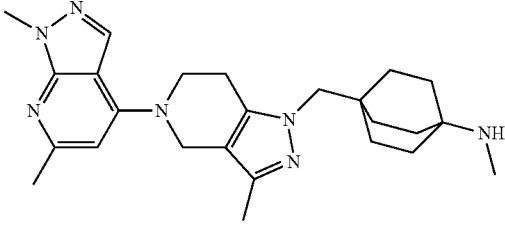<br>4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-methylbicyclo[2.2.2]octan-1-amine | 1H NMR (400 MHz, Methanol-d4) δ 8.05 (s, 1H), 6.36 (s, 1H), 4.44 (s, 2H), 3.90 (s, 3H), 3.88 (t, J = 5.8 Hz, 2H), 3.64 (s, 2H), 2.80 (t, J = 5.6 Hz, 2H), 2.44 (s, 3H), 2.17 (s, 3H), 2.13 (s, 3H), 1.49 (s, 12H). MS (ES+): 434.3 (M + 1)+. | See Example 19 |
| 51 | 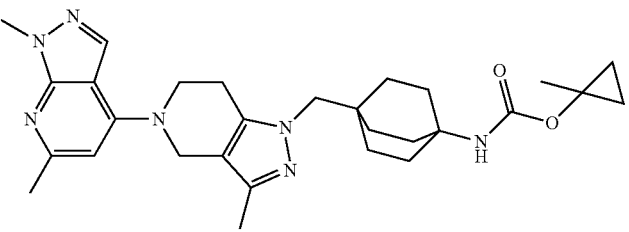<br>1-methylcyclopropyl (4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)carbamate | 1H NMR (400 MHz, Methanol-d4) δ 8.05 (s, 1H), 6.35 (s, 1H), 4.44 (s, 2H), 3.90 (s, 3H), 3.87 (t, J = 5.6 Hz, 2H), 3.61 (s, 2H), 2.80 (t, J = 5.6 Hz, 2H), 2.44 (s, 3H), 2.13 (s, 3H), 1.74-1.63 (m, 6H), 1.50-1.40 (m, 6H), 1.35 (s, 3H), 0.71-0.61 (m, 2H), 0.48-0.41 (m, 2H). MS (ES+): 518.3 (M + 1)+. | See Example 20 |
| 52 | 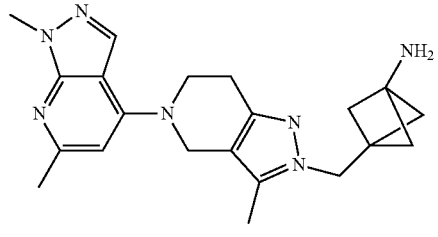<br>3-((5-(1,6-dimethyl-1H-pyrazolo[3,4-b]pyridin-4-yl)-3-methyl-4,5,6,7-tetrahydro-2H-pyrazolo[4,3-c]pyridin-2-yl)methyl)bicyclo[1.1.1]pentan-1-amine | $^1$H NMR (400 MHz, Methanol-d$_4$) δ 8.47 (s, 1H), 6.81 (s, 1H), 4.32 (s, 2H), 4.25-4.18 (m, 2H), 4.10 (s, 3H), 3.02-2.97 (m, 2H), 2.66 (s, 3H), 2.28 (s, 3H), 1.99 (s, 6H). MS (ES+): 378.2 (M + 1)+. | See Example 1 Replace (TG3) in step 1 with (TG13) |

TABLE 6-continued

Additional Exemplary Compounds

| Compound No. | Structure and Name | Characterization | Synthesis Method |
|---|---|---|---|
| 53 | 4-((5-(1-(4-methoxybenzyl)-6-methyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine | RT (method 1), 1.28 min. MS (ES+): 528.4 (M + 1)+. | See Example 2 |
| 54 | N-cyclobutyl-4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine | 1H NMR (400 MHz, Methanol-d4) δ 8.16 (s, 1H), 6.46 (s, 1H), 4.55 (s, 2H), 4.01 (s, 3H), 3.98 (t, J = 5.6 Hz, 2H), 3.72 (s, 2H), 3.32 (m, 1H), 2.90 (t, J = 5.5 Hz, 2H), 2.55 (s, 3H), 2.23 (s, 3H), 2.19 (tt, J = 11.1, 5.3 Hz, 2H), 1.93-1.77 (m, 2H), 1.68 (dd, J = 11.1, 5.7 Hz, 2H), 1.63-1.51 (m, 12H). MS (ES+): 474.4 (M + 1)+. | See example 6 Replace oxetan-3-one with cyclobutanone |
| 55 | 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-isopropylbicyclo[2.2.2]octan-1-amine | 1H NMR (400 MHz, Methanol-d4) δ 8.16 (s, 1H), 6.46 (s, 1H), 4.55 (s, 2H), 4.01 (s, 3H), 3.98 (t, J = 5.7 Hz, 2H), 3.74 (s, 2H), 3.18 (m, 1H), 2.91 (t, J = 5.6 Hz, 2H), 2.55 (s, 3H), 2.23 (s, 3H), 1.66 (q, J = 5.6, 4.5 Hz, 6H), 1.63-1.54 (m, 6H), 1.11 (d, J = 6.3 Hz, 6H). MS (ES+): 462.4 (M + 1)+. | See example 6 Replace oxetan-3-one with propan-2-one |
| 56 | 2-((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)propan-1-ol | RT (method 1): 0.21 min. MS (ES+): 478.4 (M + 1)+. | See example 6 Replace oxetan-3-one with 1-hydroxy-propan-2-one |

TABLE 6-continued

Additional Exemplary Compounds

| Compound No. | Structure and Name | Characterization | Synthesis Method |
|---|---|---|---|
| 57 | 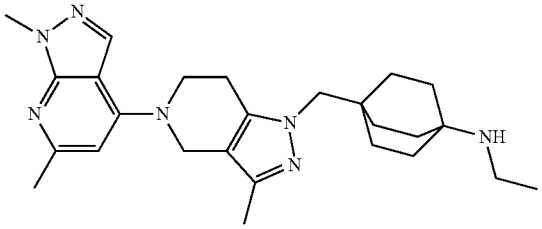<br>4-((5-(1,6-dimethyl-1H-pyraozlo[3,4-b]pyridin-4-yl)-3-methyl-4,5,6,7-tetrahydro-1H-pyrazolo[4,3-c]pyridin-1-yl)methyl)-N-ethylbicyclo[2.2.2]octan-1-amine | 1H NMR (400 MHz, Methanol-d4) δ 8.16 (s, 1H), 6.46 (s, 1H), 4.55 (s, 2H), 4.01 (s, 3H), 3.98 (t, J = 5.7 Hz, 2H), 3.75 (s, 2H), 2.91 (t, J = 5.5 Hz, 2H), 2.69 (q, J = 6.5, 5.9 Hz, 2H), 2.55 (s, 3H), 2.24 (s, 3H), 1.63 (h, J = 6.4, 5.8 Hz, 12H), 1.14 (t, J = 7.1 Hz, 3H). MS (ES+): 448.4 (M + 1)+. | See example 6 Replace oxetan-3-one with acetaldehyde |
| 58 | 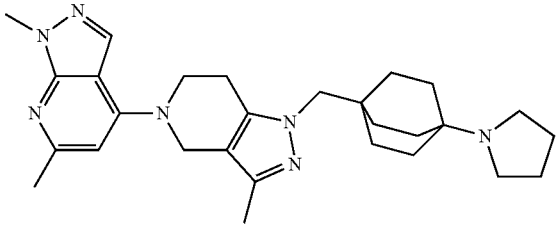<br>5-(1,6-dimethyl-1H-pyrazolo[3,4-b]pyridin-4-yl)-3-methyl-1-((4-(pyrrolidin-1-yl)bicyclo[2.2.2]octan-1-yl)methyl)-4,5,6,7-tetrahydro-1H-pyrazolo[4,3-c]pyridine | 1H NMR (400 MHz, Methanol-d4) δ 8.06 (s, 1H), 6.36 (s, 1H), 4.45 (s, 2H), 3.99 (s, 3H), 3.89 (m, 2H), 3.64 (s, 2H), 2.81 (m, 2H), 2.64 (s, 4H), 2.45 (s, 3H), 2.13 (s, 3H), 1.68 (s, 4H), 1.63 1.35 (m, 12H). ESIMS calcd. for C28H39N7 (M + H+) 475.2, found 475.2 | See Example 13 |
| 59 | 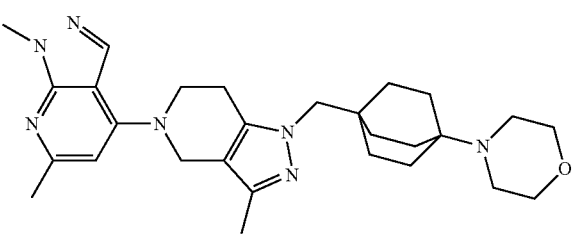<br>4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine | 1H NMR (400 MHz, Methanol-d4) δ 8.16 (s, 1H), 6.46 (s, 1H), 4.55 (s, 2H), 3.99 (d, J = 9.5 Hz, 5H), 3.73 (s, 2H), 3.68-3.51 (m, 4H), 2.91 (t, J = 5.4 Hz, 2H), 2.23 (s, 3H), 1.57 (m, 12H). ESIMS calcd. for C28H39N7O (M + H+) 491.0, found 491.0 | See Example 14 |
| 60 | 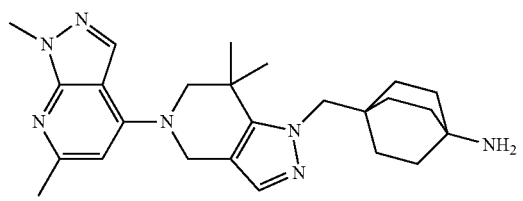<br>4-((5-(1,6-dimethyl-1H-pyrazolo[3,4-b]pyridin-4-yl)-7,7-dimethyl-4,5,6,7-tetrahydro-1H-pyrazolo[4,3-c]pyridin-1-yl)methyl)bicyclo[2.2.2]octan-1-amine | $^1$H NMR (400 MHz, Methanol-d$_4$) δ 8.51 (s, 1H), 7.47 (s, 1H), 6.83 (s, 1H), 5.02 (s, 2H), 4.13 (s, 3H), 3.97 (s, 2H), 3.95 (s, 2H), 2.66 (s, 3H), 1.79 (brs, 12H), 1.49 (s, 6H). MS (ES+): 434.3 (M + 1)+. | See Example 1 Replace (TG3) in step 1 with (TG6) |

TABLE 6-continued

Additional Exemplary Compounds

| Compound No. | Structure and Name | Characterization | Synthesis Method |
|---|---|---|---|
| 61 | 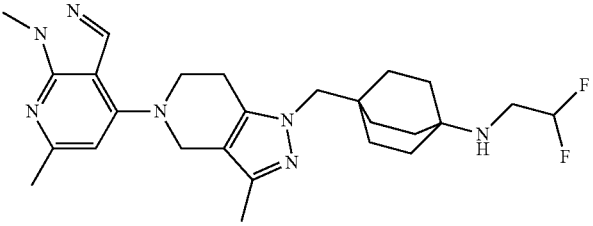<br>N-(2,2-difluoroethyl)-4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine | 1H NMR (400 MHz, Methanol-d4) δ 8.05 (s, 1H), 6.36 (s, 1H), 5.79 (tt, J = 55.9, 4.1 Hz, 1H), 4.44 (s, 2H), 3.89 (m, 5H), 3.64 (s, 2H), 2.94-2.75 (m, 4H), 2.44 (s, 3H), 2.13 (s, 3H), 1.49 (s, 12H). MS (ES+): 484.2 (M + 1)+. | See Example 21 |
| 62 | 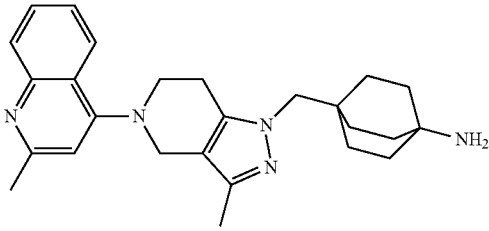<br>-((3-methyl-5-(2-methylquinolin-4-yl)-4,5,6,7-tetrahydro-1H-pyrazolo[4,3-c]pyridin-1-yl)methyl)bicyclo[2.2.2]octan-1-amine | 1H NMR of HCl salt (400 MHz, Methanol-d4) δ 8.25 (d, J = 8.6 Hz, 2H), 7.98 (ddd, J = 8.2, 6.9, 1.1 Hz, 1H), 7.94-7.89 (m, 1H), 7.75 (t, J = 7.7 Hz, 1H), 7.25 (d, J = 5.0 Hz, 1H), 4.75 (d, J = 2.9 Hz, 2H), 4.11 (t, J = 5.4 Hz, 2H), 3.92 (s, 2H), 3.20 (s, 3H), 2.80 (d, J = 1.7 Hz, 3H), 2.28 (d, J = 1.7 Hz, 3H), 2.28 (d, J = 3.3 Hz, 2H), 1.88-1.62 (m, 12H); 416.2 (M + 1), rt = 1.18 min | See Example 1 Replace (HG1) in step 1 with (HG8) |
| 63 | 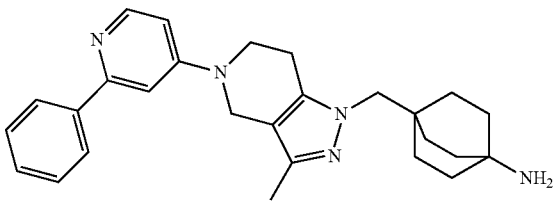<br>4-((3-methyl-5-(2-phenylpyridin-4-yl)-4,5,6,7-tetrahydro-1H-pyrazolo[4,3-c]pyridin-1-yl)methyl)bicyclo[2.2.2]octan-1-amine | 1H NMR (400 MHz, Chloroform-d) δ 8.38 (d, J = 5.9 Hz, 1H), 7.93 (dt, J = 6.4, 1.4 Hz, 2H), 7.51-7.34 (m, 3H), 7.13 (d, J = 2.6 Hz, 1H), 6.71 (dd, J = 6.0, 2.6 Hz, 1H), 4.30 (s, 2H), 3.73 (t, J = 5.6 Hz, 2H), 3.67 (s, 2H), 2.76 (t, J = 5.7 Hz, 2H), 2.23 (s, 3H), 1.50 (m, 12H); MS 428.3 (M + 1), rt-1.02 min | See Example 12 Replace 4-cyanophenyl)boronic acid in step 2 with phenylboronic acid |
| 64 | 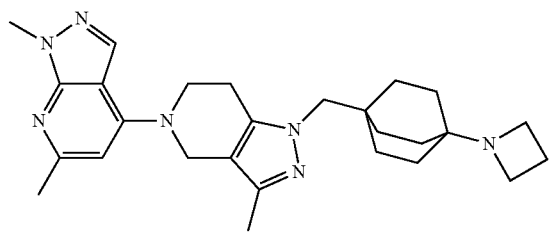<br>1-((4-azetidin-1-yl)bicyclo[2.2.2]octan-1-yl)methyl)-5-(1,6-dimethyl-1H-pyrazolo[3,4-b]pyridin-4-yl)-3-methyl-4,5,6,7-tetrahydro-1H-pyrazolo[4,3-c]pyridine | 1H NMR (400 MHz, Methanol-d4) δ 8.03 (d, J = 0.9 Hz, 1H), 6.33 (s, 1H), 4.42 (s, 2H), 3.89 (s, 3H), 3.85 (q, J = 5.6 Hz, 2H), 3.61 (s, 2H), 3.33-3.23 (m, 4H), 2.79 (t, J = 5.6 Hz, 2H), 2.43 (s, 3H), 2.12 (s, 3H), 1.95 (dt, J = 15.3, 7.6 Hz, 2H), 1.49-1.36 (m, 12H). MS (ES+): 460.4 (M + 1)+. | See Example 13 Replace 1,4-dibromo-butane with 1,3-dibromo-propane |

TABLE 6-continued

Additional Exemplary Compounds

| Compound No. | Structure and Name | Characterization | Synthesis Method |
|---|---|---|---|
| 65 | 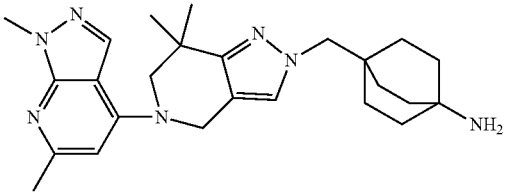<br>4-((5-(1,6-dimethyl-1H-pyrazolo[3,4-b]pyridin-4-yl)-7,7-dimethyl-4,5,6,7-tetrahydro-2H-pyrazolo[4,3-c]pyridin-2-yl)methyl)bicyclo[2.2.2]octan-1-amine | $^1$H NMR (400 MHz, Methanol-d$_4$) δ 8.49 (s, 1H), 7.47 (s, 1H), 6.83 (s, 1H), 5.08 (s, 2H), 4.09 (s, 3H), 3.95 (s, 2H), 3.92 (s, 2H), 2.66 (s, 3H), 1.80-1.70 (m, 6H), 1.68-1.58 (m, 6H), 1.41 (s, 6H). MS (ES+): 434.3 (M + 1)+. | See Example 1 Replace (TG3) in step 1 with (TG7) |
| 66 | 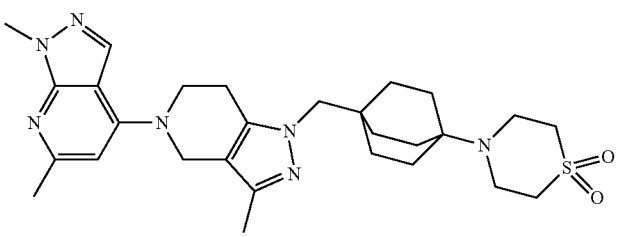<br>4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)thiomorpholine 1,1-dioxide | $^1$H NMR (400 MHz, Methanol-d$_4$) δ 8.39 (s, 1H), 6.75 (s, 1H), 4.12 (s, 2H), 4.00 (s, 4H), 3.79 (s, 3H), 3.74-3.32 (m, 7H), 2.95 (s, 2H), 2.58 (s, 3H), 2.20 (s, 3H), 1.89 (dd, J = 9.8, 5.0 Hz, 6H), 1.78-1.50 (m, 6H). MS (ES+): 538.4 (M + 1)+. | See Example 13 Replace 1,4-dibromobutane with 1-bromo-2-((2-bromoethyl)sulfonyl)ethane |
| 67 | 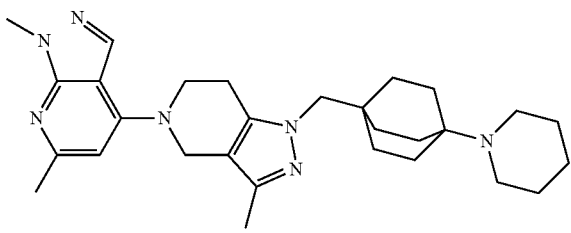<br>5-(1,6-dimethyl-1H-pyrazolo[3,4-b]pyridin-4-yl)-3-methyl-1-((4-(piperidin-1-yl)bicyclo[2.2.2]octan-1-yl)methyl)-4,5,6,7-tetrahydro-1H-pyrazolo[4,3-c]pyridine | $^1$H NMR (400 MHz, Methanol-d$_4$) δ 8.40 (s, 1H), 6.76 (s, 1H), 4.13 (s, 2H), 4.01 (s, 3H), 3.82 (s, 2H), 3.45 (d, J = 11.6 Hz, 2H), 2.97 (s, 2H), 2.73 (t, J = 12.3 Hz, 2H), 2.58 (s, 3H), 2.23 (s, 3H), 1.99-1.49 (m, 18H), 1.38 (dd, J = 14.9, 5.7 Hz, 2H). MS (ES+): 488.3 (M + 1)+. | See Example 13 Replace 1,4-dibromobutane with 1,5-dibromopentane |
| 68 | 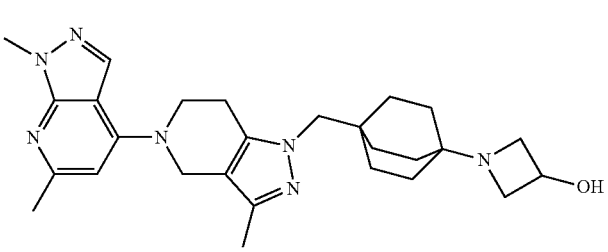<br>1-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)azetidin-3-ol | $^1$H NMR (400 MHz, Methanol-d$_4$) δ 8.50 (s, 1H), 6.87 (s, 1H), 4.61-4.34 (m, 2H), 4.24 (s, 1H), 4.06 (d, J = 6.9 Hz, 1H), 3.94 (d, J = 10.1 Hz, 3H), 3.92-3.71 (m, 2H), 3.34 (m, 2H), 3.11 (m, 2H), 2.69 (s, 3H), 2.34 (s, 3H), 1.74 (m, 12H). MS (ES+): 476.9 (M + 1)+. | See Example 13 Replace 1,4-dibromobutane with 1,3-dibromopropna-2-ol |

TABLE 6-continued

Additional Exemplary Compounds

| Compound No. | Structure and Name | Characterization | Synthesis Method |
|---|---|---|---|
| 69 | 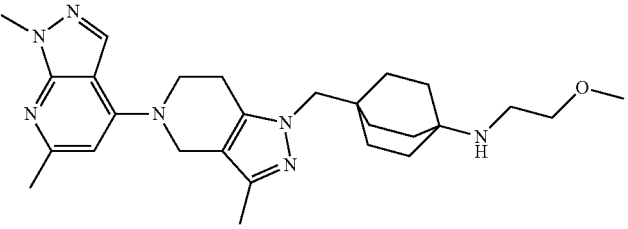<br>4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(2-methoxyethyl)bicyclo[2.2.2]octan-1-amine | 1H NMR (400 MHz, Methanol-d4) δ 8.16 (s, 1H), 8.05 (d, J = 8.2 Hz, 0H), 8.04 (s, 0H), 7.54 (d, J = 8.1 Hz, 0H), 6.46 (s, 1H), 4.54 (s, 2H), 4.00 (s, 3H), 3.98 (t, J = 5.7 Hz, 2H), 3.73 (s, 2H), 3.35 (s, 2H), 2.98 (s, 3H), 2.94 (s, 3H), 2.90 (t, J = 5.6 Hz, 2H), 2.55 (s, 3H), 2.23 (s, 3H), 1.56 (s, 12H). MS (ES+): 505.4 (M + 1)+. | See Example 22 |
| 70 | 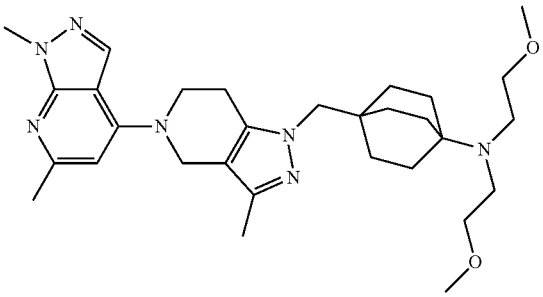<br>4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N,N-bis(2-methoxyethyl)bicyclo[2.2.2]octan-1-amine | 1H NMR (400 MHz, Methanol-d4) δ 8.15 (s, 1H), 6.45 (s, 1H), 4.54 (s, 2H), 4.00 (s, 3H), 3.97 (t, J = 5.5 Hz, 2H), 3.69 (s, 2H), 3.31 (d, J = 1.1 Hz, 6H), 2.90 (t, J = 5.6 Hz, 2H), 2.75-2.65 (m, 4H), 2.55 (s, 3H), 2.23 (s, 3H), 1.64-1.47 (m, 12H). MS (ES+): 536.4 (M + 1)+. | See Example 22 |
| 71 | 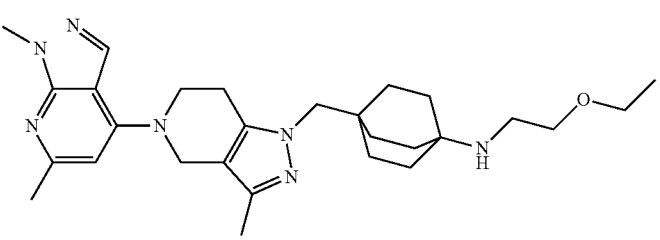<br>4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(2-ethoxyethyl)bicyclo[2.2.2]octan-1-amine | 1H NMR (400 MHz, Methanol-d4) δ 8.15 (s, 1H), 6.45 (s, 1H), 4.54 (s, 2H), 4.00 (s, 3H), 3.97 (dd, J = 7.4, 4.1 Hz, 2H), 3.73 (s, 2H), 3.52-3.46 (m, 4H), 2.90 (t, J = 5.6 Hz, 2H), 2.67 (t, J = 5.5 Hz, 2H), 2.54 (s, 3H), 2.23 (s, 3H), 1.57 (s, 12H), 1.19-1.15 (m, 3H). MS (ES+): 492.4 (M + 1)+. | See Example 22 Replace 1-bromo-2-methoxyethane with 1-bromo-2-ethoxyethane |

TABLE 6-continued

Additional Exemplary Compounds

| Compound No. | Structure and Name | Characterization | Synthesis Method |
|---|---|---|---|
| 72 | 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N,N-bis(2-ethoxyethyl)bicyclo[2.2.2]octan-1-amine | 1H NMR (400 MHz, Methanol-d4) δ 8.16 (s, 1H), 6.45 (s, 1H), 4.54 (s, 2H), 4.00 (s, 3H), 3.99-3.95 (m, 2H), 3.70 (s, 2H), 3.47 (q, J = 7.0 Hz, 4H), 3.38 (t, J = 6.8 Hz, 4H), 2.90 (t, J = 5.6 Hz, 2H), 2.71 (d, J = 7.3 Hz, 4H), 2.55 (s, 3H), 2.23 (s, 3H), 1.65-1.49 (m, 12H), 1.16 (t, J = 7.0 Hz, 6H). MS (ES+): 564.4 (M + 1)+. | See Example 22 Replace 1-bromo-2-methoxyethane with 1-bromo-2-ethoxyethane |
| 73 | 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(2-methoxyethyl)-N-methylbicyclo[2.2.2]octan-1-amine | 1H NMR (400 MHz, Methanol-d4) δ 8.16 (s, 1H), 6.46 (s, 1H), 4.54 (s, 2H), 4.00 (s, 3H), 3.98 (t, J = 5.7 Hz, 2H), 3.72 (s, 2H), 3.43 (t, J = 5.8 Hz, 2H), 2.90 (t, J = 5.6 Hz, 2H), 2.63 (s, 2H), 2.55 (s, 3H), 2.23 (s, 6H), 1.67-1.49 (m, 12H). MS (ES+): 492.4 (M + 1)+. | See Example 23 |
| 74 | (3S,4R)-1-(4-((5-(1,6-dimetthyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)pyrrolidine-3,4-diol | $^1$H NMR (400 MHz, Methanol-d$_4$) δ 8.50 (s, 1H), 6.87 (s, 1H), 4.95 (m, 2H), 4.21 (m, 4H), 4.11 (s, 3H), 3.95 (d, J = 6.5 Hz, 2H), 3.66-3.35 (m, 2H), 3.32 (m, 2H), 3.18 (m, 1H), 3.08 (s, 2H), 2.69 (s, 3H), 2.36 (d, J = 6.4 Hz, 3H), 1.88 (m, 6H), 1.79-1.57 (m, 6H). MS (ES+): 507.4 (M + 1)+. | See Example 13 Replace 1,4-dibromo-butane with (2R,3S)-1,4-dichloro-butane-2,3-diol |

TABLE 6-continued

Additional Exemplary Compounds

| Compound No. | Structure and Name | Characterization | Synthesis Method |
|---|---|---|---|
| 75 | 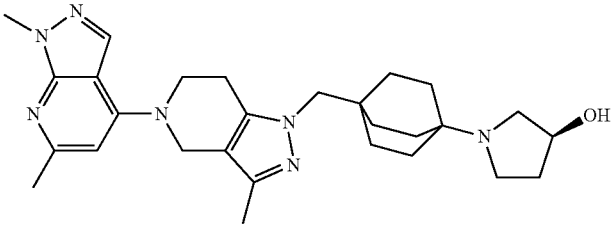<br>(S)-1-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)pyrrolidin-3-ol | $^1$H NMR (400 MHz, Methanol-d$_4$) δ 8.51 (s, 1H), 6.88 (s, 1H), 4.50 (m, 1H), 4.25 (s, 2H), 4.11 (s, 3H), 3.97 (d, J = 5.3 Hz, 2H), 3.52-3.36 (m, 4H), 3.27 (s, 2H), 3.10 (s, 2H), 2.69 (s, 3H), 2.38 (d, J = 4.8 Hz, 3H), 2.21-1.95 (m, 2H), 1.96-1.80 (m, 6H), 1.80-1.63 (m, 6H). MS (ES+): 491.3 (M + 1)+. | See Example 13 Replace 1,4-dibromo-butane with (S)-1,4-dibromo-butane-2-ol |
| 76 | 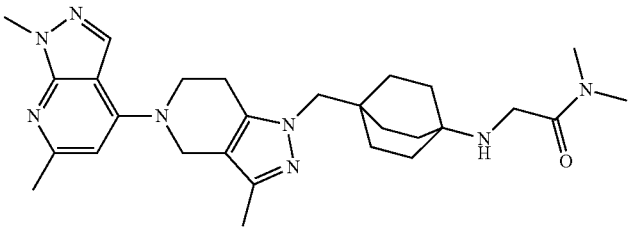<br>2-((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)-N,N-dimethylacetamide | 1H NMR (400 MHz, Methanol-d4) δ 8.17 (d, J = 1.8 Hz, 1H), 6.47 (s, 1H), 4.56 (s, 2H), 4.02 (s, 3H), 4.00 (t, J = 5.7 Hz, 2H), 3.76 (m, 2H), 3.56 (m, 2H), 3.03-2.95 (m, 6H), 2.92 (t, J = 5.6 Hz, 2H), 2.56 (s, 3H), 2.25 (s, 3H), 1.73-1.56 (m, 12H). MS (ES+): 505.4 (M + 1)+. | See Example 24 |
| 77 | 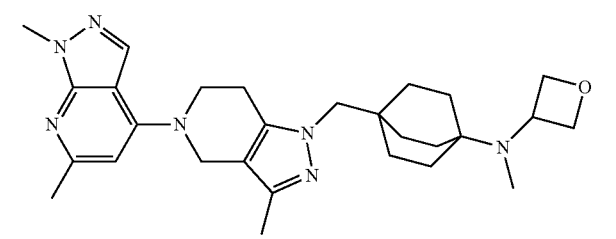<br>N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-N-methyloxetan-3-amine | 1H NMR (400 MHz, Methanol-d4) δ 8.05 (s, 1H), 6.35 (s, 1H), 4.58 (t, J = 6.9 Hz, 2H), 4.47 (t, J = 7.0 Hz, 2H), 4.44 (s, 2H), 4.25 (q, J = 7.3 Hz, 1H), 3.90 (s, 3H), 3.87 (t, J = 5.5 Hz, 2H), 3.61 (s, 2H), 2.79 (t, J = 5.6 Hz, 2H), 2.44 (s, 3H), 2.18 (s, 3H), 2.12 (s, 3H), 1.45 (s, 12H). MS (ES+): 490.4 (M + 1)+. | See Example 25 |
| 78 | 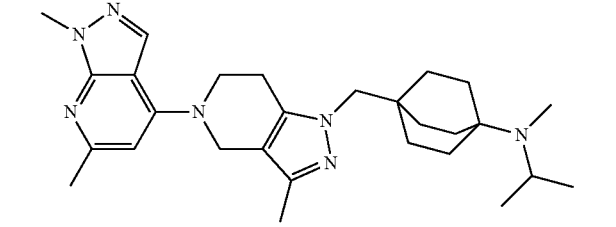<br>4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-isopropyl-N-methylbicyclo[2.2.2]octan-1-amine | 1H NMR (400 MHz, Methanol-d4) δ 8.05 (s, 1H), 6.35 (s, 1H), 4.44 (s, 2H), 3.90 (s, 3H), 3.87 (t, J = 5.6 Hz, 2H), 3.61 (s, 2H), 3.38-3.27 (m, 1H), 2.80 (t, J = 5.6 Hz, 2H), 2.44 (s, 3H), 2.13 (s, 3H), 2.05 (s, 3H), 1.58 (dd, J = 10.0, 5.4 Hz, 6H), 1.49-1.40 (m, 6H), 0.92 (d, J = 6.5 Hz, 6H). MS (ES+): 476.4 (M + 1)+. | See Example 25 Replace Compound No. 6 with Compound No. 55 |

TABLE 6-continued

Additional Exemplary Compounds

| Compound No. | Structure and Name | Characterization | Synthesis Method |
|---|---|---|---|
| 79 | 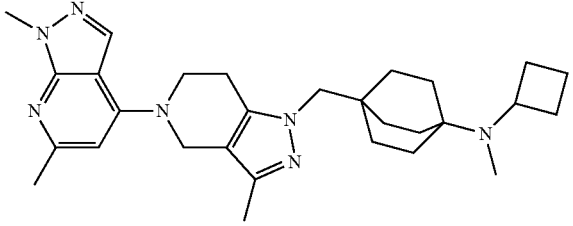<br>N-cyclobutyl-4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-methylbicyclo[2.2.2]octan-1-amine | 1H NMR (400 MHz, Methanol-d4) δ 8.00 (s, 1H), 6.30 (s, 1H), 4.39 (s, 2H), 3.85 (s, 3H), 3.82 (t, J = 5.6 Hz, 2H), 3.56 (s, 2H), 3.41-3.27 (m, 1H), 2.75 (t, J = 5.6 Hz, 2H), 2.40 (s, 3H), 2.08 (s, 3H), 1.99 (s, 3H), 1.91 (td, J = 9.8, 2.4 Hz, 2H), 1.85-1.76 (m, 2H), 1.53-1.34 (m, 14H). MS (ES+): 488.4 (M + 1)+. | See Example 25 Replace Compound No. 6 with Compound No. 54 |
| 80 | 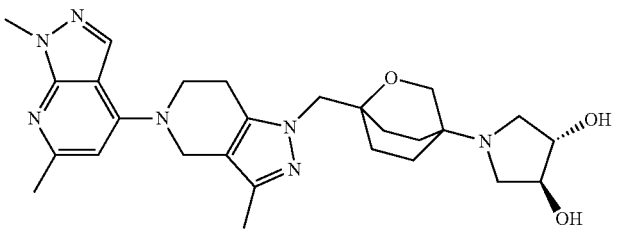<br>(3S,4S)-1-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)pyrrolidine-3,4-diol | RT (method 1): 0.97 min. MS (ES+): 507.3 (M + 1)+. | See Example 13 Replace 1,4-dibromo-butane with (2S,3S)-2,3-dihydroxy-butane-1,4-diyl bis(4-methyl-benzene-sulfonate |
| 81 | 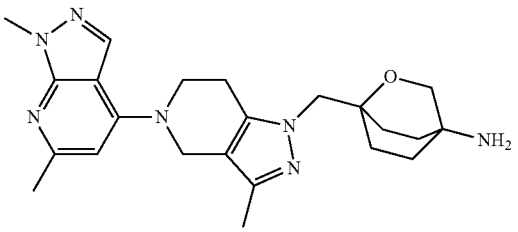<br>1-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-2-oxabicyclo[2.2.2]octan-4-amine | RT (method 2): 1.21 min. MS (ES+): 423.3 (M + 1)+ | See Example 1 Replace (TG3) in step 1 with (TG11) |
| 82 | 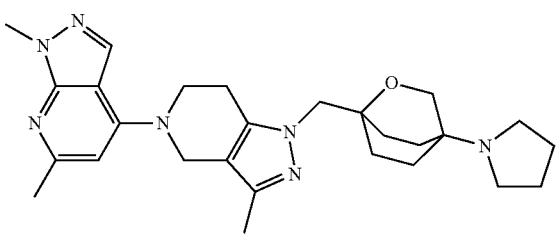<br>5-(1,6-dimethyl-1H-pyrazolo[3,4-b]pyridin-4-yl)-3-methyl-1-((4-(pyrrolidin-1-yl)-2-oxabicyclo[2.2.2]octan-1-yl)methyl)-4,5,6,7-tetrahydro-1H-pyrazolo[4,3-c]pyridine | RT (method 2): 1.23 min. MS (ES+): 477.4 (M + 1)+. | See Example 13 Replace Compound No. 1 with Compound No. 81 |

TABLE 6-continued

Additional Exemplary Compounds

| Compound No. | Structure and Name | Characterization | Synthesis Method |
|---|---|---|---|
| 83 | 4-((5-(6-(4-fluorophenyl)-1-methyl-1H-pyrazolo[3,4-d]pyrimidin-4-yl)-3-methyl-4,5,6,7-tetrahydro-1H-pyrazolo[4,3-c]pyridin-1-yl)methyl)bicyclo[2.2.2]octan-1-amine | $^1$H NMR (400 MHz, Methanol-$d_4$) δ 8.55 (dd, J = 8.7, 5.7 Hz, 2H), 8.27 (s, 1H), 7.21 (t, J = 8.8 Hz, 2H), 4.97 (s, 2H), 4.38 (brs, 2H), 4.06 (s, 3H), 3.80 (s, 2H), 2.02 (t, J = 5.4 Hz, 2H), 2.29 (s, 3H), 1.80-1.60 (m, 12H). MS (ES+): 501.3 (M + 1)+. | See Example 11 |
| 84 | 4-(4-(1-((4-aminobiyclo[2.2.2]octan-1-yl)methyl)-3-methyl-6,7-dihydro-1H-pyrazolo[4,3-c]pyridin-5(4H)-yl)pyridin-2-yl)benzonitrile | $^1$H NMR (400 MHz, Methanol-$d_4$) δ 8.25 (d, J = 7.4 Hz, 1H), 8.08-7.97 (m, 4H), 7.56 (brs, 1H), 7.36 (m, 1H), 4.71 (s, 2H), 4.09 (brs, 2H), 3.79 (s, 2H), 2.93 (t, J = 5.4 Hz, 2H), 2.25 (s, 3H), 1.82-1.60 (m, 12H). MS (ES+): 453.3 (M + 1)+. | See Example 12 |
| 85 | 3-methyl-5-(2-phenylpyridin-4-yl)-1-((4-(pyrrolidin-1-yl)bicyclo[2.2.2]octan-1-yl)methyl)-4,5,6,7-tetrahydro-1H-pyrazolo[4,3-c]pyridine | 1H NMR (400 MHz, Chloroform-d) δ 8.27 (d, J = 6.0 Hz, 1H), 7.86-7.79 (m, 2H), 7.42 (m, 2H), 7.41-7.34 (m, 1H), 7.05 (d, J = 2.6 Hz, 1H), 6.69 (dd, J = 6.1, 2.6 Hz, 1H), 4.27 (s, 2H), 3.71 (t, J = 5.6 Hz, 2H), 3.62 (s, 2H), 2.73 (t, J = 5.7 Hz, 2H), 2.53 (m, 4H), 2.19 (s, 3H), 1.68 (s, 4H), 1.63-1.38 (m, 12H); MS 482.3 (M + 1), rt = 1.13 min | See Example 13 Replace Compound No. 1 with Compound No. 63 |

TABLE 6-continued

Additional Exemplary Compounds

| Compound No. | Structure and Name | Characterization | Synthesis Method |
|---|---|---|---|
| 86 | 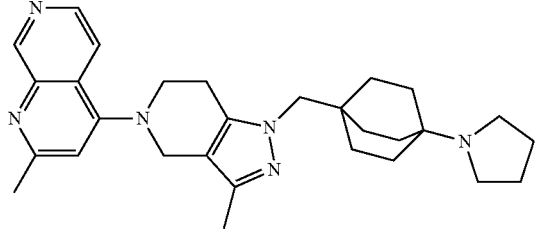<br>2-methyl-4-(3-methyl-1-((4-(pyrrolidin-1-yl)bicyclo[2.2.2]octan-1-yl)methyl)-6,7-dihydro-1H-pyrazolo[4,3-c]pyridin-5(4H)-yl)-1,7-naphthyridine | 1H NMR (400 MHz, Chloroform-d) δ 9.31 (d, J = 0.8 Hz, 1H), 8.47 (d, J = 5.8 Hz, 1H), 7.70 (dd, J = 5.8, 0.9 Hz, 1H), 6.93 (s, 1H), 4.17 (s, 2H), 3.68 (s, 2H), 3.58 (t, J = 5.6 Hz, 2H), 2.90 (t, J = 5.7 Hz, 2H), 2.70 (s, 3H), 2.62-2.50 (m, 4H), 2.20 (s, 3H), 1.71 (t, J = 3.2 Hz, 4H), 1.67-1.47 (m, 12H); MS 471.3 (M + 1), rt = 0.77 min | See Example 13 Replace Compound No. 1 with Compound No. 3 |
| 87 | 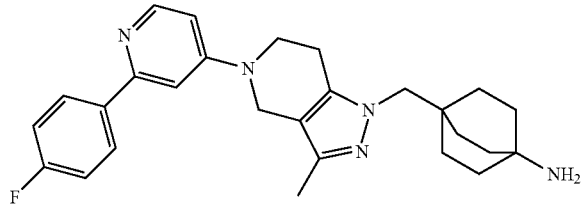<br>4-((5-(2-(4-fluorophenyl)pyridin-4-yl)-3-methyl-4,5,6,7-tetrahydro-1H-pyrazolo[4,3-c]pyridin-1-yl)methyl)bicyclo[2.2.2]octan-1-amine | ¹H NMR (400 MHz, Methanol-d₄) δ 8.25-8.16 (m, 1H), 7.96-7.88 (m, 2H), 7.48-7.29 (m, 4H), 4.70 (s, 2H), 4.07 (brs, 2H), 3.79 (s, 2H), 2.92 (t, J = 5.4 Hz, 2H), 2.25 (s, 3H), 1.86-1.60 (m, 12H). MS (ES+): 446.3 (M + 1)+. | See Example 12 Replace (4-cyanophenyl)boronic acid in step 2 with (4-fluorophenyl)boronic acid |
| 88 | 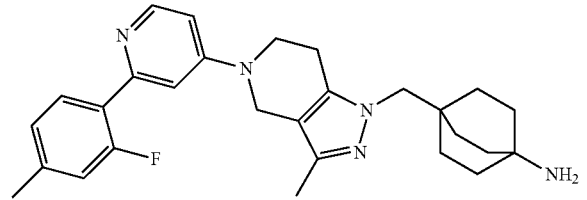<br>4-((5-(2-(2-fluoro-4-methylphenyl)pyridin-4-yl)-3-methyl-4,5,6,7-tetrahydro-1H-pyrazolo[4,3-c]pyridin-1-yl)methyl)bicyclo[2.2.2]octan-1-amine | ¹H NMR (400 MHz, Methanol-d₄) δ 8.22 (d, J = 7.4 Hz, 1H), 7.59-7.41 (m, 3H), 7.36-7.22 (m, 2H), 4.68 (s, 2H), 4.06 (t, J = 5.6 Hz, 2H), 3.79 (s, 2H), 2.91 (t, J = 5.3 Hz, 2H), 2.45 (s, 3H), 2.24 (s, 3H), 1.86-1.56 (m, 12H). MS (ES+): 460.3 (M + 1)+. | See Example 12 Replace (4-cyanophenyl)boronic acid in step 2 with (2-fluoro-4-methylphenyl)boronic acid |
| 89 | 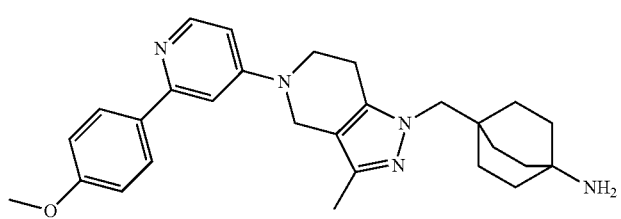<br>4-((5-(2-(4-methoxyphenyl)pyridin-4-yl)-3-methyl-4,5,6,7-tetrahydro-1H-pyrazolo[4,3-c]pyridin-1-yl)methyl)bicyclo[2.2.2]octan-1-amine | ¹H NMR (400 MHz, Methanol-d₄) δ 8.14 (d, J = 7.4 Hz, 1H), 7.86-7.80 (m, 2H), 7.41 (brs, 1H), 7.29-7.14 (m, 3H), 4.68 (s, 2H), 4.06 (brs, 2H), 3.91 (s, 3H), 3.79 (s, 2H), 2.92 (t, J = 5.4 Hz, 2H), 2.25 (s, 3H), 1.82-1.60 (m, 12H). MS (ES+): 458.3 (M + 1)+. | See Example 12 Replace (4-cyanophenyl)boronic acid in step 2 with (4-methoxyphenyl)boronic acid |

TABLE 6-continued

Additional Exemplary Compounds

| Compound No. | Structure and Name | Characterization | Synthesis Method |
|---|---|---|---|
| 90 | 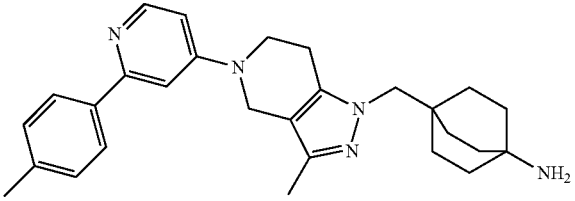<br>4-((3-methyl-5-(2-3(p-tolyl)pyridin-4-yl)-4,5,6,7-tetrahydro-1H-pyrazolo[4,3-c]pyridin-1-yl)methyl)bicyclo[2.2.2]octan-1-amine | $^1$H NMR (400 MHz, Methanol-d$_4$) δ 8.16 (d, J = 7.4 Hz, 1H), 7.76 (d, J = 8.2 Hz, 2H), 7.52-7.40 (m, 3H), 7.32-7.26 (m, 1H), 4.69 (s, 2H), 4.07 (brs, 2H), 3.79 (s, 2H), 2.92 (t, J = 5.4 Hz, 2H), 2.47 (s, 3H), 2.25 (s, 3H), 1.84-1.54 (m, 12H). MS (ES+): 442.4 (M + 1)+. | See Example 12 Replace (4-cyanophenyl) boronic acid in step 2 with p-tolylboronic acid |
| 91 | 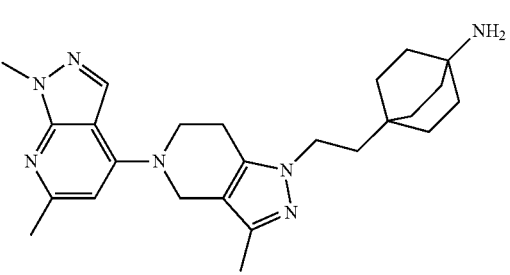<br>4-(2-(5-(1,6-dimethyl-1H-pyrazolo[3,4-b]pyridin-4-yl)-3-methyl-4,5,6,7-tetrahydro-1H-pyrazolo[4,3-c]pyridin-1-yl)ethyl)bicyclo[2.2.2]octan-1-amine | RT (method 2): 1.33 min. MS (ES+): 435.3 (M + 1)+. | See Example 1 Replace (TG3) in step 1 with (TG12) |
| 92 | 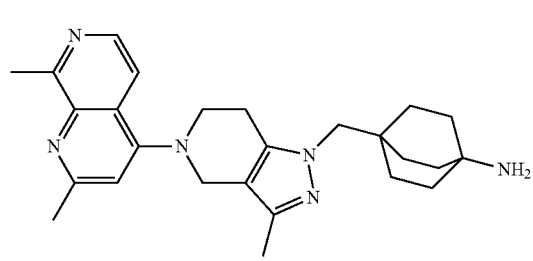<br>4-((5-(2,8-dimethyl-1,7-naphthyridin-4-yl)-3-methyl-4,5,6,7-tetrahydro-1H-pyrazolo[4,3-c]pyridin-1-yl)methyl)bicyclo[2.2.2]octan-1-amine | $^1$H NMR (400 MHz, Methanol-d$_4$) δ 8.48 (d, J = 6.3 Hz, 1H), 8.11 (d, J = 6.3 Hz, 1H), 7.42 (s, 1H), 4.56 (s, 2H), 3.92 (t, J = 5.3 Hz, 2H), 3.82 (s, 2H), 3.11 (d, J = 11.5 Hz, 8H), 2.22 (s, 3H), 1.75 (dd, J = 30.1, 8.1 Hz, 12H). MS (ES+): 431.3 (M + 1)+. | See Example 1 Replace (HG1) in step 1 with (HG10) |
| 93 | 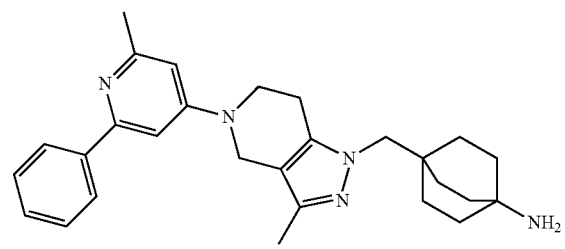<br>4-((3-methyl-5-(2-methyl-6-phenylpyridin-4-yl)-4,5,6,7-tetrahydro-1H-pyrazolo[4,3-c]pyridin-1-yl)methyl)bicyclo[2.2.2]octan-1-amine | 1H NMR (400 MHz, Methanol-d4) δ 7.86-7.76 (m, 2H), 7.50-7.40 (m, 3H), 7.04 (d, J = 2.4 Hz, 1H), 6.80 (d, J = 2.3 Hz, 1H), 4.36 (s, 2H), 3.79 (t, J = 5.6 Hz, 2H), 3.72 (s, 2H), 2.80 (t, J = 5.6 Hz, 2H), 2.49 (s, 3H), 2.22 (s, 3H), 1.57 (s, 12H); MS 442.2 (M + 1), rt = 1.00 min | See Example 12 Replace 2-chloro-4-fluoropyridine in step 1 with 2-chloro-4-fluoro-6-methylpyridine Replace 4-cyanophenyl) boronic acid in step 2 with phenylboronic acid |

TABLE 6-continued

Additional Exemplary Compounds

| Compound No. | Structure and Name | Characterization | Synthesis Method |
|---|---|---|---|
| 94 | 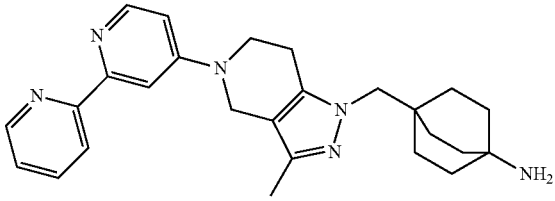<br>4-((5-([2,2'-bipyridin]-4-yl)-3-methyl-4,5,6,7-tetrahydro-1H-pyrazolo[4,3-c]pyridin-1-yl)methyl)bicyclo[2.2.2]octan-1-amine | 1H NMR (400 MHz, Chloroform-d) δ 8.60 (ddd, J = 4.8, 1.9, 0.9 Hz, 1H), 8.34-8.25 (m, 2H), 7.85 (d, J = 2.7 Hz, 1H), 7.73 (td, J = 7.7, 1.8 Hz, 1H), 7.26-7.19 (m, 1H), 6.68 (dd, J = 5.9, 2.7 Hz, 1H), 4.27 (s, 2H), 3.71 (t, J = 5.6 Hz, 2H), 3.59 (s, 2H), 2.69 (t, J = 5.7 Hz, 2H), 2.16 (s, 3H), 1.51-1.37 (m, 12H); MS 429.2 (M + 1), rt = 0.95 min | See Example 12 Replace 4-cyanophenyl) boronic acid in step 2 with pyridin-2-ylboronic acid |
| 95 | 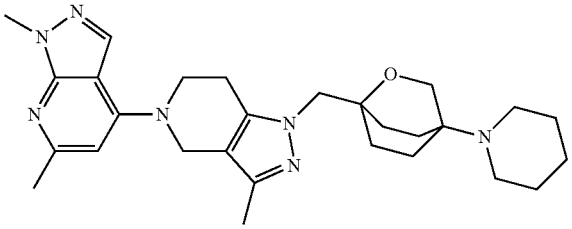<br>5-(1,6-dimethyl-1H-pyrazolo[3,4-b]pyridin-4-yl)-3-methyl-1-((4-(piperidin-1-yl)-2-oxabicyclo[2.2.2]octan-1-yl)methyl)-4,5,6,7-tetrahydro-1H-pyrazolo[4,3-c]pyridine | $^1$H NMR (400 MHz, Methanol-d$_4$) δ 8.39 (s, 1H), 6.76 (s, 1H), 4.12 (s, 2H), 4.01 (m, 5H), 3.88 (s, 2H), 3.39 (m, 3H), 3.02 (m, 2H), 2.81 (m, 2H), 2.58 (s, 3H), 2.23 (s, 3H), 2.13-1.50 (m, 14H), 1.38 (m, 1H). RT (method 2): 1.39 min. MS (ES+): 491.4 (M + 1)+. | See Example 13 Replace Compound No. 1 with Compound No. 81 and replace 1,4-dibromo-butane with 1,5-dibromo-pentane |
| 96 | 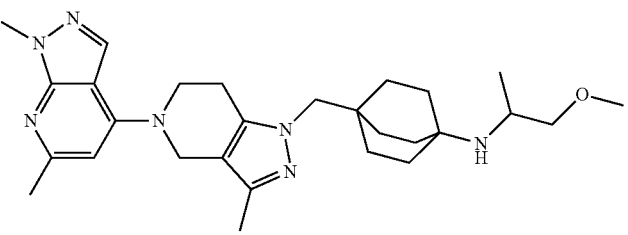<br>4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(1-methoxypropan-2-yl)bicyclo[2.2.2]octan-1-amine | 1H NMR (400 MHz, Methanol-d4) δ 8.05 (s, 1H), 6.35 (s, 1H), 4.44 (s, 2H), 3.90 (s, 3H), 3.87 (t, J = 5.7 Hz, 2H), 3.62 (s, 2H), 3.06 (dq, J = 7.7, 3.4 Hz, 2H), 3.01-2.91 (m, 1H), 2.80 (t, J = 5.6 Hz, 2H), 2.44 (s, 3H), 2.13 (s, 3H), 1.51-1.42 (m, 12H), 0.91 (d, J = 6.3 Hz, 3H). MS (ES+): 492.4 (M + 1)+. | See Example 17 Replace Compound No. 1 with Compound No. 26 and replace formaldehydr with 2-1-methoxy-propan-2-one |
| 97 | 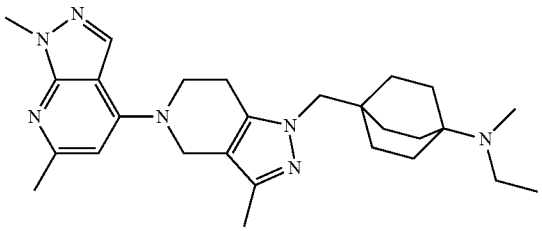<br>4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-ethyl-N-methylbicyclo[2.2.2]octan-1-amine | 1H NMR (400 MHz, Methanol-d4) δ 8.05 (s, 1H), 6.35 (s, 1H), 4.44 (s, 2H), 3.90 (s, 3H), 3.80-3.85 (m, 2H), 3.63 (s, 2H), 2.80 (t, J = 5.6 Hz, 2H), 2.48 (d, J = 7.9 Hz, 2H), 2.44 (s, 3H), 2.14 (d, J = 6.6 Hz, 6H), 1.60-1.41 (m, 12H), 0.99 (t, J = 7.1 Hz, 3H). MS (ES+): 462.4 (M + 1)+. | See Example 25 Replace Compound No. 6 with Compound No. 57 |

TABLE 6-continued

Additional Exemplary Compounds

| Compound No. | Structure and Name | Characterization | Synthesis Method |
|---|---|---|---|
| 98 | 1-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N,N-dimethyl-2-oxabicyclo[2.2.2]octan-4-amine | RT (method 2): 1.27 min. MS (ES+): 451.3 (M + 1)+. | See Example 17 Replace Compound No. 1 with Compound No. 81 |
| 99 | 2-((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)-1-(piperidin-1-yl)ethanone | 1H NMR (600 MHz, Methanol-d4) δ 8.16 (s, 1H), 6.46 (s, 1H), 4.55 (s, 2H), 4.01 (s, 3H), 4.00-3.95 (m, 2H), 3.74 (s, 2H), 3.54 (dd, J = 6.7, 4.5 Hz, 2H), 3.41-3.38 (m, 2H), 3.36 (d, J = 0.8 Hz, 2H), 2.91 (t, J = 5.6 Hz, 2H), 2.55 (s, 3H), 2.24 (s, 3H), 1.67 (ddd, J = 12.5, 7.2, 4.0 Hz, 2H), 1.57 (m, 16H). MS (ES+): 545.4 (M + 1)+. | See Example 24 Replace 2-bromo-N,N-dimethyl-acetamide with 2-bromo-1-(piperidin-1-yl)ethan-1-one |
| 100 | N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(pyrrolidin-1-yl)acetamide | 1H NMR (600 MHz, Methanol-d4) δ 8.05 (s, 1H), 6.36 (s, 1H), 4.44 (s, 2H), 3.90 (s, 3H), 3.90-3.86 (m, 2H), 3.63 (s, 2H), 3.03 (s, 2H), 2.83-2.77 (m, 2H), 2.62-2.53 (m, 4H), 2.45 (s, 3H), 2.14 (s, 3H), 1.81-1.76 (m, 6H), 1.75-1.71 (m, 4H), 1.51-.146 (m, 6H). MS (ES+): 531.4 (M + 1)+. | See Example 24 Replace 2-bromo-N,N-dimethyl-acetamide with 2-bromo-1-(pyrrolidin-1-yl)ethan-1-one |
| 101 | 4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(2-methoxy-2-methylpropyl)bicyclo[2.2.2]octan-1-amine | 1H NMR (600 MHz, Methanol-d4) δ 8.05 (d, J = 1.1 Hz, 1H), 6.35 (s, 1H), 4.44 (s, 2H), 3.90 (s, 3H), 3.90-3.85 (m, 2H), 3.64 (d, J = 6.3 Hz, 2H), 3.07 (s, 2H), 2.83-2.77 (m, 2H), 2.44 (s, 3H), 2.13 (s, 3H), 1.57-1.46 (m, 12H), 1.07 (s, 6H). MS (ES+): 506.4 (M + 1)+. | See Example 26 |

TABLE 6-continued

Additional Exemplary Compounds

| Compound No. | Structure and Name | Characterization | Synthesis Method |
|---|---|---|---|
| 102 | 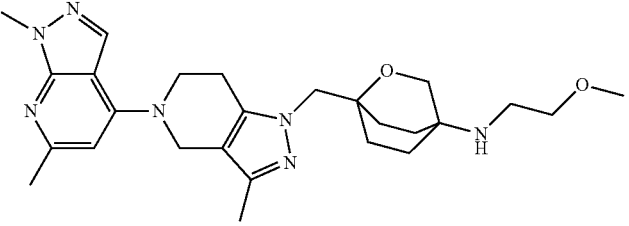<br>1-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(2-methoxyetthyl)-2-oxabicyclo[2.2.2]octan-4-amine | RT (method 2): 0.18 min. MS (ES+): 502.1 (M + Na)+. | See Example 21 Replace Compound No. 1 with Compound No. 81 and Replace 2,2-difluoroethyl trifluoromethanesulfonate with 2-bromomethoxyethane |
| 103 | 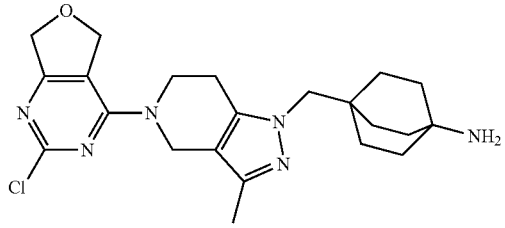<br>4-((5-(2-chloro-5,7-dihydrofuro[3,4-d]pyrimidin-4-yl)-3-methyl-4,5,6,7-tetrahydro-1H-pyrazolo[4,3-c]pyridin-1-yl)methyl)bicyclo[2.2.2]octan-1-amine | $^1$H NMR (400 MHz, Methanol-d$_4$) δ 5.34 (t, J = 2.6 Hz, 2H), 4.84 (t, J = 2.5 Hz, 2H), 4.60 (s, 2H), 3.89 (brs, 2H), 3.76 (s, 2H), 2.79 (t, J = 5.5 Hz, 2H), 2.20 (s, 3H), 1.82-1.58 (m, 12H). MS (ES+): 429.3 (M + 1)+. | See Example 1 Replace (HG1) in step 1 with (HG11) |
| 104 | 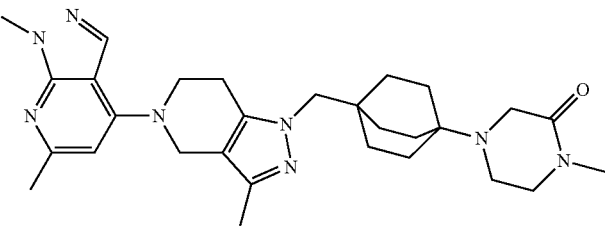<br>4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-1-methylpiperazin-2-one | 1H NMR (400 MHz, Methanol-d4) δ 8.05 (s, 1H), 6.35 (s, 1H), 4.44 (s, 2H), 3.90 (s, 3H), 3.87 (t, J = 5.5 Hz, 2H), 3.62 (s, 2H), 3.17 (dd, J = 6.3, 4.5 Hz, 2H), 3.08 (s, 2H), 2.80 (m, 5H), 2.66 (dd, J = 6.3, 4.5 Hz, 2H), 2.44 (s, 3H), 2.13 (s, 3H), 1.48 (tq, J = 9.4, 6.4, 4.7 Hz, 12H). MS (ES+): 517.3 (M + 1)+. | See Example 27 |
| 105 | 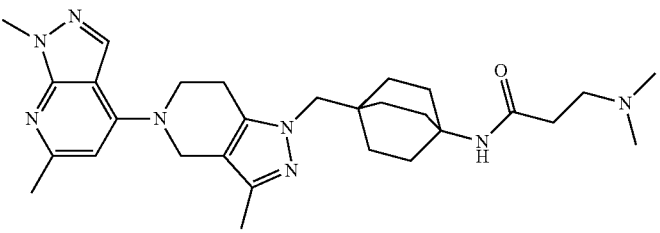<br>N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-3-(dimethylamino)propanamide | 1H NMR (400 MHz, Methanol-d4) δ 8.05 (s, 1H), 6.35 (s, 1H), 4.44 (s, 2H), 3.90 (s, 3H), 3.87 (t, J = 5.5 Hz, 2H), 3.62 (s, 2H), 2.80 (t, J = 5.5 Hz, 2H), 2.45 (m, 5H), 2.17 (dd, J = 7.9, 6.9 Hz, 2H), 2.14 (s, 6H), 2.13 (s, 3H), 1.80-1.73 (m, 6H), 1.50-1.43 (m, 6H). MS (ES+): 519.3 (M + 1)+. | See Example 7 Replace 2-(dimethylamino) acetic acid with 3-(dimethylamino) propanoic acid |

TABLE 6-continued

Additional Exemplary Compounds

| Compound No. | Structure and Name | Characterization | Synthesis Method |
|---|---|---|---|
| 106 | 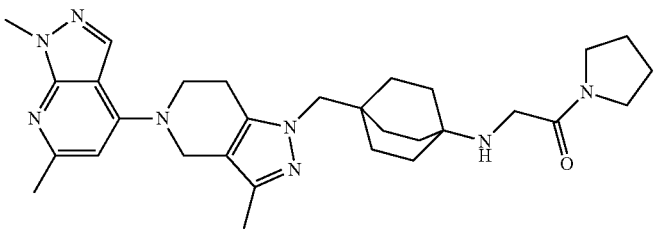<br>2-((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)-1-(pyrrolidin-1-yl)ethanone | 1H NMR (400 MHz, Methanol-d4) δ 8.47 (s, 1H), 6.82 (s, 1H), 4.87 (s, 2H), 4.20 (t, J = 5.5 Hz, 2H), 4.10 (s, 3H), 3.84 (s, 2H), 3.81 (s, 2H), 3.46 (t, J = 6.8 Hz, 4H), 3.00 (t, J = 5.6 Hz, 2H), 2.67 (s, 3H), 2.25 (s, 3H), 2.01 (p, J = 6.6 Hz, 2H), 1.92 (q, J = 6.7 Hz, 2H), 1.87-1.78 (m, 6H), 1.68 (dt, J = 8.1, 5.9 Hz, 6H). MS (ES+): 531.3 (M + 1)+ | See Example 21. Replace 2,2-difluoroethyl trifluoro-methane-sulfonate with 2-bromo-1-(pyrrolidin-1-yl)ethan-1-one |
| 107 | 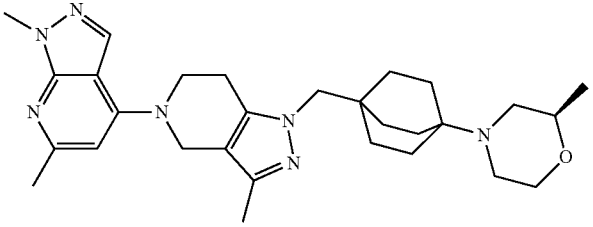<br>(R)-4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-methylmorpholine | RT (method 1): 0.14 min. MS (ES+): 505.3 (M + 1)+. | See Example 14 Replace 1-bromo-2-(2-bromoethoxy)ethane with (R)-1-bromo-2-(2-bromoethoxy)propane |
| 108 | 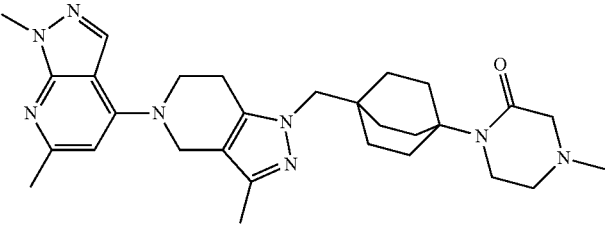<br>1-(4-((5-(1,6-dimethyl-1H-pyrazolo[3,4-b]pyridin-4-yl)-3-methyl-4,5,6,7-tetrahydro-1H-pyraozlo[4,3-c]pyridin-1-yl)methyl)bicyclo[2.2.2]octan-1-yl)-4-methylpiperazin-2-one | 1H NMR (400 MHz, Methanol-d4) δ 8.53 (s, 1H), 6.90 (s, 1H), 4.99 (s, 2H), 4.27 (s, 2H), 4.12 (s, 3H), 4.02 (s, 2H), 3.92 (d, J = 12.1 Hz, 1H), 3.75 (dd, J = 35.3, 18.9 Hz, 5H), 3.20-3.11 (m, 2H), 2.94 (s, 3H), 2.71 (s, 3H), 2.46 (s, 3H), 2.16 (d, J = 7.8 Hz, 6H), 1.67 (d, J = 6.7 Hz, 6H), MS (ES+): 517.3 (M + 1)+. | See Example 29 |
| 109 | 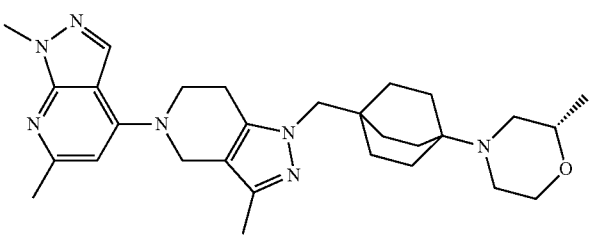<br>(S)-4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-methylmorpholine | RT (method 1): 1.09 min. MS (ES+): 505.4 (M + 1)+. | See Example 14 Replace 1-bromo-2-(2-bromoethoxy)ethane with (S)-2-(2-(tosyloxy)ethoxy)propyl 4-methyl-benzene-sulfonate |

TABLE 6-continued

Additional Exemplary Compounds

| Compound No. | Structure and Name | Characterization | Synthesis Method |
|---|---|---|---|
| 110 | 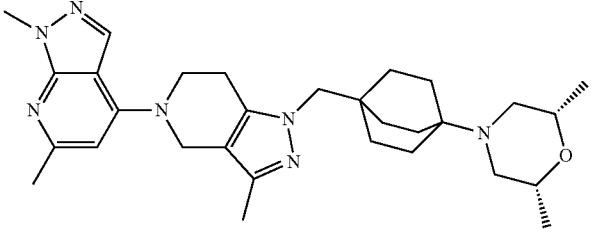<br>(2S,6R)-4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2,6-dimethylmorpholine | 1H NMR (400 MHz, Methanol-d4) δ 8.06 (s, 1H), 6.36 (s, 1H), 4.45 (s, 2H), 3.89 (d, J = 9.6 Hz, 5H), 3.63 (s, 2H), 3.56-3.41 (m, 2H), 2.81 (t, J = 5.5 Hz, 2H), 2.71 (m, 2H), 2.45 (s, 3H), 2.13 (s, 3H), 1.81 (m, 2H), 1.60-1.30 (m, 12H), 1.01 (d, J = 6.2 Hz, 6H). MS (ES+): 518.4 (M + 1)+. | See Example 14 Replace 1-bromo-2-(2-bromoethoxy)ethane with (S)-2-(((R)-1-tosyloxy-propan-2-yl)oxy)propyl 4-methyl-benzene-sulfonate |
| 111 | 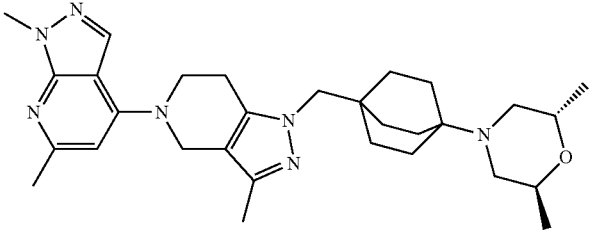<br>(2S,6S)-4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2,6-dimethylmorpholine | RT (method 1): 1.12 min. MS (ES+): 518.4 (M + 1)+. | See Example 14 Replace 1-bromo-2-(2-bromoethoxy)ethane with (S)-2-(((S)-1-tosyloxy-propan-2-yl)oxy)propyl 4-methyl-benzene-sulfonate |
| 112 | 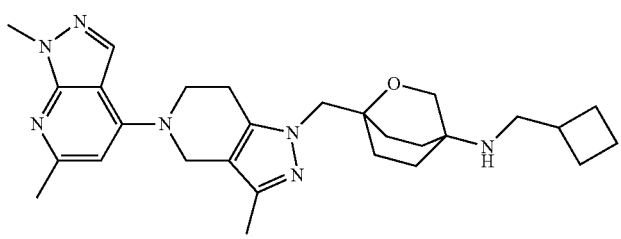<br>N-(cyclobutylmethyl)-1-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-2-oxabicyclo[2.2.2]octan-4-amine | RT (method 1): 1.13 min. MS (ES+): 490.4 (M + 1)+. | See Example 13 Replace Compound No. 1 with Compound No. 81 and replace 1,4-dibormo-butan with (bromomethyl)cyclobutane |

TABLE 6-continued

Additional Exemplary Compounds

| Compound No. | Structure and Name | Characterization | Synthesis Method |
|---|---|---|---|
| 113 | 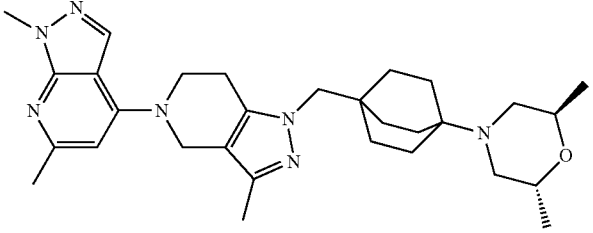<br>(2R,6R)-4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2,6-dimethylmorpholine | RT (method 1): 1.12 min. MS (ES+): 518.4 (M + 1)+. | See Example 14 Replace 1-bromo-2-(2-bromoethoxy)ethane with (R)-2-(((R)-1-tosyloxy-propan-2-yl)oxy)propyl-4-methyl-benzene-sulfonate |
| 114 | 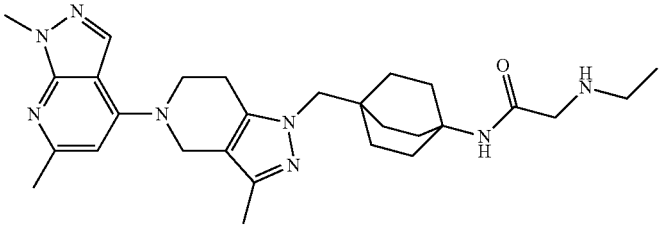<br>N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(ethylamino)acetamide | 1H NMR (400 MHz, Methanol-d4) δ 8.51 (s, 1H), 6.88 (s, 1H), 5.03-4.91 (m, 2H), 4.24 (s, 2H), 4.11 (s, 3H), 3.93 (s, 2H), 3.65 (s, 2H), 3.15-3.07 (m, 2H), 3.04 (q, J = 7.3 Hz, 3H), 2.69 (s, 3H), 2.39 (s, 3H), 2.00-1.88 (m, 6H), 1.68-1.56 (m, 6H), 1.29 (t, J = 7.3 Hz, 3H). MS (ES+): 505.3 (M + 1)+ | See Example 7 Replace dimethyl-glycine with ethylglycine |
| 115 | 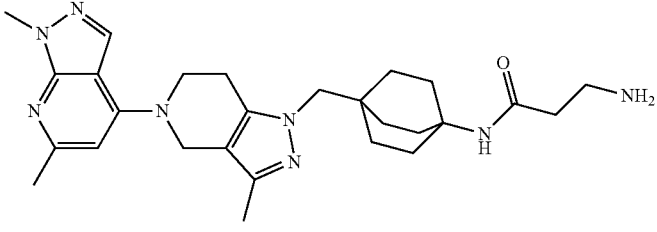<br>3-amino-N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)propanamide | 1H NMR (400 MHz, Methanol-d4) δ 8.52 (s, 1H), 6.89 (s, 1H), 5.08-4.91 (m, 2H), 4.25 (s, 2H), 4.12 (s, 3H), 3.98 (s, 2H), 3.18-3.05 (m, 4H), 2.70 (s, 3H), 2.52 (t, J = 6.5 Hz, 2H), 2.43 (s, 3H), 1.99-1.87 (m, 6H), 1.67-1.54 (m, 6H). MS (ES+): 491.3 (M + 1)+. | See example 7. Replace dimethyl-glycine with 3-((tert-butoxy-carbonyl)amino)propanoic acid |
| 116 | 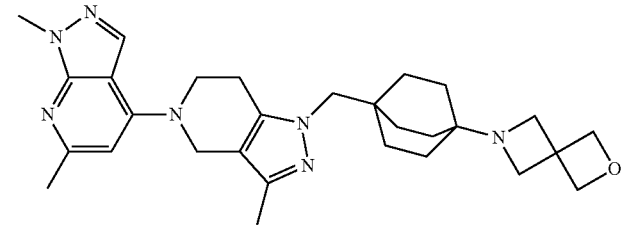<br>6-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-oxa-6-azaspiro[3.3]heptane | 1H NMR (400 MHz, Methanol-d4) δ 8.05 (s, 1H), 6.35 (s, 1H), 4.59 (s, 4H), 4.44 (s, 2H), 3.88 (d, J = 10.9 Hz, 5H), 3.62 (s, 2H), 3.40 (s, 4H), 2.70 (t, J = 5.4 Hz, 2H), 2.44 (s, 3H), 2.12 (s, 3H), 1.60-1.27 (m, 12H). MS (ES+): 503.1 (M + 1)+. | See Example 10 Replace Compound No. 26 with Compound No. 1 |

TABLE 6-continued

Additional Exemplary Compounds

| Compound No. | Structure and Name | Characterization | Synthesis Method |
|---|---|---|---|
| 117 | 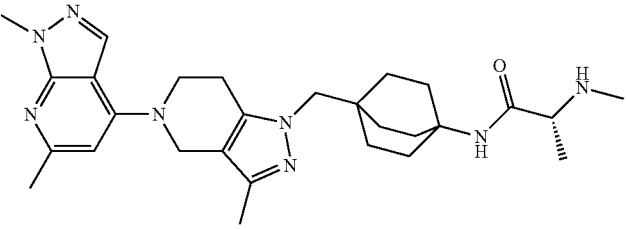<br>(R)-N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(methylamino)propanamide | 1H NMR (400 MHz, Methanol-d4) δ 8.52 (s, 1H), 6.89 (s, 1H), 5.06-4.92 (m, 2H), 4.25 (s, 2H), 4.12 (s, 3H), 3.98 (s, 2H), 3.69 (q, J = 6.2, 5.6 Hz, 1H), 3.20-3.06 (m, 2H), 2.70 (s, 3H), 2.62 (s, 3H), 2.42 (s, 3H), 2.00-1.88 (m, 6H), 1.69-1.57 (m, 6H), 1.44 (d, J = 6.9 Hz, 3H). MS (ES+): 505.3 (M + 1)+. | See Example 7. Replace dimethyl-glycine with N-(tert-butoxy-carbonyl)-N-methyl-D-alanine |
| 118 | 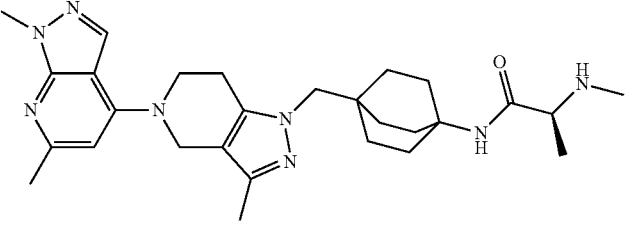<br>(S)-N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(methylamino)propanamide | 1H NMR (400 MHz, Methanol-d4) δ 8.53 (s, 1H), 6.90 (s, 1H), 5.10-4.92 (m, 2H), 4.26 (s, 2H), 4.12 (s, 3H), 4.02 (s, 2H), 3.73-3.66 (m, 1H), 3.19-3.09 (m, 2H), 2.70 (s, 3H), 2.62 (s, 3H), 2.45 (s, 3H), 2.00-1.90 (m, 6H), 1.70-1.57 (m, 6H), 1.44 (d, J = 6.9 Hz, 3H). MS (ES+): 505.3 (M + 1)+ | See example 7. Replace dimethyl-glycine with N-(tert-butoxy-carbonyl)-N-methyl-L-alanine |
| 119 | 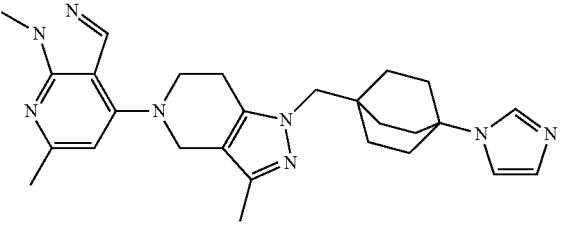<br>1-((4-(1H-imidazol-1-yl)bicyclo[2.2.2]octan-1-yl)methyl)-5-(1,6-dimethyl-1H-pyrazolo[3,4-b]pyridin-4-yl)-3-methyl-4,5,6,7-tetrahydro-1H-pyrazolo[4,3-c]pyridine | $^1$H NMR (400 MHz, Methanol-$d_4$) δ 8.06 (s, 1H), 7.66 (s, 1H), 7.13 (s, 1H), 6.85 (s, 1H), 6.36 (s, 1H), 4.45 (s, 2H), 3.90 (s, 5H), 3.71 (s, 2H), 2.83 (s, 2H), 2.45 (s, 3H), 2.14 (s, 3H), 1.93 (dd, J = 9.7, 6.0 Hz, 6H), 1.63 (dd, J = 9.7, 6.0 Hz, 6H). MS (ES+): 472.3 (M + 1)+ | See Example 15 |
| 120 | 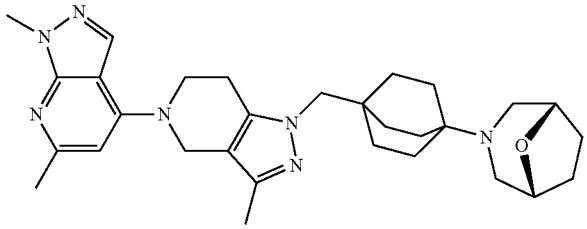<br>(1R,5S)-3-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-8-oxa-3-azabicyclo[3.2.1]octane | $^1$H NMR (400 MHz, Methanol-$d_4$) δ 8.05 (s, 1H), 6.35 (s, 1H), 4.44 (s, 2H), 4.11 (s, 2H), 4.0 (s, 3H), 3.81 (m, 2H), 3.60 (s, 2H), 2.80 (dd, J = 10.6, 5.2 Hz, 2H), 2.44 (s, 5H), 2.29 (d, J = 10.7 Hz, 2H), 2.13 (s, 3H), 1.74 (d, J = 6.4 Hz, 2H), 1.41 (s, 12H). MS (ES+): 517.0 (M + 1)+ | See Example 13 Replace 1,4-dibromo-butane with ((2R,5S)-tetrahydro-furan-2,5-diyl)bis methylene) bis(4-methyl-benzene-sulfonate |

TABLE 6-continued

Additional Exemplary Compounds

| Compound No. | Structure and Name | Characterization | Synthesis Method |
|---|---|---|---|
| 121 | 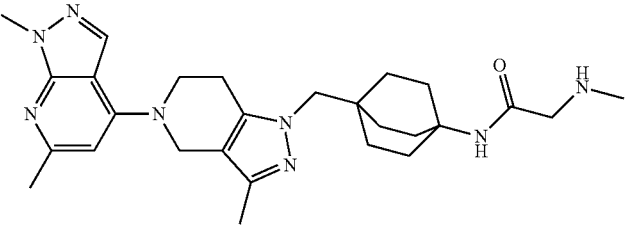<br>N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(methylamino)acetamide | 1H NMR (400 MHz, Methanol-d4) 8.52 (s, 1H), 6.89 (s, 1H), 5.07-4.93 (m, 2H), 4.25 (s, 2H), 4.12 (s, 3H), 3.98 (s, 2H), 3.66 (s, 2H), 3.13 (dt, J = 8.1, 3.2 Hz, 2H), 2.70 (s, 3H), 2.68 (s, 3H), 2.42 (s, 3H), 2.00-1.87 (m, 6H), 1.69-1.57 (m, 6H). MS (ES+): 491.3 (M + 1)+. | See example 7. Replace dimethyl-glycine with N-(tert-butoxy-carbonyl)-N-methylglycine |
| 122 | 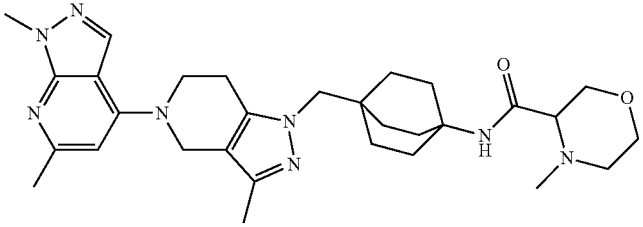<br>N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-4-methylmorpholine-3-carboxamide | 1H NMR (400 MHz, Methanol-d4) δ 8.07 (s, 1H), 6.37 (s, 1H), 4.45 (s, 2H), 3.89 (d, J = 7.9 Hz, 5H), 3.72 (dd, J = 11.7, 3.2 Hz, 2H), 3.62 (s, 2H), 3.50 (td, J = 11.6, 2.4 Hz, 1H), 3.29 (dd, J = 11.6, 10.2 Hz, 1H), 2.80 (t, J = 5.6 Hz, 2H), 2.74 (d, J = 12.0 Hz, 1H), 2.68 (s, 1H), 2.45 (s, 3H), 2.30 (d, J = 10.0 Hz, 1H), 2.19 (s, 3H), 2.13 (s, 3H), 1.83-1.72 (m, 6H), 1.53-1.42 (m, 6H). MS (ES+): 547.3 (M + 1)+. | See example 7. Replace dimethyl-glycine with 4-methyl-morpholine-3-carboxylic acid |
| 123 | 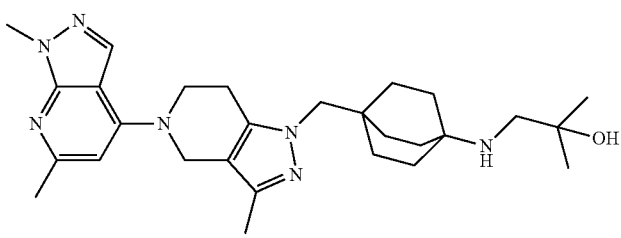<br>1-((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)-2-methylpropan-2-ol | 1H NMR (400 MHz, Methanol-d4) δ 8.52 (s, 1H), 6.89 (s, 1H), 5.06-4.92 (m, 2H), 4.25 (s, 2H), 4.12 (s, 3H), 3.98 (s, 2H), 3.12 (q, J = 5.7, 3.9 Hz, 2H), 2.90 (s, 2H), 2.70 (s, 3H), 2.39 (s, 3H), 1.96-1.81 (m, 6H), 1.79-1.63 (m, 6H), 1.29 (s, 6H). MS (ES+): 492.3 (M + 1)+ | See Example 14 Replace 1-bromo-2-(2-bromoethoxy) ethane with 2,2-dimethyl-oxirane |
| 124 | 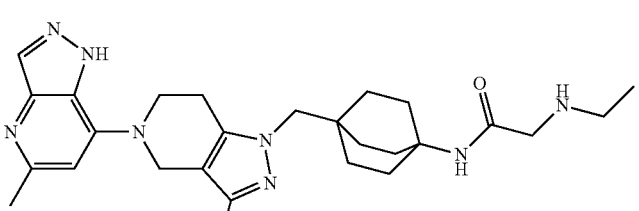<br>2-(ethylamino)-N-(4-((3-methyl-5-(5-methyl-1H-pyrazolo[4,3-b]pyridin-7-yl)-4,5,6,7-tetrahydro-1H-pyrazolo[4,3-c]pyridin-1-yl)methyl)bicyclo[2.2.2]octan-1-yl)acetamide | $^1$H NMR (400 MHz, Methanol-$d_4$) δ 8.20 (s, 1H), 6.65 (s, 1H), 4.83 (m, 4H), 3.63 (s, 2H), 3.53 (s, 2H), 3.01-2.84 (m, 4H), 2.54 (s, 3H), 2.15 (s, 3H), 1.84-1.74 (m, 6H), 1.52-1.42 (m, 6H), 1.17 (t, J = 7.3 Hz, 3H). MS (ES+): 491.4 (M + 1)+. | See Example 6 Replace HG1 with HG12 |

TABLE 6-continued

Additional Exemplary Compounds

| Compound No. | Structure and Name | Characterization | Synthesis Method |
|---|---|---|---|
| 125 | 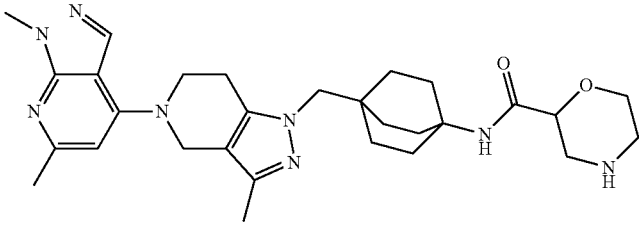<br>N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-2-carboxamide | 1H NMR (400 MHz, Methanol-d4) δ 8.15 (s, 1H), 6.45 (s, 1H), 4.53 (s, 2H), 4.00 (s, 3H), 3.97 (t, J = 5.6 Hz, 2H), 3.90 (dt, J = 11.5, 2.4 Hz, 1H), 3.78 (dd, J = 10.7, 2.8 Hz, 1H), 3.72 (s, 2H), 3.63-3.54 (m, 1H), 3.10 (dd, J = 12.7, 2.8 Hz, 1H), 2.90 (t, J = 5.6 Hz, 2H), 2.78-2.72 (m, 2H), 2.54 (s, 4H), 2.23 (s, 3H), 1.92-1.84 (m, 6H), 1.61-1.54 (m, 6H). MS (ES+): 533.3 (M + 1)+. | See Example 7 Replace dimethyl-glycine with 4-(tert-butoxy-carbonyl)morpholine-2-carboxylic acid |
| 126 | 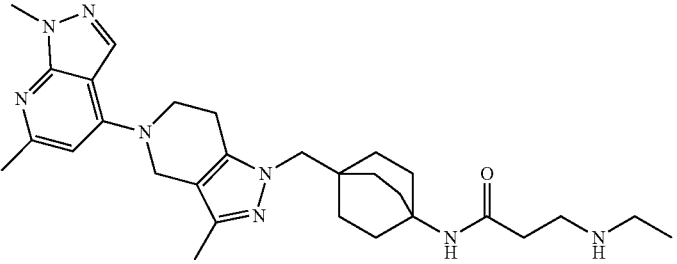<br>N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-3-(ethylamino)propanamide | 1H NMR (400 MHz, Methanol-d4) δ 851 (s, 1H), 6.87 (s, 1H), 5.04-4.93 (m, 1H), 5.03-4.95 (m, 0H), 4.95 (dddd, J = 5.4, 2.7, 2.1, 1.3 Hz, 1H), 4.24 (s, 2H), 4.11 (s, 3H), 3.91 (s, 2H), 3.17 (t, J = 6.6 Hz, 2H), 3.07 (p, J = 7.3, 6.7 Hz, 4H), 2.69 (s, 3H), 2.56 (t, J = 6.6 Hz, 2H), 2.37 (s, 3H), 1.97-1.86 (m, 6H), 1.66-1.53 (m, 6H), 1.30 (t, J = 7.3 Hz, 3H). MS (ES+): 519.3 (M + 1)+. | See Example 7 Replace dimethyl-glycine with 3-(ethylamino)propanoic acid |
| 127 | 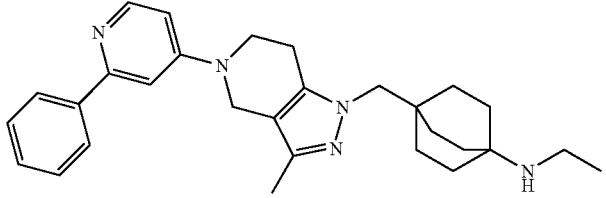<br>N-ethyl-4-((3-methyl-5-(2-phenylpyridin-4-yl)-4,5,6,7-tetrahydro-1H-pyrazolo[4,3-c]pyridin-1-yl)methyl)bicyclo[2.2.2]octan-1-amine | $^1$H NMR (400 MHz, Methanol-d$_4$) δ 8.19 (d, J = 7.4 Hz, 1H), 7.90-7.83 (m, 2H), 7.72-7.59 (m, 3H), 7.48 (s, 1H), 7.32 (d, J = 4.8 Hz, 1H), 4.70 (s, 2H), 4.08 (s, 2H), 3.79 (s, 2H), 3.03-2.88 (m, 4H), 2.25 (s, 3H), 1.84-1.62 (m, 12H), 1.26 (t, J = 7.3 Hz, 3H). MS (ES+): 456.3 (M + 1)+. | See example 6 Replace Compound No. 1 with Compound No. 63 and replace oxetan-3-one with acetaldehyde |
| 128 | 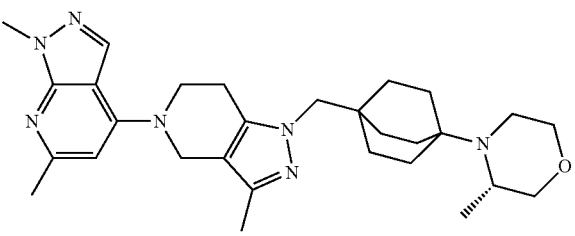<br>(S)-4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-3-methylmorpholine | RT (method 1): 1.27 min. MS (ES+): 505.3 (M + 1)+. | See Example 14 Replace 1-bromo-2-(2-bromoethoxy)ethane with (S)-1-chloro-3-(2-chloroethoxy)-2-methyl-propane |

TABLE 6-continued

Additional Exemplary Compounds

| Compound No. | Structure and Name | Characterization | Synthesis Method |
|---|---|---|---|
| 129 | 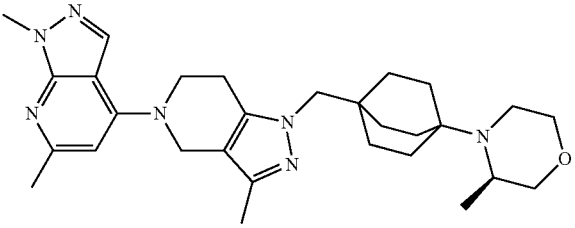<br>(R)-4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-3-methylmorpholine | NMR (DMSO-D$_6$, 400 MHz, $^1$H) δ 8.72 (d, J = 5.2, 1H), 8.16 (d, J = 1.2, 1H), 8.00 (d, J = 2.3, 1H), 7.97 (dd, J = 1.8, 5.2, 1H), 7.93 (s, 3H), 7.84 (dd, J = 2.3, 8.7, 1H), 7.50 (s, 2H), 7.29 (d, J = 8.8, 1H), 3.81 (s, 2H), 1.82-1.55 (m, 12H); ESIMS MS (ES+): 505.3 (M + 1)+. | See Example 14 Replace 1-bromo-2-(2-bromoethoxy)ethane with (R)-1-chloro-3-(2-chloroethoxy)-2-methyl-propane |
| 130 | 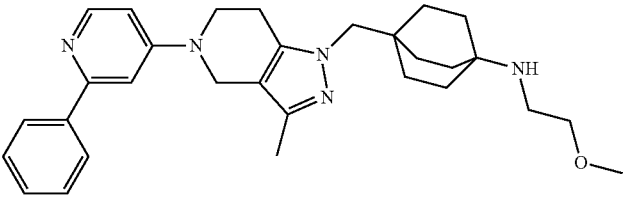<br>N-(2-methoxyethyl)-4-((3-methyl-5-(2-phenylpyridin-4-yl)-4,5,6,7-tetrahydro-1H-pyrazolo[4,3-c]pyridin-1-yl)methyl)bicyclo[2.2.2]octan-1-amine | $^1$H NMR (400 MHz, Methanol-d$_4$) δ 8.19 (d, J = 7.4 Hz, 1H), 7.88-7.83 (m, 2H), 7.68-7.62 (m, 3H), 7.48 (s, 1H), 7.32 (brs, 1H), 4.70 (s, 2H), 4.08 (brs, 2H), 3.79 (s, 2H), 3.58 (t, J = 5.0 Hz, 2H), 3.39 (s, 3H), 3.10 (t, J = 5.5 Hz, 2H), 2.92 (t, J = 5.4 Hz, 2H), 2.25 (s, 3H), 1.86-1.78 (m, 6H), 1.72-1.62 (m, 6H). MS (ES+): 486.4 (M + 1)+. | See example 6 Replace Compound No. 1 with Compound No. 63 and replace oxetan-3-one with 2-methoxy-acetaldehyde |
| 131 | 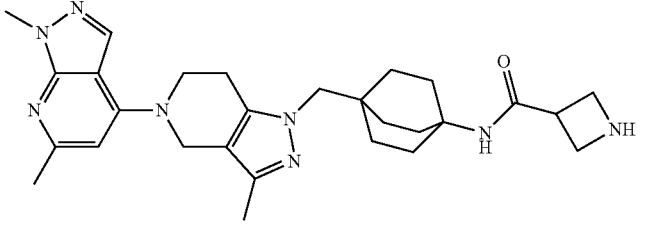<br>N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)azetidine-3-carboxamide | $^1$H NMR (400 MHz, Methanol-d$_4$) δ 8.47 (s, 1H), 6.82 (s, 1H), 4.88 (s, 2H), 4.19 (t, J = 4.8 Hz, 2H), 4.15-4.06 (m, 7H), 3.76 (s, 2H), 3.60-3.50 (m, 1H), 3.00 (t, J = 5.4 Hz, 2H), 2.69 (s, 3H), 2.26 (s, 3H), 1.93-1.84 (m, 6H), 1.63-1.53 (m, 6H). MS (ES+): 503.4 (M + 1)+. | See Example 7 Replace dimethyl-glycine with 1-(tert-butoxy-carbonyl)azetidine-3-carboxylic acid |
| 132 | 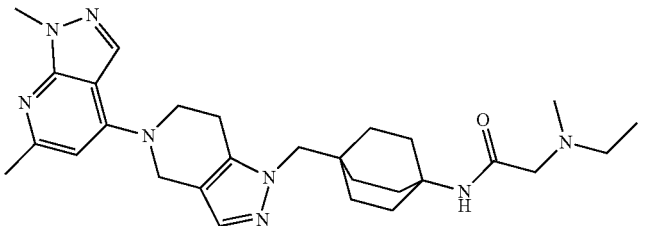<br>N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(ethyl(methyl)amino)acetamide | 1H NMR (400 MHz, Methanol-d4) δ 8.16 (s, 1H), 6.46 (s, 1H), 4.55 (s, 2H), 4.00 (s, 3H), 3.98 (t, J = 5.5 Hz, 2H), 3.73 (s, 2H), 2.91 (t, J = 5.6 Hz, 2H), 2.88 (s, 2H), 2.55 (s, 3H), 2.47 (q, J = 7.2 Hz, 2H), 2.26 (s, 3H), 2.24 (s, 3H), 1.93-1.85 (m, 6H), 1.63-1.55 (m, 6H), 1.05 (t, J = 7.2 Hz, 3H). MS (ES+): 519.3 (M + 1)+. | See Example 7 Replace dimethyl-glycine with N-ethyl-N-methylglycine |

TABLE 6-continued

Additional Exemplary Compounds

| Compound No. | Structure and Name | Characterization | Synthesis Method |
|---|---|---|---|
| 133 | 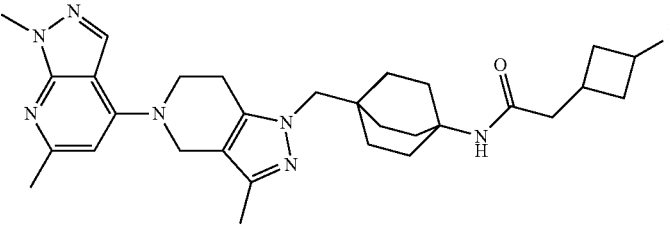<br>N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(3-fluoroazetidin-1-yl)acetamide | RT (method 1): 1.04 min. MS (ES+): 535.3 (M + 1)+. | See Example 29 |
| 134 | 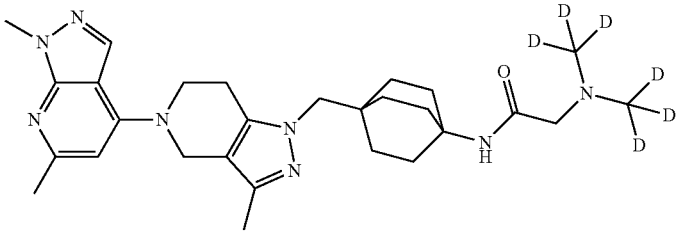<br>2-(bis(trideuteromethyl)amino)-N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)acetamide | 1H NMR (400 MHz, Methanol-d4) δ 8.05 (s, 1H), 6.35 (s, 1H), 4.44 (s, 2H), 3.90 (s, 3H), 3.87 (t, J = 5.6 Hz, 2H), 3.62 (s, 2H), 2.80 (t, J = 5.6 Hz, 2H), 2.73 (s, 2H), 2.44 (s, 3H), 2.13 (s, 3H), 1.82-1.73 (m, 6H), 1.51-1.45 (m, 6H). MS (ES+): 511.3 (M + 1)+. | See Example 7 Replace dimethyl-glycine with N,N-Dimethyl-d6-glycine HCl salt |
| 135 | 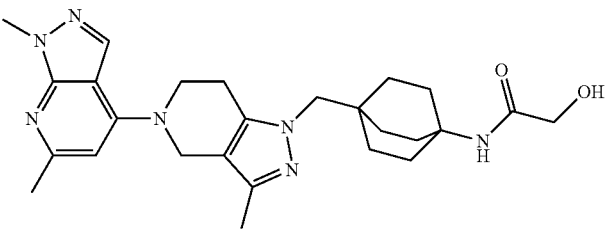<br>N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-hydroxyacetamide | RT (method 1): 1.05 min. MS (ES+): 478.3 (M + 1)+. | See Example 30 |
| 136 | 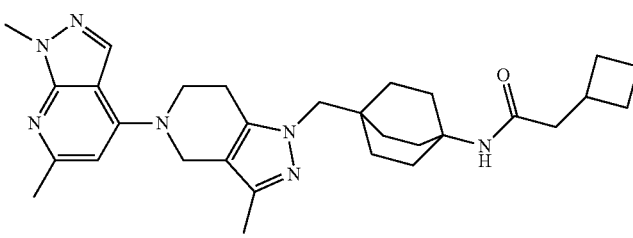<br>N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(3-hydroxyazetidin-1-yl)acetamide | RT (method 1): 0.98 min. MS (ES+): 533.3 (M + 1)+. | See Example 30 |

TABLE 6-continued

Additional Exemplary Compounds

| Compound No. | Structure and Name | Characterization | Synthesis Method |
|---|---|---|---|
| 137 | 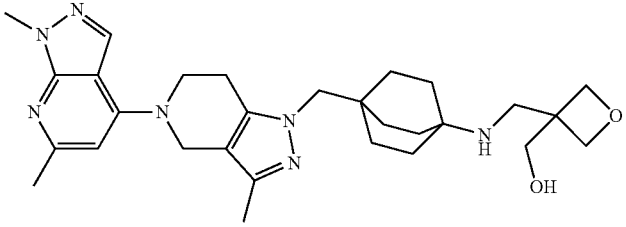<br><br>(3-(((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)methyl)oxetan-3-yl)methanol | $^1$H NMR (400 MHz, Methanol-d$_4$) δ 8.15 (s, 1H), 6.45 (s, 1H), 4.54 (s, 2H), 4.50-4.34 (m, 4H), 4.03-3.94 (m, 5H), 3.76 (s, 2H), 3.73 (s, 2H), 2.96-2.81 (m, 4H), 2.55 (s, 3H), 2.23 (s, 3H), 1.57 (m, 12H). MS (ES+): 520.4 (M + 1)+. | See Example 14 Replace 1-bromo-2-(2-bromoethoxy) ethane with (3-(bromomethyl) oxetan-3-yl)methanol |
| 138 | 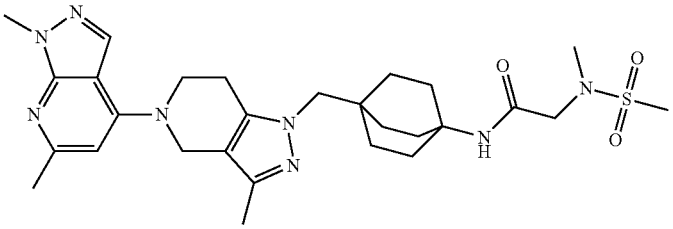<br><br>N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(N-methylmethylsulfonamido)acetamide | 1H NMR (400 MHz, Methanol-d4) δ 8.53 (s, 1H), 6.90 (s, 1H), 4.97 (d, J = 15.5 Hz, 2H), 4.26 (s, 2H), 4.12 (s, 3H), 4.01 (s, 2H), 3.77 (s, 2H), 3.20-3.09 (m, 2H), 2.95 (s, 3H), 2.88 (s, 3H), 2.70 (s, 3H), 2.45 (s, 3H), 1.98-1.88 (m, 6H), 1.62 (dd, J = 10.1, 5.8 Hz, 6H). MS (ES+): 569.2 (M + 1)+. | See Example 18 Replace Compound No. 1 with Compound No. 126 |
| 139 | 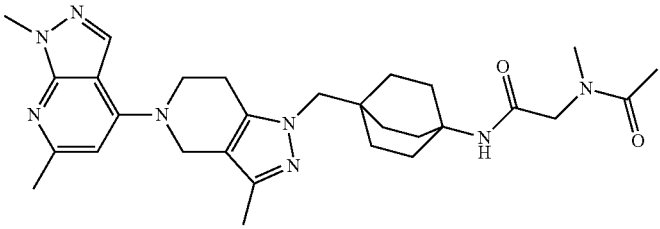<br><br>N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(N-methylacetamido)acetamide | 1H NMR (400 MHz, Methanol-d4) δ 8.54 (s, 1H), 6.91 (s, 1H), 5.07-4.95 (m, 2H), 4.27 (s, 2H), 4.12 (s, 3H), 4.03 (s, 2H), 3.94 (d, J = 14.3 Hz, 2H), 3.16 (q, J = 4.1, 2.9 Hz, 2H), 3.05 (s, 2H), 2.87 (s, 1H), 2.71 (s, 3H), 2.47 (s, 3H), 2.12 (s, 2H), 2.01 (s, 1H), 1.93 (ddd, J = 9.2, 5.5, 2.9 Hz, 6H), 1.62 (dt, J = 11.0, 5.3 Hz, 6H). MS (ES+): 533.3 (M + 1)+. | See Example 7 Replace Compound No. 1 with Compound No. 126 and replace 2-(dimethyl-amino) acetic acid with acetic acid |
| 140 | 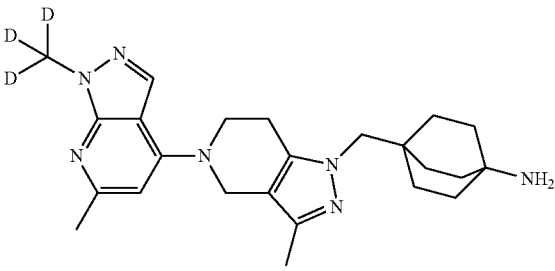<br><br>4-((3-methyl-5-(6-methyl-1-(trideuteromethyl)-1H-pyrazolo[3,4-b]pyridin-4-yl)-4,5,6,7-tetrahydro-1H-pyrazolo[4,3-c]pyridin-1-yl)methyl)bicyclo[2.2.2]octan-1-amine | 1H NMR (400 MHz, Methanol-d4) δ 8.51 (s, 1H), 6.88 (s, 1H), 5.04-4.94 (m, 2H), 4.25 (s, 2H), 3.98 (s, 2H), 3.78-3.56 (m, 2H), 3.11 (d, J = 5.1 Hz, 2H), 2.70 (s, 3H), 2.39 (s, 3H), 1.85-1.66 (m, 12H). MS (ES+): 423.3 (M + 1)+. | See Example 16 |

TABLE 6-continued

Additional Exemplary Compounds

| Compound No. | Structure and Name | Characterization | Synthesis Method |
|---|---|---|---|
| 141 | 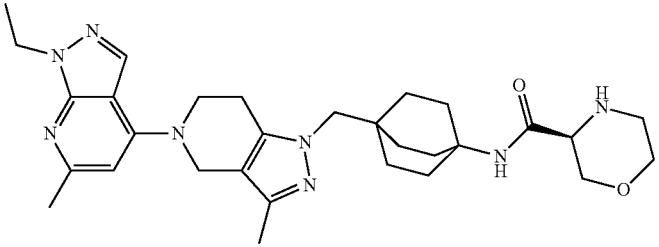<br>(S)-N-(4-((5-(1-ethyl-6-methyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide | $^1$H NMR (400 MHz, Methanol-$d_4$) δ 8.49 (s, 1H), 6.82 (s, 1H), 4.87 (s, 2H), 4.47 (q, J = 7.2 Hz, 2H), 4.22-4.10 (m, 3H), 4.02-3.86 (m, 2H), 33.77-3.53 (m, 4H), 3.31-3.16 (m, 2H), 2.99 (t, J = 5.2 Hz, 2H), 2.67 (s, 3H), 2.25 (s, 3H), 1.93-1.82 (m, 6H), 1.64-1.46 (m, 9H). MS (ES+): 547.4 (M + 1)+. | See Example 8 Replace HG1 with HG13 |
| 142 | 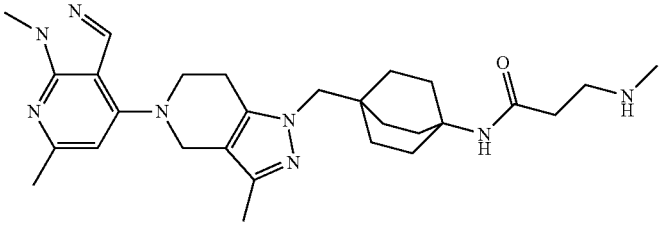<br>N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-3-(methylamino)propanamide | 1H NMR (400 MHz, Methanol-d4) δ 8.53 (s, 1H), 6.90 (s, 1H), 5.06-4.93 (m, 2H), 4.26 (s, 2H), 4.12 (s, 3H), 3.99 (s, 2H), 3.15 (dt, J = 10.7, 5.8 Hz, 4H), 2.69 (d, J = 5.5 Hz, 6H), 2.56 (t, J = 6.4 Hz, 2H), 2.44 (s, 3H), 1.99-1.88 (m, 6H), 1.67-1.56 (m, 6H). MS (ES+): 505.3 (M + 1)+. | See Example 7 Replace dimethyl-glycine with 3-(methylamino) propanoic acid |
| 143 | 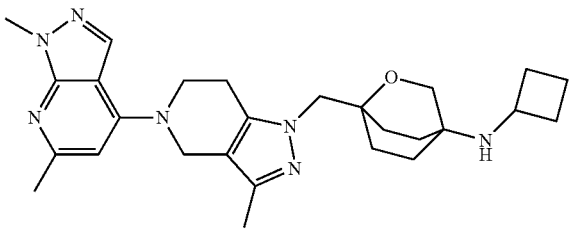<br>N-cyclobutyl-1-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-2-oxabicyclo[2.2.2]octan-4-amine | $^1$H NMR (400 MHz, Methanol-$d_4$) δ 7.96 (s, 1H), 6.27 (s, 1H), 4.36 (s, 2H), 3.84 (s, 3H), 3.72 (m, 2H), 3.64 (m, 2H), 3.41 (s, 2H), 3.14 (m, 1H), 2.80 (m, 2H), 2.36 (s, 3H), 2.04 (s, 3H), 1.69-1.26 (m, 11H). MS (ES+): 476.4 (M + 1)+. | See example 6 Replace Compound No. 1 with Compound No. 81 and replace oxetan-3-one with cyclobutanone |
| 144 | 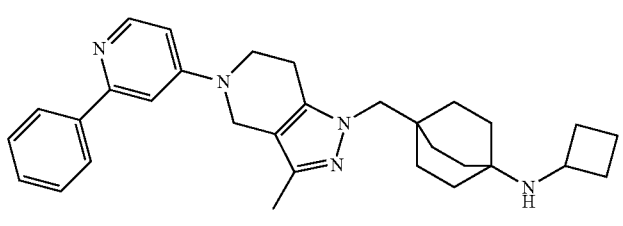<br>N-cyclobutyl-4-((3-methyl-5-(2-phenylpyridin-4-yl)-4,5,6,7-tetrahydro-1H-pyrazolo[4,3-c]pyridin-1-yl)methyl)bicyclo[2.2.2]octan-1-amine | 1H NMR (400 MHz, Methanol-d4) δ 8.22 (d, J = 6.1 Hz, 1H), 7.55 (d, J = 7.0 Hz, 2H), 7.46 (m, 3H), 7.25 (d, J = 2.4 Hz, 1H), 6.92 (dd, J = 6.1, 2.5 Hz, 1H), 4.39 (s, 2H), 3.82 (t, J = 5.5 Hz, 2H), 3.70 (s, 2H), 3.43 (m, 1H), 2.81 (t, J = 5.4 Hz, 2H), 2.23 (s, 3H), 2.11-2.01 (m, 2H), 1.78-1.64 (m, 2H), 1.62-1.51 (m, 2H), 1.54 (m, 12H); MS 482.3 (M + 1), rt = 1.05 min | See example 6 Replace Compound No. 1 with Compound No. 63 and replace oxetan-3-one with cyclobutanone |

TABLE 6-continued

Additional Exemplary Compounds

| Compound No. | Structure and Name | Characterization | Synthesis Method |
|---|---|---|---|
| 145 | 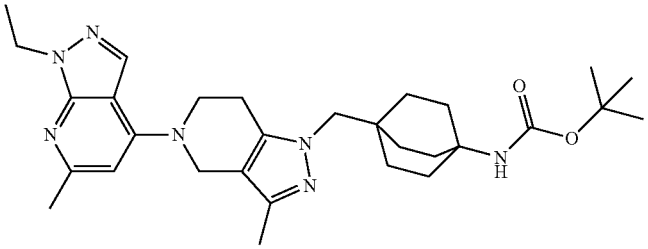<br>tert-butyl (4-((5-(1-ethyl-6-methyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)carbamate | RT (method 2): 2.24 min. MS 535.1 (M + 1) | See Compound No. 157 Product of Step 1 |
| 146 | 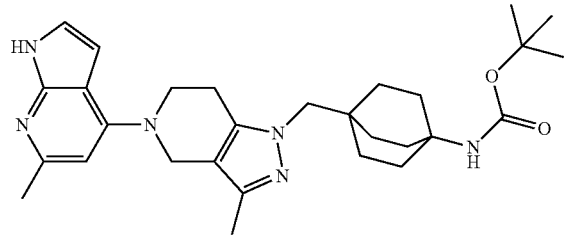<br>tert-butyl (4-((3-methyl-5-(2-methyl-7H-pyrrolo[2,3-d]pyrimidin-4-yl)-4,5,6,7-tetrahydro-1H-pyrazolo[4,3-c]pyridin-1-yl)methyl)bicyclo[2.2.2]octan-1-yl)carbamate | MS (ES+): 507.3 (M + 1)+ | See Example 4 |
| 147 | 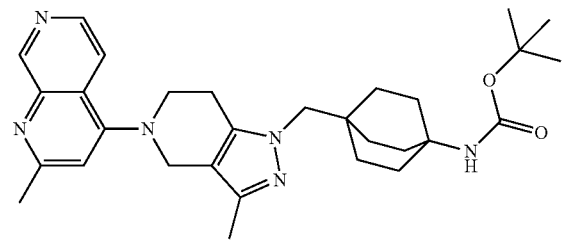<br>tert-butyl (4-((3-methyl-5-(2-methyl-1,7-naphthyridin-4-yl)-4,5,6,7-tetrahydro-1H-pyrazolo[4,3-c]pyridin-1-yl)methyl)bicyclo[2.2.2]octan-1-yl)carbamate | $^1$H NMR (400 MHz, DMSO-$d_6$) δ 9.53 (s, 1H), 8.73 (d, J = 5.9 Hz, 1H), 8.34-7.92 (m, 2H), 7.39 (s, 1H), 4.68 (s, 2H), 4.03 (t, J = 5.2 Hz, 2H), 3.72 (s, 2H), 3.08 (s, 2H), 2.78 (s, 3H), 2.51 (s, 9H), 2.12 (s, 3H), 1.80-1.45 (m, 12H). ESIMS m/z 518.0 (M$^+$ + 1) | See Example 3 |
| 148 | 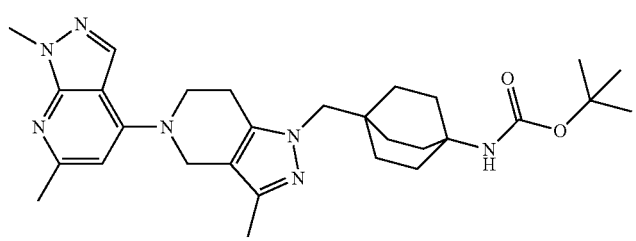<br>tert-butyl (4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.1]heptan-1-yl)carbamate | 1H NMR (600 MHz, Methanol-d4) δ 8.16 (s, 1H), 6.47 (s, 1H), 4.56 (s, 2H), 4.08 (s, 2H), 4.00 (d, J = 4.9 Hz, 5H), 2.92 (t, J = 5.7 Hz, 2H), 2.55 (s, 3H), 2.24 (s, 3H), 1.80 (s, 2H), 1.74-1.59 (m, 7H), 1.40 (s, 10H). MS (ES+): 506.3 (M + 1)+. | See Compound No 44 Product of Step 1 |

TABLE 6-continued

Additional Exemplary Compounds

| Compound No. | Structure and Name | Characterization | Synthesis Method |
|---|---|---|---|
| 149 | 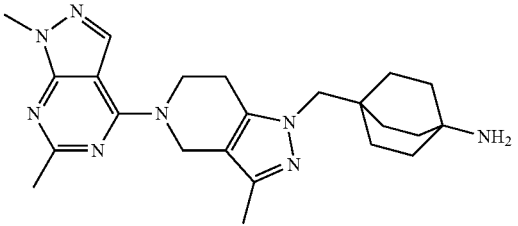<br>4-((5-(1,6-dimethyl-1H-pyrazolo[3,4-d]pyrimidin-4-yl)-3-methyl-4,5,6,7-tetrahydro-1H-pyrazolo[4,3-c]pyridin-1-yl)methyl)bicyclo[2.2.2]octan-1-amine | RT (method 1): 1.78 min. MS (ES+): 421.4 (M + 1)+ | See Example 1 Replace (HG1) in step 1 with (HG17) |
| 150 | 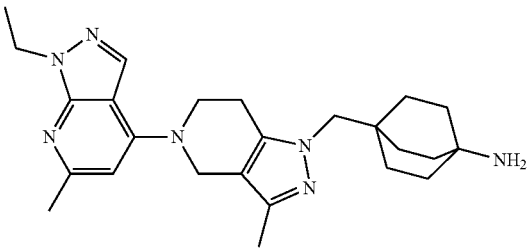<br>4-((5-(1-ethyl-6-methyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine | $^1$H NMR (400 MHz, Methanol-$d_4$) δ 8.39 (s, 1H), 6.71 (s, 1H), 4.37 (q, J = 7.2 Hz, 2H), 4.09 (t, J = 5.1 Hz, 2H), 3.70 (s, 2H), 3.25 (m, 2H), 2.89 (t, J = 5.3 Hz, 2H), 2.56 (s, 3H), 2.15 (s, 3H), 1.78-1.28 (m, 15H). MS (ES+): 434.6 (M + 1)+. | See Example 1 Replace (HG1) in step 1 with (HG14) |

Administration and Pharmaceutical Compositions

For the therapeutic uses of compounds of the invention, such compounds are administered in therapeutically effective amounts either alone or as part of a pharmaceutical composition. Accordingly, the present invention provides a pharmaceutical composition, which comprises a compound of the invention, or pharmaceutically acceptable salt thereof, and one or more pharmaceutically acceptable carriers, diluents, or excipients. For purposes of the present invention, unless designated otherwise, solvates and hydrates are generally considered compositions. Preferably, pharmaceutically acceptable carriers are sterile.

The pharmaceutical composition of the present invention can be in unit dosage of about 1-1000 mg of active ingredient(s) for a subject of about 50-70 kg. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg. The activity of a compound according to the present invention can be assessed by the following in vitro & in vivo methods.

The pharmaceutical compositions of the invention can be prepared using processes which include admixing a compound of the invention, or pharmaceutically acceptable salts thereof, with one or more pharmaceutically acceptable carriers, diluents or excipients. By way of example, the pharmaceutical compositions of the inventions are manufactured by mixing, granulating and/or coating methods using a compound of the invention in free form, or in a pharmaceutically acceptable salt form, in association with at least one pharmaceutically acceptable carrier, diluent or excipient.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention will decompose. Such agents, which are referred to herein as "stabilizers," include, but are not limited to, antioxidants such as ascorbic acid, pH buffers, or salt buffers, etc.

The pharmaceutical composition can be formulated for particular routes of administration such as oral administration, rectal administration, transdermal administration, parenteral, intravenous administration, intramuscular administration, pulmonary administration, inhalation administration, intranasal administration, ophthalmic administration and topical administration.

Oral Administration Dosage Forms

The pharmaceutical compositions of the invention can be administered orally as discrete dosage forms, wherein such dosage forms include, but are not limited to, capsules, gelatin capsules, caplets, tablets, chewable tablets, lozenges, dispersible powders, granules, syrups, flavored syrups, solutions or suspensions in aqueous or non-aqueous liquids, edible foams or whips, and oil-in-water liquid emulsions or water-in-oil liquid emulsions.

Accordingly, for oral administration the pharmaceutical compositions of the invention comprising an effective amount of a compound of the invention can be made up in a solid form (including without limitation capsules, gelatin capsules, hard or soft capsules, tablets, chewable tablets, lozenges, caplets, pills, granules or dispersible powders), or in a liquid form (including without limitation solutions, aqueous or oily suspensions, syrups, elixirs, foams, whips or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations.

Typically, the pharmaceutical compositions are tablets or gelatin capsules comprising the active ingredient together with one or more of:
 a) diluents, e.g., lactose, dextrose, sucrose, mannitol, sorbitol, cellulose and/or glycine;
 b) lubricants, e.g., silica, talcum, stearic acid, its magnesium or calcium salt and/or polyethyleneglycol; for tablets also
 c) binders, e.g., magnesium aluminum silicate, starch paste, gelatin, tragacanth, methylcellulose, sodium carboxymethylcellulose and/or polyvinylpyrrolidone; if desired
 d) disintegrants, e.g., starches, agar, alginic acid or its sodium salt, or effervescent mixtures; and
 e) absorbents, colorants, flavors and sweeteners.

Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. Tablets may be either film coated or enteric coated according to methods known in the art. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Parenteral Dosage Forms

In certain embodiments pharmaceutical compositions of the invention are administered parenterally by various routes including, but not limited to, subcutaneous, intravenous (including bolus injection), intramuscular, and intraarterial.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Topical Dosage Forms

In certain embodiments pharmaceutical compositions of the invention are administered by topical application of a pharmaceutical composition containing a compound of the invention in the form of a lotion, gel, ointment, solution, emulsion, suspension or cream.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

Rectal Administration

In certain embodiments pharmaceutical compositions of the invention of the invention are administered rectally in the form of suppositories, enemas, ointment, creams rectal foams or rectal gels. In certain embodiments such suppositories are prepared from fatty emulsions or suspensions, cocoa butter or other glycerides.

Depot Administration

In certain embodiments pharmaceutical compositions of the invention of the invention are formulated as a depot preparation. Such formulations are administered by implantation (for example subcutaneously or intramuscularly) or by intramuscular injection. In certain embodiments, such formulations include polymeric or hydrophobic materials (for example, as an emulsion in an acceptable oil) or ion exchange resins, or as sparingly soluble derivatives, for example, as a sparingly soluble salt.

Combination Treatment

Compounds of the invention and pharmaceutical compositions provided herein are administered singly or in combination with one or more additional therapeutic agents.

The combination of the present invention can be in unit dosage of about 1-1000 mg of active ingredient(s) for a subject of about 50-70 kg. The therapeutically effective dosage of the combinations is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg. The activity of a compound according to the present invention can be assessed by the following in vitro & in vivo methods.

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

The invention provides a pharmaceutical composition comprising a compound of Formula (A), Formula (I), Formula (II), Formula (Ia to Ip) or Formula (IIa to IIk), and another therapeutic agent(s). Optionally, the pharmaceutical composition may comprise a pharmaceutically acceptable carrier, as described above.

The invention provides a product comprising a compound of Formula (A), Formula (I), Formula (II), Formula (Ia to Ip) or Formula (IIa to IIk), and at least one other therapeutic agent as a combined preparation for simultaneous, separate or sequential use in therapy. In one embodiment, the therapy is the treatment of an autoimmune disease or condition mediated by activity of an endosomal Toll-like receptor (e.g. TLR7, TLR8 or TLR9), or any combinations thereof (including, but not limited to, TLR7/8, TLR7/8/9, TLR7/9, and TLR8/9). Products provided as a combined preparation include a composition comprising the compound of Formula (A), Formula (I), Formula (II), Formula (Ia to Ip) or Formula (IIa to IIk) and the other therapeutic agent(s) together in the same pharmaceutical composition, or the compound of Formula (A), Formula (I), Formula (II), Formula (Ia to Ip) or Formula (IIa to IIk) and the other therapeutic agent(s) in separate form, e.g. in the form of a kit.

In an embodiment, the invention provides a product comprising a compound of Formula (A), Formula (I), Formula (II), Formula (Ia to Ip) or Formula (IIa to IIk), and at least one other therapeutic agent as a combined preparation for simultaneous, separate or sequential use in therapy. In one embodiment, the therapy is the treatment of an autoimmune disease or condition mediated by TLR7, TLR7 and TLR8 or TLR7, TLR8 and TLR9 activity. Products provided as a combined preparation include a composition comprising the compound of Formula (A), Formula (I), Formula (II), Formula (Ia to Ip) or Formula (IIa to IIk) and the other therapeutic agent(s) together in the same pharmaceutical composition, or the compound of Formula (A), Formula (I), Formula (II), Formula (Ia to Ip) or Formula (IIa to IIk) and the other therapeutic agent(s) in separate form, e.g. in the form of a kit.

The invention provides a product comprising a compound of Formula (A), Formula (I), Formula (II), Formula (Ia to Ip) or Formula (IIa to IIk), and at least one other therapeutic agent as a combined preparation for simultaneous, separate or sequential use in therapy. In one embodiment, the therapy is the treatment of an autoimmune disease or condition mediated by activity of an endosomal Toll-like receptor (e.g. TLR7, TLR8 or TLR9) pathway, or any combinations thereof. Products provided as a combined preparation include a composition comprising the compound of Formula (A), Formula (I), Formula (II), Formula (Ia to Ip) or Formula (IIa to IIk) and the other therapeutic agent(s) together in the same pharmaceutical composition, or the compound of Formula (A), Formula (I), Formula (II), Formula (Ia to Ip) or Formula (IIa to IIk) and the other therapeutic agent(s) in separate form, e.g. in the form of a kit.

In one embodiment, the invention provides a kit comprising two or more separate pharmaceutical compositions, at least one of which contains a compound of Formula (A), Formula (I), Formula (II), Formula (Ia to Ip) or Formula (IIa to IIk). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

In certain embodiments of the combination therapies described herein, the compound of the invention and the additional therapeutics agent(s) act additively. In certain embodiments of the combination therapies described herein, the compound of the invention and the additional therapeutics agent(s) act synergistically.

The additional therapeutic agents used in combination with a compound of the invention, include, but are not limited to anti-inflammatory agents, immunomodulatory agents, immunosuppressive agents, cytokines, nonsteroidal anti-inflammatory drugs (NSAIDs), antimalarial compounds, anti-rheumatic compounds, inhibitors of B-cell activating factor (BAFF), inhibitors of B-lymphocyte stimulator (BLyS), and steroid hormones.

Nonsteroidal anti-inflammatory drugs (NSAIDs) used in combination with compounds of the invention, include, but are not limited to, salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide.

Anti-rheumatic compound used in combination with compounds of the invention, include, but are not limited to, methotrexate.

Antimalarial compound used in combination with compounds of the invention, include, but are not limited to, chloroquine and hydroxycloroquine.

Inhibitors of B-cell activating factor (BAFF), also known as inhibitors of B-lymphocyte stimulator (BLyS), used in combination with compounds of the invention, include, but are not limited to, belimumab (Benlysta®), Blisibimod and BR3-Fc.

Immunosuppressive agents used in combination with compounds of the invention, include, but are not limited to, mycophenolate mofetil (MMF), mycophenolic acid, cyclophosphamide, azathioprine and Laquinimod (5-chloro-N-ethyl-4-hydroxy-1-methyl-2-oxo-N-phenyl-1,2-dihydroquinoline-3-carboxamide).

Steroid hormones used in combination with compounds of the invention, include, but are not limited to, dehydroepiandrosterone (DHEA).

Certain aspects of the pharmaceutical compositions and combinations of the invention are provided in the following listing of additional, enumerated embodiments. It will be recognized that features specified in each embodiment may be combined with other specified features to provide further embodiments of the present invention.

Embodiment 93

A pharmaceutical composition comprising a compound of Formula (A), Formula (I), Formula (II), Formula (Ia to Ip) or Formula (IIa to IIk), or a pharmaceutically acceptable salt thereof, and a pharmaceutically acceptable carrier.

Embodiment 94

A pharmaceutical composition comprising a compound of Formula (I) or Formula (Ia to Ip), or a pharmaceutically acceptable salt thereof, and a pharmaceutically acceptable carrier.

Embodiment 95

A pharmaceutical composition comprising a compound of Formula (II) or Formula (IIa to IIk), or a pharmaceutically acceptable salt thereof, and a pharmaceutically acceptable carrier.

Embodiment 96

A pharmaceutical composition comprising a compound of Formula (A), or a pharmaceutically acceptable salt thereof, and a pharmaceutically acceptable carrier.

Embodiment 97

A pharmaceutical composition comprising a therapeutically effective amount of a compound of Formula (A), Formula (I), Formula (II), Formula (Ia to Ip) or Formula (IIa to IIk), or a pharmaceutically acceptable salt thereof, and a pharmaceutically acceptable carrier.

Embodiment 98

A pharmaceutical composition comprising a therapeutically effective amount of a compound of Formula (I) or Formula (Ia to Ip), or a pharmaceutically acceptable salt thereof, and a pharmaceutically acceptable carrier.

Embodiment 99

A pharmaceutical composition comprising a therapeutically effective amount of a compound of Formula (II) or Formula (IIa to IIk), or a pharmaceutically acceptable salt thereof, and a pharmaceutically acceptable carrier.

Embodiment 100

A pharmaceutical composition comprising a therapeutically effective amount of a compound of Formula (A), or a pharmaceutically acceptable salt thereof, and a pharmaceutically acceptable carrier.

Embodiment 101

The pharmaceutical composition of the invention further comprising one or more additional therapeutically agents independently selected from anti-inflammatory agents, immunomodulatory agents, immunosuppressive agents, cytokines, nonsteroidal anti-inflammatory drugs (NSAIDs), antimalarial compounds, anti-rheumatic compounds, inhibitors of B-cell activating factor (BAFF), inhibitors of B-lymphocyte stimulator (BLyS), and steroid hormones.

Embodiment 102

A combination comprising a therapeutically effect amount of a compound of Formula (A), Formula (I), Formula (II), Formula (Ia to Ip) or Formula (IIa to IIk), or a pharmaceutically acceptable salt thereof, and one or more additional therapeutically agents and optionally further comprising a pharmaceutically acceptable carrier, wherein the additional therapeutically agent is independently selected from anti-inflammatory agents, immunomodulatory agents, immunosuppressive agents, cytokines, nonsteroidal anti-inflammatory drugs (NSAIDs), antimalarial compounds, anti-rheumatic compounds, inhibitors of B-cell activating factor (BAFF), inhibitors of B-lymphocyte stimulator (BLyS), and steroid hormones.

Pharmacology and Utility

Compounds of the invention are generally inhibitors of an endosomal Toll-like receptor (e.g. TLR7, TLR8 or TLR9), or any combinations thereof (including, but not limited to, TLR7/8, TLR7/8/9, TLR7/9, and TLR8/9), and may therefore be useful in the treatment of autoimmune diseases associated with the activity of an endosomal Toll-like receptor (e.g. TLR7, TLR8 or TLR9), or any combinations thereof (including, but not limited to, TLR7/8, TLR7/8/9, TLR7/9, and TLR8/9). Accordingly, compounds of the invention may be useful in the treatment of autoimmune diseases, including systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis.

Compounds of the invention are typically inhibitors of TLR7, TLR7 and TLR8, or TLR7 and TLR8 and TLR9, and may therefore useful in the treatment of autoimmune diseases associated with TLR7 activity, TLR7 and TLR8 activity, or TLR7 and TLR8 and TLR9 activity. Accordingly, compounds of the invention may be useful in the treatment of autoimmune diseases, including systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis.

In addition, compounds of the invention are generally inhibitors of an endosomal Toll-like receptor (e.g. TLR7, TLR8 or TLR9) pathway, or any combinations thereof, and may therefore be useful in the treatment of autoimmune diseases associated with the activity of an endosomal Toll-like receptor (e.g. TLR7, TLR8 or TLR9) pathway, or any combinations thereof. Accordingly, compounds of the invention may be useful in the treatment of autoimmune diseases, including systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis.

The compounds of the invention, in free form or in pharmaceutically acceptable salt form, exhibit valuable pharmacological properties, e.g. as indicated in vitro and in vivo tests as provided herein, and are therefore indicated for therapy or for use as research chemicals, e.g. as tool compounds.

Thus, as a further embodiment, the present invention provides the use of a compound of the invention in therapy, wherein the therapy is the treatment of an autoimmune disease which may be treated by inhibition of an endosomal Toll-like receptor (e.g. TLR7, TLR8 or TLR9), or any combinations thereof (including, but not limited to, TLR7/8, TLR7/8/9, TLR7/9, and TLR8/9). In another embodiment, the autoimmune disease is systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis.

In a further embodiment, the therapy is the treatment of an autoimmune disease which may be treated by inhibition of TLR7, TLR7 and TLR8, or TLR7 and TLR8 and TLR9. In another embodiment, the autoimmune disease is systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis.

A further embodiment, the present invention provides the use of a compound of the invention in therapy, wherein the therapy is the treatment of an autoimmune disease which may be treated by inhibition of an endosomal Toll-like receptor (e.g. TLR7, TLR8 or TLR9) pathway, and any combinations thereof. In another embodiment, the autoimmune disease is selected from an autoimmune disease like systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis.

In another embodiment, the invention provides a method of treating an autoimmune disease which is treated by inhibition of an endosomal Toll-like receptor (e.g. TLR7, TLR8 or TLR9), or any combinations thereof (including, but not limited to, TLR7/8, TLR7/8/9, TLR7/9, and TLR8/9), wherein the method comprises administration of a therapeutically acceptable amount of a compound of Formula (A), Formula (I), Formula (II), Formula (Ia to Ip) or Formula (IIa to IIk). In a further embodiment, the autoimmune disease is systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis.

In another embodiment, the invention provides a method of treating an autoimmune disease which is treated by inhibition of TLR7, TLR7 and TLR8 or TLR7 and TLR8 and TLR9, wherein the method comprises administration of a therapeutically acceptable amount of a compound of Formula (A), Formula (I), Formula (II), Formula (Ia to Ip) or Formula (IIa to IIk). In a further embodiment, the autoimmune disease is systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis.

In another embodiment, the invention provides a method of treating an autoimmune disease which is treated by inhibition of an endosomal Toll-like receptor (e.g. TLR7, TLR8 or TLR9) pathway, or any combinations thereof, wherein the method comprises administration of a therapeutically acceptable amount of a compound of Formula (A), Formula (I), Formula (II), Formula (Ia to Ip) or Formula (IIa to IIk). In a further embodiment, the autoimmune disease is systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis.

Thus, as a further embodiment, the present invention provides the use of a compound of Formula (A), Formula (I), Formula (II), Formula (Ia to Ip) or Formula (IIa to IIk) in the manufacture of a medicament for the treatment of an autoimmune disease associated the activity of an endosomal Toll-like receptor (e.g. TLR7, TLR8 or TLR9), or any combinations thereof (including, but not limited to, TLR7/8, TLR7/8/9, TLR7/9, and TLR8/9). In another embodiment, the autoimmune disease is systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis.

In a further embodiment, the present invention provides the use of a compound of Formula (A), Formula (I), Formula (II), Formula (Ia to Ip) or Formula (IIa to IIk) in the manufacture of a medicament for the treatment of an autoimmune disease associated with the activity of TLR7, TLR7 and TLR8 or TLR7 and TLR8 and TLR9. In another embodiment, the autoimmune disease is systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis.

As a further embodiment, the present invention provides the use of a compound of Formula (A), Formula (I), Formula (II), Formula (Ia to Ip) or Formula (IIa to IIk) in the manufacture of a medicament for the treatment of an autoimmune disease associated the activity of an endosomal Toll-like receptor (e.g. TLR7, TLR8 or TLR9) pathway, or any combinations. In another embodiment, the autoimmune disease is systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis.

Certain aspects of the uses of the compounds of the invention and of the methods of treatment of the invention are provided in the following listing of additional, enumerated embodiments. It will be recognized that features specified in each embodiment may be combined with other specified features to provide further embodiments of the present invention.

Embodiment 103

A method for treating an autoimmune disease associated with the activity of an endosomal Toll-like receptor (e.g. TLR7, TLR8 or TLR9), or any combinations thereof (including, but not limited to, TLR7/8, TLR7/8/9, TLR7/9, and TLR8/9), wherein the method includes administering to a subject in need of such treatment an effective amount of a compound of Formula (A), Formula (I), Formula (II), Formula (Ia to Ip) or Formula (IIa to IIk), or pharmaceutically acceptable salt thereof, thereby treating the disease.

Embodiment 104

A method for treating an autoimmune associated with the activity of an endosomal Toll-like receptor (e.g. TLR7, TLR8 or TLR9), or any combinations thereof (including, but not limited to, TLR7/8, TLR7/8/9, TLR7/9, and TLR8/9), wherein the method includes administering to a subject in need of such treatment an effective amount of a compound of Formula (A), Formula (I), Formula (II), Formula (Ia to Ip) or Formula (IIa to IIk), or pharmaceutically acceptable salt thereof and wherein the autoimmune disease is systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis.

Embodiment 105

A method for treating an autoimmune disease associated with the activity of an endosomal Toll-like receptor (e.g. TLR7, TLR8 or TLR9) pathway, or any combinations thereof, wherein the method includes administering to a subject in need of such treatment an effective amount of a compound of Formula (A), Formula (I), Formula (II), Formula (Ia to Ip) or Formula (IIa to IIk), or pharmaceutically acceptable salt thereof, thereby treating the disease.

Embodiment 106

A method for treating an autoimmune disease associated with the activity of an endosomal Toll-like receptor (e.g. TLR7, TLR8 or TLR9) pathway, or any combinations thereof, wherein the method includes administering to a subject in need of such treatment an effective amount of a compound of Formula (A), Formula (I), Formula (II), Formula (Ia to Ip) or Formula (IIa to IIk), or pharmaceutically acceptable salt thereof and wherein the autoimmune is systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis.

Embodiment 107

A method for treating an autoimmune disease associated with
i) TLR7 activity, or
ii) TLR7 activity and TLR8 activity, or
iii) TLR7 activity and TLR8 activity and TLR9 activity, wherein the method includes administering to a subject in need of such treatment an effective amount of a compound of Formula (A), Formula (I), Formula (II), Formula (Ia to Ip) or Formula (IIa to IIk), or pharmaceutically acceptable salt thereof, thereby treating the disease.

Embodiment 108

A method for treating an autoimmune disease associated with
i) TLR7 activity, or
ii) TLR7 activity and TLR8 activity, or
iii) TLR7 activity and TLR8 activity and TLR9 activity, wherein the method includes administering to a subject in need of such treatment an effective amount of a compound of Formula (A), Formula (I), Formula (II), Formula (Ia to Ip) or Formula (IIa to IIk), or pharmaceutically acceptable salt thereof, and wherein the autoimmune disease is systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis.

Embodiment 109

A compound of Formula (A), Formula (I), Formula (II), Formula (Ia to Ip) or Formula (IIa to IIk), or pharmaceutically acceptable salt thereof, for treating an autoimmune disease associated with the activity of an endosomal Toll-like receptor (e.g. TLR7, TLR8 or TLR9), or any combinations thereof (including, but not limited to, TLR7/8, TLR7/8/9, TLR7/9, and TLR8/9.

Embodiment 110

A compound of Formula (A), Formula (I), Formula (II), Formula (Ia to Ip) or Formula (IIa to IIk), or pharmaceutically acceptable salt thereof, for treating an autoimmune disease associated with the activity of an endosomal Toll-

Embodiment 111

A compound of Formula (A), Formula (I), Formula (II), Formula (Ia to Ip) or Formula (IIa to IIk), or pharmaceutically acceptable salt thereof, for treating an autoimmune disease associated with the activity of an endosomal Toll-like receptor (e.g. TLR7, TLR8 or TLR9) pathway, or any combinations thereof.

Embodiment 112

A compound of Formula (A), Formula (I), Formula (II), Formula (Ia to Ip) or Formula (IIa to IIk), or pharmaceutically acceptable salt thereof, for treating an autoimmune disease associated with the activity of an endosomal Toll-like receptor (e.g. TLR7, TLR8 or TLR9) pathway, or any combinations thereof, wherein the autoimmune disease is systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis.

Embodiment 113

A compound of Formula (A), Formula (I), Formula (II), Formula (Ia to Ip) or Formula (IIa to IIk), or pharmaceutically acceptable salt thereof, for treating an autoimmune disease associated with
  i) TLR7 activity, or
  ii) TLR7 activity and TLR8 activity, or
  iii) TLR7 activity and TLR8 activity and TLR9 activity, wherein the autoimmune disease is systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis.

Embodiment 114

A compound of Formula (A), Formula (I), Formula (II), Formula (Ia to Ip) or Formula (IIa to IIk), or pharmaceutically acceptable salt thereof, for use in treating an autoimmune disease associated with the activity of an endosomal Toll-like receptor (e.g. TLR7, TLR8 or TLR9), or any combinations thereof (including, but not limited to, TLR7/8, TLR7/8/9, TLR7/9, and TLR8/9.

Embodiment 115

A compound of Formula (A), Formula (I), Formula (II), Formula (Ia to Ip) or Formula (IIa to IIk), or pharmaceutically acceptable salt thereof, for use in treating an autoimmune disease associated with the activity of an endosomal Toll-like receptor (e.g. TLR7, TLR8 or TLR9), or any combinations thereof (including, but not limited to, TLR7/8, TLR7/8/9, TLR7/9, and TLR8/9), wherein the autoimmune disease is systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis.

Embodiment 116

A compound of Formula (A), Formula (I), Formula (II), Formula (Ia to Ip) or Formula (IIa to IIk), or pharmaceutically acceptable salt thereof, for use in treating an autoimmune disease associated with the activity of an endosomal Toll-like receptor (e.g. TLR7, TLR8 or TLR9) pathway, or any combinations thereof.

Embodiment 117

A compound of Formula (A), Formula (I), Formula (II), Formula (Ia to Ip) or Formula (IIa to IIk), or pharmaceutically acceptable salt thereof, for use in treating an autoimmune disease associated with the activity of an endosomal Toll-like receptor (e.g. TLR7, TLR8 or TLR9) pathway, or any combinations thereof, wherein the autoimmune disease is systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis.

Embodiment 114

A compound of Formula (A), Formula (I), Formula (II), Formula (Ia to Ip) or Formula (IIa to IIk), or pharmaceutically acceptable salt thereof, for use in treating a disease associated with
  i) TLR7 activity, or
  ii) TLR7 activity and TLR8 activity, or
  iii) TLR7 activity and TLR8 activity and TLR9 activity, wherein the disease is an autoimmune disease.

Embodiment 115

Use of a compound of Formula (A), Formula (I), Formula (II), Formula (Ia to Ip) or Formula (IIa to IIk), or pharmaceutically acceptable salt thereof, in the manufacture of a medicament for treating an autoimmune disease where TLR7 activity, TLR7 and TLR8 activity, or TLR7 and TLR8 and TLR9 activity, are implicated.

Embodiment 116

Use of a compound of Formula (A), Formula (I), Formula (II), Formula (Ia to Ip) or Formula (IIa to IIk), or pharmaceutically acceptable salt thereof, in the manufacture of a medicament for treating an autoimmune disease, wherein the autoimmune disease is systemic lupus erythematosus, cutaneous lupus, discoid lupus, mixed connective tissue disease, primary biliary cirrhosis, immune thrombocytopenia purpura, hidradenitis suppurativa, dermatomyositis, polymyositis, Sjögren's syndrome, arthritis, rheumatoid arthritis or psoriasis.

Assays

Compounds of the invention were assayed in the assays described in the following paragraphs.

Test Compound Preparation

Compounds were generally serially diluted (1/3) in DMSO and plated on sterile 384 well tissue culture plates and stored until ready for use. Each ten-point dilution was typically plated in triplicate in parallel rows.

TLR7, TLR8 and TLR9 Antagonist Assays in Human PBMC's

PBMC Isolation

Fresh blood was collected from normal human donors under written informed consent in heparinized syringes on the morning of the assay. The blood was diluted in RPMI-1640 medium and the white blood cells were separated from red blood cells by centrifugation (800 g 15' 0 acceleration, 0 brake) on a Ficoll cushion. Peripheral blood mononuclear cells (PBMCs) were separated from platelets by a series of low-speed centrifugations (1000 RPM 10') in PBS+5% HI-FBS and 1 mM EDTA. Purified PBMCs were re-suspended in assay medium (RPMI-1640 w Glutamax (Invitrogen) supplemented with 5% HI-FBS, 10 mM HEPES, 50 uM β-mercaptoethanol, and 100 mG/L penicillin/streptomycin cocktail). Viable PBMCs were counted on a hemacytometer and kept on ice until ready for plating.

Agonist Treatment Bulk Transfection

A 4× concentration (4 ug/ml or 40 ug/ml for TLR8 or TLR7 assays, respectively) of the TLR7/8 agonist ssRNA40 (IDT) was complexed with 10% DOTAP (Roche) in assay medium for 30 min prior to addition to the PBMC suspension (5 million cells/ml). After addition, the final concentration of ssRNA40 in the TLR7/8 stimulated PBMC suspension was 1 µg/ml for TLR8 assay, and 10 g/mL for the TLR7 assay. The final DOTAP concentration was 2.5%.

Diluted PBMCs (5 million cells/ml) were treated with 4×TLR9 agonist ODN2216 (Invivogen). Final concentration of ODN2216 in TLR9 stimulated PBMC suspension was 0.3 M.

PBMC Plating and Compound Treatment

Agonist stimulated PBMCs were plated on the compound treated 384 well plates at 150,000 cells/well. Un-stimulated PBMCs were plated as controls on each plate. Plating volume was 40 µL per well. DMSO concentration in each well was 0.25%.

A separate plate, without compounds, with titrations of ssRNA40 and ODN2216 was included in every assay to measure agonist response of each donor's PBMC prep. Assay plates were placed in a tissue culture incubator (370C, 5% $CO_2$) for 14-16 hrs. After this incubation, the plates were centrifuged and stored at −20° C. until they were assayed.

IL-6 TR-FRET Assay for TLR8 Activity: 1) Cisbio Human IL-6 kit, 20,000 tests (62TNFPEC), and GNF High-Base TC 384 well plates (cat #789163G) were used;

2) the Anti-TIL-6 Cryptate conjugate and the Anti-IL-6 XL665 conjugate were diluted 1:20 in Reconstitution Buffer;

3) a 1:1 mixture of 3 µl/well Anti-IL-6 Cryptate conjugate and 3 µl/well Anti-IL-6 XL665 conjugate was prepared;

4) 6 µl/well HTRF dilution mastermix was added to 6 µl of transferred supernatant samples in proxiplates;

5) The plates were incubated for 3 hrs at rt in the dark; and 6) the levels of IL-6 production was measured using an Envision plate reader (665 nm (emmission)/590 nm (excitation)) with HTRF settings and ratiometric read-out: (XL665 emission/Eu Cryptate emission)×10,000.

$IFN\alpha_{2b}$ AlphaLISA Assay for TLR7 or TLR9 Activity

After thawing the assay plates, 6 µL of supernatant samples were transferred to a low-volume AlphaPlate 384SW (Perkin-Elmer). The concentration of IFNα in supernatants was measured using the $IFN\alpha_{2b}$ AlphaLISA Assay (Perkin-Elmer: AL297F). 3 µL of IFNα acceptor beads/ biotinylated antibody solution was added first, using laboratory automation. After an hour incubation, 3 µL of streptavidin acceptor bead solution was added. The plates containing this mixture were incubated in the dark for an hour and read on an appropriate plate reader at reading parameters set by the manufacturer. (Envision, EnSpire: Perkin-Elmer).

THP-1 TLR8 Antagonist TNFalpha TR-FRET Assay

Cell-Based Assay:

1) THP-1 cells were cultured in RPMI 1640 with 10% FBS, 10 mM HEPES, 1 mM Sodium Pyruvate, 1% Penicillin-Streptomycin L-glutamine, and 1% Non-Essential Amino Acids;

2) 3 sets of different passages of THP-1 cells in assay media were pooled, counted, and resuspended in the same media as culture media, but with 5% FBS;

3) Cells were diluted to 100,000 cells/well (30 µl/well) and the R848 agonist was diluted to 25 µM in 10 ul/well in media;

4) The cell and agonist dilutions were combined and 40 µl/well were added to 384-well flat bottom Greiner assay plates containing test compounds in DMSO, which were Echo pre-spotted at 50 nL per well with a 8 mM top dose and 10 point 1:3 serial dilutions—10 µM final top dose;

5) The plates were incubated overnight for 18-20 hrs at 37 degrees with 5% $CO_2$;

6) The plates were then centrifuged at 1000 rpm for 2 min at rt;

7) 10 µl/well of supernatants were transferred to 384-well low volume white Greiner proxiplates; and 8) TNFα levels were measured using the TR-FRET assay described below.

TNFalpha TR-FRET Assay:

1) Cisbio Human TNFalpha kit, 20,000 tests (62TNFPEC), and Greiner Bio-One LIA-white TC 384 well small volume plates (cat #784080) were used;

2) the Anti-TNFalpha Cryptate conjugate and the Anti-TNFalpha XL665 conjugate were diluted 1:20 in Reconstitution Buffer;

3) a 1:1 mixture of 5 µl/well Anti-TNFalpha Cryptate conjugate and 5 µl/well Anti-TNFalpha XL665 conjugate was prepared;

4) 10 µl/well HTRF dilution mastermix were added to 10 µl of transferred supernatant samples in proxiplates;

5) The plates were incubated for 3 hrs at rt in the dark; and 6) the levels of TNFalpha production was measured using an Envision plate reader (665 nm (emmission)/590 nm (excitation)).

Various compounds of the invention, in free form or in pharmaceutically acceptable salt form, exhibit pharmacological properties, for example, as indicated by the assay results presented in Table 7. The $IC_{50}$ values are given as the concentration of the test compound in question that provoke a response halfway between the baseline and maximum responses. Dashes (---) in Table 7 mean that no tests were conducted.

TABLE 7

| | Assay Results | | |
|---|---|---|---|
| Compound No. | huPBMC TLR7 Antagonist IFNα Assay $IC_{50}$ (µM) | huPBMC TLR8 Antagonist IL-6 TR-FRET Assay $IC_{50}$ (µM) | huPBMC TLR9 Antagonist IFNα Assay $IC_{50}$ (µM) |
| 1 | 0.025 | 0.236 | 1.519 |
| 2 | 0.038 | >10 | 3.134 |
| 3 | 0.054 | 0.055 | 1.934 |

TABLE 7-continued

Assay Results

| Compound No. | huPBMC TLR7 Antagonist IFNα Assay IC$_{50}$ (μM) | huPBMC TLR8 Antagonist IL-6 TR-FRET Assay IC$_{50}$ (μM) | huPBMC TLR9 Antagonist IFNα Assay IC$_{50}$ (μM) |
|---|---|---|---|
| 4 | — | 0.511 | — |
| 5 | 0.397 | 0.433 | — |
| 6 | 0.019 | 0.135 | 1.386 |
| 7 | — | 0.061 | — |
| 8 | 0.004 | 0.166 | 4.28 |
| 9 | 0.015 | 0.201 | 5.1 |
| 10 | 0.056 | 0.048 | >10 |
| 11 | 0.318 | — | >6.58 |
| 12 | 0.841 | — | >4.96 |
| 13 | 0.042 | 1.348 | 7.75 |
| 14 | 0.241 | — | >9.09 |
| 15 | 0.288 | 0.203 | 1.27 |
| 16 | 0.025 | 0.443 | >10 |
| 17 | 0.258 | 0.199 | >10 |
| 18 | 0.245 | 0.077 | >10 |
| 19 | 0.055 | 0.186 | >10 |
| 20 | 0.025 | 0.031 | >9.38 |
| 21 | 0.024 | 0.036 | >10 |
| 22 | 0.033 | 0.014 | >10 |
| 23 | 0.666 | 0.373 | >10 |
| 24 | 0.201 | 0.01 | >7.38 |
| 25 | 0.565 | 0.017 | >8.08 |
| 26 | 0.644 | 0.289 | >10 |
| 27 | 0.015 | 0.014 | >10 |
| 28 | 0.84 | 0.641 | >10 |
| 29 | 0.073 | 0.016 | >10 |
| 30 | 0.01 | 0.324 | >10 |
| 31 | 0.013 | 0.027 | 2.34 |
| 32 | 0.124 | 0.125 | — |
| 33 | 0.055 | 0.072 | >10 |
| 34 | 0.013 | 0.029 | 5.7 |
| 35 | 0.014 | >10 | >10 |
| 36 | 0.007 | 0.08 | 4.97 |
| 37 | 0.159 | 0.079 | >10 |
| 38 | 0.042 | 0.031 | >10 |
| 39 | 0.06 | 0.119 | >10 |
| 40 | 0.07 | 0.314 | 2.517 |
| 41 | 0.006 | 4.59 | 0.817 |
| 42 | 0.017 | >10 | 0.472 |
| 43 | 0.016 | 0.051 | 0.511 |
| 44 | 0.038 | 0.861 | 1.214 |
| 45 | 0.038 | 0.63 | 2.056 |
| 46 | 0.056 | >10 | >10 |
| 47 | 0.004 | >10 | >10 |
| 48 | 0.013 | >10 | >10 |
| 49 | 0.02 | >10 | 3.95 |
| 50 | 0.006 | 0.308 | 0.376 |
| 51 | 0.007 | >10 | 7.55 |
| 52 | 0.304 | >10 | 4.86 |
| 53 | 0.843 | 1.14 | 1.73 |
| 54 | 0.004 | 0.074 | 0.489 |
| 55 | 0.005 | 0.42 | 1.054 |
| 56 | 0.007 | 0.292 | 0.68 |
| 57 | 0.007 | 0.11 | 0.497 |
| 58 | 0.003 | 0.053 | 0.639 |
| 59 | 0.004 | 0.052 | 2.168 |
| 60 | 1.028 | 0.277 | — |
| 61 | 0.012 | 0.129 | — |
| 62 | — | 0.699 | — |
| 63 | 0.034 | 0.568 | — |
| 64 | 0.004 | 0.115 | 0.443 |
| 65 | — | 2.356 | — |
| 66 | — | 1.13 | — |
| 67 | 0.005 | 0.011 | — |
| 68 | — | 0.155 | — |
| 69 | 0.009 | 0.031 | 0.442 |
| 70 | — | 0.379 | — |
| 71 | 0.005 | 0.014 | 0.488 |
| 72 | 0.037 | 0.102 | 0.815 |
| 73 | — | 0.139 | — |
| 74 | 0.007 | 0.158 | 1.542 |
| 75 | 0.011 | 0.134 | 0.963 |
| 76 | — | 0.201 | — |
| 77 | 0.01 | 0.316 | 0.179 |
| 78 | — | 0.474 | — |
| 79 | 0.004 | 0.136 | 0.064 |
| 80 | 0.002 | 0.466 | 0.249 |
| 81 | — | 0.395 | — |
| 82 | — | 0.486 | — |
| 83 | — | 0.865 | — |
| 84 | 0.302 | 0.831 | 1.836 |
| 85 | 0.046 | 0.224 | 0.569 |
| 86 | 0.081 | 0.048 | 2.741 |
| 87 | — | 1.095 | — |
| 88 | — | 0.715 | — |
| 89 | — | 0.622 | — |
| 90 | — | 1.007 | — |
| 91 | 0.022 | 0.377 | 0.215 |
| 92 | 0.16 | 0.04 | 0.094 |
| 93 | — | 0.983 | — |
| 94 | — | 1.106 | — |
| 95 | — | 0.085 | — |
| 96 | — | 0.775 | — |
| 97 | — | 0.089 | — |
| 98 | — | 0.718 | — |
| 99 | 0.04 | 0.13 | 2.841 |
| 100 | 0.005 | 0.015 | 1.365 |
| 101 | 0.039 | 0.071 | 2.642 |
| 102 | 0.022 | 0.366 | 1.239 |
| 103 | — | 1.421 | — |
| 104 | 0.061 | 0.389 | >10 |
| 105 | 0.014 | 0.027 | 1.63 |
| 106 | 0.063 | 0.168 | 2.661 |
| 107 | 0.011 | 0.006 | 1.71 |
| 108 | 0.021 | 0.044 | 8.64 |
| 109 | 0.012 | 0.016 | 0.515 |
| 110 | 0.007 | 0.016 | 1.901 |
| 111 | 0.028 | 0.039 | 1.409 |
| 112 | 0.024 | 0.056 | 1.186 |
| 113 | 0.053 | 0.016 | 1.407 |
| 114 | 0.01 | 0.015 | 1.554 |
| 115 | 0.01 | 0.245 | >10 |
| 116 | 0.009 | 0.068 | 1.574 |
| 117 | 0.002 | 0.236 | 0.954 |
| 118 | 0.002 | 0.197 | 0.775 |
| 119 | 0.006 | 1.182 | 0.608 |
| 120 | 0.004 | 0.02 | — |
| 121 | 0.005 | 0.039 | 1.438 |
| 122 | — | 0.922 | — |
| 123 | 0.024 | 0.121 | 2.226 |
| 124 | 1.038 | >10 | >10 |
| 125 | 0.004 | 0.043 | 0.909 |
| 126 | 0.02 | 0.153 | 9.53 |
| 127 | 0.259 | 1.428 | 0.545 |
| 128 | 0.006 | 0.013 | 0.792 |
| 129 | 0.008 | 0.012 | 1.055 |
| 130 | 1.327 | 2.832 | 0.672 |
| 131 | 0.003 | 0.361 | >10 |
| 132 | <0.000508 | 0.008 | 0.26 |
| 133 | 0.012 | 0.806 | 1.14 |
| 134 | 0.001 | 0.093 | 0.299 |
| 135 | 0.01 | 8.44 | >10 |
| 136 | 0.006 | 0.178 | 1.169 |
| 137 | 0.072 | 0.068 | 1.279 |
| 138 | 0.006 | 2.792 | — |
| 139 | 0.067 | 3.54 | — |
| 140 | 0.027 | 0.331 | 1.803 |
| 141 | 0.032 | 2.289 | 5.17 |
| 142 | 0.047 | 0.932 | >6.59 |
| 143 | 0.041 | 0.687 | 0.841 |
| 144 | 0.073 | 0.105 | 0.139 |
| 145 | 0.061 | >10 | — |
| 146 | 0.236 | — | — |
| 147 | 0.033 | >10 | 6.24 |

TABLE 7-continued

Assay Results

| Compound No. | huPBMC TLR7 Antagonist IFNα Assay IC$_{50}$ (μM) | huPBMC TLR8 Antagonist IL-6 TR-FRET Assay IC$_{50}$ (μM) | huPBMC TLR9 Antagonist IFNα Assay IC$_{50}$ (μM) |
|---|---|---|---|
| 148 | 0.054 | >10 | >10 |
| 149 | — | 0.695 | — |
| 150 | — | 4.203 | — |

TABLE 8

Assay Results

| Compound No. | THP-1 TLR8 Antagonist TR-FRET Assay IC$_{50}$ (μM) |
|---|---|
| 11 | 8.23 |
| 12 | >10 |
| 14 | >10 |

It is understood that the examples and embodiments described herein are for illustrative purposes only and that various modifications or changes in light thereof will be suggested to persons skilled in the art and are to be included within the spirit and purview of this application and scope of the appended claims.

We claim:

1. A compound having the structure of Formula (A) or a pharmaceutically acceptable salt thereof:

Formula (A)

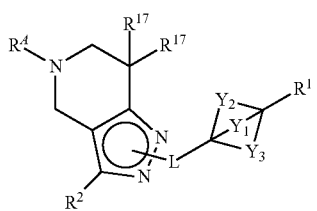

wherein:

$R^4$

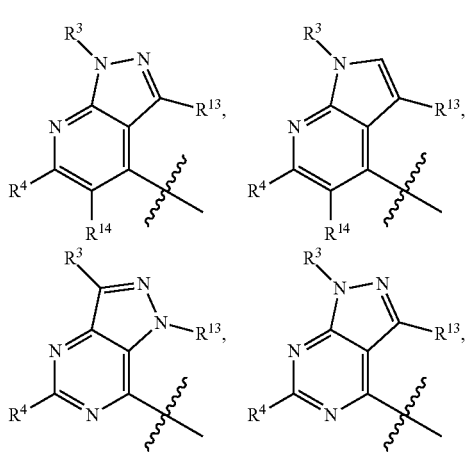

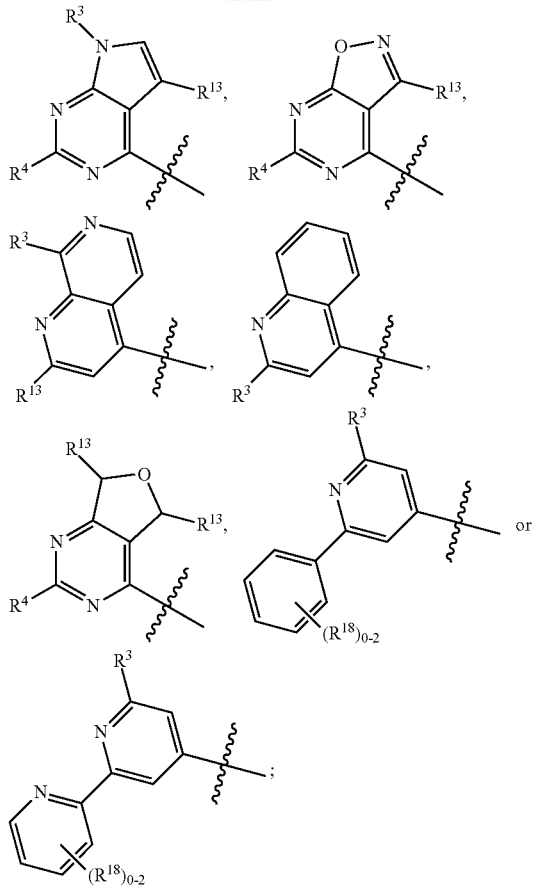

L is —CH$_2$— or —CH$_2$CH$_2$—;
Y$_1$ is —CH$_2$— or —CH$_2$CH$_2$—;
Y$_2$ is —CH$_2$— or —CH$_2$CH$_2$—;
Y$_3$ is —CH$_2$—, —XCH$_2$— or CH$_2$X—;
X is —CH$_2$— or O;
R$^1$ is —NHC(=O)R$^6$, —NHC(=O)(CH$_2$)R$^6$, —NH(CH$_2$)$_n$C(=O)R$^6$, —NHC(=O)(CH$_2$)$_m$NHR$^5$, —NHC(=O)(CH$_2$)$_m$N(R$^5$)$_2$, —NHC(=O)(CHR$^9$)$_m$NHR$^5$, —NHC(=O)(CH$_2$)$_m$NH$_2$, —NHC(=O)(CH$_2$)$_n$OR$^9$, —NHC(=O)OR$^9$, —NH(CH$_2$)$_m$C(=O)N(R$^5$)$_2$, —NH(CHR$^9$)$_n$C(=O)R$^6$, NHC(=O)(CHR$^9$)$_n$R$^6$, —NHC(=O)(CHR$^9$)$_n$N(R$^8$)$_2$, —NHC(=O)(CHR$^9$)$_n$NHR$^8$, —NH(CHR$^9$)$_n$C(=O)N(R$^8$)$_2$, —NH(CHR$^9$)$_m$C(=O)R$^6$, —NHR$^6$, —NR$^5$R$^6$, —NH$_2$, —N(R$^5$)$_2$, —NHR$^5$, —NHR$^8$, —N(R$^6$R$^8$),—NH(C(R$^9$)$_2$)$_n$R$^{10}$, —NR$^9$C(=O)OR$^{11}$, —NH(CH$_2$)$_n$R$^6$, —NH(CHR$^9$)$_n$R$^6$, —N(R$^6$)$_2$, —NHC(=O)(CH$_2$)$_n$N(CD$_3$)$_2$, —NH(CHR$^9$)$_n$CH$_2$OR$^9$, —NHCH$_2$(CHR$^9$)$_n$OR$^9$, —NH(CHR$^9$)$_n$OR$^9$, —NR$^9$(CH$_2$)$_n$OR$^9$, —NHCH$_2$C(R$^9$)$_2$)$_n$OR$^9$, —OR$^9$, —NR$^9$C(=O)R$^5$—NR$^9$C(=O)(CH$_2$)$_n$R$^5$, —NR$^9$C(=O)OR$^5$, —NHS(=O)$_2$R$^5$, —NHC(=O)(CH$_2$)NR$^9$C(=O)R$^5$, —NHC(=O)(CH$_2$)NR$^9$S(=O)$_2$R$^5$,

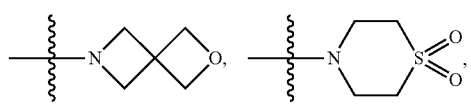 [SMILES: *N1CC2(COC2)C1 ; *N1CCS(=O)(=O)CC1 ; ","]

an 8-oxa-3-azabicyclo[3.2.1]octanyl, a 5-6 membered heteroaryl having 1 to 3 ring members independently selected from N, O and S, or a 4-6 membered heterocycloalkyl having 1 to 2 ring members independently selected from N, NH, $NR^{16}$ and O which is unsubstituted or is substituted with 1-2 $R^7$ groups;

$R^2$ is H, $C_1$-$C_6$alkyl, $C_1$-$C_6$haloalkyl or $C_1$-$C_6$alkyl substituted with 1-2 $R^{15}$ groups;

$R^3$ is H, $C_1$-$C_6$alkyl, —$CD_3$ or benzyl substituted with 1-2 $R^{10}$ groups;

$R^4$ is H, $NH_2$, $C_1$-$C_6$alkyl, halo or a phenyl substituted with 0-2 $R^{18}$ groups;

each $R^5$ is independently selected from $C_1$-$C_6$alkyl, —$CD_3$ and —$(CH_2)_nOR^9$;

$R^6$ is a $C_3$-$C_6$cycloalkyl, an oxa-3-azabicyclo[3.2.1]octane or a 4-6 membered heterocycloalkyl having 1 to 2 ring members independently selected from N, NH, $NR^{16}$ and O which is unsubstituted or is substituted with 1-2 $R^{12}$ groups;

each $R^7$ is independently selected from $C_1$-$C_6$alkyl, halo, hydroxyl, oxo and a $C_1$-$C_6$alkyl substituted with 1 to 3 —OH;

each $R^8$ is independently selected from $C_1$-$C_6$haloalkyl, —$(C(R^9)_2)_nOR^9$ and a $C_1$-$C_6$alkyl substituted with 1 to 3 —OH;

each $R^9$ is independently selected from H and $C_1$-$C_6$alkyl;

$R^{10}$ is $C_1$-$C_6$alkoxy or $C_3$-$C_6$cycloalkyl;

$R^{11}$ is a $C_3$-$C_6$cycloalkyl which is unsubstituted or is substituted with 1 to 3 $C_1$-$C_6$alkyl groups;

each $R^{12}$ is independently selected from $C_1$-$C_6$alkyl, hydroxyl, halo and a $C_1$-$C_6$alkyl substituted with 1 to 3 —OH;

$R^{13}$ is H or $C_1$-$C_6$alkyl;

$R^{14}$ is H or $C_1$-$C_6$alkyl;

$R^{15}$ is —$NHC(=O)(CH_2)_mNHR^5$, —$NHC(=O)(CH_2)_mN(R^5)_2$, —$NHC(=O)(CH_2)_mNH_2$, —$NHC(=O)(CHR^9)_nR^6$, —$NHC(=O)(CHR^9)_nN(R^8)_2$, —$NHC(=O)(CHR^9)_nNHR^8$, —$NH(CHR^9)_nC(=O)N(R^8)_2$, —$NH(CHR^9)_nC(=O)R^6$, —$NHR^6$, —$NH_2$, —$N(R^5)_2$, —$NHR^8$, —$N(R^6R^8)$, —$NH(C(R^9)_2)_nR^{10}$, —$NR^9C(=O)OR^{11}$, —$NH(CHR^9)_nR^6$, —$N(R^6)_2$, —$N(CD_3)_2$, —$NH(CHR^9)_nOR^9$ or —$NHCH_2(C(R^9)_2)_nOR^9$;

each $R^{16}$ is $C_1$-$C_6$alkyl;

each $R^{17}$ is independently selected from H and $C_1$-$C_6$alkyl;

each $R^{18}$ is independently selected from halo, —CN, $C_1$-$C_6$alkoxy and $C_1$-$C_6$alkyl;

m is 1, 2, 3, 4, 5 or 6, and n is 1, 2, 3, 4, 5 or 6.

2. The compound of claim 1 having the structure of Formula (I) or Formula (II), or a pharmaceutically acceptable salt thereof:

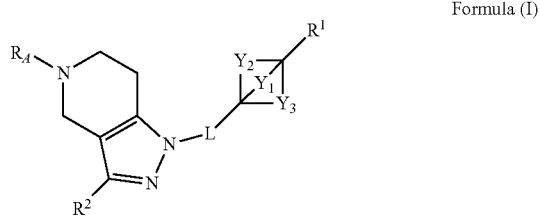

Formula (I)

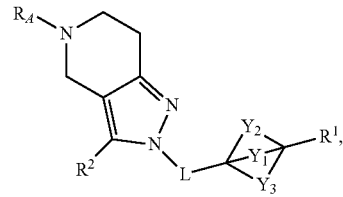

Formula (II)

wherein $Y_1$, $Y_2$, $Y_3$, L, $R^1$, $R^2$ and $R_A$ are as defined in claim 1.

3. The compound of claim 1, wherein the compound of Formula (A) has the structure of Formula (Ia), Formula (Ib), Formula (Ic), Formula (Id), Formula (Ie), Formula (If), Formula (Ig), Formula (Ih), Formula (Ii), Formula (Ij), Formula (Ik), Formula (IIa), Formula (IIb), Formula (IIc), Formula (IId), Formula (IIe), Formula (IIf), Formula (IIg), Formula (IIh), Formula (IIi), Formula (IIj) or Formula (IIk), or a pharmaceutically acceptable salt thereof:

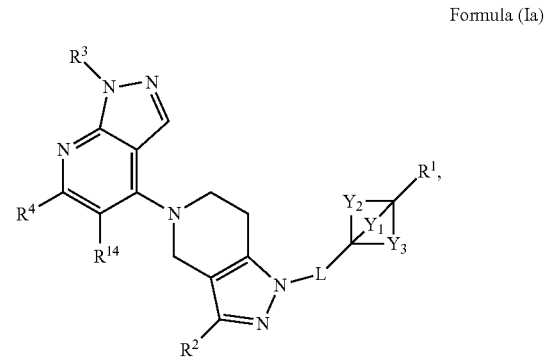

Formula (Ia)

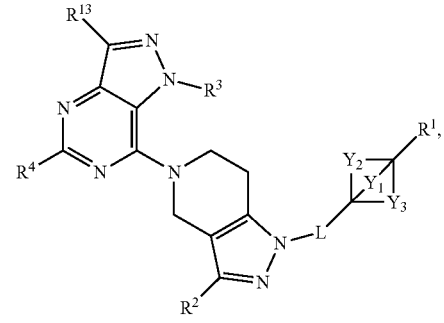

Formula (Ib)

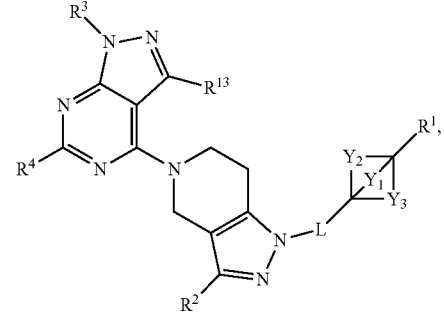

Formula (Ic)

Formula (Id)
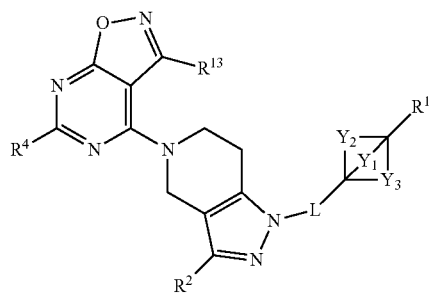
Formula (Ie)
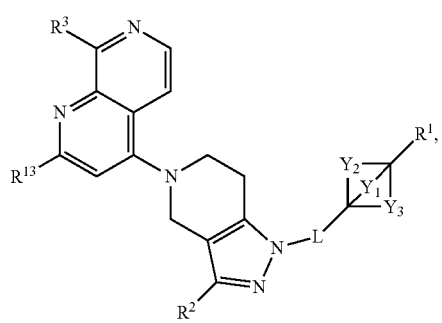
Formula (If)
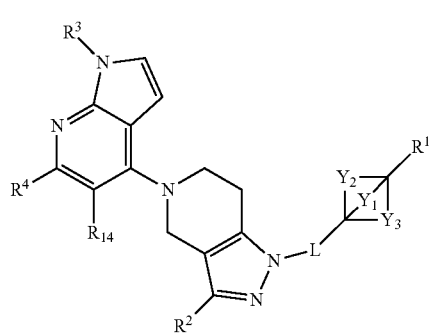
Formula (Ig)
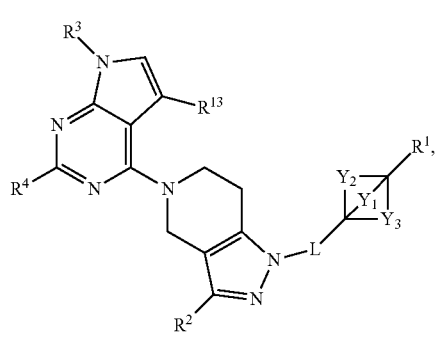
Formula (Ih)
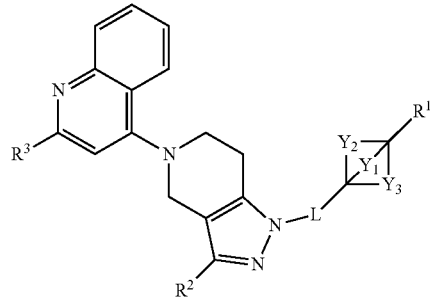
Formula (Ii)
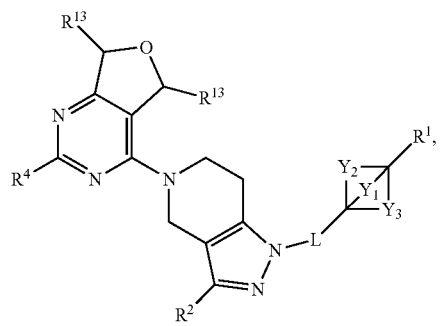
Formula (Ij)
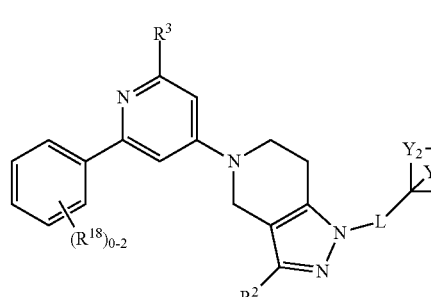
Formula (Ik)
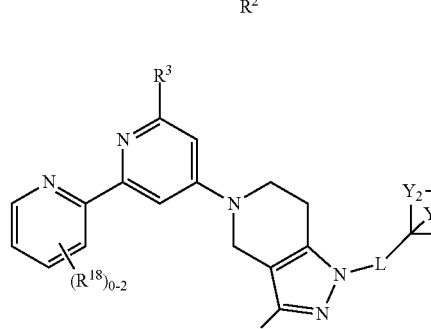
Formula (IIa)
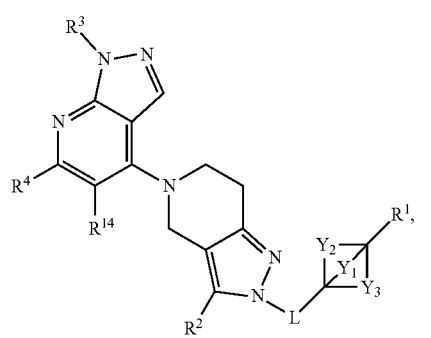

Formula (IIb)
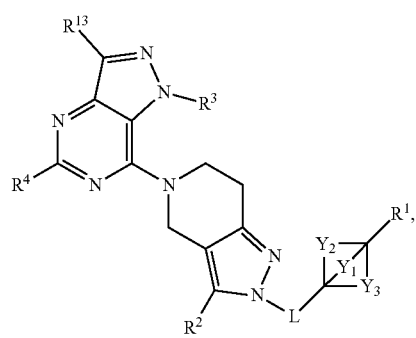
Formula (IIc)
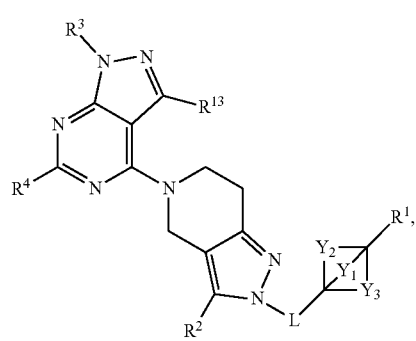
Formula (IId)
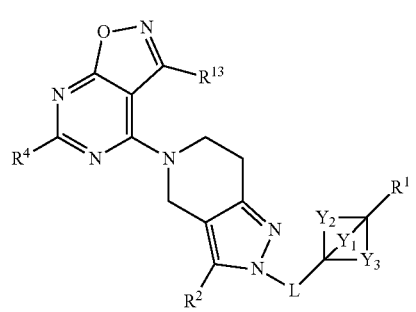
Formula (IIe)
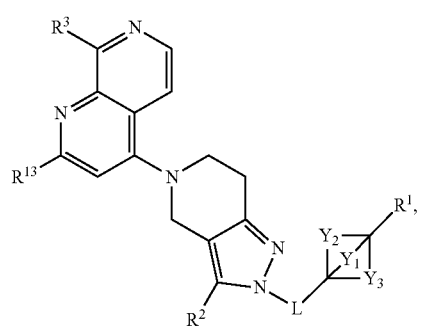
Formula (IIf)
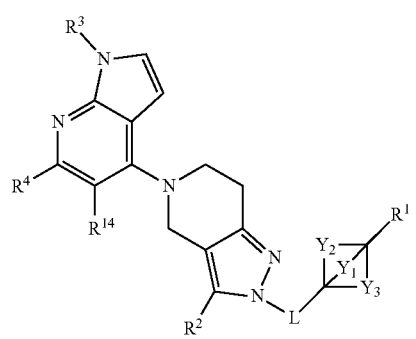
Formula (IIg)
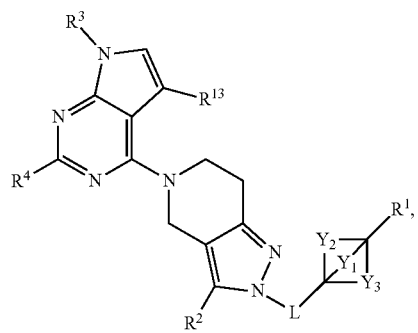
Formula (IIh)
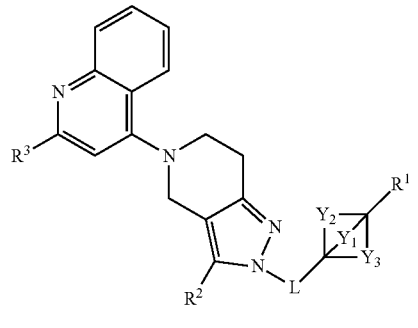
Formula (IIi)
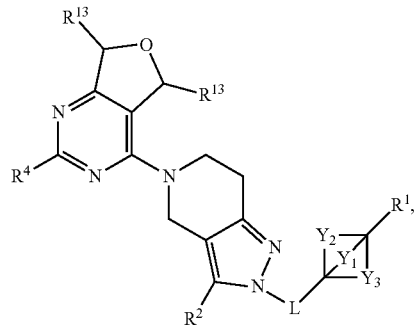
Formula (IIj)
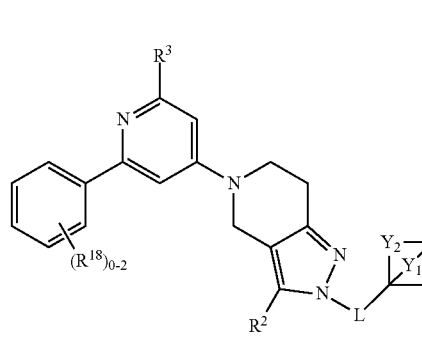
(Formula IIk)
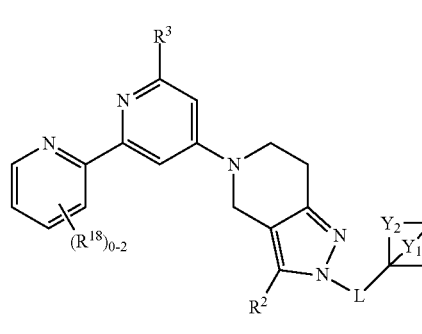

wherein $Y_1$, $Y_2$, $Y_3$, L, $R^1$, $R^2$, $R^3$, $R^4$, $R^{18}$, $R^{13}$ and $R^{14}$ are as defined in claim 1.

4. The compound of claim 1, or a pharmaceutically acceptable salt thereof, wherein:
$R^1$ is —NHC(=O)$R^6$, —NHC(=O)(CH$_2$)$_n R^6$, —NH(CH$_2$)$_n$C(=O)$R^6$, —NHC(=O)(CH$_2$)$_m$NHR$^5$, —NHC(=O)(CH$_2$)$_m$N(R$^5$)$_2$, —NHC(=O)(CHR$^9$)$_m$NHR$^5$, —NHC(=O)(CH$_2$)$_m$NH$_2$, —NHC(=O)(CH$_2$)$_n$OR$^9$, —NHC(=O)OR$^9$, —NH(CH$_2$)$_m$C(=O)N(R$^5$)$_2$, —NH(CHR$^9$)$_m$C(=O)R$^6$, —NHR$^6$, —NR$^5$R$^6$, —NH$_2$, —N(R$^5$)$_2$, —NHR$^5$, —NHR$^8$, —NR$^9$C(=O)OR$^{11}$, —NH(CH$_2$)$_n$R$^6$, —N(R$^6$)$_2$, —NHC(=O)(CH$_2$)$_n$N(CD$_3$)$_2$, —NH(CHR$^9$)$_n$CH$_2$OR$^9$, —NHCH$_2$(CHR$^9$)$_n$OR$^9$, —NH(CHR$^9$)$_n$OR$^9$, —NR$^9$(CH$_2$)$_n$OR$^9$, —NHCH$_2$(C(R$^9$)$_2$)$_n$OR$^9$, —OR$^9$, —NR$^9$C(=O)R$^5$, —NR$^9$C(=O)OR$^5$, —NHS(=O)$_2$R$^5$, —NHC(=O)(CH$_2$)$_n$NR$^9$C(=O)R$^5$, or —NHC(=O)(CH$_2$)$_n$NR$^9$S(=O)$_2$R$^5$.

5. The compound of claim 1, or a pharmaceutically acceptable salt thereof, wherein:
$R^1$ is —NHC(=O)$R^6$, —NHC(=O)(CH$_2$)$_n R^6$, —NH(CH$_2$)$_n$C(=O)$R^6$, —NHC(=O)(CH$_2$)$_m$NHR$^5$, —NHC(=O)(CH$_2$)$_m$N(R$^5$)$_2$, —NHC(=O)(CHR$^9$)$_m$NHR$^5$, —NHC(=O)(CH$_2$)$_m$NH$_2$, —NH(CH$_2$)$_m$C(=O)N(R$^5$)$_2$, —NH(CHR$^9$)$_n$C(=O)R$^6$, —NHR$^6$, —NH$_2$, —N(R$^5$)$_2$, —NHR$^5$, —NHR$^8$, —NH(CHR$^9$)$_n$OR$^9$ or —NHCH$_2$(C(R$^9$)$_2$)$_n$OR$^9$.

6. The compound of claim 1, or a pharmaceutically acceptable salt thereof, wherein:
$R^1$ is —NHC(=O)$R^6$, —NHC(=O)(CHR$^9$)$_n R^6$, —NH(CHR$^9$)$_n$C(=O)$R^6$ or —NHR$^6$.

7. The compound of claim 1, or a pharmaceutically acceptable salt thereof, wherein:
L is —CH$_2$— or —CH$_2$CH$_2$—;
$Y_1$ is —CH$_2$— or —CH$_2$CH$_2$—;
$Y_2$ is —CH$_2$— or —CH$_2$CH$_2$—;
$Y_3$ is —CH$_2$— or —XCH$_2$—;
X is —CH$_2$— or O;
$R^1$ is —NH(CH$_2$)$_n$C(=O)$R^6$, —NH(CH$_2$)$_m$C(=O)N(R$^5$)$_2$, —NH(CHR$^9$)$_n$C(=O)$R^6$, —NH(CHR$^9$)$_n$C(=O)N(R$^8$)$_2$, —NH(CHR$^9$)$_m$C(=O)$R^6$, —NH(C(R$^9$)$_2$)$_n$R$^{10}$, —NH(CH$_2$)$_n$R$^6$, —NH(CHR$^9$)$_n$R$^6$, —NH(CHR$^9$)$_n$CH$_2$OR$^9$, —NHCH$_2$(CHR$^9$)$_n$OR$^9$, —NH(CHR$^9$)$_n$OR$^9$, —NR$^9$(CH$_2$)$_n$OR$^9$, or —NHCH$_2$(C(R$^9$)$_2$)$_n$OR$^9$;
$R^2$ is H, C$_1$-C$_6$alkyl or C$_1$-C$_6$haloalkyl;
$R^3$ is H, C$_1$-C$_6$alkyl or —CD$_3$;
$R^4$ is H, NH$_2$, C$_1$-C$_6$alkyl or halo;
each $R^5$ is independently C$_1$-C$_6$alkyl, —CD$_3$ or —(CH$_2$)$_n$OR$^9$;
$R^6$ is a C$_3$-C$_6$cycloalkyl or a 4-6 membered heterocycloalkyl having 1 to 2 ring members independently selected from N, NH, NR$^{16}$ and O which is unsubstituted or is substituted with 1-2 R$^{12}$ groups;
each $R^8$ is independently selected from C$_1$-C$_6$haloalkyl, —(C(R$^9$)$_2$)$_n$OR$^9$ and a C$_1$-C$_6$alkyl substituted with 1 to 3 —OH;
each $R^9$ is independently selected from H and C$_1$-C$_6$alkyl;
$R^{10}$ is C$_1$-C$_6$alkoxy or C$_3$-C$_6$cycloalkyl;
each $R^{12}$ is independently selected from C$_1$-C$_6$alkyl, hydroxyl, halo and a C$_1$-C$_6$alkyl substituted with 1 to 3 —OH;
$R^{13}$ is H or C-C6alkyl;
$R^{14}$ is H or C$_1$-C$_6$alkyl;
each $R^{16}$ is C$_1$-C$_6$alkyl;
each $R^{17}$ is independently H or C$_1$-C$_6$alkyl;
each $R^{18}$ is independently halo, —CN, C$_1$-C$_6$alkoxy or C$_1$-C$_6$alkyl;

m is 1, 2, 3, 4, 5 or 6, and
n is 1, 2, 3, 4, 5 or 6.

8. The compound of claim 1, or a pharmaceutically acceptable salt thereof, wherein:
L is —CH$_2$— or —CH$_2$CH$_2$—;
$Y_1$ is —CH$_2$— or —CH$_2$CH$_2$—;
$Y_2$ is —CH$_2$— or —CH$_2$CH$_2$—;
$Y_3$ is —CH$_2$— or —XCH$_2$—;
X is —CH$_2$— or O;
$R^1$ is —NHR$^6$, —NR$^5$R$^6$, —NH$_2$, —N(R$^5$)$_2$, —NHR$^5$, —NHR$^8$, —N(R$^6$R$^8$) or —N(R$^6$)$_2$;
$R^2$ is H, C$_1$-C$_6$alkyl or C$_1$-C$_6$haloalkyl;
$R^3$ is H, C$_1$-C$_6$alkyl or —CD$_3$;
$R^4$ is H, NH$_2$, C$_1$-C$_6$alkyl or halo;
each $R^5$ is independently C$_1$-C$_6$alkyl, —CD$_3$ or —(CH$_2$)$_n$OR$^9$;
$R^6$ is a C$_3$-C$_6$cycloalkyl or a 4-6 membered heterocycloalkyl having 1 to 2 ring members independently selected from N, NH, NR$^{16}$ and O which is unsubstituted or is substituted with 1-2 R$^{12}$ groups;
each $R^8$ is independently selected from C$_1$-C$_6$haloalkyl, —(C(R$^9$)$_2$)$_n$OR$^9$ and a C$_1$-C$_6$alkyl substituted with 1 to 3 —OH;
each $R^{12}$ is independently selected from C$_1$-C$_6$alkyl, hydroxyl, halo and a C$_1$-C$_6$alkyl substituted with 1 to 3 —OH;
$R^{13}$ is H or C$_1$-C$_6$alkyl;
$R^{14}$ is H or C$_1$-C$_6$alkyl;
each $R^{16}$ is C$_1$-C$_6$alkyl;
each $R^{17}$ is independently H or C$_1$-C$_6$alkyl;
each $R^{18}$ is independently halo, —CN, C$_1$-C$_6$alkoxy or C$_1$-C$_6$alkyl;
m is 1, 2, 3, 4, 5 or 6, and
n is 1, 2, 3, 4, 5 or 6.

9. The compound of claim 1, or a pharmaceutically acceptable salt thereof, wherein
$R^6$ is a unsubstituted 4-6 membered heterocycloalkyl having 1 to 2 ring members independently selected from N, NH and O.

10. The compound of claim 1, or a pharmaceutically acceptable salt thereof, wherein
$R^6$ is cyclobutyl, oxetanyl, piperidinyl, pyrrolidinyl, morpholinyl or azetadinyl.

11. The compound of claim 1 selected from:
4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine;
4-((3-methyl-5-(6-methyl-1H-pyrazolo[3,4-b]pyridin-4-yl)-4,5,6,7-tetrahydro-1H-pyrazolo[4,3-c]pyridin-1-yl)methyl)bicyclo[2.2.2]octan-1-amine;
4-((3-methyl-5-(2-methyl-1,7-naphthyridin-4-yl)-4,5,6,7-tetrahydro-1H-pyrazolo[4,3-c]pyridin-1-yl)methyl)bicyclo[2.2.2]octan-1-amine;
4-((3-methyl-5-(2-methyl-7H-pyrrolo[2,3-d]pyrimidin-4-yl)-4,5,6,7-tetrahydro-1H-pyrazolo[4,3-c]pyridin-1-yl)methyl)bicyclo[2.2.2]octan-1-amine;
4-((5-(1,6-dimethyl-1H-pyrrolo[2,3-b]pyridin-4-yl)-3-methyl-4,5,6,7-tetrahydro-1H-pyrazolo[4,3-c]pyridin-1-yl)methyl)bicyclo[2.2.2]octan-1-amine;
N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)oxetan-3-amine;
N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(dimethylamino)acetamide (S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide;

(R)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide;

6-(4-((3-methyl-5-(1,3,5-trimethyl-H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)-2-oxa-6-azaspiro[3.3]heptane;

4-(1-((4-aminobicyclo[2.2.2]octan-1-yl)methyl)-6,7-dihydro-1H-pyrazolo[4,3-c]pyridin-5(4H)-yl)-1-methyl-1H-pyrazolo[3,4-d]pyrimidin-6-amine;

4-(2-((4-aminobicyclo[2.2.2]octan-1-yl)methyl)-6,7-dihydro-2H-pyrazolo[4,3-c]pyridin-5(4H)-yl)-1-methyl-1H-pyrazolo[3,4-d]pyrimidin-6-amine;

4-(1-((4-aminobicyclo[2.2.2]octan-1-yl)methyl)-3-methyl-6,7-dihydro-1H-pyrazolo[4,3-c]pyridin-5(4H)-yl)-1-methyl-1H-pyrazolo[3,4-d]pyrimidin-6-amine;

4-(2-((4-aminobicyclo[2.2.2]octan-1-yl)methyl)-3-methyl-6,7-dihydro-2H-pyrazolo[4,3-c]pyridin-5(4H)-yl)-1-methyl-1H-pyrazolo[3,4-d]pyrimidin-6-amine;

4-((5-(5-chloro-1-methyl-1H-pyrazolo[4,3-d]pyrimidin-7-yl)-3-methyl-4,5,6,7-tetrahydro-1H-pyrazolo[4,3-c]pyridin-1-yl)methyl)bicyclo[2.2.2]octan-1-amine;

1,6-dimethyl-4-(3-methyl-1-((4-(pyrrolidin-1-yl)bicyclo[2.2.2]octan-1-yl)methyl)-6,7-dihydro-1H-pyrazolo[4,3-c]pyridin-5(4H)-yl)-1H-pyrazolo[3,4-d]pyrimidine;

1,3,5-trimethyl-7-(3-methyl-1-((4-(pyrrolidin-1-yl)bicyclo[2.2.2]octan-1-yl)methyl)-6,7-dihydro-1H-pyrazolo[4,3-c]pyridin-5(4H)-yl)-1H-pyrazolo[4,3-d]pyrimidine;

N-(2-methoxyethyl)-4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-amine;

4-(4-((5-(1,6-dimethyl-1H-pyrazolo[3,4-d]pyrimidin-4-yl)-3-methyl-4,5,6,7-tetrahydro-1H-pyrazolo[4,3-c]pyridin-1-yl)methyl)bicyclo[2.2.2]octan-1-yl)morpholine;

2-(ethylamino)-N-(4-((3-methyl-5-(6-methyl-1H-pyrazolo[3,4-d]pyrimidin-4-yl)-4,5,6,7-tetrahydro-1H-pyrazolo[4,3-c]pyridin-1-yl)methyl)bicyclo[2.2.2]octan-1-yl)acetamide;

4-(4-((3-methyl-5-(6-methyl-1H-pyrazolo[3,4-d]pyrimidin-4-yl)-4,5,6,7-tetrahydro-1H-pyrazolo[4,3-c]pyridin-1-yl)methyl)bicyclo[2.2.2]octan-1-yl)morpholine;

2-(ethylamino)-N-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)acetamide;

4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)-N-(oxetan-3-ylmethyl)bicyclo[2.2.2]octan-1-amine;

3-(dimethylamino)-N-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)propanamide;

4-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)morpholine;

4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-amine;

N-cyclobutyl-4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-amine;

N,N-dicyclobutyl-4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-amine;

6-methyl-4-(3-methyl-1-((4-(piperidin-1-yl)bicyclo[2.2.2]octan-1-yl)methyl)-6,7-dihydro-1H-pyrazolo[4,3-c]pyridin-5(4H)-yl)-1H-pyrazolo[3,4-d]pyrimidine;

6-methyl-4-(3-methyl-1-((4-(pyrrolidin-1-yl)bicyclo[2.2.2]octan-1-yl)methyl)-6,7-dihydro-1H-pyrazolo[4,3-c]pyridin-5(4H)-yl)-1H-pyrazolo[3,4-d]pyrimidine;

(3-(((4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)amino)methyl)oxetan-3-yl)methanol;

N-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)azetidine-3-carboxamide;

(S)—N-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)morpholine-3-carboxamide;

(S)—N-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)morpholine-2-carboxamide;

(R)—N-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)morpholine-3-carboxamide;

(R)—N-(4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)morpholine-2-carboxamide;

3,6-dimethyl-4-(3-methyl-1-((4-morpholinobicyclo[2.2.2]octan-1-yl)methyl)-6,7-dihydro-1H-pyrazolo[4,3-c]pyridin-5(4H)-yl)isoxazolo[5,4-d]pyrimidine;

1,3,5-trimethyl-7-(3-methyl-1-((4-(piperidin-1-yl)bicyclo[2.2.2]octan-1-yl)methyl)-6,7-dihydro-1H-pyrazolo[4,3-c]pyridin-5(4H)-yl)-1H-pyrazolo[4,3-d]pyrimidine;

1,6-dimethyl-4-(3-methyl-1-((4-(piperidin-1-yl)bicyclo[2.2.2]octan-1-yl)methyl)-6,7-dihydro-1H-pyrazolo[4,3-c]pyridin-5(4H)-yl)-1H-pyrazolo[3,4-d]pyrimidine;

4-((3-methyl-5-(1,3,5-trimethyl-1H-pyrazolo[4,3-d]pyrimidin-7-yl)-4,5,6,7-tetrahydro-1H-pyrazolo[4,3-c]pyridin-1-yl)methyl)-N,N-bis(trideuteromethyl)bicyclo[2.2.2]octan-1-amine;

4-((3-methyl-5-(1H-pyrazolo[3,4-b]pyridin-4-yl)-4,5,6,7-tetrahydro-1H-pyrazolo[4,3-c]pyridin-1-yl)methyl)bicyclo[2.2.2]octan-1-amine;

4-((3-methyl-5-(1H-pyrazolo[3,4-b]pyridin-4-yl)-4,5,6,7-tetrahydro-2H-pyrazolo[4,3-c]pyridin-2-yl)methyl)bicyclo[2.2.2]octan-1-amine;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N,N-dimethylbicyclo[2.2.2]octan-1-amine;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.1]heptan-1-amine;

4-((5-(1,6-dimethyl-1H-pyrazolo[3,4-b]pyridin-4-yl)-3-(trifluoromethyl)-4,5,6,7-tetrahydro-1H-pyrazolo[4,3-c]pyridin-1-yl)methyl)bicyclo[2.2.2]octan-1-amine;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-ol;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)acetamide;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)methanesulfonamide;

tert-butyl (4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)(methyl)carbamate;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-methylbicyclo[2.2.2]octan-1-amine;

1-methylcyclopropyl (4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)carbamate;

3-((5-(1,6-dimethyl-1H-pyrazolo[3,4-b]pyridin-4-yl)-3-methyl-4,5,6,7-tetrahydro-2H-pyrazolo[4,3-c]pyridin-2-yl)methyl)bicyclo[1.1.1]pentan-1-amine;

4-((5-(1-(4-methoxybenzyl)-6-methyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine;

N-cyclobutyl-4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-isopropylbicyclo[2.2.2]octan-1-amine;

2-((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)propan-1-ol;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-ethylbicyclo[2.2.2]octan-1-amine;

5-(1,6-dimethyl-1H-pyrazolo[3,4-b]pyridin-4-yl)-3-methyl-1H-((4-(pyrrolidin-1-yl)bicyclo[2.2.2]octan-1-yl)methyl)-4,5,6,7-tetrahydro-1H-pyrazolo[4,3-c]pyridine;

4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine;

4-((5-(1,6-dimethyl-1H-pyrazolo[3,4-b]pyridin-4-yl)-7,7-dimethyl-4,5,6,7-tetrahydro-1H-pyrazolo[4,3-c]pyridin-1-yl)methyl)bicyclo[2.2.2]octan-1-amine;

N-(2,2-difluoroethyl)-4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine;

-((3-methyl-5-(2-methylquinolin-4-yl)-4,5,6,7-tetrahydro-1H-pyrazolo[4,3-c]pyridin-1-yl)methyl)bicyclo[2.2.2]octan-1-amine;

4-((3-methyl-5-(2-phenylpyridin-4-yl)-4,5,6,7-tetrahydro-1H-pyrazolo[4,3-c]pyridin-1-yl)methyl)bicyclo[2.2.2]octan-1-amine;

1-((4-(azetidin-1-yl)bicyclo[2.2.2]octan-1-yl)methyl)-5-(1,6-dimethyl-1H-pyrazolo[3,4-b]pyridin-4-yl)-3-methyl-4,5,6,7-tetrahydro-1H-pyrazolo[4,3-c]pyridine;

4-((5-(1,6-dimethyl-1H-pyrazolo[3,4-b]pyridin-4-yl)-7,7-dimethyl-4,5,6,7-tetrahydro-2H-pyrazolo[4,3-c]pyridin-2-yl)methyl)bicyclo[2.2.2]octan-1-amine;

4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)thiomorpholine 1,1-dioxide;

5-(1,6-dimethyl-1H-pyrazolo[3,4-b]pyridin-4-yl)-3-methyl-1-((4-(piperidin-1-yl)bicyclo[2.2.2]octan-1-yl)methyl)-4,5,6,7-tetrahydro-1H-pyrazolo[4,3-c]pyridine;

1-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)azetidin-3-ol;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(2-methoxyethyl)bicyclo[2.2.2]octan-1-amine;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N,N-bis(2-methoxyethyl)bicyclo[2.2.2]octan-1-amine;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(2-ethoxyethyl)bicyclo[2.2.2]octan-1-amine;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N,N-bis(2-ethoxyethyl)bicyclo[2.2.2]octan-1-amine;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(2-methoxyethyl)-N-methylbicyclo[2.2.2]octan-1-amine;

(3S,4R)-1-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)pyrrolidine-3,4-diol;

(S)-1-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)pyrrolidin-3-ol;

2-((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)-N,N-dimethylacetamide;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-N-methyloxetan-3-amine;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-isopropyl-N-methylbicyclo[2.2.2]octan-1-amine;

N-cyclobutyl-4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-methylbicyclo[2.2.2]octan-1-amine;

(3S,4S)-1-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)pyrrolidine-3,4-diol;

1-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-2-oxabicyclo[2.2.2]octan-4-amine;

5-(1,6-dimethyl-1H-pyrazolo[3,4-b]pyridin-4-yl)-3-methyl-1-((4-(pyrrolidin-1-yl)-2-oxabicyclo[2.2.2]octan-1-yl)methyl)-4,5,6,7-tetrahydro-1H-pyrazolo[4,3-c]pyridine;

4-((5-(6-(4-fluorophenyl)-1-methyl-1H-pyrazolo[3,4-d]pyrimidin-4-yl)-3-methyl-4,5,6,7-tetrahydro-1H-pyrazolo[4,3-c]pyridin-1-yl)methyl)bicyclo[2.2.2]octan-1-amine;

4-(4-(1-((4-aminobicyclo[2.2.2]octan-1-yl)methyl)-3-methyl-6,7-dihydro-1H-pyrazolo[4,3-c]pyridin-5(4H)-yl)pyridin-2-yl)benzonitrile;

3-methyl-5-(2-phenylpyridin-4-yl)-1-((4-(pyrrolidin-1-yl)bicyclo[2.2.2]octan-1-yl)methyl)-4,5,6,7-tetrahydro-1H-pyrazolo[4,3-c]pyridine;

2-methyl-4-(3-methyl-1-((4-(pyrrolidin-1-yl)bicyclo[2.2.2]octan-1-yl)methyl)-6,7-dihydro-1H-pyrazolo[4,3-c]pyridin-5(4H)-yl)-1,7-naphthyridine;

4-((5-(2-(4-fluorophenyl)pyridin-4-yl)-3-methyl-4,5,6,7-tetrahydro-1H-pyrazolo[4,3-c]pyridin-1-yl)methyl)bicyclo[2.2.2]octan-1-amine;

4-((5-(2-(2-fluoro-4-methylphenyl)pyridin-4-yl)-3-methyl-4,5,6,7-tetrahydro-1H-pyrazolo[4,3-c]pyridin-1-yl)methyl)bicyclo[2.2.2]octan-1-amine;

4-((5-(2-(4-methoxyphenyl)pyridin-4-yl)-3-methyl-4,5,6,7-tetrahydro-1H-pyrazolo[4,3-c]pyridin-1-yl)methyl)bicyclo[2.2.2]octan-1-amine;

4-((3-methyl-5-(2-(p-tolyl)pyridin-4-yl)-4,5,6,7-tetrahydro-1H-pyrazolo[4,3-c]pyridin-1-yl)methyl)bicyclo[2.2.2]octan-1-amine;

4-(2-(5-(1,6-dimethyl-1H-pyrazolo[3,4-b]pyridin-4-yl)-3-methyl-4,5,6,7-tetrahydro-1H-pyrazolo[4,3-c]pyridin-1-yl)ethyl)bicyclo[2.2.2]octan-1-amine;

4-((5-(2,8-dimethyl-1,7-naphthyridin-4-yl)-3-methyl-4,5,6,7-tetrahydro-1H-pyrazolo[4,3-c]pyridin-1-yl)methyl)bicyclo[2.2.2]octan-1-amine;

4-((3-methyl-5-(2-methyl-6-phenylpyridin-4-yl)-4,5,6,7-tetrahydro-1H-pyrazolo[4,3-c]pyridin-1-yl)methyl)bicyclo[2.2.2]octan-1-amine;

4-((5-([2,2'-bipyridin]-4-yl)-3-methyl-4,5,6,7-tetrahydro-1H-pyrazolo[4,3-c]pyridin-1-yl)methyl)bicyclo[2.2.2]octan-1-amine;

5-(1,6-dimethyl-1H-pyrazolo[3,4-b]pyridin-4-yl)-3-methyl-1-((4-(piperidin-1-yl)-2-oxabicyclo[2.2.2]octan-1-yl)methyl)-4,5,6,7-tetrahydro-1H-pyrazolo[4,3-c]pyridine;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(1-methoxypropan-2-yl)bicyclo[2.2.2]octan-1-amine;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-ethyl-N-methylbicyclo[2.2.2]octan-1-amine;

1-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N,N-dimethyl-2-oxabicyclo[2.2.2]octan-4-amine;

2-((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)-1-(piperidin-1-yl)ethanone;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(pyrrolidin-1-yl)acetamide;

4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(2-methoxy-2-methylpropyl)bicyclo[2.2.2]octan-1-amine;

1-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-N-(2-methoxyethyl)-2-oxabicyclo[2.2.2]octan-4-amine;

4-((5-(2-chloro-5,7-dihydrofuro[3,4-d]pyrimidin-4-yl)-3-methyl-4,5,6,7-tetrahydro-1H-pyrazolo[4,3-c]pyridin-1-yl)methyl)bicyclo[2.2.2]octan-1-amine;

4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-1-methylpiperazin-2-one;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-3-(dimethylamino)propanamide;

2-((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)-1-(pyrrolidin-1-yl)ethanone;

(R)-4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-methylmorpholine;

1-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-4-methylpiperazin-2-one;

(S)-4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-methylmorpholine;

(2S,6R)-4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2,6-dimethylmorpholine;

(2S,6S)-4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2,6-dimethylmorpholine;

N-(cyclobutylmethyl)-1-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-2-oxabicyclo[2.2.2]octan-4-amine;

(2R,6R)-4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2,6-dimethylmorpholine;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(ethylamino)acetamide;

3-amino-N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)propanamide;

6-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-oxa-6-azaspiro[3.3]heptane;

(R)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(methylamino)propanamide;

(S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(methylamino)propanamide;

1-((4-(1H-imidazol-1-yl)bicyclo[2.2.2]octan-1-yl)methyl)-5-(1,6-dimethyl-1H-pyrazolo[3,4-b]pyridin-4-yl)-3-methyl-4,5,6,7-tetrahydro-1H-pyrazolo[4,3-c]pyridine;

(1R,5S)-3-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-8-oxa-3-azabicyclo[3.2.1]octane;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(methylamino)acetamide;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-4-methylmorpholine-3-carboxamide;

1-((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)-2-methylpropan-2-ol;

2-(ethylamino)-N-(4-((3-methyl-5-(5-methyl-1H-pyrazolo[4,3-b]pyridin-7-yl)-4,5,6,7-tetrahydro-1H-pyrazolo[4,3-c]pyridin-1-yl)methyl)bicyclo[2.2.2]octan-1-yl)acetamide;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-2-carboxamide;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-3-(ethylamino)propanamide;

N-ethyl-4-((3-methyl-5-(2-phenylpyridin-4-yl)-4,5,6,7-tetrahydro-1H-pyrazolo[4,3-c]pyridin-1-yl)methyl)bicyclo[2.2.2]octan-1-amine;

(S)-4-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-3-methylmorpholine;

(R)-4-(4-((5-(1,6-dimethyl-H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-3-methylmorpholine;

N-(2-methoxyethyl)-4-((3-methyl-5-(2-phenylpyridin-4-yl)-4,5,6,7-tetrahydro-1H-pyrazolo[4,3-c]pyridin-1-yl)methyl)bicyclo[2.2.2]octan-1-amine;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)azetidine-3-carboxamide;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(ethyl(methyl)amino)acetamide;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(3-fluoroazetidin-1-yl)acetamide;

2-(bis(trideuteromethyl)amino)-N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)acetamide;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-hydroxyacetamide;

N-(4-((5-(1,6-dimethyl-1H-pyrazolo[3,4-b]pyridin-4-yl)-3-methyl-4,5,6,7-tetrahydro-H-pyrazolo[4,3-c]pyridin-1-yl)methyl)bicyclo[2.2.2]octan-1-yl)-2-(3-hydroxyazetidin-1-yl)acetamide;

(3-(((4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)amino)methyl)oxetan-3-yl)methanol;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(N-methylmethylsulfonamido)acetamide;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(N-methylacetamido)acetamide 4-((3-methyl-5-(6-methyl-1-(trideuteromethyl)-1H-pyrazolo[3,4-b]pyridin-4-yl)-4,5,6,7-tetrahydro-1H-pyrazolo[4,3-c]pyridin-1-yl)methyl)bicyclo[2.2.2]octan-1-amine;

(S)—N-(4-((5-(1-ethyl-6-methyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide;

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-3-(methylamino)propanamide;

N-cyclobutyl-1-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)-2-oxabicyclo[2.2.2]octan-4-amine;

N-cyclobutyl-4-((3-methyl-5-(2-phenylpyridin-4-yl)-4,5,6,7-tetrahydro-1H-pyrazolo[4,3-c]pyridin-1-yl)methyl)bicyclo[2.2.2]octan-1-amine;

tert-butyl (4-((5-(1-ethyl-6-methyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)carbamate;

tert-butyl (4-((3-methyl-5-(2-methyl-7H-pyrrolo[2,3-d]pyrimidin-4-yl)-4,5,6,7-tetrahydro-1H-pyrazolo[4,3-c]pyridin-1-yl)methyl)bicyclo[2.2.2]octan-1-yl)carbamate;

tert-butyl (4-((3-methyl-5-(2-methyl-1,7-naphthyridin-4-yl)-4,5,6,7-tetrahydro-1H-pyrazolo[4,3-c]pyridin-1-yl)methyl)bicyclo[2.2.2]octan-1-yl)carbamate;

tert-butyl (4-((5-(1,6-dimethyl-H-pyrazolo[3,4-b]pyridin-4-yl)-3-methyl-4,5,6,7-tetrahydro-1H-pyrazolo[4,3-c]pyridin-1-yl)methyl)bicyclo[2.2.1]heptan-1-yl)carbamate;

4-((5-(1,6-dimethyl-1H-pyrazolo[3,4-d]pyrimidin-4-yl)-3-methyl-4,5,6,7-tetrahydro-1H-pyrazolo[4,3-c]pyridin-1-yl)methyl)bicyclo[2.2.2]octan-1-amine, and 4-((5-(1-ethyl-6-methyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-amine.

12. The compound of claim 1 selected from:
N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)oxetan-3-amine;
N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)-2-(dimethylamino)acetamide;
(S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide;
(R)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide, and
6-(4-((3-methyl-5-(1,3,5-trimethyl-H-pyrazolo[4,3-d]pyrimidin-7-yl)-4,5,6,7-tetrahydro-1H-pyrazolo[4,3-c]pyridin-1-yl)methyl)bicyclo[2.2.2]octan-1-yl)-2-oxa-6-azaspiro[3.3]heptane.

13. A pharmaceutical composition comprising a therapeutically effective amount a compound of a compound of claim 1, or a pharmaceutically acceptable salt thereof, and a pharmaceutically acceptable carrier.

14. A method for inhibiting activity of an endosomal Toll-Like Receptor selected from TLR7, TLR8 and TLR9, or a combination thereof, wherein the method comprises administering to a subject in need of such inhibition a therapeutically effective amount of a compound of claim 1, or a pharmaceutically acceptable salt thereof.

15. A method for inhibiting activity of an endosomal Toll-Like Receptor pathway selected from TLR7 pathway, TLR8 pathway and TLR9 pathway, or a combination thereof, wherein the method comprises administering to a subject in need of such inhibition a therapeutically effective amount of a compound of claim 1, or a pharmaceutically acceptable salt thereof.

16. A method for treating an autoimmune disease associated with
  i) TLR7 activity, or
  ii) TLR7 activity and TLR8 activity, or
  iii) TLR7 activity and TLR8 activity and TLR9 activity,
wherein the method comprises administering to a subject in need of such treatment a therapeutically effective amount of a compound of claim 1, or a pharmaceutically acceptable salt thereof, wherein the autoimmune disease is systemic lupus erythematosus, cutaneous lupus, mixed connective tissue disease, primary biliary cirrhosis, immune thrombocytopenia purpura, dermatomyositis, polymyositis, Sjögren's syndrome, arthritis, rheumatoid arthritis or psoriasis.

17. A combination comprising a therapeutically effect amount of a compound of claim 1, or a pharmaceutically acceptable salt thereof, and one or more additional therapeutic agents, wherein the additional therapeutic agent is independently selected from anti-inflammatory agents, immunomodulatory agents, immunosuppressive agents, cytokines, nonsteroidal anti-inflammatory drugs (NSAIDs), antimalarial compounds, anti-rheumatic compounds, inhibitors of B-cell activating factor (BAFF), inhibitors of B-lymphocyte stimulator (BLyS), and steroid hormones.

18. The compound of Formula (Ia) of claim 3, or a pharmaceutically acceptable salt thereof, wherein:
L is —CH$_2$—;
Y$_1$ is —CH$_2$CH$_2$—;
Y$_2$ is —CH$_2$CH$_2$—;
Y$_3$ is —XCH$_2$—;
X is —CH$_2$—;
R$^1$ is —NHC(=O)R$^6$;
R$^2$ is C$_1$-C$_6$alkyl;
R$^3$ is C$_1$-C$_6$alkyl;
R$^4$ is C$_1$-C$_6$alkyl;
R$^6$ is an unsubstituted 4-6 membered heterocycloalkyl having 1 to 2 ring members independently selected from N, NH, and O; and
R$^{14}$ is H.

19. The compound of claim 18, or a pharmaceutically acceptable salt thereof, wherein the compound is

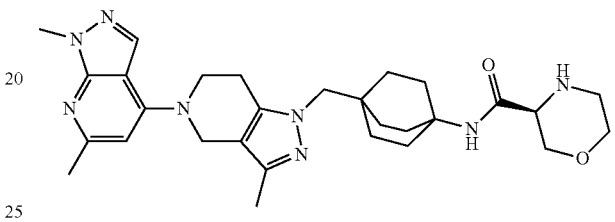

(S)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide;

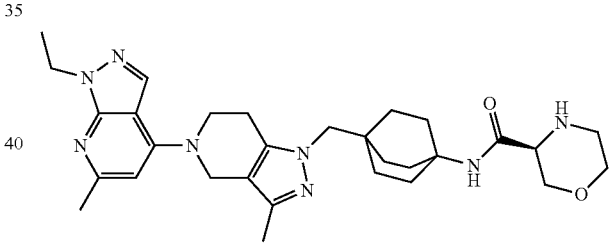

(S)—N-(4-((5-(1-ethyl-6-methyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide;

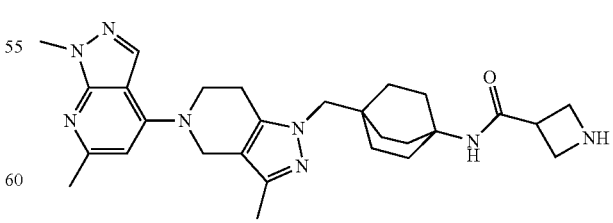

N-(4-((5-(1,6-dimethyl-H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)azetidine-3-carboxamide;

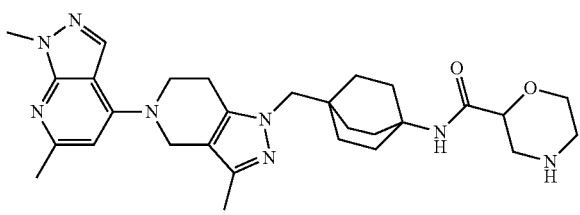 [SMILES: Cc1cc(N2CCc3c(c(C)nn3CC34CCC(NC(=O)C5CNCCO5)(CC3)CC4)C2)c2cnn(C)c2n1]

N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-2-carboxamide; or

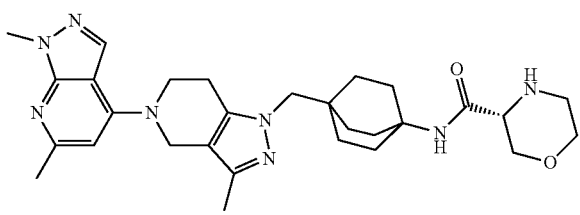 [SMILES: Cc1cc(N2CCc3c(c(C)nn3CC34CCC(NC(=O)[C@H]5COCCN5)(CC3)CC4)C2)c2cnn(C)c2n1]

(R)—N-(4-((5-(1,6-dimethyl-1H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide.

20. A pharmaceutical composition comprising a therapeutically effective amount a compound of claim 18, or a pharmaceutically acceptable salt thereof, and a pharmaceutically acceptable carrier.

21. A method for treating an autoimmune disease associated with the activity of an endosomal Toll-Like Receptor selected from TLR7, TLR8 and TLR9, or a combination thereof, wherein the method comprises administering to a subj t in need of such treatment a therapeutically effective amount of a compound of claim 18, or a pharmaceutically acceptable salt thereof, wherein the autoimmune disease is systemic lupus erythematosus, cutaneous lupus, mixed connective tissue disease, primary biliary cirrhosis, immune thrombocytopenia purpura, dermatomyositis, polymyositis, Sjögren's syndrome, arthritis, rheumatoid arthritis or psoriasis.

22. A method for treating an autoimmune disease associated with the activity of an endosomal Toll-Like Receptor pathway selected from TLR7 pathway, TLR8 pathway and TLR9 pathway, or a combination thereof, wherein the method comprises administering to a subject in need of such treatment a therapeutically effective amount of a compound of claim 18, or a pharmaceutically acceptable salt thereof, wherein the autoimmune disease is systemic lupus erythematosus, cutaneous lupus, mixed connective tissue disease, primary biliary cirrhosis, immune thrombocytopenia purpura, dermatomyositis, polymyositis, Sjögren's syndrome, arthritis, rheumatoid arthritis or psoriasis.

23. A method for treating an autoimmune disease associated with
  i) TLR7 activity, or
  ii) TLR7 activity and TLR8 activity, or
  iii) TLR7 activity and TLR8 activity and TLR9 activity,
    wherein the method comprises administering to a subject in need of such treatment a therapeutically effective amount of a compound of claim 18, or a pharmaceutically acceptable salt thereof, wherein the autoimmune disease is systemic lupus erythematosus, cutaneous lupus, mixed connective tissue disease, primary biliary cirrhosis, immune thrombocytopenia purpura, dermatomyositis, polymyositis, Sjögren's syndrome, arthritis, rheumatoid arthritis or psoriasis.

24. A combination comprising a therapeutically effect amount of a compound of claim 18, or a pharmaceutically acceptable salt thereof, and one or more additional therapeutic agents, wherein the additional therapeutic agent is independently selected from anti-inflammatory agents, immunomodulatory agents, immunosuppressive agents, cytokines, nonsteroidal anti-inflammatory drugs (NSAIDs), antimalarial compounds, anti-rheumatic compounds, inhibitors of B-cell activating factor (BAFF), inhibitors of B-lymphocyte stimulator (BLyS), and steroid hormones.

25. A compound, which is (S)—N-(4-((5-(1,6-dimethyl-H-pyrazolo[3,4-b]pyridin-4-yl)-3-methyl-4,5,6,7-tetrahydro-1H-pyrazolo[4,3-c]pyridin-1-yl)methyl)bicyclo[2.2.2]octan-1-yl)morpholine-3-carboxamide.

26. A pharmaceutical composition comprising a therapeutically effective amount a compound of claim 25, or a pharmaceutically acceptable salt thereof, and a pharmaceutically acceptable carrier.

27. A combination comprising a therapeutically effect amount of the compound of claim 25, or a pharmaceutically acceptable salt thereof, and one or more additional therapeutic agents, wherein the additional therapeutic agent is independently selected from anti-inflammatory agents, immunomodulatory agents, immunosuppressive agents, cytokines, nonsteroidal anti-inflammatory drugs (NSAIDs), antimalarial compounds, anti-rheumatic compounds, inhibitors of B-cell activating factor (BAFF), inhibitors of B-lymphocyte stimulator (BLyS), and steroid hormones.

28. A method for inhibiting activity of an endosomal Toll-Like Receptor selected from TLR7, TLR8 and TLR9, or a combination thereof, wherein the method comprises administering to a subject in need of such inhibition a therapeutically effective amount of the compound of claim 25, or a pharmaceutically acceptable salt thereof.

29. A method for inhibiting activity of an endosomal Toll-Like Receptor pathway selected from TLR7 pathway, TLR8 pathway and TLR9 pathway, or a combination thereof, wherein the method comprises administering to a subject in need of such inhibition a therapeutically effective amount of the compound of claim 25, or a pharmaceutically acceptable salt thereof.

30. A method for treating an autoimmune disease associated with
  i) TLR7 activity, or
  ii) TLR7 activity and TLR8 activity, or
  iii) TLR7 activity and TLR8 activity and TLR9 activity,
    wherein the method comprises administering to a subject in need of such treatment a therapeutically effective amount of the compound of claim 25, or a pharmaceutically acceptable salt thereof, wherein the autoimmune disease is systemic lupus erythematosus, cutaneous lupus, mixed connective tissue disease, primary biliary cirrhosis, immune thrombocytopenia purpura, dermatomyositis, polymyositis, Sjögren's syndrome, arthritis, rheumatoid arthritis or psoriasis.

* * * * *